(12) United States Patent
Chang et al.

(10) Patent No.: US 12,090,212 B2
(45) Date of Patent: *Sep. 17, 2024

(54) CONJUGATED BIOLOGICAL MOLECULES, PHARMACEUTICAL COMPOSITIONS AND METHODS

(71) Applicant: OBI Pharma, Inc., Taipei (TW)

(72) Inventors: Michael Nientse Chang, Taipei (TW); Jiann-Shiun Lai, Taipei (TW); Wan-Fen Li, Taipei (TW); I-Ju Chen, Taipei (TW); Yi-Chien Tsai, Taipei (TW); Kai-Chuan Chen, Taipei (TW)

(73) Assignee: OBI Pharma, Inc., Taipei (TW)

( * ) Notice: Subject to any disclaimer, the term of this patent is extended or adjusted under 35 U.S.C. 154(b) by 38 days.

This patent is subject to a terminal disclaimer.

(21) Appl. No.: 17/133,388

(22) Filed: Dec. 23, 2020

(65) Prior Publication Data

US 2021/0113711 A1   Apr. 22, 2021

Related U.S. Application Data

(62) Division of application No. 15/820,309, filed on Nov. 21, 2017, now Pat. No. 11,000,601.

(Continued)

(51) Int. Cl.
*A61K 47/68* (2017.01)
*A61K 39/395* (2006.01)
(Continued)

(52) U.S. Cl.
CPC .... *A61K 47/6855* (2017.08); *A61K 39/39558* (2013.01); *A61K 45/06* (2013.01);
(Continued)

(58) Field of Classification Search
None
See application file for complete search history.

(56) References Cited

U.S. PATENT DOCUMENTS 3,773,919 A   11/1973   Boswell et al.
RE30,985 E    6/1982    Cartaya
(Continued)

FOREIGN PATENT DOCUMENTS

CN   1871025 A    11/2006
CN   103108654 A   5/2013
(Continued)

OTHER PUBLICATIONS

Final Office Action issued in U.S. Appl. No. 16/454,750 on May 27, 2021.

(Continued)

*Primary Examiner* — Karl J Puttlitz
(74) *Attorney, Agent, or Firm* — Prosyla Group PC

(57) ABSTRACT

Antibody drug conjugates (ADC's) comprising a drug conjugated to antibody or antigen binding fragments thereof that bind to Globo series antigen disclosed herein, as well as methods of use thereof. Methods of use include, without limitation, cancer therapies and diagnostics. The antibodies of the disclosure can bind to certain cancer cell surfaces. Exemplary targets of the antibodies disclosed herein can include carcinomas, such as sarcoma, skin cancer, leukemia, lymphoma, brain cancer, glioblastoma, lung cancer, breast cancer, oral cancer, head-and-neck cancer, nasopharyngeal cancer, esophagus cancer, stomach cancer, liver cancer, bile duct cancer, gallbladder cancer, bladder cancer, pancreatic cancer, intestinal cancer, colorectal cancer, kidney cancer, cervix cancer, endometrial cancer, ovarian cancer, testical cancer, buccal cancer, oropharyngeal cancer, laryngeal cancer and prostate cancer.

8 Claims, 40 Drawing Sheets

Specification includes a Sequence Listing.

Related U.S. Application Data

(60) Provisional application No. 62/424,851, filed on Nov. 21, 2016.

(51) Int. Cl.
| | |
|---|---|
| *A61K 45/06* | (2006.01) |
| *A61K 49/00* | (2006.01) |
| *A61K 49/16* | (2006.01) |
| *A61K 51/10* | (2006.01) |
| *A61P 35/00* | (2006.01) |
| *A61P 35/04* | (2006.01) |
| *C07K 16/18* | (2006.01) |
| *C07K 16/30* | (2006.01) |
| *C07K 16/44* | (2006.01) |
| *C08B 37/00* | (2006.01) |
| *G01N 33/574* | (2006.01) |
| *A61K 39/00* | (2006.01) |

(52) U.S. Cl.
CPC ...... *A61K 47/6803* (2017.08); *A61K 47/6811* (2017.08); *A61K 47/6817* (2017.08); *A61K 47/6843* (2017.08); *A61K 47/6857* (2017.08); *A61K 47/6859* (2017.08); *A61K 47/6863* (2017.08); *A61K 49/0058* (2013.01); *A61K 49/16* (2013.01); *A61K 51/1018* (2013.01); *A61K 51/1051* (2013.01); *A61K 51/1054* (2013.01); *A61K 51/1057* (2013.01); *A61K 51/1063* (2013.01); *A61P 35/00* (2018.01); *A61P 35/04* (2018.01); *C07K 16/18* (2013.01); *C07K 16/3076* (2013.01); *C07K 16/44* (2013.01); *C08B 37/0006* (2013.01); *G01N 33/57492* (2013.01); *A61K 2039/505* (2013.01); *A61K 2039/54* (2013.01); *A61K 2039/545* (2013.01); *C07K 2317/24* (2013.01); *C07K 2317/56* (2013.01); *C07K 2317/565* (2013.01); *C07K 2317/567* (2013.01)

(56) References Cited

U.S. PATENT DOCUMENTS

| | | |
|---|---|---|
| 4,419,446 A | 12/1983 | Howley et al. |
| 4,522,811 A | 6/1985 | Eppstein et al. |
| 4,560,655 A | 12/1985 | Baker |
| 4,601,903 A | 7/1986 | Frasch |
| 4,601,978 A | 7/1986 | Karin |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,849,222 A | 7/1989 | Broaddus |
| 4,927,762 A | 5/1990 | Darfler |
| 4,943,533 A | 7/1990 | Mendelsohn et al. |
| 4,965,199 A | 10/1990 | Capon et al. |
| 4,975,278 A | 12/1990 | Senter et al. |
| 5,004,697 A | 4/1991 | Pardridge |
| 5,057,540 A | 10/1991 | Kensil et al. |
| 5,061,620 A | 10/1991 | Tsukamoto et al. |
| 5,100,669 A | 3/1992 | Hyon et al. |
| 5,112,596 A | 5/1992 | Malfroy-Camine |
| 5,122,469 A | 6/1992 | Mather et al. |
| 5,212,290 A | 5/1993 | Vogelstein et al. |
| 5,264,365 A | 11/1993 | Georgiou et al. |
| 5,268,164 A | 12/1993 | Kozarich et al. |
| 5,500,362 A | 3/1996 | Robinson et al. |
| 5,506,206 A | 4/1996 | Kozarich et al. |
| 5,508,192 A | 4/1996 | Georgiou et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,569,825 A | 10/1996 | Lonberg et al. |
| 5,571,894 A | 11/1996 | Wels et al. |
| 5,580,717 A | 12/1996 | Dower et al. |
| 5,587,458 A | 12/1996 | King et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,648,237 A | 7/1997 | Carter |
| 5,661,016 A | 8/1997 | Lonberg et al. |
| 5,686,416 A | 11/1997 | Kozarich et al. |
| 5,733,743 A | 3/1998 | Johnson et al. |
| 5,804,396 A | 9/1998 | Plowman |
| 5,814,344 A | 9/1998 | Tice et al. |
| 5,821,337 A | 10/1998 | Carter et al. |
| 5,840,523 A | 11/1998 | Simmons et al. |
| 5,869,046 A | 2/1999 | Presta et al. |
| 5,891,996 A | 4/1999 | Mateo de Acosta del Rio et al. |
| 6,004,940 A | 12/1999 | Marasco et al. |
| 6,027,888 A | 2/2000 | Georgiou et al. |
| 6,083,715 A | 7/2000 | Georgiou et al. |
| 6,265,150 B1 | 7/2001 | Terstappen et al. |
| 6,329,173 B1 | 12/2001 | Marasco et al. |
| 6,524,584 B2 | 2/2003 | Kensil |
| 6,544,952 B1 | 4/2003 | Danishefsky et al. |
| 6,703,019 B1 | 3/2004 | Malfroy-Camine |
| 7,595,292 B2 | 9/2009 | Brocchini et al. |
| 8,268,969 B2 | 9/2012 | Wong et al. |
| 10,815,307 B2 | 10/2020 | Yu et al. |
| 2002/0025313 A1 | 2/2002 | Micklus et al. |
| 2002/0038086 A1 | 3/2002 | Hynynen et al. |
| 2002/0065259 A1 | 5/2002 | Schatzberg et al. |
| 2003/0073713 A1 | 4/2003 | Schoenhard |
| 2003/0083299 A1 | 5/2003 | Ferguson |
| 2003/0104402 A1 | 6/2003 | Zauderer et al. |
| 2003/0129186 A1 | 7/2003 | Beliveau et al. |
| 2003/0153492 A1 | 8/2003 | Danishefsky et al. |
| 2003/0162695 A1 | 8/2003 | Schatzberg et al. |
| 2004/0018194 A1 | 1/2004 | Francisco et al. |
| 2004/0131692 A1 | 7/2004 | Kreuter et al. |
| 2004/0204354 A1 | 10/2004 | Nelson et al. |
| 2004/0208884 A1 | 10/2004 | Danishefsky et al. |
| 2004/0229310 A1 | 11/2004 | Simmons |
| 2004/0247608 A1 | 12/2004 | Krantz et al. |
| 2005/0048572 A1 | 3/2005 | Reilly et al. |
| 2005/0089473 A1 | 4/2005 | Black et al. |
| 2005/0124533 A1 | 6/2005 | Schatzberg et al. |
| 2006/0035267 A1 | 2/2006 | Livingston et al. |
| 2007/0059769 A1 | 3/2007 | Blixt et al. |
| 2009/0317411 A1 | 12/2009 | Wong et al. |
| 2010/0136042 A1 | 6/2010 | Wong et al. |
| 2010/0166790 A1 | 7/2010 | Agadjanyan et al. |
| 2010/0286035 A1 | 11/2010 | Ohtaki et al. |
| 2011/0117009 A1 | 5/2011 | Kratz et al. |
| 2012/0237532 A1 | 9/2012 | Olbrich et al. |
| 2012/0294859 A1 | 11/2012 | Goletz et al. |
| 2012/0321583 A1 | 12/2012 | Yurkovetskiy et al. |
| 2012/0328646 A1 | 12/2012 | Wong et al. |
| 2013/0095173 A1 | 4/2013 | Danishefsky et al. |
| 2013/0232589 A1 | 9/2013 | Papkoff et al. |
| 2014/0363455 A1 | 12/2014 | Stull et al. |
| 2015/0030669 A1 | 1/2015 | Platscher et al. |
| 2015/0297696 A1 | 10/2015 | Yu et al. |
| 2015/0316556 A1 | 11/2015 | Hardt et al. |
| 2015/0344551 A1 | 12/2015 | Wong et al. |
| 2016/0051672 A1 | 2/2016 | Stewart et al. |
| 2016/0074522 A1 | 3/2016 | Okuda et al. |
| 2016/0102151 A1* | 4/2016 | Wong .................. C07K 16/44 |
| | | 530/387.3 |
| 2016/0339089 A1 | 11/2016 | Yu et al. |
| 2017/0067885 A1 | 3/2017 | Yu et al. |
| 2017/0101462 A1 | 4/2017 | Yu et al. |
| 2017/0283488 A1 | 10/2017 | Yu et al. |
| 2017/0283489 A1 | 10/2017 | Bosio et al. |
| 2017/0304419 A1 | 10/2017 | Yu et al. |
| 2018/0028629 A1 | 2/2018 | Yu et al. |
| 2018/0193481 A1 | 7/2018 | Chang et al. |

(56) References Cited

U.S. PATENT DOCUMENTS

| | | | |
|---|---|---|---|
| 2018/0291109 A1* | 10/2018 | Lin | G01N 33/92 |
| 2018/0339061 A1 | 11/2018 | Yu et al. | |

FOREIGN PATENT DOCUMENTS

| | | | |
|---|---|---|---|
| EP | 0404097 A2 | 12/1990 | |
| EP | 1391213 A1 | 2/2004 | |
| EP | 2500035 A1 | 9/2012 | |
| EP | 2993182 A1 | 3/2016 | |
| JP | 2006-507233 A | 3/2006 | |
| JP | 2011524375 A | 9/2011 | |
| JP | 2011524417 A | 9/2011 | |
| JP | 2012-500880 | 1/2012 | |
| JP | 2016500256 A | 1/2016 | |
| JP | 2017512759 A | 5/2017 | |
| JP | 2018510844 A | 4/2018 | |
| JP | 2016-504385 | 6/2018 | |
| KR | 10-2012-0014238 A | 2/2012 | |
| NO | 2014107652 A2 | 7/2014 | |
| WO | WO 87/00195 A1 | 1/1987 | |
| WO | WO 90/03184 A1 | 4/1990 | |
| WO | WO 90/03430 A1 | 4/1990 | |
| WO | WO 91/00360 A1 | 1/1991 | |
| WO | WO 91/10741 A1 | 7/1991 | |
| WO | WO 92/00373 A1 | 1/1992 | |
| WO | WO 92/09690 A2 | 6/1992 | |
| WO | WO 93/01161 A1 | 1/1993 | |
| WO | WO 93/06213 A1 | 4/1993 | |
| WO | WO 93/007861 A1 | 4/1993 | |
| WO | WO 93/08829 A1 | 5/1993 | |
| WO | WO 93/16185 A2 | 8/1993 | |
| WO | WO 94/04690 A1 | 3/1994 | |
| WO | WO 94/011026 A2 | 5/1994 | |
| WO | WO 95/011010 A1 | 4/1995 | |
| WO | WO 96/07754 A1 | 3/1996 | |
| WO | WO 96/11711 A1 | 4/1996 | |
| WO | WO 96/30347 A1 | 10/1996 | |
| WO | WO 96/33735 A1 | 10/1996 | |
| WO | WO 96/33978 | 10/1996 | |
| WO | WO 96/33980 | 10/1996 | |
| WO | WO 96/34096 A1 | 10/1996 | |
| WO | WO 96/40210 | 12/1996 | |
| WO | WO 97/38983 | 10/1997 | |
| WO | WO 98/24893 A2 | 6/1998 | |
| WO | WO 98/36772 A1 | 8/1998 | |
| WO | WO 98/43960 A1 | 10/1998 | |
| WO | WO 99/06378 A1 | 2/1999 | |
| WO | WO 99/06396 A1 | 2/1999 | |
| WO | WO 99/09016 A1 | 2/1999 | |
| WO | WO 99/042130 A1 | 8/1999 | |
| WO | WO 2000/41720 A1 | 7/2000 | |
| WO | WO 2000/48630 A1 | 8/2000 | |
| WO | WO-2000/49412 A1 | 8/2000 | |
| WO | WO 2003/015796 A1 | 2/2003 | |
| WO | WO 2003/043583 A2 | 5/2003 | |
| WO | WO 2003/077945 A1 | 9/2003 | |
| WO | WO 2004/011476 A1 | 2/2004 | |
| WO | WO 2004/032828 A2 | 4/2004 | |
| WO | WO 2005/007197 A2 | 1/2005 | |
| WO | WO 2006/105152 A2 | 10/2006 | |
| WO | WO 2006/134423 A2 | 12/2006 | |
| WO | WO 2007/026190 A2 | 3/2007 | |
| WO | 2007047764 A2 | 4/2007 | |
| WO | WO 2007/044515 A1 | 4/2007 | |
| WO | WO 2009/035494 A2 | 3/2009 | |
| WO | WO 2009/126737 A2 | 10/2009 | |
| WO | 2010005735 A3 | 3/2010 | |
| WO | WO-2011/156774 A2 | 12/2011 | |
| WO | WO 2014/107652 A2 | 7/2014 | |
| WO | WO 2014/178195 A1 | 11/2014 | |
| WO | 2016044326 | 9/2015 | |
| WO | WO 2015/143123 A2 | 9/2015 | |
| WO | 2015157629 * | 10/2015 | |
| WO | 2015157629 A2 | 10/2015 | |
| WO | WO 2015/159118 A2 | 10/2015 | |
| WO | WO 2016/026742 A1 | 2/2016 | |
| WO | 2016044326 A1 | 3/2016 | |
| WO | 2016118961 A1 | 7/2016 | |
| WO | 2017004150 A1 | 1/2017 | |
| WO | 2017172990 | 3/2017 | |
| WO | WO 2017/041027 A1 | 3/2017 | |
| WO | 2017062792 * | 4/2017 | |
| WO | 2017185089 | 4/2017 | |
| WO | WO 2017/062792 A1 | 4/2017 | |
| WO | 2016044326 A9 | 5/2017 | |
| WO | 2018022933 | 7/2017 | |
| WO | 2018023121 | 7/2017 | |
| WO | 2017185089 A2 | 10/2017 | |
| WO | WO 2017/172990 A1 | 10/2017 | |
| WO | 2018094414 | 11/2017 | |
| WO | 2018022933 | 2/2018 | |
| WO | WO 2018/023121 A1 | 2/2018 | |
| WO | WO 2018/094414 A1 | 5/2018 | |
| WO | 2019232519 | 6/2019 | |
| WO | 2020006176 | 6/2019 | |
| WO | 2022109601 | 11/2021 | |

OTHER PUBLICATIONS

Substantive Examination Report, Office Paper No. 7, issued in Philippines Application No. 1-2017-500478 dated Oct. 21, 2020.

Substantive Examination Report, Office Paper No. 9, issued in Philippines Application No. 1-2017-500478 dated Jun. 10, 2021.

Eller, Chelcie et al., "Affinity of monoclonal antibodies for Globo-series glycans," Carbohydrate Research, (2014), 397, 1-6.

Gebauer, Wolfgang et al., "Keyhole Limpet Hemocyanin Type 2 (KLH2): Detection and Immunolocalization of a Labile Functional Unit h," J Structrual Biology, vol. 128, p. 280-286, 1999.

Gilewski, T et al., "Immunization of of metastatic breast cancer patients with a fully synthetic globo H conjugate: A phase I trial," PNAS, 98(6), pp. 3270-3275, Mar. 13, 2001.

International Search Report issued on Mar. 24, 2022, in International Patent Publication No. WO 2022/072513.

Lin, Yuan et al., "Improved affinity of a chicken single-chain antibody to avian infectious bronchitis virus by site-directed mutagenesis of complementarity-determining region H3", African Journal of Biotechnology, vol. 10(79), pp. 18294-18302, Dec. 12, 2011.

Lou, Yi-Wei et al., "Stage-specific embryonic antigen-4 as a potential therapeutic target in glioblastoma multiforme and other cancers," PNAS, (2014), 111(7): 2482-2487.

Mariuzza, R.A. et al., "The Structural Basis of Antigen-Antibody Recognition", Ann. Rev. Biophys. Chem, 1987, vol. 16, pp. 139-159.

McCarthy, Barry J., et al. "Altering the find specificity of an anti-Legionella single chain antibody by a single amino acid insertion", Journal of Immunological Methods, 2001, vol. 251, pp. 137-149.

Ragupathi, G., et al., "A fully synthetic globo H carbohydrate vaccine induces a focused humoral response in prostate cancer patients: a proof of principle," Angewandte Chemie International Edition 38.4 (1999): 569-566. Feb. 24, 1999.

Sasikumar et al., "Small-Molecule Immune Checkpoint INhibitors Targeting PD-1/PD-L1 and Other Emerging Checkpoint Pathways," BioDrugs, 2018, 32:481-497.

Abrahmsén et al., "Analysis of signals for secretion in the staphylococcal protein A gene," EMBO J., Dec. 30, 1985, 4(13B):3901-3906.

Allen, P. Z. et al., Immunochemical Studies on a Sophorosyl-Azoprotein Conjugate, Biochemistry, 1967, 6(10), 3029-3036.

Arié et al., "Chaperone function of FkpA, a heat shock prolyl isomerase, in the periplasm of *Escherichia coli*," Mol. Microbiol., Jan. 2001, 39(1):199-210.

Arigi, Emma, et al. "Design of a covalently bonded glycosphingolipid microarray." Glycoconjugate Journal 29.1 (2012): 1-12.

Avery, Oswald et al., Chemo-Immunological Studies on Conjugated Carbohydrate-Proteins, J. Exp. Med., 1929, 50, 533-550.

Bachmann, Cellular and Molecular Biology, vol. 2, Chapter 72: Derivations and Genotypes of Some Mutant Derivatives of *Escherichia*

(56) References Cited

OTHER PUBLICATIONS coli K-12, Neidhardt et al., eds., 1987, pp. 1190-1219, American Society for Microbiology, Washington, D.C.
Baldwin et al., "Monoclonal antibodies in cancer treatment," Lancet, Mar. 15, 1986, 327(8481):603-605.
Barbas et al., "Assembly of combinatorial antibody libraries on phage surfaces: the gene III site," Proc. Natl. Acad. Sci. U.S.A., Sep. 15, 1991, 88(18):7978-7982.
Barbas, C.F. et al., "Semisynthetic combinatorial antibody libraries: a chemical solution to the diversity problem" Proc. Natl. Acad. Sci. USA, May 15, 1992, 89(10): 4457-4461.
Barbas et al., "In vitro evolution of a neutralizing human antibody to human immunodeficiency virus type 1 to enhance affinity and broaden strain cross-reactivity," Proc. Nat. Acad. Sci. U.S.A., Apr. 26, 1994, 91(9):3809-3813.
Barnes et al., "Methods for growth of cultured cells in serum-free medium," Anal. Biochem., Mar. 1, 1980, 102(2):255-270.
Bass et al., "Hormone phage: an enrichment method for variant proteins with altered binding properties," Proteins, 1990, 8(4):309-314.
Berenbaum, M. C., What is Synergy?, Pharmacol. Rev. 41(2) :93-141, 1989.
Bergman, Jan, and Lennart Venemalm. "Efficient synthesis of 2-chloro-, 2-bromo-, and 2-iodoindole." The Journal of Organic Chemistry 57.8 (1992): 2495-2497.
Bertozzi, CR et al., Glycans in Cancer and Inflammation-Potential for Therapeutics and Diagnostics, Nat Rev Drug Discovery, 2005, 4, 477-488.
Bhaskar, Vinay et al., E-Electin Up-Regulation Allows for Targeted Drug Delivery in Prostate Cancer, Cancer Res. 63 :6387-6394, 2003.
Bird, R.E. et al., Single-Chain Antigen-Binding Proteins, Science, 1988, 242:423-426.
Bliss, C.I., The Calculation of Microbial Assays, Bacterial. Rev. 20:243-258, 1956.
Bobo et al., "Convection-enhanced delivery of macromolecules in the brain," Proc. Natl. Acad. Sci. U.S.A., Mar. 15, 1994, 91(6) 2076-2080.
Boerner et al., "Production of antigen-specific human monoclonal antibodies from in vitro-primed human splenocytes," J. Immunol., Jul. 1, 1991, 147(1):86-95.
Borisy, Alexis et al., Systematic Discovery of Multicomponent Therapeutics, Proc. Natl. Acad. Sci. 100(13):7977-7982, 2003.
Bosse, Folkert et al., Linear Synthesis of the Tumor-Associated Carbohydrate Antigens Globo-H, SSEA-3, and Gb3, J Org Chem. 67(19):6659-70, 2002.
Bothmann et al., "The periplasmic Escherichia coli peptidylprolyl cis,trans-isomerase FkpA. I. Increased functional expression of antibody fragments with and without cis-prolines," J. Biol. Chem., Jun. 2, 2000, 275(22):17100-17105.
Bowie, Ju et al., Deciphering the Message in Protein Sequences: Tolerance to Amino Acid Substitutions, Science, 247: 1306-1310 (1990).
Bremer, Eric et al., Characterization of Glycosphingolipid Antigen Defined By The Monoclonal Antibody MBr1 Expressed in Normal and Neoplastic Epithelial Cells of Human Mammary Gland, J Biol Chem 259: 14773-14777, 1984.
Brennan et al., "Preparation of bispecific antibodies by chemical recombination of monoclonal immunoglobulin G1 fragments," Science, Jul. 5, 1985, 229(4708):81-83.
Brodeur et al., Monoclonal Antibody Production Techniques and Applications, Chapter 4: Mouse-Human Myeloma Partners for the Production of Heterohybridomas, Schook, ed., 1987, pp. 51-63, Marcel Dekker, Inc., New York.
Brüggemann et al., "Designer mice: the production of human antibody repertoires in transgenic animals," Year in Immunol., 1993, 7:33-40.
Carter et al., "High level Escherichia coli expression and production of a bivalent humanized antibody fragment," Nature Biotechnology, Feb. 1992, 10(2):163-167.
Carter et al., "Humanization of an anti-p185$^{HER2}$ antibody for human cancer therapy," Proc. Natl. Acad. Sci. U.S.A., May 15, 1992, 89(10):4285-4289.
Casset, Florence, et al. "A peptide mimetic of an anti-CD4 monoclonal antibody by rational design." Biochemical and Biophysical Research Communications 307.1 (2003): 198-205.
Chang et al., "Potent immune-modulating and anticancer effects of NKT cell stimulatory glycolipids," Proc. Natl. Acad. Sci. USA, Jun. 19, 2007, 104(25):10299-10304.
Chang et al., "Expression of Globo H and SSEA3 in breast cancer stem cells and the involvement of fucosyl transferases 1 and 2 in Globo H synthesis," Proc. Natl. Acad. Sci. U.S.A., Aug. 19, 2008, 105(33):11667-11672.
Chen et al., "Chaperone activity of DsbC," J. Bio. Chem., Jul. 9, 1999, 274(28):19601-19605.
Chen et al., "Selection and analysis of an optimized anti-VEGF antibody: crystal structure of an affinity-matured Fab in complex with antigen," J. Mol. Biol., Nov. 5, 1999, 293(4):865-881.
Chen et al., "Selective killing of transformed cells by cyclin/cyclin-dependent kinase 2 antagonists," Proc. Natl. Acad. Sci. U.S.A., Apr. 13, 1999, 96(8):4325-4329.
Chen, Wei, et al. "Determination of thiols and disulfides via HPLC quantification of 5-thio-2-nitrobenzoic acid." Journal of Pharmaceutical and Biomedical Analysis 48.5 (2008): 1375-1380.
Chothia et al., "Canonical structures for the hypervariable regions of immunoglobulins," J. Mol. Biol., Aug. 20, 1987, 196(4):901-917.
Chou, Ting-Chao and Talalay, Paul, A Simple Generalized Equation for the Analysis of Multiple Inhibitions of Michaelis-Menten Kinetic Systems, J. Biol. Chem. 252:6438-6442, 1977.
Chou, T. C. and Talalay, P., Quantitative Analysis of Dose-Effect Relationships: The Combined Effects of Multiple Drugs or Enzyme Inhibitors. Adv. Enzyme Regul. 22:27-55, 1984.
Clackson et al., "Making antibody fragments using phage display libraries," Nature, Aug. 15, 1991, 352(6336):624-628.
ClinicalTrials.gov [Internet]. Bethesda (MD): National Library of Medicine (US). Jan. 24, 2012-. Trial of Active Imunotherapy with Globo H-KLH (OPT-822) in Metastatic Breast Cancer Subjects); Jan. 24, 2012 [cited Oct. 11, 2017]; [about 7 screens]. Available from: https:clinicaltrials.gov/ct2/show/NCT01516307.
Cunningham et al., "High-resolution epitope mapping of hGH-receptor interactions by alanine-scanning mutagenesis," Science, Jun. 2, 1989, 244(4908):1081-1085.
Clynes, Raphael, et al. "Fc receptors are required in passive and active immunity to melanoma." Proceedings of the National Academy of Sciences 95.2 (1998): 652-656.
Colman, P.M., "Effects of amino acid sequence changes on antibody-antigen interactions," Research in Immunology 145:33-36, 1994.
Cuzick, J., et al. "Overview of the main outcomes in breast-cancer prevention trials." The Lancet 361.9354 (2003): 296-300.
Danishefsky, Samuel J., et al. "Development of Globo-H cancer vaccine." Accounts of Chemical Research 48.3 (2015): 643-652.
De Pascalis, Roberto, et al. "Grafting of "abbreviated" complementarity-determining regions containing specificity-determining residues essential for ligand contact to engineer a less immunogenic humanized monoclonal antibody." The Journal of Immunology 169.6 (2002): 3076-3084.
Doronina, Svetlana et al., Development of Potent Monoclonal Antibody Auristatin Conjugates for Cancer Therapy, Nature Biotechnology 21(7):778-784, 2003.
Eller, Chelcie et al., Human Cancer Antigen Globo H Is a Cell-Surface Ligand for Human Ribonuclease 1, ACS Central Science. vol. 1, p. 181-90, Jul. 13, 2015.
Embleton et al., "In-cell PCR from mRNA: amplifying and linking the rearranged immunoglobulin heavy and light chain V-genes within single cells," Nucl. Acids Res., Aug. 11, 1992, 20(15):3831-3837.
Engels et al., "Gene synthesis [new synthetic methods (77)]," Angew. Chem. Int. Ed. Engl., Jun. 1989, 28(6):716-734.
Evans, T. R. J., and S. B. Kaye. "Vaccine therapy for cancer-fact or fiction?" Q J Med 92.6 (1999): 299-307.
Extended European Search Report, Application No. 15842660.1, Mailed Mar. 12, 2018, 9 pages.

(56) References Cited

OTHER PUBLICATIONS

Extended European Search Report from corresponding European App. No. 16843131.0, Feb. 14, 2019, 13 Pages.
Fellouse et al., "Synthetic antibodies from a four-amino-acid code: a dominant role for tyrosine in antigen recognition," Proc. Natl. Acad. Sci. U.S.A., Aug. 24, 2004, 101(34):12467-12472.
Feng, Li. "Probing lipid-protein interactions using lipid microarrays." Prostaglandins & other lipid mediators 77.1-4 (2005): 158-167.
Fielder, R. J. et al., An Immunogenic Polysaccharide-Protein Conjugate, J. Immunol., 1970, 105(1), 265-267.
Fishwild et al., "High-avidity human IgGκ monoclonal antibodies from a novel strain of minilocus transgenic mice," Nature Biotechnol., Jul. 1996, 14(7):845-851.
Fitzgerald, Jonathan et al., Systems Biology and Combination Therapy in the Quest for Clinical Efficacy, Nature Chem. Biol. 2(9):458-466, 2006.
Francisco, Joseph et al., cAC10-vcMMAE, an Anti-CD30-Monomethyl Auristatin E Conjugate With Potent and Selective Antitumor Activity, Blood 102(4): 1458-1465, 2003.
Galfrè et al., "Preparation of monoclonal antibodies: strategies and procedures," Methods Enzymol., 1981, 73(Pt B):3-46.
Gazzano-Santoro, Hélène, et al. "A non-radioactive complement-dependent cytotoxicity assay for anti-CD20 monoclonal antibody." Journal of Immunological Methods 202.2 (1997): 163-171.
Gijsen, H.J. et al., Recent Advances in the Chemoenzymatic Synthesis of Carbohydrates and Carbohydrate Mimetics, Chem. Rev., 96, 443-473, 1996.
Gilewski, Teresa et al., Immunization of Metastatic Breast Cancer Patients with a Fully Synthetic Globo H Conjugate: A Phase I Trial, Proc Natl Acad Sci USA 98:3270-3275, 2001.
Gill et al., "Direct brain infusion of glial cell line-derived neurotrophic factor in Parkinson disease," Nature Med., May 2003, 9(5):589-595 and Addendum from Apr. 2006, 12(4):479.
Goding, Monoclonal Antibodies: Principles and Practice 2nd ed., Chapter 3: Production of Monoclonal Antibodies, 1986, pp. 59-103, Academic Press, London.
Goebel, Walther et al., Chemo-immunological Studies on Conjugated Carbohydrate-Proteins, J. Exp. Med., 1929, 50, 521-531.
Gonnet, GH et al., Exhaustive Matching of the Entire Protein Sequence Database, Science 256: 1443-45 (1992).
Graham et al., "Characteristics of a human cell line transformed by DNA from human adenovirus type 5," J. Gen. Virol., Jul. 1977, 36(1):59-72.
Gram et al., "In vitro selection and affinity maturation of antibodies from a naive combinatorial immunoglobulin library," Proc. Natl. Acad. Sci. U.S.A., Apr. 15, 1992, 89(8):3576-3580.
Grant, Oliver C., et al. "Presentation, presentation, presentation! Molecular-level insight into linker effects on glycan array screening data." Glycobiology 24.1 (2014): 17-25.
Greco, William et al., The Search for Synergy: A Critical Review From a Response Surface Perspective, Pharmacol. Rev. 47(2):331-385, 1995.
Griffiths et al., "Human anti-self antibodies with high specificity from phage display libraries," EMBO J., Feb. 1993, 12(2):725-734.
Gruber et al., "Efficient tumor cell lysis mediated by a bispecific single chain antibody expressed in Escherichia coli," J. Immunol., Jun. 1, 1994, 152(11):5368-5374.
Guss et al., "Structure of the IgG-binding regions of streptococcal protein G," EMBO J., Jul. 1986, 5(7):1567-1575.
Hakomori et al., "Glycosphingolipid antigens and cancer therapy," Chem. & Biol., Feb. 1997, 4(2):97-104.
Hakomori, Sen-Itiroh, Tumor-associated carbohydrate antigens defining tumor malignancy: Basis for development of and-cancer vaccines, 2001, Advances in Experimental Medicine and Biology. 491 :369-402.
Ham, Richard et al., Media and Growth Requirements, Meth. Enz 58, 44-93 (1979).
Hammerling et al., in: Monoclonal Antibodies and T-Cell Hybridomas 563-681, 1981.

Hara et al., "Overproduction of penicillin-binding protein 7 suppresses thermosensitive growth defect at low osmolarity due to an spr mutation of Escherichia coli," Microbial Drug Resistance, Spring 1996, 2(1):63-72.
Harris, J. Robin, et al. "Keyhole limpet hemocyanin (KLH), II: Characteristic reassociation properties of purified KLH1 and KLH2." Micron 28.1 (1997): 43-56.
Harris, J. R., and J. Mark l. "Keyhole limpet hemocyanin (KLH): a biomedical review." Micron 30.6 (1999): 597-623.
Harris, "Production of humanized monoclonal antibodies for in vivo imaging and therapy," Biochem. Soc. Transactions, Nov. 1995, 23(4):1035-1038.
Hawkins et al., "Selection of phage antibodies by binding affinity. Mimicking affinity maturation," J. Mol. Biol., 1992, 226(3):889-896.
Heffernan, Michael J., et al. "In vivo efficacy of a chitosan/IL-12 adjuvant system for protein-based vaccines." Biomaterials 32.3 (2011): 926-932.
Hernández-Ledesma, Blanca, Chia-Chien Hsieh, and O. Ben. "Lunasin, a novel seed peptide for cancer prevention." Peptides 30.2 (2009): 426-430.
Himmelspach, K. et al., Use of l-(m-aminophenyl)flavazoles for the Preparation of Immunogens with Oligosaccharide Determinant Groups, Eur. J. Immunol., 1971, 1(2), 106-112.
Hinman et al., "Preparation and characterization of monoclonal antibody conjugates of the calicheamicins: a novel and potent family of antitumor antibiotics," Cancer Res., Jul. 15, 1993, 53(14):3336-3342.
Hirabayashi, J. et al., Oligosaccharide Microarrays for Glycomics, Trends in Biotechnology 21 (4): 141-143, 2003.
Hirano, Fumiya, et al. "Blockade of B7-H1 and PD-1 by monoclonal antibodies potentiates cancer therapeutic immunity." Cancer Research 65.3 (2005): 1089-1096.
Hogrefe, H.H. et al., "A bacteriophage lambda vector for the cloning and expression of immunoglobulin Fab fragments on the surface of filamentous phage" Gene, 1993, 128(1): 119-126.
Holliger et al., "'Diabodies': small bivalent and bispecific antibody fragments," Proc. Natl. Acad. Sci. U.S.A., Jul. 15, 1993, 90(14):6444-6448.
Holm, Patrik, Rozbeh Jafari, and Birgitta E. Sundström. "Functional mapping and single chain construction of the anti-cytokeratin 8 monoclonal antibody TS1." Molecular Immunology 44.6 (2007): 1075-1084.
Hoogenboom et al., "By-passing immunisation: Human antibodies from synthetic repertoires of germline VH gene segments rearranged in vitro," J. Mol. Biol., Sep. 20, 1992, 227(2):381-388.
Hoogenboom et al., "Multi-subunit proteins on the surface of filamentous phage: methodologies for displaying antibody (Fab) heavy and light chains," Nucl. Acids Res., Aug. 11, 1991 19(15):4133-4137.
Huang, Cheng-Yuan et al., Carbohydrate Microarray for Profiling the Antibodies Interacting with Globo H Tumor Antigen, Proc Natl Acad Sci, 103:15-20, 2006.
Huang, Yen-Lin, and Chung-Yi Wu. "Carbohydrate-based vaccines: challenges and opportunities." Expert Review of Vaccines 9.11 (2010): 1257-1274.
Huang, Yen-Lin, et al. "Carbohydrate-based vaccines with a glycolipid adjuvant for breast cancer." Proceedings of the National Academy of Sciences 110.7 (2013): 2517-2522.
Hurle et al., "Protein engineering techniques for antibody humanization," Curr. Opin. Biotechnol., Aug. 1994, 5(4):428-433.
Huston, James et al., Protein Engineering of Antibody Binding Sites: Recovery of Specific Activity in an Anti-Digoxin Single-Chain Fv Analogue Produced in Escherichia coli, Proc. Natl. Acad. Sci. USA, 1988, 85:5879-5883.
International Search Report issued Jan. 8, 2016 in counterpart application PCT/IB2014/002744, 3 pages.
International Search Report and Written Opinion of the International Searching Authority, from corresponding International Patent Application No. PCT/US2015/050270, Dec. 15, 2015, 14 Pages.
International Search Report and Written Opinion of the International Searching Authority, from corresponding International Patent Application No. PCT/US16/50252, Nov. 17, 2016, 12 Pages.

(56) References Cited

OTHER PUBLICATIONS

International Search Report and Written Opinion dated Jul. 7, 2017, from corresponding International Patent Application No. PCT/US2017/024853, by Yu, Cheng-Der Tony et al., "Antibodies, Pharmaceutical Compositions and Methods", filed Mar. 29, 2017, 21 pages.
International Search Report/Written Opinion issued Oct. 31, 2017 in counterpart PCT Application No. PCT/US2017/044244, 13 pages.
International Search Report issued Nov. 28, 2017 in counterpart application PCT/US2017/044713, 6 pages.
Jackson et al., "In vitro antibody maturation: Improvement of a high affinity, neutralizing antibody against IL-1β," J. Immunol., Apr. 1, 1995, 154(7):3310-3319.
Jakobovits et al., "Analysis of homozygous mutant chimeric mice: deletion of the immunoglobulin heavy-chain joining region blocks B-cell development and antibody production," Proc. Natl. Acad. Sci. U.S.A., Mar. 15, 1993, 90(6):2551-2555.
Jakobovits et al., "Germ-line transmission and expression of a human-derived yeast artificial chromosome," Nature, Mar. 18, 1993, 362(6417):255-258.
Jeon, Insik et al., A Practical Total Synthesis of Globo-H for Use in Anticancer Vaccines, J. Org. Chem., 2009, 74(21), pp. 8452-8455.
Jones et al., "Rapid PCR-cloning of full-length mouse immunoglobulin variable regions," Nature Biotechnol., Jan. 1991, 9(1):88-89.
Jones, "Analysis of polypeptides and proteins," Adv. Drug Delivery Rev., Jan.-Apr. 1993, 10(1):29-90.
Jones et al., "Replacing the complementarity-determining regions in a human antibody with those from a mouse," Nature, May 29-Jun. 4, 1986, 321(6069):522-525.
Kam et al., "Carbon nanotubes as multifunctional biological transporters and near-infrared agents for selective cancer cell destruction," Proc. Natl. Acad. Sci. U.S.A., Aug. 16, 2005, 102(33):11600-11605.
Kannagi et al., "New globoseries glycosphingolipids in human teratocarcinoma reactive with the monoclonal antibody directed to a developmentally regulated antigen, stage-specific embryonic antigen 3," J. Biol. Chem., Jul. 25, 1983, 258(14):8934-8942.
Kannagi, Reiji et al., Stage-Specific Embryonic Antigens (SSEA-3 and -4) are Epitopes of a Unique Globo-Series Ganglioside Isolated From Human Teratocarcinoma Cells, EMBO J, 2:2355-2361, 1983.
Klussman, Kerry et al., Secondary mAb-vcMMAE Conjugates are Highly Sensitive Reporters of Antibody Internalization Via the Lysosome Pathway, Bioconjugate Chemistry 15(4):765-773, 2004.
Koeller, Kathryn et al., Enzymes for Chemical Synthesis, Nature, 409, 232-240, 2001.
Köhler et al., "Continuous cultures of fused cells secreting antibody of predefined specificity," Nature, Aug. 7, 1975, 256(5517):495-497.
Komenaka, Ian, Heidi Hoerig, and Howard L. Kaufman. "Immunotherapy for melanoma." Clinics in Dermatology 22.3 (2004): 251-265.
Konecny, G. et al., Drug Interactions and Cytotoxic Effects of Paclitaxel in Combination with Carboplatin, Epirubicin, Gemcitabine or Vinorelbine in Breast Cancer Cell Lines and Tumor Samples, Breast Cancer Res. and Treatment 67:223-233, 2001.
Kontermann, "Intrabodies as therapeutic agents," Methods, Oct. 2004, 34(2):163-170.
Kostelny et al., "Formation of a bispecific antibody by the use of leucine zippers," J. Immunol., Mar. 1, 1992, 148(5):1547-1553.
Kozbor, "A human hybrid myeloma for production of human monoclonal antibodies," J. Immunol., Dec. 1984, 133(6):3001-3005.
Krainer, Florian et al., An Updated View on Horseradish Peroxidases: Recombinant Production and Biotechnological Applications, Applied Microbiology and Biotechnology, vol. 99, p. 1611-1625, Jan. 11, 2015.
Kufer, P. et al., A Revival of Bispecific Antibodies, Trends Biotechnol. 22:238-244, 2004.

Lee et al. "Immunogenicity study of Globo H analogues with modification at the reducing or nonreducing end of the tumor antigen" Journal of the American Chemical Society, (2014) 136(48), 16844-16853.
Lee et al., "Bivalent antibody phage display mimics natural immunoglobulin," J. Immunol. Methods, Jan. 2004, 284(1-2):119-132.
Lee et al., "High-affinity human antibodies from phage-displayed synthetic Fab libraries with a single framework scaffold," J. Mol. Biol., Jul. 23, 2004, 340(5):1073-1093.
Lehninger, Biochemistry: The Molecular Basis of Cell Structure and Function, 2nd ed., 1975, pp. 73-75, Worth Publishers, New York.
Leung et al., "A method for random mutagenesis of a defined DNA segment using a modified polymerase chain reaction," Technique—A Journal of Methods in Cell and Molecular Biology, Aug. 1989, 1(1):11-15.
Liang, Pi-Hui, et al. "Quantitative Microarray Analysis of Intact Glycolipid-CD1d Interaction and Correlation with Cell-Based Cytokine Production." Journal of the American Chemical Society 130.37 (2008): 12348-12354.
Lindmark et al., "Binding of immunoglobulins to protein A and immunoglobulin levels in mammalian sera," J. Immunol. Meth., Aug. 12, 1983, 62(1):1-13.
Liu et al., "Eradication of large colon tumor xenografts by targeted delivery of maytansinoids," Proc. Natl., Acad. Sci. U.S.A., Aug. 6, 1996, 93(16):8618-8623.
Liu, Gui, et al. "QS-21 structure/function studies: effect of acylation on adjuvant activity." Vaccine 20.21-22 (2002): 2808-2815.
Livingston, Philip, "Augmenting the immunogenicity of carbohydrate tunor antigens" Seminars in Cancer Biology, Cancer Biol, 6(6):357-366, 1995.
Lloyd, Kenneth, "Tumor Antigens Known to be Immunogenic in Man" in Specific Immunotherapy of Cancer with Vaccines, 1993, 690, 50-58.
Lode et al., "Targeted therapy with a novel enediyene antibiotic calicheamicin ϴI1 effectively suppresses growth and dissemination of liver metastases in a syngeneic model of murine neuroblastoma," Cancer Res., Jul. 15, 1998, 58(14):2925-2928.
Lonberg et al., "Antigen-specific human antibodies from mice comprising four distinct genetic modifications," Nature, Apr. 28, 1994, 368(6474):856-859.
Lonberg et al., "Human antibodies from transgenic mice," Int. Rev. Immunol., 1995, 13(1):65-93.
Lou, et al., Stage-specific embryonic antigent-4 as a potential therapeutic target in glioblastoma multiforms and other cancers. Proc Natl Acad Sci USA 2014, 111(7):2482-7.
Lucas, A.H. et al., Carbohydrate Moieties as Vaccine Candidates: Meeting Summary, Vaccine, vol. 28(4), Jan. 2010, pp. 1121-1131.
Mandler et al., "Immunoconjugates of geldanamycin and anti-HER2 monoclonal antibodies: antiproliferative activity on human breast carcinoma cell lines," J. Nat. Cancer Inst., Oct. 4, 2000, 92(19):1573-1581.
Mandler et al., "Modifications in synthesis strategy improve the yield and efficacy of geldanamycin-herceptin immunoconjugates," Bioconjugate Chem., Jul.-Aug. 2002, 13(4):786-791.
Mandler et al., "Synthesis and evaluation of antiproliferative activity of a geldanamycin-Herceptin™ immunoconjugate," Bioorganic & Med. Chem. Letters, May 15, 2000, 10(10):1025-1028.
Mao, Shenlan, et al. "Phage-display library selection of high-affinity human single-chain antibodies to tumor-associated carbohydrate antigens sialyl Lewisx and Lewisx." Proceedings of the National Academy of Sciences 96.12 (1999): 6953-6958.
Mao, Weiguang et al., EphB2 as a Therapeutic Antibody DrugTarget for the Treatment of Colorectal Cancer, Cancer Research 64(3):781-788, 2004.
Marasco et al., "Design, intracellular expression, and activity of a human anti-human immunodeficiency virus type 1 gp120 single-chain antibody," Proc. Natl. Acad. Sci. U.S.A., Aug. 15, 1993, 90(16):7889-7893.
Marasco, "Intrabodies: turning the humoral immune system outside in for intracellular immunization," Gene Therapy, Jan. 1997, 4(1):11-15.

(56) References Cited

OTHER PUBLICATIONS

Marks et al., "By-passing immunization. Human antibodies from V-gene libraries displayed on phage," *J. Mol. Biol.*, Dec. 5, 1991, 222(3):581-597.
Marks et al., "By-passing immunization: Building high affinity human antibodies by chain shuffling," *Nature Biotechnology*, Jul. 1992, 10(7):779-783.
Martineau, R.S. et al., Immunochemical Studies on a Panosyl-Azoprotein conjugate, Immunochemistry, vol. 8, 705-718, 1971.
Mather et al., "Culture of testicular cells in hormone-supplemented serum-free medium," Annals N.Y. Acad. Sci., 1982, 383:44-68.
Mather, "Establishment and characterization of two distinct mouse testicular epithelial cell lines," Biol. Reprod., Aug. 1980, 23(1):243-252.
Matsuda, F. et al., "Structure and physical map of 64 variable segments in the 3' 0.8- megabase region of the human immunoglobulin heavy-chain locus." Nature Genet., 1993, 3: 88-94.
McCafferty et al., "Phage antibodies: Filamentous phage displaying antibody variable domains," *Nature*, Dec. 6, 1990, 348:552-554.
Menard S et al., Generation of Monoclonal Antibodies Reacting with Normal and Cancer Cells of Human Breast, Cancer Res 43: 1295-1300, 1983.
Milstein, C & Cuello, AC, Hybrid Hydridomas and their use in immunohistochemistry, Nature 305, 537-540, Oct. 1993.
Miller, Kathy et al., Design, Construction, and In Vitro Analyses of Multivalent Antibodies, Jour. Of Immunology 170:4854-4861, 2003.
Morimoto et al., "Single-step purification of F(ab')2 fragments of mouse monoclonal antibodies (immunoglobulins G1) by hydrophobic interaction high performance liquid chromatography using TSKgel Phenyl-5PW," J. Biochem. Biophys. Meth., Mar. 1992, 24(1-2):107-117.
Morrison et al., "Chimeric human antibody molecules: mouse antigen-binding domains with human constant region domains," *Proc. Natl. Acad. Sci. U.S.A.*, Nov. 1984, 81(21):6851-6855.
Morrison, "Immunology. Success in specification," *Nature*, Apr. 28, 1994, 368(6474):812-813.
Munson et al., "Ligand: a versatile computerized approach for characterization of ligand-binding systems," *Anal. Biochem.*, Sep. 1, 1980, 107(1):220-239.
Neuberger et al., "Recombinant antibodies possessing novel effector functions," Nature, Dec. 13-19, 1984, 312(5995):604-608.
Neuberger, "Generating high-avidity human Mabs in mice," *Nature Biotechnol.*, Jul. 1996, 14(7):826.
Nicolaou, K.C. et al., "Calicheamicin $\Theta^I{}_1$: A rationally designed molecule with extremely potent and selective DNA cleaving properties and apoptosis inducing activity." Angew. Chem. Intl. Ed. Engl., Feb. 1, 1994, 33(2):183-186.
Nikula, Kristen et al., Animal Models of Chronic Bronchitis and Their Relevance to Studies of Particle-Induced Disease, Inhal. Toxicol. 4(12): 123-153, 2000.
Niculescu-Duvaz et al., "Antibody-directed enzyme prodrug therapy (ADEPT): A review," *Adv. Drg. Del. Rev.*, Jul. 7, 1997, 26(2-3):151-172.
Office Action issued in corresponding Taiwan patent application No. 103131876, mailed Dec. 26, 2016, 7 pages.
Orlandi et al., "Cloning immunoglobulin variable domains for expression by the polymerase chain reaction," Proc. Natl. Acad. Sci. U.S.A., May 1989, 86(10):3833-3837.
Ørum et al., "Efficient method for constructing comprehensive murine Fab antibody libraries displayed on phage." Nucleic Acids Res., Sep. 25, 1993, 21(19):4491-4498.
Oxenius, Annette, et al. "CpG-containing oligonucleotides are efficient adjuvants for induction of protective antiviral immune responses with T-cell peptide vaccines." Journal of Virology 73.5 (1999): 4120-4126.
Papanastassiou et al., "The potential for efficacy of the modified (ICP 34.5-) herpes simplex virus HSV1716 following intratumoural injection into human malignant glioma: a proof of principle study," Gene Therapy, Mar. 2002, 9(6):398-406.

Paul, William E. "Structure and Function of Immunoglobulins, Fundamental Immunology." Chapter 9 (1993), 3rd Edition: 292-295.
Pearson, William, Using the FASTA Program to Search Protein and DNA Sequence Databases, Methods Mol. Biol. 243:307-31, 1994.
Pegram, Mark et al., Inhibitory Effects of Combinations of HER-2/neu Antibody and Chemotherapeutic Agents Used for Treatment of Human Breast Cancers, Oncogene 18:2241-2251, 1999.
Pegram, Mark et al., Rational Combinations of Trastuzumab With Chemotherapeutic Drugs Used in the Treatment of Breast Cancer, J. of the Nat. Cancer Inst. 96(10):739-749, 2004.
Pluckthun, *Handbook of Experimental Pharmacology, vol. 113: The Pharacology of Monoclonal Antibodies, Chapter 11: Antibodies from Escherichia coli*, Rosenberg et al., eds., 1994, pp. 269-315, Springer-Verlag, Berlin.
Presta et al., "Humanization of an antibody directed against IgE," *J. Immunol.*, Sep. 1, 1993, 151(5):2623-2632.
Presta, "Antibody engineering," *Curr. Opin. Struct. Biol.*, Aug. 1992, 2(4):593-596.
Presta et al., "Humanization of an anti-vascular endothelial growth factor monoclonal antibody for the therapy of solid tumors and other disorders," Cancer Res., Oct. 15, 1997, 57(20):4593-4599.
Presta, Leonard G. "Antibody engineering." Current Opinion in Biotechnology 3.4 (1992): 394-398.
Proba et al., "Functional antibody single-chain fragments from the cytoplasm of *Escherichia coli*: influence of thioredoxin reductase (TrxB)," Gene, Jul. 4, 1995, 159(2):203-207.
Queen, Cary et al, A Humanized Antibody that Binds to the Interleukin 2 Receptor, Proc Natl Acad Sci., 86: 10029-10033 (1989).
Ragupathi, Govindaswami et al., Immunization of Mice with a Fully Synthetic Globo H Antigen Results in Antibodies against Human Cancer Cells: A Combined Chemical—Immunological Approach to the Fashioning of an Anticancer Vaccine, Angew Chem Int, 36(1-2), 125-128, Feb. 1997.
Ragupathi, Govindaswami, et al. "Constructing an adenocarcinoma vaccine: Immunization of mice with synthetic KH-1 nonasaccharide stimulates anti-KH-1 and anti-Ley antibodies." International Journal of Cancer 99.2 (2002): 207-212.
Ramm et al., "The periplasmic *Escherichia coli* peptidylprolyl cis,trans-isomerase FkpA. II. Isomerase-independent chaperone activity in vitro," J. Biol. Chem., Jun. 2, 2000, 275(22):17106-17113.
Ravetch et al., "Fc receptors," Annu. Rev. Immunol., 1991, 9:457-492.
Reyes et al., "Expression of human β-interferon cDNA under the control of a thymidine kinase promoter from herpes simplex virus," Nature, Jun. 17, 1982, 297(5867):598-601.
Riechmann et al., "Reshaping human antibodies for therapy," *Nature*, Mar. 24, 1988, 332(6162):323-327.
Rowland et al, "Drug localisation and growth inhibition studies of vindesine-monoclonal anti-CEA conjugates in a human tumour xenograft," *Cancer Immunol. Immunother.*, 1986, 21(3):183-187.
Rüde, Erwin et al., Synthesis of the N-carboxy-α-amino Acid Anhydrides of Several O-acetylated Serine Glycosides, Carbohydr. Research, 1968, 8(2), 219-232.
Rudikoff, Stuart, et al. "Single amino acid substitution altering antigen-binding specificity." Proceedings of the National Academy of Sciences 79.6 (1982): 1979-1983.
Sastry et al., "Cloning of the immunological repertoire in *Escherichia coli* for generation of monoclonal catalytic antibodies: construction of a heavy chain variable region-specific cDNA library," Proc. Natl. Acad. Sci. U.S.A., Aug. 1989, 86(15):5728-5732.
Schier et al., "Identification of functional and structural amino-acid residues by parsimonious mutagenesis," Gene, Mar. 9, 1996, 169(2):147-155.
Schiffman, Mark, and Philip E. Castle. "The promise of global cervical-cancer prevention." New England Journal of Medicine 353.20 (2005): 2101-2104.
Schwarz, Mikael, et al. "A new kind of carbohydrate array, its use for profiling antiglycan antibodies, and the discovery of a novel human cellulose-binding antibody." Glycobiology 13.11 (2003): 749-754.

(56) References Cited

OTHER PUBLICATIONS

Search Report issued in corresponding Taiwan patent application No. 103131876, prepared Dec. 20, 2016, 1 page.
Shalaby et al., "Development of humanized bispecific antibodies reactive with cytotoxic lymphocytes and tumor cells overexpressing the HER2 protooncogene," J. Exp. Med., Jan. 1, 1992, 175(1):217-225.
Sidhu et al., "Phage-displayed antibody libraries of synthetic heavy chain complementarity determining regions," J. Mol. Biol., Apr. 23, 2004, 338(2):299-310.
Siebenlist et al., "E. coli RNA polymerase interacts homologously with two different promoters," Cell, Jun. 1980, 20(2):269-281.
Sigma-Aldrich, Product Information for Hemocyanin From Megathura Crenulata, Catalog No. H7017, 1 Page, 2016.
Simmons et al., "Expression of full-length immunoglobulins in Escherichia coli: Rapid and efficient production of aglycosylated antibodies," J. Immunol. Methods, May 1, 2002, 263(1-2):133-147.
Sims et al., "A humanized CD18 antibody can block function without cell destruction," J. Immunol., Aug. 15, 1993, 151(4):2296-2308.
Sjölander, A., et al. "ISCOMs: an adjuvant with multiple functions." J. Leukocyte Biol. 64.6 (1998): 713-723.
Skerra, "Bacterial expression of immunoglobulin fragments," Curr. Opinion in Immunol., Apr. 1993, 5(2):256-262.
Slovin, S.F. et al., Carbohydrate Vaccines in Cancer: Immunogenicity of a Fully Synthetic Globo H Hexasaccharide Conjugate in Man, Proc Natl Acad Sci, 96:5710-5715, May 1999.
Sonderstrup, Grete, Development of Humanized Mice as a Model of Inflammatory Arthritis, Springer Sem. Immunopathol. 25: 35-45, 2003.
Speed, Margaret A., Daniel IC Wang, and Jonathan King. "Multimeric intermediates in the pathway to the aggregated inclusion body state for P22 tailspike polypeptide chains." Protein Science 4.5 (1995): 900-908.
Sun, Hongfan, Kevin GJ Pollock, and James M. Brewer. "Analysis of the role of vaccine adjuvants in modulating dendritic cell activation and antigen presentation in vitro." Vaccine 21.9-10 (2003): 849-855.
Suresh et al., "Bispecific monoclonal antibodies from hybrid hybridomas," Methods in Enzymology, 1986, 121:210-228.
Syrigos et al., "Antibody directed enzyme prodrug therapy (ADEPT): a review of the experimental and clinical considerations," Anticancer Research, Jan.-Feb. 1999, 19(1A):605-614.
Takeda et al., "Construction of chimaeric processed immunoglobulin genes containing mouse variable and human constant region sequences," Nature, Apr. 4-10, 1985, 314(6010):452-454.
Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506.
Tomlinson, I.M. et al., "The repertoire of human germline $V_H$ sequences reveals about fifty groups of $V_H$ segments with different hypervariable loops" J. Mol. Biol., Oct. 5, 1992, 227(3): 776-798.
Toyokuni, Tatsushi et al., Synthetic Vaccines: Synthesis of a Dimeric Tn Antigen-Lipopeptide Conjugate That Elicits Immune Responses Against Tn-Expressing Glycoproteins, J. Am. Chem. Soc., 1994, 116(1), 395-396.
Traunecker et al., "Bispecific single chain molecules (Janusins) target cytotoxic lymphocytes on HIV infected cells," EMBO J., Dec. 1991, 10(12):3655-3659.
Tutt et al., "Trispecific F(ab')$_3$ derivatives that use cooperative signaling via the TCR/CD3 complex and CD2 to activate and redirect resting cytotoxic T cells," J. Immunol., Jul. 1, 1991, 147(1):60-69.
Urlaub et al., "Isolation of Chinese hamster cell mutants deficient in dihydrofolate reductase activity." Proc. Natl. Acad. Sci. U.S.A., Jul. 1980, 77(7):4216-4220.
Vajdos, Felix F., et al. "Comprehensive functional maps of the antigen-binding site of an anti-ErbB2 antibody obtained with shotgun scanning mutagenesis." Journal of Molecular Biology 320.2 (2002): 415-428.

Vaswani et al., "Humanized antibodies as potential therapeutic drugs," Ann. Allergy, Asthma Immunol., Aug. 1998, 81(2):105-116, 119.
Verhoeyen et al., "Reshaping human antibodies: grafting an antilysozyme activity," Science, Mar. 25, 1988, 239(4847):1534-1536.
Wakimoto, Hiroaki, et al. "Intensified antitumor immunity by a cancer vaccine that produces granulocyte-macrophage colony-stimulating factor plus interleukin 4." Cancer Research 56.8 (1996): 1828-1833.
Wallner, Fredrik K., et al. "Solid-phase synthesis of serine-based glycosphingolipid analogues for preparation of glycoconjugate arrays." Organic & Biomolecular Chemistry 3.2 (2005): 309-315.
Wang et al., "Glycan microarray of Globo H and related structures for quantitative analysis of breast cancer," Proc. Natl. Acad. Sci. U.S.A., Aug. 19, 2008, 105(33):11661-11666.
Ward et al., "Binding activities of a repertoire of single immunoglobulin variable domains secreted from Escherichia coli," Nature, Oct. 12, 1989, 341(6242):544-546.
Waterhouse et al., "Combinatorial infection and in vivo recombination: a strategy for making large phage antibody repertoires," Nuc. Acids Res., May 11, 1993, 21(9):2265-2266.
Wilen et al., "Strategies in optical resolutions," Tetrahedron, 1977, 33(21):2725-2736.
Williams, S.C. and Winter, G. "Cloning and sequencing of human immunoglobulin $V_\lambda$ gene segments" Eur. J. Immunol., 1993, 23: 1456-1461.
Wilman, "Prodrugs in Cancer Chemotherapy" Biochemical Society Transactions, 14, pp. 375-382, 615th Meeting Belfast, 1986.
Winter et al., "Making antibodies by phage display technology," Annu. Rev. Immunol., 1994, 12:433-455.
Wymer, Nathan et al., Enzyme-Catalyzed Synthesis of Carbohydrates, Curr. Opin. Chem. Biol., 4, 110-119, 2000.
Yaniv, Moshe, Enhancing Elements for Activation of Eukaryotic Promoters, Nature 297: 17-18, 1982.
Yansura et al., "Nucleotide sequence selection for increased expression of heterologous genes in Escherichia coli," Methods: A Companion to Methods in Enzymol., Aug. 1992, 4(2):151-158.
Yelton et al., "Affinity maturation of the BR96 anti-carcinoma antibody by codon-based mutagenesis." J. Immunol., Aug. 15, 1995, 155(4):1994-2004.
Zhang et al., "Selection of tumor antigens as targets for immune attack using immunohistochemistry: I. Focus on gangliosides," Int. J. Cancer, Sep. 26, 1997,73(1):42-49.
Zhou, Zhifang et al., A Fully Synthetic Self-Adjuvanting Globo H-Based Vaccine Elicited Strong T Cell-Mediated Antitumor Immunity, Chem. Sci., 2015, 6, 7112-7121.
Zhu, Jianglong et al., From Synthesis to Biologics: Preclinical Data on a Chemistry Derived Anticancer Vaccine, J. Am. Chem. Soc. 131(26):9298-9303, 2009.
Bremer, Eric et al., Characterization of Glycosphingolipid Antigen Defined By The Monoclonal Antibody MBr1 Expressed in Normal and Neoplastic Epithelial Cells of Human Mammary Gland, J Biol Chem 259: 14773-14777, 1984.
Plückthun, "Mono- and bivalent antibody fragments produced in Escherichia coli: Engineering, folding and antigen binding," Immunol. Rev., Dec. 1992, 130:151-188.
Chen et al., "Chaperone activity of DsbC," J. Bio. Chem., July 9. 1999, 274(28):19601-19605.
Cheung, Sarah et al., Stage-Specific Embryonic Antigen-3 (SSEA-3) and β3GalT5 are cancer specific and Significant Markers for Breast Cancer Stem Cells, PNAS, Jan. 26, 2016, vol. 113, No. 4, pp. 960-965.
Himmelspach, K. et al., Use of 1-(m-aminophenyl)flavazoles for the Preparation of Immunogens with Oligosaccharide Determinant Groups, Eur. J. Immunol., 1971, 1(2), 106-112.
International Search Report/Written Opinion issued Mar. 12, 2018 in counterpart PCT Application No. PCT/US17/062886.
Lode et al., "Targeted therapy with a novel enediyne antibiotic calicheamicin θ11 effectively suppresses growth and dissemination of liver metastases in a syngeneic model of murine neuroblastoma," Cancer Res., Jul. 15, 1998, 58(14):2925-2928.

(56) References Cited

OTHER PUBLICATIONS

Sedlik, Christine et al., Effective Antitumor Therapy Based on a Novel Antibody-Drug Conjugate Targeting the Tn Carbohydrate Antigen, Oncoimmunology, Jul. 2016, vol. 5, No. 7, e1171434-1-13.

Blast alignment of GenBank AN126084.1 and SEQ ID No. 1 (downloaded Nov. 20, 2020). (Year: 2020).

First Examination Report issued on Jul. 5, 2021 in India Patent Application No. 201717013151.

NCBI GenBank: AN126084.1 (submitted Jun. 8, 2016). (Year: 2016).

Non-Final Office Action issued in U.S. Appl. No. 14/855,260 on Jul. 27, 2021.

Chang, W.W. et al., "Expression of Globo H and SSEA3 in breast cancer stem cells and the involvement of fucosyl transferases 1 and 2 in Globo H synthesis," PNAS, Aug. 19, 2008, vol. 105 No. 33, pp. 11667-11672.

Genbank: CAG28308.1, May 13, 2004.

Genbank: CAG28309.2, Nov. 26, 2013.

NCT01516307—Trial of Active Immunotherapy with Globo H-KLH (OPT-822) in Metastatic Breast Cancer Subjects. Full Text Review. ClinicalTrials.gov. Jan. 2012. (https:/clinicaltrials.gov/ct2/show/NCT01516307).

Pravetoni, M et al. "Structurally distinct nicotine immunogens elicit antibodies with non-overlapping specificities," Biochem Pharmacol, Feb. 15, 2012, vol. 83. No. 4, 543-550. 19 pages.

Sledzinska, Anna et al. "Negative immune checkpoints on T lymphocytes and their relevance to cancer immunotherapy," Molecular Oncology, 2015, vol. 9, pp. 1936-1965 (30 pages).

Wang, Z.-G. et al., "Polyclonal antibodies from patients immunized with a globo H-keyhole limpet hemocyanin vaccine: Isolation, quantification, and characterization of immune responses by using totally synthetic immobilized tumor antigens," PNAS, Mar. 14, 2000, vol. 97, No. 6, pp. 2719-2724.

Cheung, Sarah K. C. et al., "Stage-specific embryonic antigen-3 (SSEA-3) and beta3GalT5 are cancer specific and significant markers for breast cancer stem cells", PNAS, (Jan. 26, 2016), vol. 113, No. 4, pp. 960-965, DOI: http://dx.doi.org/10.1073/pnas.1522602113.

Sedlik, Christine et al., "Effective antitumor therapy based on a novel antibody-drug conjugate targeting the Tn carbohydrate antigen", Oncoimmunology, (Apr. 22, 2016), vol. 5, No. 7, pp. 1-13, DOI: http://dx.doi.org/10.1080/2162402X.2016.1171434.

Danishefsky, S.J., et al., "Development of Globo-H Cancer Vaccine," ACS, 48:643-652. (D1).

Kushner, Brian H. et al., "Phase I Trial of a Bivalent Gangliosides Vaccine in Combination with [beta]-Glucan for High-Risk Neuroblastoma in Second or Later Remission," Clin Cancer Res, Mar. 2014, vol. 20, No. 5, pp. 1375-1382 (22 pages).

Nikkei Biotec Online Article Dated Feb. 25, 2016 by Kiyomi Morishita entitled, "Taiwan OBI Pharma's OBI-822/821 fails to meet its primary endpoint in breast cancer phase II/III." Downloaded on Feb. 13, 2024. https://bio.nikkeibp.co.jp/atcl/news/p1/16/02/24/00272/.

Bioconjugate Techniques (Third edition), 2013; pp. 839-865, Chapter 19—Vaccines and Immunogen Conjugates.

Ragupathi, G. et al, "A novel and efficient method for synthetic carbohydrate conjugate vaccine preparation: synthesis of sialyl Tn-KLH conjugate using a 4-(4-N-maleimidomethyl) cyclohexane-1-carboxyl hydrazide (MMCCH) linker arm," Glycoconjugate Journal (1998) 15: 217-221 retrieved from https://link.springer.com/content/pdf/10.1023/A:1006936826730.pdf on Jul. 14, 2023.

* cited by examiner

Hydrophobic Interaction Chromatogram

Size Exclusion Chromatogram

Group 1: Vehicle (25 mM Sodium Citrate, pH 6.5+100 mM NaCl) 10 mL/kg × 6, IV, once weekly Group 2: Vehicle (25 mM Sodium Citrate, pH 6.5+100 mM NaCl) 10 mL/kg × 2, IV, once weekly Group 3: ADC (OBI-999) 10 mg/kg × 2, IV, once weekly Group 4: ADC (OBI-999) 0.3 mg/kg × 6, IV, once weekly Group 5: ADC (OBI-999) 1 mg/kg × 6, IV, once weekly Group 6: ADC (OBI-999) 3 mg/kg × 6, IV, once weekly Group 7: OBI-888 10 mg/kg × 2, IV, once weekly Group 8: OBI-888 0.3 mg/kg × 6, IV, once weekly Group 9: OBI-888 1 mg/kg × 6, IV, once weekly Group 10: OBI-888 3 mg/kg × 6, IV, once weekly Group 11: MMAE 0.057 mg/kg × 2, IV, once weekly Group 1: Vehicle (25 mM Sodium Citrate, 100 mM NaCl, pH 6.5), IV, 10 mL/kg, qwk x 4
+
Vehicle (PBS, pH7.4), IP, 10 mL/kg, qwk x 4 (Day 53)

Group 2: ADC (OBI-999), IV, 1 mg/kg, qwk x 4 (Day 100)

Group 3: ADC (OBI-999), IV, 3 mg/kg, qwk x 4 (Day 100)

Group 4: ADC (OBI-999), IV, 10 mg/kg, qwk x 4 (Day 100)

Group 5: OBI-888, IV, 10 mg/kg, qwk x 4 (Day72)

Group 6: Anti-CD30 ADC (OBI-910), IV, 3 mg/kg, qwk x 4 (Day100)

Group 7: MMAE, IP, 0.191 mg/kg, qwk x 4 + OBI-888, IV, 10 mg/kg, qwk x 4 (Day100)

Group 8: MMAE, IP, 0.191 mg/kg, qwk x 4 (Day100)

Group 1: Vehicle, IP, 10mL/kg, qwk x 4 + Vehicle, IV, 10mL/kg, qwk x 4

Group 2: ADC (OBI-999), IV, 10 mg/kg, qwk x 4

Group 3: OBI-888, IV, 10 mg/kg, qwk x 4

Group 4: MMAE, IP, 0.191 mg/kg, qwk x 4 +OBI-888, IV, 10 mg/kg, qwk x 4

Group 5: MMAE, IP, 0.191 mg/kg, qwk x 4

CONJUGATED BIOLOGICAL MOLECULES, PHARMACEUTICAL COMPOSITIONS AND METHODS

RELATED APPLICATIONS

This application is a divisional of U.S. patent application Ser. No. 15/820,309, filed Nov. 21, 2017, which claims the benefit of and priority to U.S. Provisional Patent Application No. 62/424,851, filed on Nov. 21, 2016, both of which are incorporated herein by reference in their entirety.

FIELD

The present disclosure is directed to antibody-drug conjugates (ADCs) compositions and methods of use thereof to treat cancer. Also described herein are methods of using antibody-drug conjugate compounds for treatment of mammalian cells associated with pathological conditions. The present disclosure relates to antibodies and binding fragments thereof to Globo series antigens (Globo H, SSEA-3 and SSEA-4), including pharmaceutical compositions comprising said antibody and/or binding fragments. Further, methods are provided for administering ADCs to a subject in an amount effective to inhibit cancer cells.

BACKGROUND OF THE INVENTION

Numerous surface carbohydrates are expressed in malignant tumor cells. For example, the carbohydrate antigen Globo H (Fuc α 1→2 Gal β 1→3 GalNAc β 1→3 Gal α 1→4 Gal β 1→4 Glc) was first isolated as a ceramide-linked Glycolipid and identified in 1984 from breast cancer MCF-7 cells. (Bremer E G, et al. (1984) J Biol Chem 259:14773-14777). Previous studies have also shown that Globo H and stage-specific embryonic antigen 3 (Gal β 1→3GalNAc β 1→3Gal α 1→4Gal β 1→4Glc β 1) (SSEA-3, also called Gb5) were observed on breast cancer cells and breast cancer stem cells (WW Chang et al. (2008) Proc Natl Acad Sci USA, 105(33): 11667-11672). In addition, SSEA-4 (stage-specific embryonic antigen-4) (Neu5Ac α 2→3Gal β 1→3GalNAc β 1→3Gal α 1→4Gal β 1→4Glc β 1) has been commonly used as a cell surface marker for pluripotent human embryonic stem cells and has been used to isolate mesenchymal stem cells and enrich neural progenitor cells (Kannagi R et al. (1983) EMBO J, 2:2355-2361). These findings support that Globo series antigens (Globo H, SSEA-3 and SSEA-4) are unique targets for cancer therapies and can be used to direct therapeutic agents to targeting cancer cells effectively. It is of great interest to identify glycan markers associated with and/or predictive of cancers, and develop antibody-drug conjugates (ADCs) against the markers for use in diagnosing and treating a broad spectrum of cancers. Globo series antigens can be designed as an ADC by combining its specific antibodies with therapeutic agents through different linkers.

The use of antibody-drug conjugates (ADCs) for the local delivery of cytotoxic or cytostatic agents, e.g., drugs to kill or inhibit tumor cells in the treatment of cancer (Syrigos and Epenetos (1999) Anticancer Research 19:605-614; Niculescu-Duvaz and Springer (1997) Adv. Drg. Del. Rev. 26:151-172; U.S. Pat. No. 4,975,278) theoretically allows targeted delivery of the drug moiety to tumors, and intracellular accumulation therein, while systemic administration of these unconjugated drug agents may result in unacceptable levels of toxicity to normal cells as well as the tumor cells sought to be eliminated (Baldwin et al., 1986, Lancet pp. (Mar. 15, 1986):603-05; Thorpe, 1985, "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., 1986, Cancer Immunol. Immunother. 21:183-87). Drugs used in these methods include daunomycin, doxorubicin, methotrexate, and vindesine (Rowland et al., 1986, supra). Some cytotoxic drugs tend to be inactive or less active when conjugated to large antibodies or protein receptor ligands.

The auristatin peptides, auristain E (AE) and monomethylauristatin (MMAE), synthetic analogs of dolastatin, were conjugated to: (i) chimeric monoclonal antibodies cBR96 (specific to Lewis Y on carcinomas); (ii) cAC10 which is specific to CD30 on hematological malignancies (Klussman, et al. (2004), Bioconjugate Chemistry 15(4):765-773; Doronina et al. (2003) Nature Biotechnology 21(7):778-784; "Monomethylvaline Compounds Capable of Conjugation to Ligands"; Francisco et al. (2003) Blood 102(4):1458-1465; U.S. Publication 2004/0018194; (iii) anti-CD20 antibodies such as RITUXAN® (WO 04/032828) for the treatment of CD20-expressing cancers and immune disorders; (iv) anti-EphB2 antibodies 2H9 and anti-IL-8 for treatment of colorectal cancer (Mao, et al. (2004) Cancer Research 64(3): 781-788); (v) E-selectin antibody (Bhaskar et al. (2003) Cancer Res. 63:6387-6394); and (vi) other anti-CD30 antibodies (WO 03/043583).

SUMMARY OF THE INVENTION

Accordingly, the present disclosure is based on the discovery that Globo series antigens are aberrantly expressed in a broad spectrum of cancers, but not on normal cells. Cancers expressing Globo series antigens include, but are not limited to, sarcoma, skin cancer, leukemia, lymphoma, brain cancer, glioblastoma, lung cancer, breast cancer, oral cancer, head-and-neck cancer, nasopharyngeal cancer, esophagus cancer, stomach cancer, liver cancer, bile duct cancer, gallbladder cancer, bladder cancer, pancreatic cancer, intestinal cancer, colorectal cancer, kidney cancer, cervix cancer, endometrial cancer, ovarian cancer, testical cancer, buccal cancer, oropharyngeal cancer, laryngeal cancer and prostate cancer.

In one aspect, the present disclosure features an antibody or binding fragment thereof specific to Globo series antigens.

In certain embodiments, the antibody is an Anti-Globo H antibody.

In certain embodiments, the Anti-Globo H antibody is OBI-888. Exemplary OBI antibody 888 is as described in US2017/0101462 (WO2017/062792), the contents of which are incorporated by reference in its entirety.

In certain embodiments, the antibody is an Anti-SSEA4 antibody.

In certain embodiments, the Anti-SSEA4 antibody is OBI-898. Exemplary OBI antibody 898 is as described in US 2017/283488 (WO2017/172990), the contents of which are incorporated by reference in its entirety.

In one aspect, the invention provides antibody-drug conjugates (ADCs), comprising an antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). In certain embodiments, the present disclosure features an antibody-drug conjugate (ADC) thereof specific to Globo series antigens.

In certain embodiments, the drug is monomethyl auristatin E (MMAE).

In one aspect, the present disclosure provides a method for inhibiting the proliferation of cancer cells, comprising the administering of an effective amount of an exemplary ADC (OBI-999) to a subject in need thereof, wherein the proliferation of cancer cells is inhibited.

In certain embodiments, the present disclosure provides a method of treating cancer in a subject, the method comprising administering to a subject in need thereof an effective amount of the exemplary ADC (OBI-999) described herein.

In the disclosed compositions, both the ADC or any other relevant components are present in immunogenically effective amounts. For each specific ADC, the optimal immunogenically effective amount should be determined experimentally (taking into consideration specific characteristics of a given patient and/or type of treatment). Generally, this amount is in the range of 0.01 µg-250 mg per kilogram body weight of an antibody which was specifically targeting a Globo series antigen. In some embodiments, a therapeutically effective amount of a therapeutic composition (i.e., an effective dosage) may range from about 0.001 µg/kg to about 250 mg/kg, 0.01 µg/kg to 100 mg/kg, or 0.1 µg/kg to 50 mg/kg or about or at least: 0.001, 0.002, 0.003, 0.004, 0.005, 0.006, 0.007, 0.008, 0.009; 0.01, 0.02, 0.03, 0.04, 0.05, 0.06, 0.07, 0.08, 0.09; 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, or 250 grams or micrograms per kilogram of patient body weight, or any range between any of the numbers listed herein, or other ranges that would be apparent and understood by artisans without undue experimentation. The skilled artisan will appreciate that certain factors can influence the dosage and timing required to effectively treat a subject, including but not limited to the severity of the disease or disorder, previous treatments, the general health or age of the subject, and other diseases present.

In certain embodiments, the cancer is selected from the group consisting of sarcoma, skin cancer, leukemia, lymphoma, brain cancer, glioblastoma, lung cancer, breast cancer, oral cancer, head-and-neck cancer, nasopharyngeal cancer, esophagus cancer, stomach cancer, liver cancer, bile duct cancer, gallbladder cancer, bladder cancer, pancreatic cancer, intestinal cancer, colorectal cancer, kidney cancer, cervix cancer, endometrial cancer, ovarian cancer, testical cancer, buccal cancer, oropharyngeal cancer, laryngeal cancer and prostate cancer.

The details of one or more embodiments of the invention are set forth in the description below. Other features or advantages of the present invention will be apparent from the following drawings and detailed description of several embodiments, and also from the appending claims.

BRIEF DESCRIPTION OF THE FIGURES

A more complete understanding of the invention may be obtained by reference to the accompanying drawings, when considered in conjunction with the subsequent detailed description. The embodiments illustrated in the drawings are intended only to exemplify the invention and should not be construed as limiting the invention to the illustrated embodiments.

DETAILED DESCRIPTION OF THE INVENTION

Figure 1A:
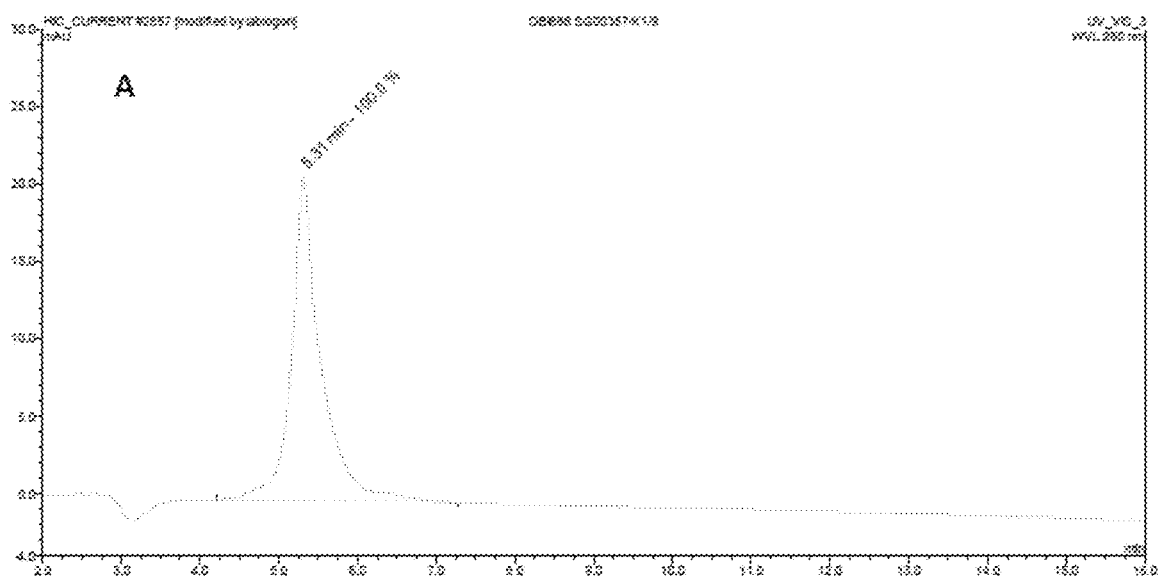
FIGS. 1A and 1B show hydrophobic interaction chromatogram (HIC) for OBI-888 (FIG. 1A) and ADC (OBI-999) (FIG. 1B).

Accordingly, antibody-drug conjugate (ADC) methods and compositions directed to the markers for use in diagnosing and treating a broad spectrum of cancers are provided. An antibody-drug conjugate (ADC) comprising a drug conjugated to an antibody or an antigen-binding fragment that binds Globo series antigens was developed and disclosed herein. Methods of use include, without limitation, cancer therapies and diagnostics. The ADC described herein can bind to a broad spectrum of Globo series antigens-expressing cancer cells, thereby facilitating cancer diagnosis and treatment. Cells that can be targeted by the antibodies include carcinomas, such as those in skin, blood, lymph node, brain, lung, breast, mouse, esophagus, stomach, liver, bile duct, pancreas, colon, kidney, cervix, ovary, prostate cancer, etc.

General Definitions

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press, 1989); DNA Cloning, Volumes I and II (D. N. Glover ed., 1985); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Antibodies: A Laboratory Manual, by Harlow and Lane s (Cold Spring Harbor Laboratory Press, 1988); and Handbook Of Experimental Immunology, Volumes I-IV (D. M. Weir and C. C. Blackwell, eds., 1986).

As used herein, the term "glycan" refers to a polysaccharide, or oligosaccharide. Glycan is also used herein to refer to the carbohydrate portion of a glycoconjugate, such as a glycoprotein, glycolipid, glycopeptide, glycoproteome, peptidoglycan, lipopolysaccharide or a proteoglycan. Glycans usually consist solely of O-glycosidic linkages between monosaccharides. For example, cellulose is a glycan (or more specifically a glucan) composed of β-1,4-linked D-glucose, and chitin is a glycan composed of β-1,4-linked N-acetyl-D-glucosamine. Glycans can be homo or heteropolymers of monosaccharide residues, and can be linear or branched. Glycans can be found attached to proteins as in glycoproteins and proteoglycans. They are generally found on the exterior surface of cells. O- and N-linked glycans are very common in eukaryotes but may also be found, although less commonly, in prokaryotes. N-Linked glycans are found attached to the R-group nitrogen (N) of asparagine in the sequon. The sequon is a Asn-X-Ser or Asn-X-Thr sequence, where X is any amino acid except praline.

As used herein, the term "antigen" is defined as any substance capable of eliciting an immune response.

As used herein, the term "immunogenicity" refers to the ability of an immunogen, antigen, or vaccine to stimulate an immune response.

As used herein, the term "epitope" is defined as the parts of an antigen molecule which contact the antigen binding site of an antibody or a T cell receptor.

As used herein, the term "vaccine" refers to a preparation that contains an antigen, consisting of whole disease-causing organisms (killed or weakened) or components of such organisms, such as proteins, peptides, or polysaccharides, that is used to confer immunity against the disease that the organisms cause. Vaccine preparations can be natural, synthetic or derived by recombinant DNA technology.

As used herein, the term "antigen specific" refers to a property of a cell population such that supply of a particular antigen, or a fragment of the antigen, results in specific cell proliferation.

As used herein, the term "specifically binding," refers to the interaction between binding pairs (e.g., an antibody and an antigen). In various instances, specifically binding can be embodied by an affinity constant of about $10^{-6}$ moles/liter, about $10^{-7}$ moles/liter, or about $10^{-8}$ moles/liter, or less.

The phrase "substantially similar," "substantially the same", "equivalent", or "substantially equivalent", as used herein, denotes a sufficiently high degree of similarity between two numeric values (for example, one associated with a molecule and the other associated with a reference/comparator molecule) such that one of skill in the art would consider the difference between the two values to be of little or no biological and/or statistical significance within the context of the biological characteristic measured by said values (e.g., Kd values, anti-viral effects, etc.). The difference between said two values is, for example, less than about 50%, less than about 40%, less than about 30%, less than about 20%, and/or less than about 10% as a function of the value for the reference/comparator molecule.

The phrase "substantially reduced," or "substantially different", as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which generally lack antigen specificity. Polypeptides of the latter kind are, for example, produced at low levels by the lymph system and at increased levels by myelomas.

The terms "antibody" and "immunoglobulin" are used interchangeably in the broadest sense and include monoclonal antibodies (e.g., full length or intact monoclonal antibodies), polyclonal antibodies, monovalent, multivalent antibodies, multispecific antibodies (e.g., bispecific antibodies so long as they exhibit the desired biological activity) and may also include certain antibody fragments (as described in greater detail herein). An antibody can be chimeric, human, humanized and/or affinity matured.

The "variable region" or "variable domain" of an antibody refers to the amino-terminal domains of heavy or light chain of the antibody. These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. Cellular and Mol. Immunology, 4th ed. (2000). An antibody may be part of a larger fusion molecule, formed by covalent or non-covalent association of the antibody with one or more other proteins or peptides.

The terms "full length antibody," "intact antibody" and "whole antibody" are used herein interchangeably, to refer to an antibody in its substantially intact form, not antibody fragments as defined below. The terms particularly refer to an antibody with heavy chains that contain the Fc region.

"Antibody fragments" comprise only a portion of an intact antibody, wherein the portion retains at least one, and as many as most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise an antigen binding arm linked to an Fc sequence capable of conferring in vivo stability to the fragment.

The term "monoclonal antibody" as used herein refers to an antibody obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., Nature, 256: 495 (1975); Harlow et al., Antibodies: A Laboratory Manual, (Cold Spring Harbor Laboratory Press, 2nd ed. 1988); Hammerling et al., in: Monoclonal Antibodies and T-Cell hybridomas 563-681 (Elsevier, N.Y., 1981)), recombinant DNA methods (see, e.g., U.S. Pat. No. 4,816, 567), phage display technologies (See, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO98/24893; WO96/34096; WO96/33735; WO91/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; 5,661,016; Marks et al., Bio. Technology 10: 779-783 (1992); Lonberg et al., Nature 368: 856-859 (1994); Morrison, Nature 368: 812-813 (1994); Fishwild et al., Nature Biotechnol. 14: 845-851

(1996); Neuberger, Nature Biotechnol. 14: 826 (1996) and Lonberg and Huszar, Intern. Rev. Immunol. 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

Antibodies of the present invention also include chimerized or humanized monoclonal antibodies generated from antibodies of the present invention.

The antibodies can be full-length or can comprise a fragment (or fragments) of the antibody having an antigen-binding portion, including, but not limited to, Fab, F(ab')$_2$, Fab', F(ab)', Fv, single chain Fv (scFv), bivalent scFv (bi-scFv), trivalent scFv (tri-scFv), Fd, dAb fragment (e.g., Ward et al, Nature, 341:544-546 (1989)), an CDR, diabodies, triabodies, tetrabodies, linear antibodies, single-chain antibody molecules, and multispecific antibodies formed from antibody fragments. Single chain antibodies produced by joining antibody fragments using recombinant methods, or a synthetic linker, are also encompassed by the present invention. Bird et al. Science, 1988, 242:423-426. Huston et al, Proc. Natl. Acad. Sci. USA, 1988, 85:5879-5883.

The antibodies or antigen-binding portions thereof of the present invention may be monospecific, bi-specific or multispecific.

All antibody isotypes are encompassed by the present invention, including IgG (e.g., IgG$_1$, IgG$_2$, IgG$_3$, IgG$_4$), IgM, IgA (IgA$_1$, IgA$_2$), IgD or IgE (all classes and subclasses are encompassed by the present invention). The antibodies or antigen-binding portions thereof may be mammalian (e.g., mouse, human) antibodies or antigen-binding portions thereof. The light chains of the antibody may be of kappa or lambda type.

Thus, anti-cancer antibodies of the present invention include in combination with a heavy chain or light chain variable region, a heavy chain or light chain constant region, a framework region, or any portion thereof, of non-murine origin, preferably of human origin, which can be incorporated into an antibody of the present invention.

Antibodies with a variable heavy chain region and a variable light chain region that are at least about 70%, at least about 75%, at least about 80%, at least about 81%, at least about 82%, at least about 83%, at least about 84%, at least about 85%, at least about 86%, at least about 87%>, at least about 88%>, at least about 89%>, at least about 90%>, at least about 91>, at least about 92%>, at least about 93%>, at least about 94%>, at least about 95%), at least about 96%>, at least about 97%>, at least about 98%>, at least about 99%> or about 100% homologous to the variable heavy chain region and variable light chain region of the antibody produced by the reference antibody, and can also bind to Globo series antigens (Globo H, SSEA-3 and SSEA-4). Homology can be present at either the amino acid or nucleotide sequence level.

The antibodies or antigen-binding portions may be peptides. Such peptides can include variants, analogs, orthologs, homologs and derivatives of peptides, that exhibit a biological activity, e.g., binding of a carbohydrate antigen. The peptides may contain one or more analogs of an amino acid (including, for example, non-naturally occurring amino acids, amino acids which only occur naturally in an unrelated biological system, modified amino acids from mammalian systems etc.), peptides with substituted linkages, as well as other modifications known in the art.

Also within the scope of the invention are antibodies or antigen-binding portions thereof in which specific amino acids have been substituted, deleted or added. In an exemplary embodiment, these alternations do not have a substantial effect on the peptide's biological properties such as binding affinity. In another exemplary embodiment, antibodies may have amino acid substitutions in the framework region, such as to improve binding affinity of the antibody to the antigen. In yet another exemplary embodiment, a selected, small number of acceptor framework residues can be replaced by the corresponding donor amino acids. The donor framework can be a mature or germline human antibody framework sequence or a consensus sequence. Guidance concerning how to make phenotypically silent amino acid substitutions is provided in Bowie et al., Science, 247: 1306-1310 (1990). Cunningham et al, Science, 244: 1081-1085 (1989). Ausubel (ed.), Current Protocols in Molecular Biology, John Wiley and Sons, Inc. (1994). T. Maniatis, E. F. Fritsch and J. Sambrook, Molecular Cloning: A Laboratory Manual, Cold Spring Harbor laboratory, Cold Spring Harbor, N.Y. (1989). Pearson, Methods Mol. Biol. 243:307-31 (1994). Gonnet et al., Science 256: 1443-45 (1992).

The antibody, or antigen-binding portion thereof, can be derivatized or linked to another functional molecule. For example, an antibody can be functionally linked (by chemical coupling, genetic fusion, noncovalent interaction, etc.) to one or more other molecular entities, such as another antibody, a detectable agent, a cytotoxic agent, a pharmaceutical agent, a protein or peptide that can mediate association with another molecule (such as a streptavidin core region or a polyhistidine tag), amino acid linkers, signal sequences, immunogenic carriers, or ligands useful in protein purification, such as glutathione-S-transferase, histidine tag, and staphylococcal protein A. One type of derivatized protein is produced by crosslinking two or more proteins (of the same type or of different types). Suitable crosslinkers include those that are heterobifunctional, having two distinct reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, 111. Useful detectable agents with which a protein can be derivatized (or labeled) include fluorescent compounds, various enzymes, prosthetic groups, luminescent materials, bioluminescent materials, and radioactive materials. Non-limiting, exemplary fluorescent detectable agents include fluorescein, fluorescein isothiocyanate, rhodamine, and, phycoerythrin. A protein or antibody can also be derivatized with detectable enzymes, such as alkaline phosphatase, horseradish peroxidase, beta-galactosidase, acetylcholinesterase, glucose oxidase and the like. A protein can also be derivatized with a prosthetic group (e.g., streptavidin/biotin and avidin/biotin).

Nucleic acids encoding a functionally active variant of the present antibody or antigen-binding portion thereof are also encompassed by the present invention. These nucleic acid molecules may hybridize with a nucleic acid encoding any of the present antibody or antigen-binding portion thereof under medium stringency, high stringency, or very high stringency conditions. Guidance for performing hybridization reactions can be found in Current Protocols in Molecular Biology, John Wiley & Sons, N.Y. 6.3.1-6.3.6, 1989, which is incorporated herein by reference. Specific hybridization conditions referred to herein are as follows: 1) medium stringency hybridization conditions: 6×SSC at about 45° C., followed by one or more washes in 0.2×SSC, 0.1% SDS at 60° C.; 2) high stringency hybridization conditions: 6×SSC at about 45° C., followed by one or more washes in 0.2×SSC, 0.1% SDS at 65° C.; and 3) very high stringency hybridization conditions: 0.5 M sodium phosphate, 7% SDS at 65° C., followed by one or more washes at 0.2×SSC, 1% SDS at 65° C.

A nucleic acid encoding the present antibody or antigen-binding portion thereof may be introduced into an expression vector that can be expressed in a suitable expression system, followed by isolation or purification of the expressed antibody or antigen-binding portion thereof. Optionally, a nucleic acid encoding the present antibody or antigen-binding portion thereof can be translated in a cell-free translation system. U.S. Pat. No. 4,816,567. Queen et al, Proc Natl Acad Sci USA, 86: 10029-10033 (1989).

The present antibodies or antigen-binding portions thereof can be produced by host cells transformed with DNA encoding light and heavy chains (or portions thereof) of a desired antibody. Antibodies can be isolated and purified from these culture supernatants and/or cells using standard techniques. For example, a host cell may be transformed with DNA encoding the light chain, the heavy chain, or both, of an antibody. Recombinant DNA technology may also be used to remove some or all of the DNA encoding either or both of the light and heavy chains that is not necessary for binding, e.g., the constant region.

The present nucleic acids can be expressed in various suitable cells, including prokaryotic and eukaryotic cells, e.g., bacterial cells, (e.g., *E. coli*), yeast cells, plant cells, insect cells, and mammalian cells. A number of mammalian cell lines are known in the art and include immortalized cell lines available from the American Type Culture Collection (ATCC). Non-limiting examples of the cells include all cell lines of mammalian origin or mammalian-like characteristics, including but not limited to, parental cells, derivatives and/or engineered variants of monkey kidney cells (COS, e.g., COS-1, COS-7), HEK293, baby hamster kidney (BHK, e.g., BHK21), Chinese hamster ovary (CHO), NSO, PerC6, BSC-1, human hepatocellular carcinoma cells (e.g., Hep G2), SP2/0, HeLa, Madin-Darby bovine kidney (MDBK), myeloma and lymphoma cells. The engineered variants include, e.g., glycan profile modified and/or site-specific integration site derivatives.

The present invention also provides for cells comprising the nucleic acids described herein. The cells may be a hybridoma or transfectant.

Alternatively, the present antibody or antigen-binding portion thereof can be synthesized by solid phase procedures well known in the art. Solid Phase Peptide Synthesis: A Practical Approach by E. Atherton and R. C. Sheppard, published by IRL at Oxford University Press (1989). Methods in Molecular Biology, Vol. 35: Peptide Synthesis Protocols (ed. M. W. Pennington and B. M. Dunn), chapter 7. Solid Phase Peptide Synthesis, 2nd Ed., Pierce Chemical Co., Rockford, Ill. (1984). G. Barany and R. B. Merrifield, The Peptides: Analysis, Synthesis, Biology, editors E. Gross and J. Meienhofer, Vol. 1 and Vol. 2, Academic Press, New York, (1980), pp. 3-254. M. Bodansky, Principles of Peptide Synthesis, Springer-Verlag, Berlin (1984).

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region of the recipient are replaced by residues from a hypervariable region of a non-human species (donor antibody) such as mouse, rat, rabbit or nonhuman primate having the desired specificity, affinity, and/or capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)).

"Framework" or "FW" residues are those variable domain residues other than the hypervariable region residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv see Pluckthun, in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO93/1161; and Hollinger et al., Proc. Natl. Acad. Sci. USA 90: 6444-6448 (1993).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more HVRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of CDR and/or framework residues is described by: Barbas et al. Proc Nat. Acad. Sci. USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al, J. Mol. Biol. 226:889-896 (1992).

A "blocking" antibody or an "antagonist" antibody is one which inhibits or reduces biological activity of the antigen it binds. Certain blocking antibodies or antagonist antibodies substantially or completely inhibit the biological activity of the antigen.

An "agonist antibody", as used herein, is an antibody which mimics at least one of the functional activities of a polypeptide of interest.

A "disorder" is any condition that would benefit from treatment with an antibody of the invention. This includes chronic and acute disorders or diseases including those pathological conditions which predispose the mammal to the disorder in question. Non-limiting examples of disorders to be treated herein include cancer.

The terms "cell proliferative disorder" and "proliferative disorder" refer to disorders that are associated with some degree of abnormal cell proliferation. In one embodiment, the cell proliferative disorder is cancer.

"Tumor" as used herein, refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing or decreasing inflammation and/or tissue/organ damage, decreasing the rate of disease progression, amelioration or palliation of the disease state, and remission or improved prognosis. In some embodiments, antibodies of the invention are used to delay development of a disease or disorder.

An "individual" or a "subject" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, the vertebrate is a human.

"Mammal" for purposes of treatment refers to any animal classified as a mammal, including humans, domestic and farm animals, and zoo, sports, or pet animals, such as dogs, horses, cats, cows, etc. In certain embodiments, the mammal is human.

An "effective amount" refers to an amount effective, at dosages and for periods of time necessary, to achieve the desired therapeutic or prophylactic result.

A "therapeutically effective amount" of a substance/molecule of the invention may vary according to factors such as the disease state, age, sex, and weight of the individual, and the ability of the substance/molecule, to elicit a desired response in the individual. A therapeutically effective amount is also one in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount would be less than the therapeutically effective amount.

A "combination" refers to combination therapy would be the amount of the antibody-drug conjugate and/or the amount of other biological or chemical drugs that when administered together (either as co-administration and/or co-formulation), either sequentially or simultaneously, on the same or different days during a treatment cycle, have a synergistic effect that is therapeutically effective and more than therapeutically additive.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies.

The term "cytotoxic agent" as used herein refers to a substance that inhibits or prevents the function of cells and/or causes destruction of cells. The term is intended to include radioactive isotopes, (e.g. $^{211}$At, $^{131}$I, $^{125}$I, $^{90}$Y, $^{186}$Re, $^{188}$Re, $^{153}$Sm, $^{212}$Bi, $^{32}$P, $^{60}$C, and radioactive isotopes of lutetium-177, strontium-89 and samarium (153Sm)), chemotherapeutic agents, and toxins such as small molecule toxins or enzymatically active toxins of bacterial, fungal, plant or animal origin, including synthetic analogs and derivatives thereof.

The term "photodynamic therapy (PDT)", sometimes called photochemotherapy, is a form of phototherapy involving light and a photosensitizing chemical substance, used in conjunction with molecular oxygen to elicit cell death (phototoxicity). It is used clinically to treat a wide range of medical conditions, including wet age-related macular degeneration, psoriasis, atherosclerosis and has shown some efficacy in anti-viral treatments, including herpes. It also treats malignant cancers including head and neck, lung, bladder, skin and prostate cancer (Wang, S S et al. Cancer Journal. 8 (2): 154-63. 2002). The "photodynamic therapeutic agent" is selected from Photofrin, Laserphyrin, Aminolevulinic acid (ALA), Silicon Phthalocyanine Pc 4, m-tetra-hydroxyphenylchlorin (mTHPC), chlorin e6 (Ce6), Allumera, Levulan, Foscan, Metvix, Hexvix, Photochlor, Photosens, Photrex, Lumacan, Visonac, Amphinex, Verteporfin, Purlytin, ATMPn, Zinc phthalocyanine (ZnPc), Protoporphyrin IX (PpIX), Pyropheophorbidea (PPa) or Pheophorbide a (PhA).

A "chemotherapeutic agent" is a chemical compound useful in the treatment of cancer. Examples of chemotherapeutic agents include Monomethyl auristatin E (MMAE), Monomethyl auristatin F (MMAF), mertansine (also called DM1), anthracycline, pyrrolobenzodiazepine, α-amanitin, tubulysin, benzodiazepine, erlotinib (TARCEVA®), Genentech/OSI Pharm.), bortezomib (VELCADE®, Millenium Pharm.), fulvestrant (FASLODEX®, Astrazeneca), sunitinib (SUTENT®, SU11248, Pfizer), letrozole (FEMARA®), Novartis), imatinib mesylate (GLEEVEC®, Novartis), PTK787/ZK 222584 (Novartis), oxaliplatin (ELOXATIN®, Sanofi), leucovorin, rapamycin (Sirolimus, RAPAMUNE®, Wyeth), lapatinib (TYKERB®, GSK572016, GlaxoSmithKline), lonafarnib (SARASAR®, SCH 66336), sorafenib (NEXAVAR®, BAY43-9006, Bayer Labs.), and gefitinib (IRESSA®, Astrazeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, especially calicheamicin gamma1I and calicheamicin omega1I (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine (XELODA®, Roche); and pharmaceutically acceptable salts, acids or derivatives of any of the above.

Also included in this definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON. toremifene; (ii) aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVIS OR® vorozole, FEMARA® letrozole, and ARIMIDEX® anastrozole; (iii) anti-androgens such as flutamide, nilutamide, bicalutamide, leuprolide, and goserelin; as well as troxacitabine (a 1,3-dioxolane nucleoside cytosine analog); (iv) aromatase inhibitors; (v) protein kinase inhibitors; (vi) lipid kinase inhibitors; (vii) antisense oligonucleotides, particularly those which inhibit expression of genes in signaling pathways implicated in abherant cell proliferation, such as, for example, PKC-alpha, Ralf and H-Ras; (viii) ribozymes such as a VEGF expression inhibitor (e.g., ANGIOZYME® ribozyme) and a HER2 expression inhibitor; (ix) vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; (x) antiangiogenic agents such as bevacizumab (AVASTIN®, Genentech); and (xi) pharmaceutically acceptable salts, acids or derivatives of any of the above.

Protein kinase inhibitors include tyrosine kinase inhibitors which inhibit to some extent tyrosine kinase activity of a tyrosine kinase such as an ErbB receptor. Examples of tyrosine kinase inhibitors include EGFR-targeted drugs such as: (i) antibodies which bind to EGFR, including MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBITUX®, Imclone) and reshaped human 225 (H225) (WO 96/40210, Imclone Systems Inc.); antibodies that bind type II mutant EGFR (U.S. Pat. No. 5,212,290); humanized and chimeric antibodies that bind EGFR (U.S. Pat. No. 5,891,996); and human antibodies that bind EGFR, such as ABX-EGF (WO 98/50433); (ii) anti-EGFR antibody conjugated with a cyotoxic agent (EP 659439A2); and small molecules that bind to EGFR including ZD1839 or Gefitinib (IRESSA™; Astra Zeneca), Erlotinib HCl (CP-358774, TARCEVA™; Genentech/OSI) and AG1478, AG1571 (SU 5271; Sugen), quinazolines such as PD 153035,4-(3-chloroanilino) quinazoline, pyridopyrimidines, pyrimidopyrimidines, pyrrolopyrimidines, such as CGP 59326, CGP 60261 and CGP 62706, and pyrazolopyrimidines, 4-(phenylamino)-7H-pyrrolo[2,3-d]pyrimidines, curcumin (diferuloyl methane, 4,5-bis(4-fluoroanilino)phthalimide), tyrphostines containing nitrothiophene moieties; PD-0183805 (Warner-Lambert); antisense molecules (e.g., those that bind to ErbB-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); panErbB inhibitors such as CI-1033 (Pfizer); Affinitac (ISIS 3521; Isis/Lilly); Imatinib mesylate (Gleevac; Novartis); PKI 166 (Novartis); GW2016 (Glaxo SmithKline); CI-1033 (Pfizer); EKB-569 (Wyeth); Semaxanib (Sugen); ZD6474 (AstraZeneca); PTK-787 (Novartis/Schering AG); INC-1C11 (Imclone); or as described in: U.S. Pat. No. 5,804,396; WO 99/09016 (American Cyanamid); WO 98/43960 (American Cyanamid); WO 97/38983 (Warner Lambert); WO 99/06378 (Warner Lambert); WO 99/06396 (Warner Lambert); WO 96/30347 (Pfizer, Inc); WO 96/33978 (Zeneca); WO 96/3397 (Zeneca); and WO 96/33980 (Zeneca).

An "anti-angiogenic agent" refers to a compound which blocks, or interferes with to some degree, the development of blood vessels. The anti-angiogenic factor may, for instance, be a small molecule or antibody that binds to a growth factor or growth factor receptor involved in promoting angiogenesis. An exemplary anti-angiogenic agent is an antibody that binds to Vascular Endothelial Growth Factor (VEGF) such as bevacizumab (AVASTIN®, Genentech).

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified pro drugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

A "liposome" is a small vesicle composed of various types of lipids, phospholipids and/or surfactant which is useful for delivery of a drug (such as the anti-ErbB2 antibodies disclosed herein and, optionally, a chemotherapeutic agent) to a mammal. The components of the liposome are commonly arranged in a bilayer formation, similar to the lipid arrangement of biological membranes.

The phrase "pharmaceutically acceptable salt," as used herein, refers to pharmaceutically acceptable organic or inorganic salts of an ADC. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

"Pharmaceutically acceptable solvate" refers to an association of one or more solvent molecules and an ADC. Examples of solvents that form pharmaceutically acceptable solvates include, but are not limited to, water, isopropanol, ethanol, methanol, DMSO, ethyl acetate, acetic acid, and ethanolamine.

General Features of Exemplary Antibody-Drug Conjugates

The compounds of the invention include those with utility for anticancer activity. In particular, the compounds include an antibody conjugated, i.e. covalently attached by a linker, to a drug moiety where the drug when not conjugated to an antibody has a cytotoxic or cytostatic effect. The biological activity of the drug moiety is thus modulated by conjugation to an antibody. The antibody-drug conjugates (ADCs) of the invention may selectively deliver an effective dose of a cytotoxic agent to tumor tissue whereby greater selectivity, i.e. a lower efficacious dose may be achieved.

Antibody-drug conjugates (ADCs) may be represented by Formula I:

$$Ab\text{-}(L\text{-}D)_n \qquad (I)$$

or a pharmaceutically acceptable salt or solvate thereof, wherein:
Ab is an antibody which binds Globo series antigen, or which binds to one or more tumor-associated antigens or cell-surface receptors; n is the Drug-to-antibody ratio (DAR) and ranging from 1 to 8.

An antibody-drug conjugate (ADC) comprise an antibody covalently attached by a linker to one or more MMAE moieties. ADC may be represented by Formula I:

$$Ab\text{-}(L\text{-}D)_n \qquad (I)$$

wherein one or more MMAE drug moieties (D) are covalently linked by L to an antibody (Ab).
Ab is an antibody which targets Globo series antigens or which binds to one or more tumor-associated antigens or cell-surface receptors. The linker L may be stable outside a cell, i.e. extracellular.

In one embodiment, a substantial amount of the drug moiety is not cleaved from the antibody until the antibody-drug conjugate enters a cell with a cell-surface receptor specific for the antibody of the antibody-drug conjugate, and the drug moiety is cleaved from the antibody when the antibody-drug conjugate does enter the cell.

In another embodiment, the ADC specifically binds to a Globo series antigen, such as Globo H, SSEA-3, or SSEA-4. The ADC may specifically bind to Globo H, SSEA-4, SSEA-3. The ADC may inhibit growth of tumor cells which expresses Globo series antigens.

In another embodiment, the antibody (Ab) of Formula I is a human, chimeric or humanized antibody.

Another aspect of the invention is a pharmaceutical composition including a Formula I compound, or a pharmaceutically acceptable salt or solvate thereof, and a pharmaceutically acceptable diluent, carrier, or excipient.

Another aspect provides a pharmaceutical combination comprising a Formula I compound and a second compound having anti-cancer properties or other therapeutic effects.

Another aspect includes diagnostic and therapeutic uses for the compounds and compositions disclosed herein.

Another aspect is a method for killing or inhibiting the proliferation of tumor cells or cancer cells comprising treating the cells with an amount of an antibody-drug conjugate, or a pharmaceutically acceptable salt or solvate thereof, being effective to kill or inhibit the proliferation of the tumor cells or cancer cells.

Another aspect are methods of treating cancer comprising administering to a patient a formulation of a Formula I compound. One method is for the treatment of cancer in a mammal, wherein the cancer is characterized by the expression of the Globo series antigens. The mammal optionally does not respond, or responds poorly, to treatment with an unconjugated Anti-Globo series antigen antibody. The method comprises administering to the mammal a therapeutically effective amount of an antibody-drug conjugate compound.

Another aspect is a method of inhibiting the growth of tumor cells that expresses Globo H, SSEA-4, and/or SSEA-3 comprising administering to a patient an antibody-drug conjugate compound which binds specifically to said growth factor receptor and a chemotherapeutic agent wherein said antibody-drug conjugate and said chemotherapeutic agent are each administered in amounts effective to inhibit growth of tumor cells in the patient.

Another aspect is a method for the treatment of a human patient susceptible to or diagnosed with a disorder characterized by expression of Globo series antigens, comprising administering a combination of an antibody-drug conjugate compound of Formula I and a chemotherapeutic agent.

Another aspect is an assay method for detecting cancer cells comprising: exposing cells to an antibody-drug conjugate compound, and determining the extent of binding of the antibody-drug conjugate compound to the cells.

Another aspect concerns methods of screening ADC drug candidates for the treatment of a disease or disorder where the disease or disorder is characterized by the expression of Globo series antigens.

Another aspect includes articles of manufacture, i.e. kits, comprising an antibody-drug conjugate, a container, and a package insert or label indicating a treatment.

Another aspect includes methods of treating a disease or disorder characterized by the overexpression of Globo series antigens in a patient with the antibody-drug conjugate compounds.

Another aspect includes methods of making, methods of preparing, methods of synthesis, methods of conjugation, and methods of purification of the antibody-drug conjugate compounds, and the intermediates for the preparation, synthesis, and conjugation of the antibody-drug conjugate compounds.

ADCs: Antibodies:

The antibody unit (Ab-) of Formula I includes within its scope any unit of an antibody that binds or reactively associates or complexes with a receptor, antigen or other receptive moiety associated with a given target-cell population. An antibody can be any protein or protein-like molecule that binds to, complexes with, or reacts with a moiety of a cell population sought to be therapeutically or otherwise biologically modified. In one aspect, the antibody unit acts to deliver the maytansinoid drug moiety to the particular target cell population with which the antibody unit reacts. Such antibodies include, but are not limited to, large molecular weight proteins such as, full-length antibodies and antibody fragments.

Antibodies comprising the antibody-drug conjugates of the invention preferably retain the antigen binding capability of their native, wild type counterparts. Thus, antibodies of the invention are capable of binding, preferably specifically, to antigens.

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al (2003) Jour. of Immunology 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) *Immuno Biology*, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

For example, the antibodies can be full-length or can comprise a fragment (or fragments) of the antibody having an antigen-binding portion, including, but not limited to, Fab, F(ab')2, Fab', F(ab)', Fv, single chain Fv (scFv), bivalent scFv (bi-scFv), trivalent scFv (tri-scFv), Fd, dAb fragment (e.g., Ward et al., Nature, 341:544-546 (1989)), an isolated CDR, diabodies, triabodies, tetrabodies, linear antibodies, single-chain antibody molecules, and multispecific antibodies formed from antibody fragments. Single chain antibodies produced by joining antibody fragments using recombinant methods, or a synthetic linker, are also encompassed by the present invention. Bird et al. Science, 1988, 242:423-426. Huston et al., Proc. Natl. Acad. Sci. USA, 1988, 85:5879-5883.

For example, the antibodies or antigen-binding portions thereof of the present invention may be monospecific, bi-specific or multispecific. Multispecific or bi-specific antibodies or fragments thereof may be specific for different epitopes of one target carbohydrate (e.g., Globo H) or may contain antigen-binding domains specific for more than one target carbohydrate (e.g., antigen-binding domains specific for Globo H, SSEA-3 and SSEA-4). In one embodiment, a multispecific antibody or antigen-binding portion thereof comprises at least two different variable domains, wherein each variable domain is capable of specifically binding to a separate carbohydrate antigen or to a different epitope on the same carbohydrate antigen. Tutt et al., 1991, J. Immunol. 147:60-69. Kufer et al., 2004, Trends Biotechnol. 22:238-244. The present antibodies can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity.

All antibody isotypes are encompassed by the present invention, including IgG (e.g., IgG1, IgG2, IgG3, IgG4), IgM, IgA (IgA1, IgA2), IgD or IgE (all classes and subclasses are encompassed by the present invention). The antibodies or antigen-binding portions thereof may be mammalian (e.g., mouse, human) antibodies or antigen-binding portions thereof. The light chains of the antibody may be of kappa or lambda type.

The variable regions of the present antibodies or antigen-binding portions thereof can be from a non-human or human source. The framework of the present antibodies or antigen-binding portions thereof can be human, humanized, non-human (e.g., a murine framework modified to decrease antigenicity in humans), or a synthetic framework (e.g., a consensus sequence).

In one embodiment, the present antibodies, or antigen-binding portions thereof, comprise at least one heavy chain variable region and/or at least one light chain variable region.

The present antibodies or antigen-binding portions thereof specifically bind to Globo H with a dissociation constant ($K_D$) of less than about 10E-7 M, less than about 10E-8 M, less than about 10E-9 M, less than about 10E-10 M, less than about 10E-11 M, or less than about 10E-12 M. In one embodiment, the antibody or the antibody binding portion thereof has a dissociation constant ($K_D$) of 1~10× 10E-9 or less. In another embodiment, the Kd is determined by surface plasmon resonance.

Antibodies comprising the antibody-drug conjugates of the invention preferably retain the antigen binding capability of their native, wild type counterparts. Thus, antibodies of the invention are capable of binding, preferably specifically, to antigens. Such antigens include, for example, tumor-associated antigens (TAA), cell surface receptor proteins and other cell surface molecules, cell survival regulatory factors, cell proliferation regulatory factors, molecules associated with (for e.g., known or suspected to contribute functionally to) tissue development or differentiation, lymphokines, cytokines, molecules involved in cell cycle regulation, molecules involved in vasculogenesis and molecules associated with (for e.g., known or suspected to contribute functionally to) angiogenesis. The tumor-associated antigen may be a cluster differentiation factor (i.e., a CD protein). An antigen to which an antibody of the invention is capable of binding may be a member of a subset of one of the above-mentioned categories, wherein the other subset(s) of said category comprise other molecules/antigens that have a distinct characteristic (with respect to the antigen of interest).

In one embodiment, the antibody of the antibody-drug conjugates (ADCs) specifically binds to a Globo series antigen Globo H, SSEA-4 and/or SSEA-3.

In some embodiments, the antibodies or antigen-binding portions thereof include, for example, the variable heavy chains and/or variable light chains of the Anti-Globo series antigens antibodies (Globo H: OBI-888, SSEA-4: OBI-999), as shown in Table 1.

In related embodiments, the exemplary antibodies or antigen-binding portions thereof include, for example, the CDRs of the variable heavy chains and/or the CDRs of the variable light chains of Anti-Globo series antigens antibodies (Globo H: OBI-888, SSEA-4: OBI-999). The exemplary CDRs and frameworks of the variable heavy chains and the variable light chains from these hybridoma clones are shown in Table 1.

TABLE 1-1

Anti-Globo H antibody (OBI-888) amino acid sequence
[Details described in US2017/0101462 (WO2017/062792)]

| Variable Region | Amino Acid Sequences | SEQ ID NO. |
| --- | --- | --- |
| Heavy Chain CDR1 | GFSLYTFDMGVG | 1 |
| Heavy Chain CDR2 | HIWWDDDKYYNPALKS | 2 |
| Heavy Chain CDR3 | VRGLHDYYYWFAY | 3 |
| Humanized Heavy Chain FW1 | QITLKESGPTLVKPTQTLTLTCTFS | 4 |
| Humanized Heavy Chain FW2 | WIRQPPGKGLEWLA | 5 |
| Humanized Heavy Chain FW3 | RLTISKDTSKNQVVLTMTNMDPVDTATYYCAR | 6 |
| Light Chain CDR1 | RASSSVSYMH | 7 |
| Light Chain CDR2 | ATSNLAS | 8 |
| Light Chain CDR3 | QQWSRNPFT | 9 |
| Humanized Light Chain FW1 | EIVLTQSPATLSLSPGERATLSC | 10 |
| Humanized Light Chain FW2 | WYQQKPGKSPKPWIY | 11 |
| Humanized Light Chain FW3 | GVPSRFSGSGSGTDFTFTISSLQPEDIATYYC | 12 |
| Heavy Chain Variable Region of Humanized Antibody | QITLKESGPTLVKPTQTLTLTCTFSGFSLYTFDMGVGWIRQPPGKGLEWLAHIWWDDDKYYNPALKSRLTISKDTSKNQVVLTMTNMDPVDTATYYCARVRGLHDYYYWFAY | 13 |
| Light Chain Variable Region of Humanized Antibody | EIVLTQSPATLSLSPGERATLSCRASSSVSYMHWYQQKPGKSPKPWIYATSNLASGVPSRFSGSGSGTDFTFTISSLQPEDIATYYCQQWSRNPFT | 14 |
| Heavy Chain Variable Region of Chimeric Antibody | QVTLKESGPGILQPSQTLSLTCSFSGFSLYTFDMGVGWIRQPSGKGLEWLAHIWWDDDKYYNPALKSRLTVSKDTSKNQVFLKIPNVDTADSATYYCARVRGLHDYYYWFAY | 15 |
| Light Chain Variable Region of Chimeric Antibody | QIVLSQSPTILSASPGEKVTMTCRASSSVSYMHWYQQKPGSSPKPWIYATSNLASGVPARFSGSGSGTSYSLTISRVEAEDAATYFCQQWSRNPFT | 16 |
| Heavy Chain Variable Region of Modified Antibody (Humanized R28 mAb) | QITLKESGPTLVKPTQTLTLTCTFSGFSLYTFDMGVGWIRQPPGKGLEWLAHIWWDGDKYYNPALKSRLTISKDTSKNQVVLTMTNMDPVDTATYYCARVRGLHRYYYWFAYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 17 |
| Light Chain Variable Region of Modified Antibody (Humanized R28 mAb) | EIVLTQSPATLSLSPGERATLSCRASSSVSYMHWYQQKPGKSPKPWIYATSNKASGVPSRFSGSGSGTDFTFTISSLQPEDIATYYCQQWSRRPFTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | 18 |

TABLE 1-2

Anti-SSEA4 antibody (OBI-898) amino acid sequence
[Details described in US 2017/283488 (WO2017/172990)]

| Variable Region | Amino Acid Sequences | SEQ ID NO. |
|---|---|---|
| Heavy Chain Variable Region (VH) | QVQLKESGPGLVAPSQSLSITCTVSGFSLISYGVDWVR QPPGKGLEWLGVIWGGGNTNYNSSLMSRLSISKDNS KSQVFLKMNSLQTDDTAMYYCAKTGTGYALEYWGQ GTSVTVSS | 19 |
| Light Chain Variable Region (VL) | ENVLTQSPAIMSASPGEKVTMTCSARSSVSYMHWYQ QKSTASPKLWIYDTSKLASGVPGRFSGSGSGNSYSLTI SSMEAEDVATYYCFQASGYPLTFGAGTKLELKR | 20 |
| VL FW1 | ENVLTQSPAIMSASPGEKVTMTC | 21 |
| VL CDR1 | SARSSVSYMH | 22 |
| VL FW2 | WYQQKSTASPKLWIY | 23 |
| VL CDR2 | DTSKLAS | 24 |
| VL FW3 | GVPGRFSGSGSGNSYSLTISSMEAEDVATYYC | 25 |
| VL CDR3 | FQASGYPLT | 26 |
| VL FW4 | FGAGTKLELKR | 27 |
| VH FW1 | QVQLKESGPGLVAPSQSLSITCTVS | 28 |
| VH CDR1 | GFSLISYGVD | 29 |
| VH FW2 | WVRQPPGKGLEWLG | 30 |
| VH CDR2 | VIWGGGNTNYNSSLMS | 31 |
| VH FW3 | RLSISKDNSKSQVFLKMNSLQTDDTAMYYCAK | 32 |
| VH CDR3 | TGTGYALEY | 33 |
| VH FW4 | WGQGTSVTVSS | 34 |

Antibodies with a variable heavy chain region and a variable light chain region that are at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% or about 100% homologous to the variable heavy chain region and variable light chain region of the antibody produced by clone 2C2, and can also bind to a carbohydrate antigen (e.g. Globo H). Homology can be present at either the amino acid or nucleotide sequence level.

ADC Targeting Globo Series Antigen

One aspect of the present disclosure features the new ADC (OBI-999) specific to Globo H. The Anti-Globo H antibody of the ADC binds to Fucα1→2 Galβ1→3 GalNAcβ1→3 Galα1→4 Galβ1→4 Glc.

Any of the antibodies described herein can be a full length antibody or an antigen-binding fragment thereof. In some examples, the antigen binding fragment is a Fab fragment, a F(ab')$_2$ fragment, or a single-chain Fv fragment. In some examples, the antigen binding fragment is a Fab fragment, a F(ab')$_2$ fragment, or a single-chain Fv fragment. In some examples, the antibody is a human antibody, a humanized antibody, a chimeric antibody, or a single-chain antibody.

Any of the antibodies described herein has one or more characteristics of: (a) is a recombinant antibody, a monoclonal antibody, a chimeric antibody, a humanized antibody, a human antibody, an antibody fragment, a bispecific antibody, a monospecific antibody, a monovalent antibody, an IgG$_1$ antibody, an IgG$_2$ antibody, or derivative of an antibody; (b) is a human, murine, humanized, or chimeric antibody, antigen-binding fragment, or derivative of an antibody; (c) is a single-chain antibody fragment, a multibody, a Fab fragment, and/or an immunoglobulin of the IgG, IgM, IgA, IgE, IgD isotypes and/or subclasses thereof; (d) has one or more of the following characteristics: (i) mediates ADCC and/or CDC of cancer cells; (ii) induces and/or promotes apoptosis of cancer cells; (iii) inhibits proliferation of target cells of cancer cells; (iv) induces and/or promotes phagocytosis of cancer cells; and/or (v) induces and/or promotes the release of cytotoxic agents; (e) specifically binds the tumor-associated carbohydrate antigen, which is a tumor-specific carbohydrate antigen; (f) does not bind an antigen expressed on non-cancer cells, non-tumor cells, benign cancer cells and/or benign tumor cells; and/or (g) specifically binds a tumor-associated carbohydrate antigen expressed on cancer stem cells and on normal cancer cells.

Preferably the binding of the antibodies to their respective antigens is specific. The term "specific" is generally used to refer to the situation in which one member of a binding pair will not show any significant binding to molecules other than its specific binding partner (s) and e.g. has less than about 30%, preferably 20%, 10%, or 1% cross-reactivity with any other molecule other than those specified herein.

Production of Antibodies

Various methods have been employed to produce monoclonal antibodies (MAbs). Hybridoma technology, which refers to a cloned cell line that produces a single type of antibody, uses the cells of various species, including mice (murine), hamsters, rats, and humans. Other methods to prepare MAbs, including chimeric and humanized antibodies, uses genetic engineering, i.e. recombinant DNA techniques.

Polyclonal antibodies may be raised in animals by multiple subcutaneous (sc) or intraperitoneal (ip) injections of the relevant antigen and an adjuvant. Monoclonal antibodies are obtained from a population of substantially homogeneous antibodies, i.e., the individual antibodies comprising the population are identical except for possible naturally occurring mutations that may be present in minor amounts.

Human myeloma and mouse-human heteromyeloma cell lines also have been described for the production of human monoclonal antibodies (Kozbor, (1984) J. Immunol., 133: 3001, and Brodeur et al., *Monoclonal Antibody Production Techniques and Applications*, pp. 51-63 (Marcel Dekker, Inc., New York, 1987)). Culture medium in which hybridoma cells are growing is assayed for production of monoclonal antibodies directed against the antigen. Binding specificity of monoclonal antibodies produced by hybridoma cells may be determined by immunoprecipitation or by an in vitro binding assay, such as radioimmunoassay (RIA) or enzyme-linked immunoabsorbent assay (ELISA). The binding affinity of the monoclonal antibody can, for example, be determined by the Scatchard analysis of Munson et al (1980) Anal. Biochem. 107:220.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells (US 2005/0048572; US 2004/0229310). Review articles on recombinant expression in bacteria of DNA encoding the antibody include Skerra et al (1993) Curr. Opinion in Immunol. 5:256-262 and Plückthun (1992) Immunol. Revs. 130:151-188.

In a further embodiment, monoclonal antibodies or antibody fragments can be isolated from antibody phage libraries generated using the techniques described in McCafferty et al (1990) Nature 348:552-554; Clackson et al (1991) Nature 352:624-628; and Marks et al (1991) J. Mol. Biol., 222:581-597 describe the isolation of murine and human antibodies, respectively, using phage libraries. Subsequent publications describe the production of high affinity (nM range) human antibodies by chain shuffling (Marks et al (1992) Bio/Technology 10:779-783), as well as combinatorial infection and in vivo recombination as a strategy for constructing very large phage libraries (Waterhouse et al (1993) Nuc. Acids. Res. 21:2265-2266). Thus, these techniques are viable alternatives to traditional monoclonal antibody hybridoma techniques for isolation of monoclonal antibodies.

The DNA also may be modified, for example, by substituting the coding sequence for human heavy chain and light chain constant domains in place of the homologous murine sequences (U.S. Pat. No. 4,816,567); and Morrison et al (1984) Proc. Natl. Acad. Sci. USA 81:6851), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

ADCs: the Linkers:

Exemplary ADC Linker

Suitable exemplary linkers for the ADC are described in, for example, U.S. Pat. No. 7,595,292 (WO2005/007197). The entire content directed to linkers is hereby incorporated by reference herein. The linker, L, attaches the antibody to a drug moiety through covalent bond(s), not comprising a disulfide group. The linker is a bifunctional or multifunctional moiety which can be used to link one or more Drug moieties (D) and an antibody unit (Ab) to form antibody-drug conjugates (ADCs) of Formula I. Antibody-drug conjugates (ADCa) can be conveniently prepared using a linker having reactive functionality for binding to the Drug and to the Antibody. A cysteine thiol, or an amine, e.g. N-terminus or amino acid side chain such as lysine, of the antibody (Ab) can form a bond with a functional group of a linker reagent, drug moiety or drug-linker reagent.

The linkers are preferably stable extracellularly. Before transport or delivery into a cell, the antibody-drug conjugate (ADC) is preferably stable and remains intact, i.e. the antibody remains linked to the drug moiety. The linkers are stable outside the target cell and may be cleaved at some efficacious rate inside the cell. An effective linker will: (i) maintain the specific binding properties of the antibody; (ii) allow intracellular delivery of the conjugate or drug moiety; (iii) remain stable and intact, i.e. not cleaved, until the conjugate has been delivered or transported to its targeted site; and (iv) maintain a cytotoxic, cell-killing effect or a cytostatic effect of the maytansinoid drug moiety. Stability of the ADC may be measured by standard analytical techniques such as mass spectroscopy, HPLC, and the separation/analysis technique LC/MS.

Covalent attachment of the antibody and the drug moiety requires the linker to have two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Hermanson, G. T. (1996) *Bioconjugate Techniques*; Academic Press: New York, p234-242).

Exemplary ADC Linkers can include biologically active compounds of the general formula II in which one of X and X' represents a polymer (especially a toxin), and the other represents a hydrogen atom; each Q independently represents a linking group; W represents an electron-withdrawing moiety or a moiety preparable by reduction of an electron-withdrawing moiety; or, if X' represents a polymer, X-Q-W- together may represent an electron withdrawing group; and in addition, if X represents a polymer, X' and electron withdrawing group W together with the interjacent atoms may form a ring; each of $Z^1$ and $Z^2$ independently represents a group derived from a biological molecule, each of which is linked to A and B via a nucleophilic moiety; or $Z^1$ and $Z^2$ together represent a single group derived from a biological molecule which is linked to A and B via two nucleophilic moieties; A is a $C_{1-5}$ alkylene or alkenylene chain; and B is a bond or a $C_{1-4}$ alkylene or alkenylene chain; are formed by conjugating a suitable polymer to a suitable biologically active molecule via nucleophilic groups in said molecule, preferably via a disulphide bridge.

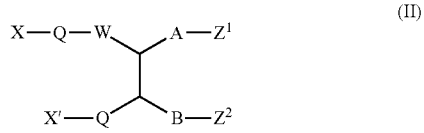

In certain embodiments, the disclosure provides a protein-polymer conjugate of formula III:

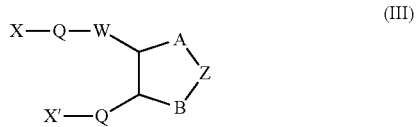

wherein X is a homo- or co-polymer (especially a toxin) selected from the group consisting of polyalkylene glycols, polyvinylpyrrolidones, polyacrylates, polymethacrylates, polyoxazolines, polyvinylalcohols, polyacrylamides, polymethacrylamides, HPMA copolymers, polyesters, polyacetals, poly(ortho ester)s, polycarbonates, poly(imino carbonate)s, polyamides, copolymers of divinylether-maleic anhydride and styrene-maleic anhydride, polysacoharides, and polyglutamic acids; Q is a linking group selected from the group consisting of a direct bond, alkylenes, optionally-substituted aryls, and optionally-substituted heteroaryls, wherein the alkylene, aryl, or heteroaryl may be terminated or interrupted by one or more oxygen atoms, sulphur atoms, keto groups, —O—CO— groups, —CO—O— groups, or —NR groups in which R is an alkyl or aryl group; W is selected from the group consisting of a keto group, an ester group, a sulphone group, a reduced keto group, a reduced ester group, and a reduced sulphone group; X'-Q is hydrogen; A is a $C_{1-5}$ alkylene or alkenylene chain; B is a bond or a $C_{1-4}$ alkylene or alkenylene chain; and Z is a single protein linked to A and B via two thiol groups generated by reduction of a disulfide bridge in the protein.

Activity Assays Demonstrating the Efficacy of the Exemplary ADCs

ADC of the invention (OBI-999) can be characterized for their physical/chemical properties and biological functions by various assays known in the art.

Antibodies, or antigen-binding fragments, variants or derivatives thereof of the present disclosure can also be described or specified in terms of their binding affinity to an antigen. The affinity of an antibody for a carbohydrate antigen can be determined experimentally using any suitable method (see, e.g., Berzofsky et al, "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein). The measured affinity of a particular antibody-carbohydrate antigen interaction can vary if measured under different conditions {e.g., salt concentration, pH). Thus, measurements of affinity and other antigen-binding parameters (e.g., $K_D$, $K_a$, Ka) are preferably made with standardized solutions of antibody and antigen, and a standardized buffer.

The present antibodies or antigen-binding portions thereof have in vitro and in vivo therapeutic, prophylactic, and/or diagnostic utilities. For example, these antibodies can be administered to cells in culture, e.g., in vitro or ex vivo, or to a subject, e.g., in vivo, to treat, inhibit, prevent relapse, and/or diagnose cancer.

Purified antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

Where necessary, antibodies are analyzed for their biological activity. In some embodiments, antibodies of the invention are tested for their antigen binding activity. The antigen binding assays that are known in the art and can be used herein include without limitation any direct or competitive binding assays using techniques such as western blots, radioimmunoassays, ELISA (enzyme linked immunosorbent assay), "sandwich" immunoassays, immunoprecipitation assays, fluorescent immunoassays, chemiluminescent immunoassays, nanoparticle immunoassays, aptamer immunoassays, and protein A immunoassays.

Humanized Antibodies

The invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) Nature 321:522-525; Riechmann et al. (1988) Nature 332:323-327; Verhoeyen et al. (1988) Science 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) J. Immunol. 151:2296; Chothia et al. (1987) J. Mol. Biol. 196:901. Another method uses a particular framework derived from the consensus sequence of all human antibodies of a particular subgroup of light or heavy chains. The same framework may be used for several different humanized antibodies (Carter et al. (1992) Proc. Natl. Acad. Sci. USA, 89:4285; Presta et al. (1993) J. Immunol., 151:2623.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Uses

An ADC of the invention (OBI-999) may be used in, for example, in vitro, ex vivo and in vivo therapeutic methods. ADC of the invention (OBI-999) can be used as an antagonist to partially or fully block the specific antigen activity in vitro, ex vivo and/or in vivo. Accordingly, ADCs of the invention (OBI-999) can be used to inhibit a specific antigen activity, e.g., in a cell culture containing the antigen, in human subjects or in other mammalian subjects having the antigen with which an ADC of the invention (OBI-999) cross-reacts (e.g. chimpanzee, baboon, marmoset, cynomolgus and rhesus, pig or mouse). In one embodiment, an ADC of the invention (OBI-999) can be used for inhibiting antigen activities by contacting the ADC (OBI-999) with the antigen such that antigen activity is inhibited. In one embodiment, the antigen is a human protein molecule.

In one embodiment, an ADC of the invention (OBI-999) can be used in a method for inhibiting an antigen in a subject suffering from a disorder in which the antigen activity is detrimental, comprising administering to the subject an ADC of the invention (OBI-999) such that the antigen activity in the subject is inhibited. In one embodiment, the antigen is a human protein molecule and the subject is a human subject. Alternatively, the subject can be a mammal expressing the antigen with which an ADC of the invention (OBI-999) binds. Still further the subject can be a mammal into which the antigen has been introduced (e.g., by administration of the antigen or by expression of an antigen transgene). An ADC of the invention (OBI-999) can be administered to a human subject for therapeutic purposes. Moreover, an ADC of the invention (OBI-999) can be administered to a non-human mammal expressing an antigen with which the ADC (OBI-999) cross-reacts (e.g., a primate, pig or mouse) for veterinary purposes or as an animal model of human disease. Regarding the latter, such animal models may be useful for evaluating the therapeutic efficacy of ADCs of the invention (OBI-999) (e.g., testing of dosages and time courses of administration). ADCs of the invention (OBI-999) can be used to treat, inhibit, delay progression of, prevent/delay recurrence of, ameliorate, or prevent diseases, disorders or conditions associated with abnormal expression and/or activity of Globo series antigens, including but not limited to cancer, muscular disorders, ubiquitin-pathway-related genetic disorders, immune/inflammatory disorders, neurological disorders, and other ubiquitin pathway-related disorders.

ADCs of the invention (OBI-999) can be used either alone or in combination with other compositions in a therapy. For instance, an ADC of the invention (OBI-999) may be co-administered with another antibody, and/or adjuvant/therapeutic agents (e.g., steroids). For instance, an ADC of the invention (OBI-999) may be combined with an anti-inflammatory and/or antiseptic in a treatment scheme, e.g. in treating any of the diseases described herein, including cancer, muscular disorders, ubiquitin-pathway-related genetic disorders, immune/inflammatory disorders, neurological disorders, and other ubiquitin pathway-related disorders. Such combined therapies noted above include combined administration (where the two or more agents are included in the same or separate formulations), and separate administration, in which case, administration of the ADC of the invention (OBI-999) can occur prior to, and/or following, administration of the adjunct therapy or therapies.

An ADC of the invention (OBI-999) can be administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the ADC (OBI-999) is suitably administered by pulse infusion, particularly with declining doses of the ADC (OBI-999). Dosing can be by any suitable route, e.g. by injections, such as intravenous or subcutaneous injections, depending in part on whether the administration is brief or chronic.

Therapeutic Applications

Described herein are therapeutic methods that include administering to a subject in need of such treatment a therapeutically effective amount of a composition that includes one or more ADCs (OBI-999) described herein.

In some embodiments, the subject (e.g., a human patient) in need of the treatment is diagnosed with, suspected of having, or at risk for cancer. Examples of the cancer include, but are not limited to, sarcoma, skin cancer, leukemia, lymphoma, brain cancer, glioblastoma, lung cancer, breast cancer, oral cancer, head-and-neck cancer, nasopharyngeal cancer, esophagus cancer, stomach cancer, liver cancer, bile duct cancer, gallbladder cancer, bladder cancer, pancreatic cancer, intestinal cancer, colorectal cancer, kidney cancer, cervix cancer, endometrial cancer, ovarian cancer, testical cancer, buccal cancer, oropharyngeal cancer, laryngeal cancer or prostate cancer.

In preferred embodiments, the ADC (OBI-999) is capable of targeting Globo series antigens-expressing cancer cells. In some embodiments, the ADC (OBI-999) is capable of targeting Globo series antigens on cancer cells. In some embodiments, the ADC (OBI-999) is capable of targeting Globo series antigens in cancers.

The treatment results in reduction of tumor size, elimination of malignant cells, prevention of metastasis, prevention of relapse, reduction or killing of disseminated cancer, prolongation of survival and/or prolongation of time to tumor cancer progression.

In some embodiments, the treatment further comprises administering an additional therapy to said subject prior to, during or subsequent to said administering of the ADCs (OBI-999). In some embodiments, the additional therapy is treatment with a chemotherapeutic agent. In some embodiments, the additional therapy is radiation therapy.

The methods of the invention are particularly advantageous in treating and preventing early stage tumors, thereby preventing progression to the more advanced stages resulting in a reduction in the morbidity and mortality associated with advanced cancer. The methods of the invention are also advantageous in preventing the recurrence of a tumor or the regrowth of a tumor, for example, a dormant tumor that persists after removal of the primary tumor, or in reducing or preventing the occurrence of a tumor.

In some embodiments, the methods as disclosed herein are useful for the treatment or prevention of a cancer, for example where a cancer is characterized by increased Globo H, SSEA-3 and/or SSEA-4 expression. In some embodiments the cancer comprises a cancer stem cell. In some embodiments, the cancer is a pre-cancer, and/or a malignant cancer and/or a therapy resistant cancer. In some embodiments, the cancer is a brain cancer.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having cancer, which include, but not limited to, sarcoma, skin cancer, leukemia, lymphoma, brain cancer, lung cancer, breast cancer, oral cancer, esophagus cancer, stomach cancer, liver cancer, bile duct cancer, pancreas cancer, colon cancer, kidney cancer, cervix cancer, ovary cancer and prostate cancer. A subject having cancer can be identified by routine medical examination.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

As used herein, the term "treating" refers to the application or administration of a composition including one or more active agents to a subject, who has cancer, a symptom of cancer, or a predisposition toward cancer, with the purpose to cure, heal, alleviate, relieve, alter, remedy, ameliorate, improve, or affect cancer, the symptom of cancer, or the predisposition toward cancer.

"Development" or "progression" of cancer means initial manifestations and/or ensuing progression of cancer. Development of cancer can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of cancer includes initial onset and/or recurrence.

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble ADCs (OBI-999) can be administered by the drip method, whereby a pharmaceutical formulation containing the ADC (OBI-999) and a physiologically acceptable excipients is infused. Physiologically acceptable excipients may include, for example, 5% dextrose, 0.9% saline, Ringer's solution or other suitable excipients.

Administration of Antibody-Drug Conjugate Pharmaceutical Formulations

Therapeutic antibody-drug conjugates (ADCs) may be administered by any route appropriate to the condition to be treated. The ADC will typically be administered parenterally, i.e. infusion, subcutaneous, intramuscular, intravenous, intradermal, intrathecal, bolus, intratumor injection or epidural (Shire et al (2004) J. Pharm. Sciences 93(6):1390-1402). Pharmaceutical formulations of therapeutic antibody-drug conjugates (ADCs) are typically prepared for parenteral administration with a pharmaceutically acceptable parenteral vehicle and in a unit dosage injectable form. An antibody-drug conjugate (ADC) having the desired degree of purity is optionally mixed with pharmaceutically acceptable diluents, carriers, excipients or stabilizers, in the form of a lyophilized formulation or an aqueous solution (Remington's Pharmaceutical Sciences (1980) 16th edition, Osol, A. Ed.).

Acceptable parenteral vehicles, diluents, carriers, excipients, and stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/ or non-ionic surfactants such as TWEEN™, PLURONICS™ or polyethylene glycol (PEG). For example, lyophilized anti-ErbB2 antibody formulations are described in WO 97/04801, expressly incorporated herein by reference. An exemplary formulation of an ADC such as trastuzumab-SMCC-DM1 contains about 100 mg/ml of trehalose (2-(hydroxymethyl)-6-[3,4,5-trihydroxy-6-(hydroxymethyl) tetrahydropyran-2-yl]oxy-tetrahydropyran-3,4,5-triol; $C_{12}H_{22}O_{11}$; CAS Number 99-20-7) and about 0.1% TWEEN™ 20 (polysorbate 20; dodecanoic acid 2-[2-[3,4-bis(2-hydroxyethoxy)tetrahydrofuran-2-yl]-2-(2-hydroxyethoxy)ethoxy]ethyl ester; $C_{26}H_{50}O_{10}$; CAS Number 9005-64-5) at approximately pH 6.

Pharmaceutical formulations of a therapeutic antibody-drug conjugate (ADC) may contain certain amounts of unreacted drug moiety (D), antibody-linker intermediate (Ab-L), and/or drug-linker intermediate (D-L), as a consequence of incomplete purification and separation of excess reagents, impurities, and by-products, in the process of making the ADC; or time/temperature hydrolysis or degradation upon storage of the bulk ADC or formulated ADC composition.

The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semi permeable matrices of solid hydrophobic polymers containing the ADC, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile, which is readily accomplished by filtration through sterile filtration membranes.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Aqueous suspensions contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of ADC may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, an aqueous solution intended for intravenous infusion may contain from about 3 to 500 μg of the active ingredient per milliliter of solution in order that infusion of a suitable volume at a rate of about 30 mL/hr can occur. Subcutaneous (bolus) administration may be effected with about 1.5 ml or less of total volume and a concentration of about 100 mg ADC per ml. For ADC that require frequent and chronic administration, the subcutaneous route may be employed, such as by pre-filled syringe or autoinjector device technology.

As a general proposition, the initial pharmaceutically effective amount of ADC administered per dose will be in the range of about 0.01-100 mg/kg, namely about 0.1 to 20 mg/kg of patient body weight per day, with the typical initial range of compound used being 0.3 to 15 mg/kg/day. For example, human patients may be initially dosed at about 1.5 mg ADC per kg patient body weight. The dose may be escalated to the maximally tolerated dose (MTD). The dosing schedule may be about every 3 weeks, but according to diagnosed condition or response, the schedule may be more or less frequent. The dose may be further adjusted during the course of treatment to be at or below MTD which can be safely administered for multiple cycles, such as about 4 or more.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Although oral administration of protein therapeutics are generally disfavored due to poor bioavailability due to limited absorption, hydrolysis or denaturation in the gut, formulations of ADC suitable for oral administration may be prepared as discrete units such as capsules, cachets or tablets each containing a predetermined amount of the ADC.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Exemplary unit dosage formulations contain a daily dose or unit daily sub-dose, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

For the prevention or treatment of disease, the appropriate dosage of an ADC will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 µg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 µg/kg to 100 mg/kg or more, depending on the factors mentioned above. An exemplary dosage of ADC to be administered to a patient is in the range of about 0.1 to about 10 mg/kg of patient weight.

For repeated administrations over several days or longer, depending on the condition, the treatment is sustained until a desired suppression of disease symptoms occurs. An exemplary dosing regimen comprises administering an initial loading dose of about 4 mg/kg, followed by a weekly maintenance dose of about 2 mg/kg of the anti-ErbB2 antibody. Other dosage regimens may be useful. The progress of this therapy is easily monitored by conventional techniques and assays.

Combination Therapy

An antibody-drug conjugate (ADC) may be combined in a pharmaceutical combination formulation, or dosing regimen as combination therapy, with a second compound having anti-cancer properties. The second compound of the pharmaceutical combination formulation or dosing regimen preferably has complementary activities to the ADC of the combination such that they do not adversely affect each other.

The second compound may be a chemotherapeutic agent, cytotoxic agent, cytokine, growth inhibitory agent, anti-hormonal agent, aromatase inhibitor, protein kinase inhibitor, lipid kinase inhibitor, anti-androgen, antisense oligonucleotide, ribozyme, gene therapy vaccine, anti-angiogenic agent and/or cardioprotectant. Such molecules are suitably present in combination in amounts that are effective for the purpose intended. A pharmaceutical composition containing an ADC may also have a therapeutically effective amount of a chemotherapeutic agent such as a tubulin-forming inhibitor, a topoisomerase inhibitor, or a DNA binder.

Metabolite products may be identified by preparing a radiolabelled (e.g. $^{14}$C or $^{3}$H) ADC, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS, LC/MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the ADC compounds.

Metabolites include the products of in vivo cleavage of the ADC where cleavage of any bond occurs that links the drug moiety to the antibody. Metabolic cleavage may thus result in the naked antibody, or an antibody fragment. The antibody metabolite may be linked to a part, or all, of the linker. Metabolic cleavage may also result in the production a drug moiety or part thereof. The drug moiety metabolite may be linked to a part, or all, of the linker.

Articles of Manufacture

In another embodiment, an article of manufacture, or "kit", containing ADC and materials useful for the treatment of the disorders described above is provided. The article of manufacture comprises a container and a label or package insert on or associated with the container. Suitable containers include, for example, bottles, vials, syringes, or blister pack. The containers may be formed from a variety of materials such as glass or plastic. The container holds an antibody-drug conjugate (ADC) composition which is effective for treating the condition and may have a sterile access port (for example the container may be an intravenous solution bag or a vial having a stopper pierceable by a hypodermic injection needle). At least one active agent in the composition is an ADC. The label or package insert indicates that the composition is used for treating the condition of choice, such as cancer.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Antibody Drug Conjugation

Figure 37:
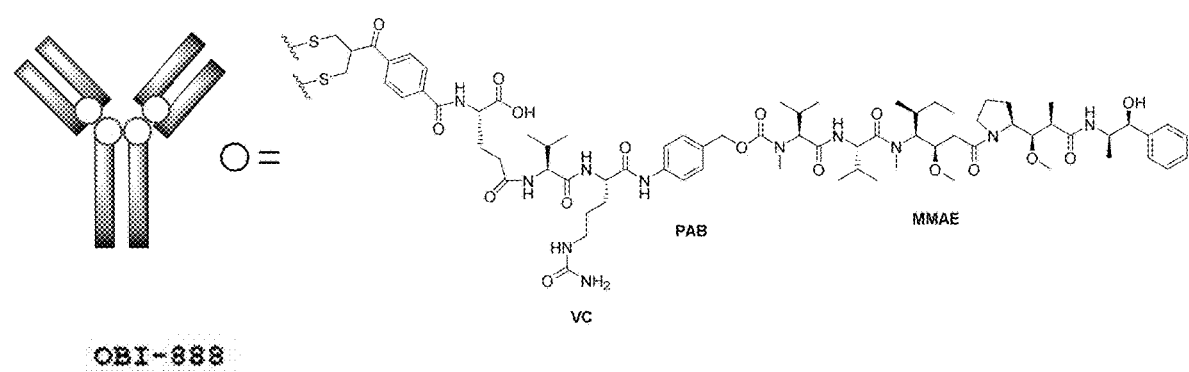
FIG. 37 showed the entire chemical structure of OBI-999 (DAR=4).

PolyTherics performed the conjugation of a MMAE reagent to OBI-888 monoclonal antibody to prepare the antibody drug conjugate (ADC; OBI-999). The disulfide conjugation linker is as disclosed in PCT publication number: U.S. Pat. No. 7,595,292 (WO2005/007197); OBI-888 is an Anti-Globo H monoclonal antibody which is as disclosed in US20170101462 (WO2017/062792); monomethyl auristatin E (MMAE) is a commercially available antineoplastic agent. Pilot scale reaction and purification were carried out to identify the appropriate conditions. It was found that the reduced antibody was not prone to aggregation. Subsequent screening of reduction and conjugation conditions resulted in significantly improved conjugation yields. The entire chemical structure of OBI-999 (DAR=4) is indicated in FIG. 37.

Example 2: The Analysis of Antibody Drug Conjugate (OBI-999)

2.1 Appearance

The appearance of the product solution was inspected visually for colour and transparency.

2.2 HIC Analysis

Analytical HIC (hydrophobic interaction chromatography) was carried out using a TOSOH, TSKgel Butyl-NPR column (3.5 cm×4.6 mm) connected to a Dionex Ultimate 3000RS HPLC system. The mobile phase was buffer A (1.5 M ammonium sulfate in 50 mM sodium phosphate, pH 7.0). A gradient was applied using buffer B (20% isopropanol (v/v) in 50 mM sodium phosphate, pH 7.0) from 20% to 86% (over 18.4 min at a flow rate of 1.2 mL/min). The column temperature was maintained at 30° C. throughout the analysis and UV detection was carried out at 280 nm. For each analysis 10 μg of native OBI-888 or conjugated product was injected.

2.3 SEC Analysis

SEC (size exclusion chromatography) was carried out using a TOSOH Bioscience TSKgel Super SW 3000 column (4.6 mm×30 cm, 4 μm) and guard column (4.6 mm×4 cm), connected to an Agilent Infinity 1260 Bioinert system. The mobile phase was 0.2 M Potassium phosphate buffer, pH 6.8 (0.2 M potassium chloride, 15% isopropanol). The flow rate was kept constant at 0.35 mL/min. The column was maintained at ambient temperature throughout the analysis. The analysis was carried out in a 20 min isocratic elution with UV detection at 280 nm. For each analysis, 10 μg of conjugated product was injected. The percentage purity & percentage aggregation present were calculated by comparing the peak areas of the main peaks and early eluting peaks respectively with total peak area.

2.4 SDS-PAGE Analysis

SDS-PAGE analysis was carried out using NuPAGE 4-12% Bis-Tris gels (Invitrogen, Cat #NP0321BOX) under reducing conditions with MES buffer. For analysis, 1 μg of sample (based on protein) was loaded onto the gel per lane. Electrophoresis was carried out at 200 V for 35 min. The gel were stained with InstantBlue (Expedeon, Cat #ISB1LUK) for protein detection and analysed using ImageQuant imaging equipment (GE Healthcare).

2.5 Concentration Determination by Bradford Assay & UV Absorbance.

Concentration of the conjugate was determined against a native OBI-888 standard curve (0-100 μg/mL) by Bradford microplate assay. The assay was performed in a flat bottomed, 96 well plate by mixing 100 μL of each calibration standard and sample with 200 μL of Bradford reagent (Expedeon, BFU1L) in triplicate. The optical density at 595 nm was read and the sample concentration was determined against the native OBI-888 standard curve. The concentration of the conjugate (based on protein) was also determined by UV absorbance (A280) using a Nanodrop spectrophotometer. Measurements were taken in triplicate and the average value was used to determine the antibody concentration:

$c = Abs/\varepsilon.1$ c=concentration (mg/mL); Abs=absorbance at 280 nm; ε=extinction coefficient (mL/mg·cm); l=length (cm).

Figure 1B:
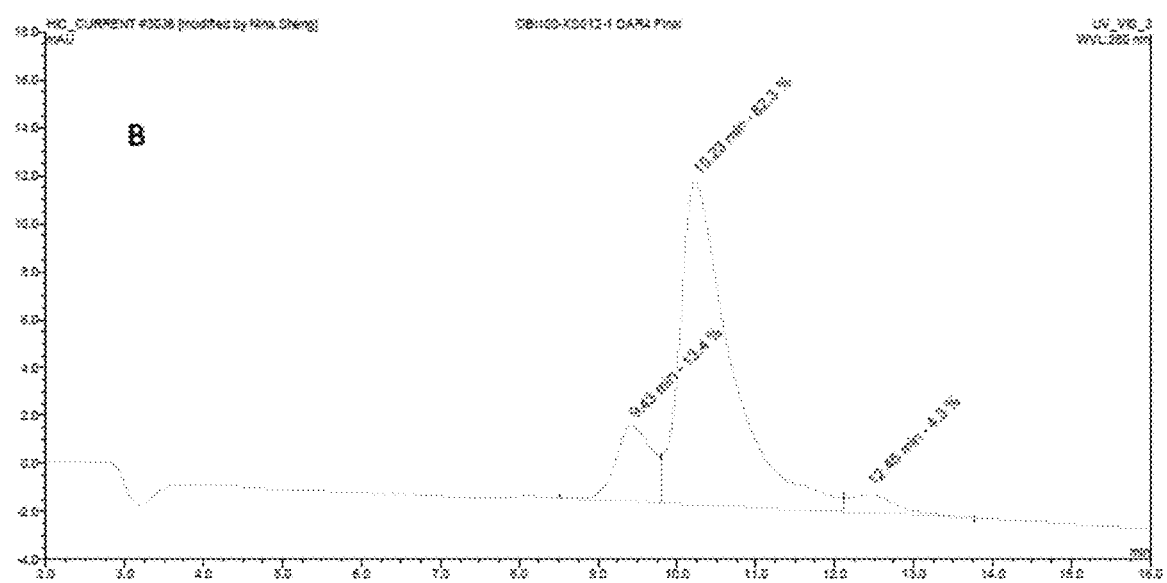
Figure 2A:
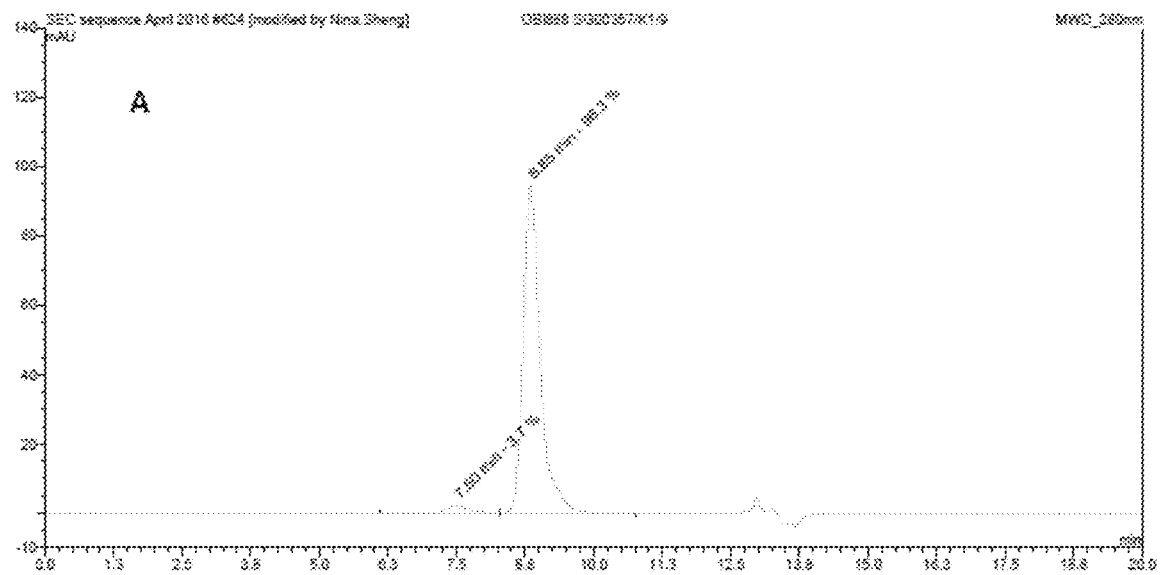
FIGS. 2A and 2B show size exclusion chromatogram (SEC) for OBI-888 (FIG. 2A) and ADC (OBI-999) (FIG. 2B).
Figure 2B:
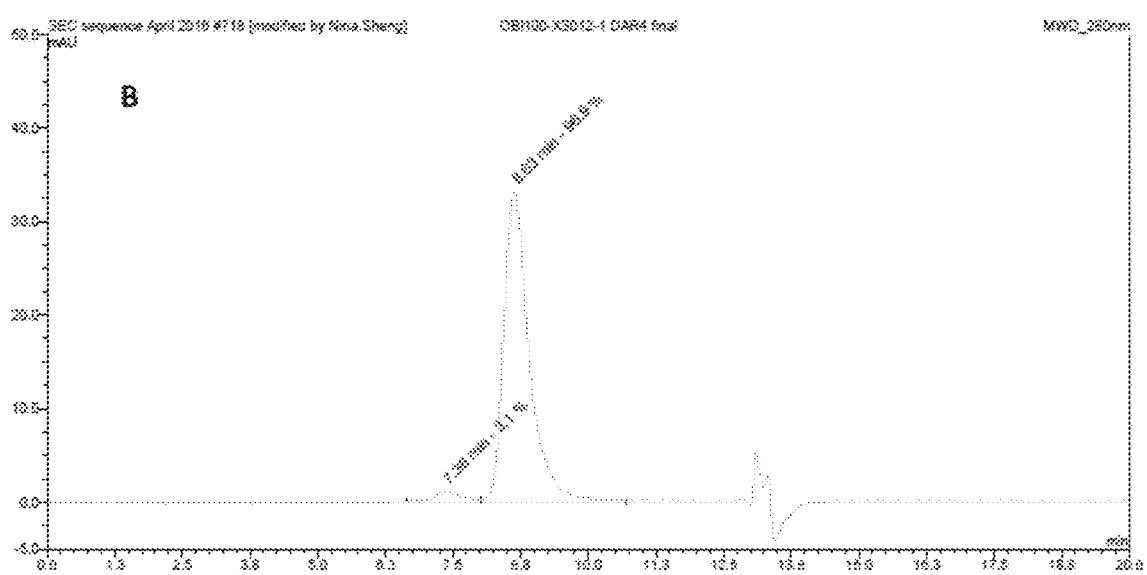
Figure 3:
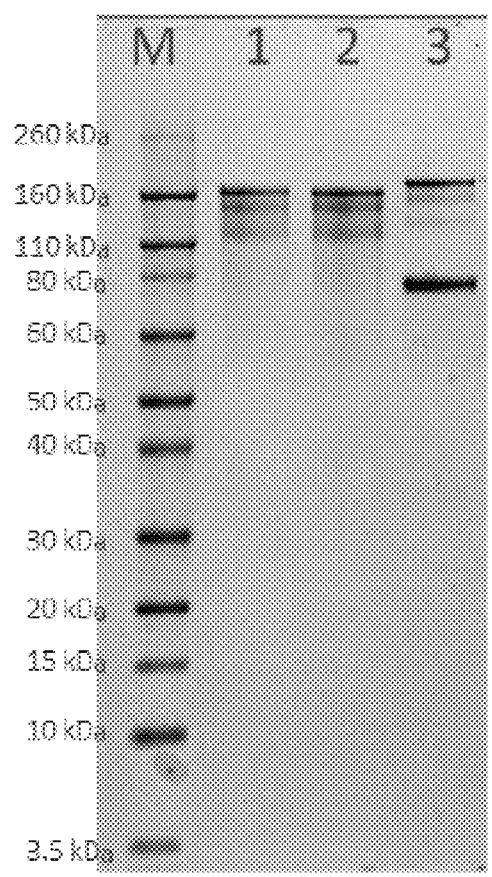
FIG. 3 showed SDS-PAGE analysis of OBI-888 and ADC (OBI-999). Lane M: Novex Sharp Marker; Lane 1: Native OBI-888 in formulation buffer; Lane 2: Native OBI-888 in reaction buffer; Lane 3: ADC (OBI-999).

One ADC sample (OBI-999) was isolated from a larger scale conjugation with a drug to antibody ratio of four and total amount of ADC (OBI-999) isolated was 14.5 mg (by Bradford). The drug to antibody ratio distribution was conducted by using hydrophobic interaction chromatography and showed in FIGS. 1A and 1B. FIG. 1(A) shows a single peak (100%) of OBI-888 by HIC and FIG. 1(B) shows a major peak (82.3%) of ADC (OBI-999) represented the drug to antibody ratio of four. The purities of OBI-888 (FIG. 2A) and ADC (OBI-999) (FIG. 2B) were conducted by using size exclusion chromatography. The purities were both over 96%. Finally, the SDS-PAGE analysis of OBI-888 and ADC (OBI-999) was shown in FIG. 3. The sample was shown to be a homogenous product (>82% single drug to antibody ratio) with low aggregation (<5%). The analytical summary was listed in Table 2.

TABLE 2

The analytical summary of ADC (OBI-999)

| Analysis | Results |
| --- | --- |
| Appearance | Clear colorless solution |
| % Purity (HIC) | Drug to Antibody Ratio = 3: 13.4% |
|  | Drug to Antibody Ratio = 4: 82.3% |
|  | Drug to Antibody Ratio = >4: 4.3% |
| % Purity (SEC) | 96.9% monomeric |
| Amount (by Bradford) | 14.5 mg |

Example 3: Measurement of the Anti-Tumor Activity of the Exemplary Antibody in Nude Mice (Breast Cancer)

In a xenograft tumor model of human breast adenocarcinoma, MCF-7 (ATCC HTB-22) cells were subcutaneously (SC) implanted ($2.0 \times 10^7$ cells in 1:1 matrigel/media mixture at 0.2 mL/mouse) into the right flank of female athymic (nu/nu) nude mice. Supplemental injections of estradiol cyclopentyl propionate (100 μg/mouse) were administered subcutaneously between the scapulae twice weekly, from one week prior to cell implantation to study completion. Tumor-implanted mice were divided into eleven treatment groups, each group containing six animals, and test agent administrations were initiated one day after cell implantation (denoted as Day 1).

3.1 Test Substances and Dosing Pattern

Test substances ADC (OBI-999), OBI-888, and MMAE were formulated by diluting stock with a 25 mM sodium citrate, 100 mM NaCl buffer (pH 6.5) daily and administered intravenously (IV) once weekly for two or six weeks. Two control groups received intravenous injections of vehicle (25 mM Sodium Citrate, pH 6.5+100 mM NaCl) once weekly for either six weeks (group 1) or two weeks (group 2). Test substance, ADC (OBI-999), was dosed at 10 mg/kg once weekly for 2 weeks, and at 0.3, 1, and 3 mg/kg once weekly for six weeks. Test substance, OBI-888, was dosed at 10 mg/kg once weekly for 2 weeks, and at 0.3, 1 and 3 mg/kg once weekly for six weeks. Test substance, MMAE, was dosed at 0.057 mg/kg once weekly for six weeks. All test substances were administered in a dose volume of 10 mL/kg except ADC (OBI-999) was administered at 10 mg/kg with the dose volume of 12.5 mL/kg.

TABLE 3

Study Design for Anti-Tumor Activity of the exemplary antibody in Nude Mice (Breast cancer)

| Group | Test Compound | Route | Conc. mg/mL | Dosage mL/kg | Dosage mg/kg | Mice (nu/nu) (female) |
|---|---|---|---|---|---|---|
| 1 | Vehicle[a] | IV | NA | 10 | 0 × 6[c] | 6 |
| 2 | Vehicle[a] | IV | NA | 10 | 0 × 2[b] | 6 |
| 3 | ADC (OBI-999) | IV | 0.8 | 12.5 | 10 × 2[b] | 6 |
| 4 | ADC (OBI-999) | IV | 0.03 | 10 | 0.3 × 6[c] | 6 |
| 5 | ADC (OBI-999) | IV | 0.1 | 10 | 1 × 6[c] | 6 |
| 6 | ADC (OBI-999) | IV | 0.3 | 10 | 3 × 6[c] | 6 |
| 7 | OBI-888 | IV | 1 | 10 | 10 × 2[b] | 6 |
| 8 | OBI-888 | IV | 0.03 | 10 | 0.3 × 6[c] | 6 |
| 9 | OBI-888 | IV | 0.1 | 10 | 1 × 6[c] | 6 |
| 10 | OBI-888 | IV | 0.3 | 10 | 3 × 6[c] | 6 |
| 11 | MMAE | IV | 0.0057 | 10 | 0.057 × 6[c] | 6 |

[a] 25 mM Sodium Citrate, pH 6.5 + 100 mM NaCl
[b] Dosing: once weekly for 2 weeks starting day after tumor implantation (Day 1)
[c] Dosing: once weekly for 6 weeks starting day after tumor implantation (Day 1) Monitor and provide tumor size and body weight record twice a week till Day 43 or the tumor size reaches 500 mm$^3$. Tumor photographed at the endpoint of study.

3.2 Cell Line

Human breast adenocarcinoma tumor cell line, MCF-7 (ATCC HTB-22, breast adenocarcinoma), was provided by the Sponsor. The tumor cells were prepared and cultured by the Sponsor ($1 \times 10^8$ cells/mL), and 0.2 mL MCF-7 tumor cell inoculum containing $2 \times 10^7$ cells (mixture of matrigel and medium; 1:1) was implanted subcutaneously in the right flank of each mouse.

3.3 Animals

Female (nu/nu) nude mice aged 6-7 weeks obtained from BioLasco Taiwan (under Charles River Laboratories Licensee) were used. The animals were housed in individually ventilated cages (IVC, 36 Mini Isolator System). The allocation for 3-5 animals was 27×20×14 in cm. All animals were maintained in a hygienic environment under controlled temperature (20-24° C.) and humidity (30-70%) with 12-hour light/dark cycle. Free access to standard lab diet (Oriental Yeast Co., Ltd., Japan) and autoclaved tap water were granted. All aspects of this work including housing, experimentation, and animal disposal were performed in general accordance with the "Guide for the Care and Use of Laboratory Animals: Eighth Edition" (National Academies Press, Washington, D.C., 2011) in our AAALAC-accredited laboratory animal facility. In addition, the animal care and use protocol was reviewed and approved by the IACUC at Eurofins Panlabs Taiwan, Ltd.

3.4 Chemicals

Estol-Depot Inj. (estradiol cyclopentyl propionate) (Astar, Taiwan) and BD Matrigel Matrix (BD Biosciences, US) were used in this experiment.

3.5 Equipment

Calipers (Mitutoyo, Japan), Centrifuge 5810R (Eppendorf, Germany), $CO_2$ Incubator (Forma Scientific Inc., USA), Hemacytometer (Hausser Scientific Horsham, USA), Individually Ventilated Cages (36 Mini Isolator system, Tecniplast, Italy), Inverted Microscope CK-40 (Olympus, Japan), System Microscope E-400 (Nikon, Japan) and Vertical laminar flow (Tsao-Hsin, Taiwan).

3.6 Methods

The tumor volumes, body weights, mortality, and signs of overt toxicity were monitored and recorded twice weekly for 77 days. Tumor volume (mm$^3$) was calculated according to the formula for a prolate ellipsoid: length (mm)×[width (mm)]$^2$×0.5. Tumor growth inhibition was calculated as T/C (treatment/control)×100%. A T/C value ≤42% was considered significant anti-tumor activity. Two-way ANOVA followed by Bonferroni test was used to ascertain the statistical significance of groups compared to respective vehicle control (*$p<0.05$).

3.7 Results

TABLE 4-1

Tumor volume, Xenograft, Breast, MCF-7 in Nude Mice (Day 1-Day 26)

| Gr. | Treatment | Dose (mg/kg) (Route) | No. | Day1 | Day5 | Day8 | Day12 | Day15 | Day19 | Day22 | Day26 |
|---|---|---|---|---|---|---|---|---|---|---|---|
| 1 | Vehicle (25 mM Sodium Citrate, pH 6.5 + 100 mM NaCl) | 10 mL/kg × 6 IV (Once weekly) | 1 | 131 | 119 | 133 | 134 | 175 | 220 | 240 | 258 |
| | | | 2 | 171 | 115 | 160 | 168 | 164 | 219 | 240 | 296 |
| | | | 3 | 173 | 137 | 150 | 150 | 176 | 194 | 243 | 286 |
| | | | 4 | 155 | 125 | 121 | 171 | 142 | 185 | 202 | 240 |
| | | | 5 | 166 | 117 | 123 | 181 | 138 | 169 | 171 | 203 |
| | | | 6 | 157 | 125 | 139 | 157 | 171 | 228 | 275 | 306 |
| | | | Mean | 159 | 123 | 138 | 160 | 161 | 203 | 229 | 265 |
| | | | SEM | 6 | 3 | 6 | 7 | 7 | 10 | 15 | 16 |
| 2 | Vehicle (25 mM Sodium Citrate, pH 6.5 + 100 mM NaCl) | 10 mL/kg × 2 IV (Once weekly) | 1 | 169 | 148 | 137 | 207 | 210 | 268 | 300 | 322 |
| | | | 2 | 149 | 137 | 146 | 189 | 189 | 234 | 282 | 337 |
| | | | 3 | 169 | 139 | 148 | 262 | 279 | 300 | 307 | 317 |
| | | | 4 | 184 | 133 | 139 | 133 | 123 | 127 | 146 | 231 |
| | | | 5 | 143 | 113 | 113 | 184 | 131 | 154 | 205 | 210 |
| | | | 6 | 160 | 121 | 127 | 142 | 153 | 174 | 174 | 166 |
| | | | Mean | 162 | 132 | 135 | 186 | 181 | 210 | 236 | 264 |
| | | | SEM | 6 | 5 | 5 | 19 | 24 | 28 | 28 | 29 |
| | | | % T/C | 102 | 107 | 98 | 116 | 112 | 103 | 103 | 100 |
| 3 | ADC (OBI-999) | 10 mg/kg × 2 IV (Once weekly) | 1 | 155 | 126 | 119 | 168 | 104 | 97 | 108 | 89 |
| | | | 2 | 139 | 123 | 115 | 123 | 90 | 89 | 89 | 94 |
| | | | 3 | 164 | 117 | 121 | 131 | 89 | 76 | 85 | 74 |
| | | | 4 | 152 | 119 | 110 | 88 | 100 | 97 | 85 | 75 |
| | | | 5 | 166 | 110 | 108 | 87 | 94 | 57 | 56 | 54 |
| | | | 6 | 127 | 125 | 118 | 129 | 101 | 104 | 93 | 85 |
| | | | Mean | 151 | 120 | 115 | 121 | 96 | 87 | 86 | 79 |
| | | | SEM | 6 | 2 | 2 | 12 | 3 | 7 | 7 | 6 |
| | | | % T/C | 93 | 91 | 85 | 65 | 53 | 41 | 36 | 30 |

TABLE 4-1-continued

Tumor volume, Xenograft, Breast, MCF-7 in Nude Mice (Day 1-Day 26)

| Gr. | Treatment | Dose (mg/kg) (Route) | No. | Tumor Volume (mm$^3$) | | | | | | | |
|---|---|---|---|---|---|---|---|---|---|---|---|
| | | | | Day1 | Day5 | Day8 | Day12 | Day15 | Day19 | Day22 | Day26 |
| 4 | ADC (OBI-999) | 0.3 mg/ kg × 6 IV (Once weekly) | 1 | 139 | 117 | 113 | 159 | 123 | 160 | 160 | 152 |
| | | | 2 | 176 | 139 | 131 | 143 | 141 | 144 | 176 | 195 |
| | | | 3 | 146 | 121 | 143 | 155 | 125 | 174 | 187 | 220 |
| | | | 4 | 153 | 119 | 126 | 168 | 156 | 186 | 198 | 197 |
| | | | 5 | 148 | 117 | 94 | 146 | 130 | 154 | 155 | 124 |
| | | | 6 | 135 | 103 | 113 | 141 | 143 | 145 | 163 | 166 |
| | | | Mean | 150 | 119 | 120 | 152 | 136 | 161 | 173 | 176 |
| | | | SEM | 6 | 5 | 7 | 4 | 5 | 7 | 7 | 14 |
| | | | % T/C | 94 | 97 | 87 | 95 | 84 | 79 | 76 | 66 |
| 5 | ADC (OBI-999) | 1 mg/ kg × 6 IV (Once weekly) | 1 | 197 | 161 | 149 | 175 | 145 | 135 | 138 | 125 |
| | | | 2 | 162 | 101 | 107 | 74 | 95 | 113 | 110 | 78 |
| | | | 3 | 157 | 131 | 148 | 126 | 124 | 148 | 135 | 121 |
| | | | 4 | 152 | 133 | 125 | 136 | 124 | 144 | 141 | 120 |
| | | | 5 | 131 | 101 | 108 | 127 | 113 | 106 | 117 | 112 |
| | | | 6 | 116 | 104 | 112 | 108 | 73 | 76 | 67 | 65 |
| | | | Mean | 153 | 122 | 125 | 124 | 112 | 120 | 118 | 104 |
| | | | SEM | 11 | 10 | 8 | 14 | 10 | 11 | 11 | 10 |
| | | | % T/C | 96 | 99 | 91 | 78 | 70 | 59 | 52 | 39 |
| 6 | ADC (OBI-999) | 3 mg/ kg × 6 IV (Once weekly) | 1 | 156 | 129 | 129 | 117 | 98 | 89 | 93 | 79 |
| | | | 2 | 194 | 108 | 108 | 125 | 88 | 86 | 88 | 70 |
| | | | 3 | 129 | 112 | 83 | 72 | 44 | 38 | 24 | 21 |
| | | | 4 | 139 | 108 | 94 | 88 | 81 | 82 | 51 | 37 |
| | | | 5 | 143 | 111 | 108 | 80 | 74 | 76 | 55 | 45 |
| | | | 6 | 139 | 108 | 94 | 88 | 81 | 88 | 83 | 55 |
| | | | Mean | 150 | 113 | 103 | 95 | 78 | 77 | 66 | 51 |
| | | | SEM | 9 | 3 | 7 | 9 | 8 | 8 | 11 | 9 |
| | | | % T/C | 94 | 92 | 75 | 59 | 48 | 38 | 29 | 19 |
| 7 | OBI-888 | 10 mg/ kg × 2 IV (Once weekly) | 1 | 123 | 94 | 123 | 100 | 162 | 161 | 154 | 137 |
| | | | 2 | 155 | 114 | 141 | 123 | 161 | 207 | 207 | 214 |
| | | | 3 | 150 | 97 | 127 | 111 | 104 | 115 | 133 | 145 |
| | | | 4 | 144 | 125 | 123 | 113 | 109 | 106 | 106 | 101 |
| | | | 5 | 159 | 125 | 100 | 120 | 145 | 187 | 202 | 213 |
| | | | 6 | 141 | 110 | 110 | 117 | 108 | 130 | 133 | 125 |
| | | | Mean | 145 | 111 | 121 | 114 | 132 | 151 | 156 | 156 |
| | | | SEM | 5 | 5 | 6 | 3 | 11 | 17 | 17 | 19 |
| | | | % T/C | 90 | 84 | 90 | 61 | 73 | 74 | 68 | 59 |
| 8 | OBI-888 | 0.3 mg/ kg × 6 IV (Once weekly) | 1 | 154 | 110 | 111 | 106 | 119 | 131 | 133 | 98 |
| | | | 2 | 231 | 123 | 104 | 106 | 111 | 141 | 157 | 197 |
| | | | 3 | 129 | 104 | 137 | 123 | 117 | 167 | 189 | 203 |
| | | | 4 | 153 | 119 | 117 | 106 | 113 | 113 | 119 | 115 |
| | | | 5 | 157 | 98 | 123 | 121 | 108 | 142 | 181 | 180 |
| | | | 6 | 150 | 101 | 127 | 101 | 104 | 109 | 121 | 164 |
| | | | Mean | 162 | 109 | 120 | 111 | 112 | 134 | 150 | 160 |
| | | | SEM | 14 | 4 | 5 | 4 | 2 | 9 | 12 | 18 |
| | | | % T/C | 102 | 89 | 87 | 69 | 70 | 66 | 66 | 60 |
| 9 | OBI-888 | 1 mg/ kg × 6 IV (Once weekly) | 1 | 146 | 133 | 113 | 115 | 83 | 97 | 92 | 86 |
| | | | 2 | 164 | 113 | 127 | 113 | 119 | 146 | 141 | 133 |
| | | | 3 | 127 | 63 | 69 | 80 | 69 | 81 | 89 | 88 |
| | | | 4 | 146 | 139 | 108 | 129 | 94 | 144 | 122 | 119 |
| | | | 5 | 215 | 136 | 115 | 130 | 145 | 200 | 198 | 206 |
| | | | 6 | 146 | 119 | 106 | 109 | 93 | 119 | 119 | 122 |
| | | | Mean | 157 | 117 | 106 | 113 | 101 | 131 | 127 | 126 |
| | | | SEM | 12 | 12 | 8 | 7 | 11 | 17 | 16 | 18 |
| | | | % T/C | 99 | 95 | 77 | 71 | 63 | 65 | 55 | 48 |
| 10 | OBI-888 | 3 mg/ kg × 6 IV (Once weekly) | 1 | 146 | 108 | 127 | 87 | 88 | 96 | 92 | 115 |
| | | | 2 | 137 | 125 | 131 | 125 | 115 | 124 | 137 | 153 |
| | | | 3 | 126 | 94 | 109 | 94 | 93 | 95 | 99 | 119 |
| | | | 4 | 136 | 119 | 125 | 124 | 124 | 143 | 138 | 114 |
| | | | 5 | 135 | 84 | 89 | 91 | 69 | 85 | 86 | 77 |
| | | | 6 | 181 | 108 | 129 | 121 | 91 | 103 | 108 | 102 |
| | | | Mean | 144 | 106 | 118 | 107 | 97 | 108 | 110 | 113 |
| | | | SEM | 8 | 6 | 7 | 7 | 8 | 9 | 9 | 10 |
| | | | % T/C | 91 | 86 | 86 | 67 | 60 | 53 | 48 | 43 |
| 11 | MMAE | 0.057 mg/ kg × 6 IV (Once weekly) | 1 | 162 | 145 | 139 | 133 | 127 | 125 | 137 | 119 |
| | | | 2 | 186 | 104 | 131 | 115 | 105 | 121 | 138 | 154 |
| | | | 3 | 152 | 106 | 131 | 103 | 137 | 148 | 164 | 179 |
| | | | 4 | 188 | 128 | 146 | 129 | 121 | 135 | 143 | 144 |
| | | | 5 | 141 | 110 | 121 | 101 | 102 | 137 | 123 | 135 |
| | | | 6 | 139 | 123 | 125 | 104 | 101 | 113 | 137 | 127 |
| | | | Mean | 161 | 119 | 132 | 114 | 116 | 130 | 140 | 143 |
| | | | SEM | 9 | 6 | 4 | 6 | 6 | 5 | 5 | 9 |
| | | | % T/C | 101 | 97 | 96 | 71 | 72 | 64 | 61 | 54 |

TABLE 4-2

Tumor volume, Xenograft, Breast, MCF-7 in Nude Mice (Day 29-Day 49)

| Gr. | Treatment | Dose (mg/kg) (Route) | No. | Tumor Volume (mm³) | | | | | | |
|---|---|---|---|---|---|---|---|---|---|---|
| | | | | Day29 | Day33 | Day36 | Day40 | Day43 | Day46 | Day49 |
| 1 | Vehicle (25 mM Sodium Citrate, pH 6.5 + 100 mM NaCl) | 10 mL/ kg × 6 IV (Once weekly) | 1 | 281 | 312 | 343 | 372 | 399 | 435 | 455 |
| | | | 2 | 295 | 325 | 340 | 348 | 368 | 376 | 419 |
| | | | 3 | 307 | 328 | 351 | 363 | 388 | 432 | 465 |
| | | | 4 | 255 | 277 | 295 | 307 | 330 | 355 | 387 |
| | | | 5 | 214 | 228 | 243 | 259 | 307 | 321 | 351 |
| | | | 6 | 316 | 370 | 386 | 424 | 432 | 436 | 476 |
| | | | Mean | 278 | 307 | 326 | 346 | 371 | 393 | 426 |
| | | | SEM | 16 | 20 | 20 | 23 | 19 | 20 | 20 |
| 2 | Vehicle (25 mM Sodium Citrate, pH 6.5 + 100 mM NaCl) | 10 mL/ kg × 2 IV (Once weekly) | 1 | 356 | 389 | 432 | 458 | 503 | 612 | 738 |
| | | | 2 | 344 | 364 | 402 | 402 | 429 | 470 | 484 |
| | | | 3 | 381 | 402 | 411 | 415 | 415 | 433 | 456 |
| | | | 4 | 252 | 279 | 341 | 389 | 422 | 451 | 499 |
| | | | 5 | 266 | 317 | 325 | 332 | 340 | 356 | 368 |
| | | | 6 | 169 | 189 | 194 | 197 | 203 | 203 | 203 |
| | | | Mean | 295 | 323 | 351 | 366 | 385 | 421 | 458 |
| | | | SEM | 33 | 33 | 36 | 38 | 42 | 55 | 72 |
| | | | % T/C | 106 | 105 | 108 | 106 | 104 | 107 | 108 |
| 3 | ADC (OBI-999) | 10 mg/ kg × 2 IV (Once weekly) | 1 | 73 | 66 | 66 | 57 | 53 | 51 | 49 |
| | | | 2 | 91 | 85 | 83 | 70 | 66 | 53 | 48 |
| | | | 3 | 75 | 79 | 79 | 62 | 56 | 49 | 45 |
| | | | 4 | 75 | 76 | 78 | 72 | 65 | 62 | 56 |
| | | | 5 | 48 | 42 | 39 | 32 | 32 | 31 | 30 |
| | | | 6 | 86 | 82 | 79 | 66 | 62 | 60 | 58 |
| | | | Mean | 75 | 72 | 71 | 60 | 56 | 51 | 48 |
| | | | SEM | 6 | 7 | 7 | 6 | 5 | 5 | 4 |
| | | | % T/C | 27 | 23 | 22 | 17 | 15 | 13 | 11 |
| 4 | ADC (OBI-999) | 0.3 mg/ kg × 6 IV (Once weekly) | 1 | 176 | 222 | 240 | 269 | 296 | 307 | 340 |
| | | | 2 | 218 | 238 | 260 | 270 | 276 | 295 | 333 |
| | | | 3 | 284 | 388 | 405 | 580 | 700 | 756 | 828 |
| | | | 4 | 241 | 254 | 264 | 285 | 312 | 326 | 353 |
| | | | 5 | 143 | 168 | 190 | 198 | 209 | 221 | 233 |
| | | | 6 | 174 | 211 | 225 | 234 | 243 | 259 | 269 |
| | | | Mean | 206 | 247 | 264 | 306 | 339 | 361 | 393 |
| | | | SEM | 21 | 31 | 30 | 56 | 74 | 81 | 89 |
| | | | % T/C | 74 | 80 | 81 | 88 | 91 | 92 | 92 |
| 5 | ADC (OBI-999) | 1 mg/ kg × 6 IV (Once weekly) | 1 | 140 | 140 | 140 | 153 | 165 | 167 | 182 |
| | | | 2 | 85 | 95 | 117 | 127 | 147 | 154 | 158 |
| | | | 3 | 141 | 160 | 174 | 181 | 192 | 179 | 187 |
| | | | 4 | 126 | 143 | 143 | 154 | 180 | 200 | 219 |
| | | | 5 | 121 | 113 | 121 | 127 | 127 | 129 | 137 |
| | | | 6 | 69 | 56 | 64 | 70 | 72 | 74 | 74 |
| | | | Mean | 114 | 118 | 127 | 135 | 147 | 151 | 160 |
| | | | SEM | 12 | 16 | 15 | 15 | 18 | 18 | 21 |
| | | | % T/C | 41 | 38 | 39 | 39 | 40 | 38 | 38 |
| 6 | ADC (OBI-999) | 3 mg/ kg × 6 IV (Once weekly) | 1 | 79 | 79 | 73 | 60 | 58 | 56 | 56 |
| | | | 2 | 86 | 83 | 80 | 56 | 53 | 51 | 50 |
| | | | 3 | 18 | 0 | 0 | 0 | 0 | 0 | 0 |
| | | | 4 | 37 | 40 | 47 | 31 | 31 | 29 | 0 |
| | | | 5 | 39 | 44 | 51 | 30 | 29 | 25 | 23 |
| | | | 6 | 59 | 41 | 39 | 0 | 0 | 0 | 0 |
| | | | Mean | 53 | 48 | 48 | 30 | 29 | 27 | 22 |
| | | | SEM | 11 | 12 | 12 | 11 | 10 | 10 | 11 |
| | | | % T/C | 19 | 16 | 15 | 9 | 8 | 7 | 5 |
| 7 | OBI-888 | 10 mg/ kg × 2 IV (Once weekly) | 1 | 174 | 200 | 249 | 272 | 292 | 313 | 332 |
| | | | 2 | 236 | 244 | 273 | 291 | 296 | 293 | 308 |
| | | | 3 | 139 | 173 | 202 | 249 | 292 | 354 | 425 |
| | | | 4 | 117 | 111 | 119 | 117 | 122 | 128 | 134 |
| | | | 5 | 241 | 247 | 264 | 296 | 312 | 347 | 378 |
| | | | 6 | 159 | 174 | 197 | 200 | 205 | 213 | 230 |
| | | | Mean | 178 | 192 | 217 | 238 | 253 | 275 | 301 |
| | | | SEM | 21 | 21 | 24 | 28 | 30 | 36 | 43 |
| | | | % T/C | 64 | 63 | 67 | 69 | 68 | 70 | 71 |
| 8 | OBI-888 | 0.3 mg/ kg × 6 IV (Once weekly) | 1 | 97 | 110 | 119 | 127 | 137 | 167 | 179 |
| | | | 2 | 213 | 265 | 331 | 385 | 416 | 486 | 508 |
| | | | 3 | 211 | 217 | 240 | 246 | 265 | 286 | 310 |
| | | | 4 | 106 | 104 | 121 | 139 | 150 | 152 | 152 |
| | | | 5 | 241 | 294 | 372 | 397 | 455 | 493 | 539 |
| | | | 6 | 189 | 217 | 245 | 274 | 287 | 295 | 298 |
| | | | Mean | 176 | 201 | 238 | 261 | 285 | 313 | 331 |
| | | | SEM | 25 | 32 | 43 | 47 | 54 | 61 | 66 |
| | | | % T/C | 63 | 65 | 73 | 75 | 77 | 80 | 78 |

TABLE 4-2-continued

Tumor volume, Xenograft, Breast, MCF-7 in Nude Mice (Day 29-Day 49)

| Gr. | Treatment | Dose (mg/kg) (Route) | No. | Tumor Volume (mm$^3$) | | | | | | |
|---|---|---|---|---|---|---|---|---|---|---|
| | | | | Day29 | Day33 | Day36 | Day40 | Day43 | Day46 | Day49 |
| 9 | OBI-888 | 1 mg/ kg × 6 IV (Once weekly) | 1 | 104 | 108 | 119 | 117 | 127 | 133 | 139 |
| | | | 2 | 153 | 160 | 174 | 181 | 187 | 192 | 200 |
| | | | 3 | 98 | 127 | 136 | 158 | 178 | 199 | 211 |
| | | | 4 | 123 | 139 | 145 | 147 | 161 | 163 | 178 |
| | | | 5 | 255 | 331 | 354 | 379 | 416 | 450 | 491 |
| | | | 6 | 142 | 145 | 157 | 168 | 185 | 199 | 201 |
| | | | Mean | 146 | 168 | 181 | 192 | 209 | 223 | 237 |
| | | | SEM | 23 | 33 | 35 | 39 | 42 | 47 | 52 |
| | | | % T/C | 53 | 55 | 56 | 55 | 56 | 57 | 56 |
| 10 | OBI-888 | 3 mg/ kg × 6 IV (Once weekly) | 1 | 123 | 139 | 146 | 152 | 162 | 181 | 192 |
| | | | 2 | 167 | 181 | 231 | 256 | 269 | 272 | 292 |
| | | | 3 | 149 | 171 | 183 | 207 | 221 | 236 | 248 |
| | | | 4 | 117 | 145 | 154 | 163 | 166 | 170 | 174 |
| | | | 5 | 79 | 83 | 86 | 91 | 101 | 112 | 116 |
| | | | 6 | 103 | 107 | 107 | 105 | 110 | 112 | 116 |
| | | | Mean | 123 | 138 | 151 | 162 | 172 | 181 | 190 |
| | | | SEM | 13 | 15 | 21 | 25 | 26 | 26 | 29 |
| | | | % T/C | 44 | 45 | 46 | 47 | 46 | 46 | 45 |
| 11 | MMAE | 0.057 mg/ kg × 6 IV (Once weekly) | 1 | 119 | 133 | 152 | 156 | 186 | 222 | 235 |
| | | | 2 | 156 | 168 | 201 | 223 | 242 | 258 | 301 |
| | | | 3 | 194 | 216 | 256 | 285 | 296 | 332 | 351 |
| | | | 4 | 160 | 177 | 218 | 226 | 240 | 259 | 264 |
| | | | 5 | 146 | 162 | 171 | 184 | 186 | 204 | 210 |
| | | | 6 | 131 | 152 | 154 | 186 | 239 | 261 | 270 |
| | | | Mean | 151 | 168 | 192 | 210 | 232 | 256 | 272 |
| | | | SEM | 11 | 11 | 17 | 18 | 17 | 18 | 20 |
| | | | % T/C | 54 | 55 | 59 | 61 | 63 | 65 | 64 |

TABLE 4-3

Tumor volume, Xenograft, Breast, MCF-7 in Nude Mice (Day 53-Day 77)

| Gr. | Treatment | Dose (mg/kg) (Route) | No. | Tumor Volume (mm$^3$) | | | | | | |
|---|---|---|---|---|---|---|---|---|---|---|
| | | | | Day53 | Day56 | Day60 | Day63 | Day67 | Day70 | Day74 | Day77 |
| 1 | Vehicle (25 mM Sodium Citrate, pH 6.5 + 100 mM NaCl) | 10 mL/ kg × 6 IV (Once weekly) | 1 | 489 | 519 | 535 | 565 | 645 | 684 | 744 | 853 |
| | | | 2 | 445 | 469 | 509 | 519 | 557 | 579 | 584 | 601 |
| | | | 3 | 519 | 578 | 688 | 785 | 890 | 972 | 986 | 1155 |
| | | | 4 | 405 | 416 | 454 | 465 | 514 | 518 | 578 | 796 |
| | | | 5 | 375 | 450 | 509 | 579 | 622 | 652 | 681 | 881 |
| | | | 6 | 499 | 530 | 585 | 629 | 752 | 776 | 862 | 1032 |
| | | | Mean | 455 | 494 | 547 | 590 | 663 | 697 | 739 | 886 |
| | | | SEM | 23 | 24 | 33 | 45 | 56 | 66 | 66 | 78 |
| 2 | Vehicle (25 mM Sodium Citrate, pH 6.5 + 100 mM NaCl) | 10 mL/ kg × 2 IV (Once weekly) | 1 | 803 | 950 | 1113 | 1247 | 1439 | 1509 | 1870 | 2222 |
| | | | 2 | 488 | 528 | 547 | 575 | 597 | 627 | 663 | 780 |
| | | | 3 | 465 | 494 | 515 | 525 | 578 | 583 | 647 | 828 |
| | | | 4 | 605 | 708 | 793 | 877 | 968 | 1014 | 1030 | 1102 |
| | | | 5 | 368 | 407 | 414 | 423 | 465 | 465 | 535 | 754 |
| | | | 6 | 208 | 222 | 243 | 267 | 361 | 433 | 526 | 615 |
| | | | Mean | 490 | 552 | 604 | 652 | 735 | 772 | 879 | 1050 |
| | | | SEM | 83 | 103 | 125 | 145 | 164 | 170 | 212 | 243 |
| | | | % T/C | 108 | 112 | 110 | 111 | 111 | 111 | 119 | 119 |
| 3 | ADC (OBI-999) | 10 mg/ kg × 2 IV (Once weekly) | 1 | 48 | 47 | 46 | 45 | 44 | 42 | 42 | 40 |
| | | | 2 | 46 | 45 | 44 | 42 | 41 | 41 | 41 | 43 |
| | | | 3 | 45 | 43 | 41 | 39 | 37 | 37 | 37 | 37 |
| | | | 4 | 55 | 56 | 55 | 48 | 46 | 45 | 44 | 43 |
| | | | 5 | 29 | 55 | 55 | 23 | 23 | 23 | 23 | 25 |
| | | | 6 | 58 | 29 | 29 | 55 | 53 | 51 | 51 | 50 |
| | | | Mean | 47 | 46 | 45 | 42 | 41 | 40 | 40 | 40 |
| | | | SEM | 4 | 4 | 4 | 4 | 4 | 4 | 4 | 3 |
| | | | % T/C | 10 | 9 | 8 | 7 | 6 | 6 | 5 | 5 |
| 4 | ADC (OBI-999) | 0.3 mg/ kg × 6 IV (Once weekly) | 1 | 356 | 385 | 411 | 428 | 490 | 607 | 665 | 834 |
| | | | 2 | 361 | 371 | 444 | 476 | 536 | 630 | 681 | 819 |
| | | | 3 | 992 | 1120 | 1276 | 1299 | 1532 | 1882 | 1950 | 2177 |
| | | | 4 | 400 | 484 | 530 | 575 | 641 | 725 | 849 | 1028 |
| | | | 5 | 235 | 241 | 276 | 298 | 362 | 408 | 473 | 575 |
| | | | 6 | 272 | 292 | 328 | 371 | 390 | 492 | 545 | 704 |
| | | | Mean | 436 | 482 | 544 | 575 | 659 | 791 | 861 | 1023 |

TABLE 4-3-continued

Tumor volume, Xenograft, Breast, MCF-7 in Nude Mice (Day 53-Day 77)

| Gr. | Treatment | Dose (mg/kg) (Route) | No. | Day53 | Day56 | Day60 | Day63 | Day67 | Day70 | Day74 | Day77 |
|---|---|---|---|---|---|---|---|---|---|---|---|
|  |  |  | SEM | 114 | 132 | 151 | 150 | 180 | 223 | 224 | 239 |
|  |  |  | % T/C | 96 | 98 | 99 | 97 | 99 | 113 | 117 | 115 |
| 5 | ADC (OBI-999) | 1 mg/kg × 6 IV (Once weekly) | 1 | 188 | 197 | 205 | 222 | 237 | 264 | 292 | 373 |
|  |  |  | 2 | 160 | 176 | 183 | 205 | 217 | 245 | 256 | 277 |
|  |  |  | 3 | 197 | 200 | 219 | 228 | 228 | 233 | 233 | 231 |
|  |  |  | 4 | 236 | 257 | 296 | 331 | 409 | 497 | 552 | 770 |
|  |  |  | 5 | 145 | 172 | 195 | 224 | 259 | 291 | 304 | 368 |
|  |  |  | 6 | 70 | 73 | 74 | 76 | 77 | 77 | 78 | 78 |
|  |  |  | Mean | 166 | 179 | 195 | 214 | 238 | 268 | 286 | 350 |
|  |  |  | SEM | 23 | 25 | 29 | 33 | 43 | 55 | 63 | 95 |
|  |  |  | % T/C | 36 | 36 | 36 | 36 | 36 | 38 | 39 | 40 |
| 6 | ADC (OBI-999) | 3 mg/kg × 6 IV (Once weekly) | 1 | 54 | 52 | 52 | 51 | 51 | 51 | 51 | 52 |
|  |  |  | 2 | 49 | 47 | 46 | 44 | 42 | 42 | 42 | 41 |
|  |  |  | 3 | 0 | 0 | 0 | 0 | 0 | 0 | 0 | 0 |
|  |  |  | 4 | 0 | 0 | 0 | 0 | 0 | 0 | 0 | 0 |
|  |  |  | 5 | 23 | 22 | 21 | 21 | 21 | 21 | 21 | 23 |
|  |  |  | 6 | 0 | 0 | 0 | 0 | 0 | 0 | 0 | 0 |
|  |  |  | Mean | 21 | 20 | 20 | 19 | 19 | 19 | 19 | 19 |
|  |  |  | SEM | 10 | 10 | 10 | 10 | 9 | 9 | 9 | 9 |
|  |  |  | % T/C | 5 | 4 | 4 | 3 | 3 | 3 | 3 | 2 |
| 7 | OBI-888 | 10 mg/kg × 2 IV (Once weekly) | 1 | 377 | 399 | 420 | 496 | 940 | 1180 | 1250 | 1710 |
|  |  |  | 2 | 333 | 348 | 372 | 436 | 451 | died | died | died |
|  |  |  | 3 | 610 | 162 | 188 | 701 | 746 | 849 | 952 | 1476 |
|  |  |  | 4 | 160 | 462 | 519 | 194 | 198 | 265 | 313 | 402 |
|  |  |  | 5 | 441 | 239 | 242 | 547 | 605 | 609 | 677 | 768 |
|  |  |  | 6 | 233 | 657 | 682 | 262 | 268 | 271 | 284 | 325 |
|  |  |  | Mean | 359 | 378 | 404 | 439 | 535 | 635 | 695 | 936 |
|  |  |  | SEM | 65 | 71 | 74 | 76 | 116 | 175 | 186 | 281 |
|  |  |  | % T/C | 79 | 77 | 74 | 74 | 81 | 91 | 94 | 106 |
| 8 | OBI-888 | 0.3 mg/kg × 6 IV (Once weekly) | 1 | 181 | 202 | 213 | 243 | 284 | 350 | 419 | 658 |
|  |  |  | 2 | 528 | 573 | 711 | 717 | 744 | 781 | 955 | 1080 |
|  |  |  | 3 | 332 | 155 | 157 | 428 | 451 | 510 | 552 | 589 |
|  |  |  | 4 | 152 | 733 | 841 | 157 | 157 | 157 | 157 | 162 |
|  |  |  | 5 | 673 | 318 | 341 | 910 | 992 | 1138 | 1180 | 1392 |
|  |  |  | 6 | 307 | 372 | 381 | 353 | 378 | 436 | 475 | 616 |
|  |  |  | Mean | 362 | 392 | 441 | 468 | 501 | 562 | 623 | 750 |
|  |  |  | SEM | 83 | 91 | 112 | 118 | 127 | 142 | 153 | 175 |
|  |  |  | % T/C | 80 | 79 | 81 | 79 | 76 | 81 | 84 | 85 |
| 9 | OBI-888 | 1 mg/kg × 6 IV (Once weekly) | 1 | 147 | 161 | 163 | 168 | 183 | 194 | 201 | 221 |
|  |  |  | 2 | 259 | 265 | 322 | 360 | 385 | 429 | 475 | 596 |
|  |  |  | 3 | 220 | 226 | 248 | 337 | 365 | 379 | 443 | 579 |
|  |  |  | 4 | 213 | 653 | 784 | 254 | 321 | 335 | 341 | 377 |
|  |  |  | 5 | 632 | 210 | 217 | 847 | 883 | 932 | 962 | 1289 |
|  |  |  | 6 | 203 | 240 | 273 | 223 | 228 | 291 | 299 | 394 |
|  |  |  | Mean | 279 | 293 | 335 | 365 | 394 | 427 | 454 | 576 |
|  |  |  | SEM | 72 | 73 | 93 | 101 | 103 | 106 | 109 | 154 |
|  |  |  | % T/C | 61 | 59 | 61 | 62 | 59 | 61 | 61 | 65 |
| 10 | OBI-888 | 3 mg/kg × 6 IV (Once weekly) | 1 | 203 | 324 | 356 | 303 | 352 | 389 | 460 | 629 |
|  |  |  | 2 | 309 | 316 | 381 | 356 | 378 | 378 | 396 | 603 |
|  |  |  | 3 | 294 | 176 | 179 | 411 | 469 | 508 | 581 | 678 |
|  |  |  | 4 | 174 | 125 | 138 | 181 | 181 | 181 | 181 | 215 |
|  |  |  | 5 | 124 | 127 | 131 | 143 | 162 | 177 | 206 | 270 |
|  |  |  | 6 | 121 | 219 | 269 | 134 | 137 | 139 | 159 | 161 |
|  |  |  | Mean | 204 | 215 | 242 | 255 | 280 | 295 | 331 | 426 |
|  |  |  | SEM | 33 | 36 | 45 | 48 | 56 | 61 | 71 | 96 |
|  |  |  | % T/C | 45 | 44 | 44 | 43 | 42 | 42 | 45 | 48 |
| 11 | MMAE | 0.057 mg/kg × 6 IV (Once weekly) | 1 | 268 | 325 | 383 | 494 | 598 | 603 | 681 | 760 |
|  |  |  | 2 | 319 | 329 | 373 | 418 | 455 | 493 | 570 | 632 |
|  |  |  | 3 | 373 | 399 | 453 | 496 | 505 | 523 | 568 | 807 |
|  |  |  | 4 | 270 | 328 | 358 | 412 | 489 | 528 | 695 | 887 |
|  |  |  | 5 | 216 | 305 | 312 | 286 | 307 | 333 | 365 | 410 |
|  |  |  | 6 | 291 | 249 | 262 | 422 | 458 | 591 | 625 | 922 |
|  |  |  | Mean | 290 | 323 | 357 | 421 | 469 | 512 | 584 | 736 |
|  |  |  | SEM | 22 | 20 | 27 | 31 | 39 | 40 | 49 | 77 |
|  |  |  | % T/C | 64 | 65 | 65 | 71 | 71 | 73 | 79 | 83 |

TABLE 5-1

Body weight, Xenograft, Breast, MCF-7 in Nude Mice (Day 1-Day 26)

| Gr. | Treatment | Dose (mg/kg) (Route) | No. | Day1 | Day5 | Day8 | Day12 | Day15 | Day19 | Day22 | Day26 |
|---|---|---|---|---|---|---|---|---|---|---|---|
| 1 | Vehicle (25 mM Sodium Citrate, pH 6.5 + 100 mM NaCl) | 10 mL/ kg × 6 IV (Once weekly) | 1 | 25 | 25 | 26 | 27 | 27 | 26 | 26 | 25 |
| | | | 2 | 24 | 24 | 26 | 28 | 29 | 29 | 29 | 27 |
| | | | 3 | 23 | 24 | 25 | 26 | 26 | 26 | 26 | 27 |
| | | | 4 | 23 | 24 | 26 | 27 | 27 | 27 | 26 | 26 |
| | | | 5 | 23 | 24 | 25 | 27 | 27 | 27 | 28 | 27 |
| | | | 6 | 21 | 22 | 24 | 24 | 24 | 24 | 25 | 24 |
| | | | Mean | 23.2 | 23.8 | 25.3 | 26.5 | 26.7 | 26.5 | 26.7 | 26.0 |
| | | | SEM | 0.5 | 0.4 | 0.3 | 0.6 | 0.7 | 0.7 | 0.6 | 0.5 |
| 2 | Vehicle (25 mM Sodium Citrate, pH 6.5 + 100 mM NaCl) | 10 mL/ kg × 2 IV (Once weekly) | 1 | 21 | 23 | 23 | 25 | 25 | 25 | 25 | 25 |
| | | | 2 | 20 | 21 | 22 | 24 | 25 | 25 | 25 | 25 |
| | | | 3 | 18 | 19 | 20 | 21 | 22 | 22 | 23 | 22 |
| | | | 4 | 24 | 24 | 24 | 26 | 26 | 25 | 26 | 27 |
| | | | 5 | 23 | 25 | 27 | 28 | 28 | 27 | 27 | 28 |
| | | | 6 | 23 | 24 | 25 | 26 | 27 | 26 | 27 | 27 |
| | | | Mean | 21.5 | 22.7 | 23.5 | 25.0 | 25.5 | 25.0 | 25.5 | 25.7 |
| | | | SEM | 0.9 | 0.9 | 1.0 | 1.0 | 0.8 | 0.7 | 0.6 | 0.9 |
| | | | $p < 0.05$ | | | | | | | | |
| 3 | ADC (OBI-999) | 10 mg/ kg × 2 IV (Once weekly) | 1 | 22 | 22 | 25 | 26 | 27 | 26 | 26 | 26 |
| | | | 2 | 21 | 21 | 22 | 23 | 23 | 23 | 24 | 23 |
| | | | 3 | 23 | 25 | 26 | 26 | 27 | 27 | 26 | 27 |
| | | | 4 | 21 | 20 | 21 | 21 | 23 | 21 | 22 | 21 |
| | | | 5 | 20 | 20 | 21 | 22 | 23 | 23 | 24 | 24 |
| | | | 6 | 22 | 23 | 23 | 24 | 24 | 24 | 25 | 25 |
| | | | Mean | 21.5 | 21.8 | 23.0 | 23.7 | 24.5 | 24.0 | 24.5 | 24.3 |
| | | | SEM | 0.4 | 0.8 | 0.9 | 0.8 | 0.8 | 0.9 | 0.6 | 0.9 |
| | | | $p < 0.05$ | | | | | | | | |
| 4 | ADC (OBI-999) | 0.3 mg/ kg × 6 IV (Once weekly) | 1 | 22 | 22 | 23 | 24 | 25 | 25 | 25 | 25 |
| | | | 2 | 23 | 24 | 25 | 27 | 26 | 25 | 26 | 26 |
| | | | 3 | 21 | 21 | 22 | 23 | 23 | 23 | 25 | 25 |
| | | | 4 | 23 | 23 | 24 | 25 | 24 | 25 | 25 | 26 |
| | | | 5 | 21 | 22 | 23 | 24 | 24 | 24 | 25 | 24 |
| | | | 6 | 21 | 21 | 23 | 24 | 24 | 25 | 25 | 25 |
| | | | Mean | 21.8 | 22.2 | 23.3 | 24.5 | 24.3 | 24.5 | 25.2 | 25.2 |
| | | | SEM | 0.4 | 0.5 | 0.4 | 0.6 | 0.4 | 0.3 | 0.2 | 0.3 |
| | | | $p < 0.05$ | | | | | | | | |
| 5 | ADC (OBI-999) | 1 mg/ kg × 6 IV (Once weekly) | 1 | 22 | 22 | 24 | 24 | 24 | 24 | 24 | 24 |
| | | | 2 | 22 | 23 | 25 | 26 | 26 | 26 | 26 | 26 |
| | | | 3 | 21 | 20 | 22 | 22 | 23 | 23 | 24 | 23 |
| | | | 4 | 23 | 25 | 25 | 26 | 27 | 26 | 27 | 26 |
| | | | 5 | 22 | 23 | 24 | 25 | 25 | 25 | 25 | 25 |
| | | | 6 | 23 | 24 | 25 | 26 | 27 | 25 | 26 | 25 |
| | | | Mean | 22.2 | 22.8 | 24.2 | 24.8 | 25.3 | 24.8 | 25.3 | 24.8 |
| | | | SEM | 0.3 | 0.7 | 0.5 | 0.7 | 0.7 | 0.5 | 0.5 | 0.5 |
| 6 | ADC (OBI-999) | 3 mg/ kg × 6 IV (Once weekly) | 1 | 22 | 22 | 24 | 26 | 26 | 26 | 26 | 26 |
| | | | 2 | 22 | 21 | 23 | 24 | 23 | 23 | 23 | 24 |
| | | | 3 | 22 | 22 | 23 | 24 | 24 | 24 | 24 | 24 |
| | | | 4 | 22 | 23 | 24 | 26 | 26 | 26 | 26 | 26 |
| | | | 5 | 22 | 22 | 22 | 23 | 23 | 23 | 23 | 23 |
| | | | 6 | 20 | 21 | 22 | 23 | 24 | 24 | 24 | 23 |
| | | | Mean | 21.7 | 21.8 | 23.0 | 24.3 | 24.3 | 24.3 | 24.3 | 24.3 |
| | | | SEM | 0.3 | 0.3 | 0.4 | 0.6 | 0.6 | 0.6 | 0.6 | 0.6 |
| | | | $p < 0.05$ | | | | | | | | |
| 7 | OBI-888 | 10 mg/ kg × 2 IV (Once weekly) | 1 | 21 | 21 | 22 | 23 | 24 | 23 | 24 | 24 |
| | | | 2 | 24 | 24 | 25 | 26 | 27 | 27 | 28 | 28 |
| | | | 3 | 21 | 22 | 23 | 24 | 25 | 24 | 24 | 24 |
| | | | 4 | 22 | 24 | 24 | 25 | 26 | 26 | 26 | 26 |
| | | | 5 | 21 | 21 | 22 | 23 | 25 | 25 | 25 | 25 |
| | | | 6 | 21 | 22 | 24 | 23 | 25 | 24 | 25 | 24 |
| | | | Mean | 21.7 | 22.3 | 23.3 | 24.0 | 25.3 | 24.8 | 25.3 | 25.2 |
| | | | SEM | 0.5 | 0.6 | 0.5 | 0.5 | 0.4 | 0.6 | 0.6 | 0.7 |
| | | | $p < 0.05$ | | | | | | | | |
| 8 | OBI-888 | 0.3 mg/ kg × 6 IV (Once weekly) | 1 | 21 | 23 | 23 | 25 | 25 | 25 | 25 | 24 |
| | | | 2 | 19 | 19 | 21 | 22 | 22 | 22 | 23 | 22 |
| | | | 3 | 19 | 19 | 21 | 22 | 23 | 23 | 24 | 24 |
| | | | 4 | 20 | 21 | 22 | 23 | 23 | 23 | 24 | 23 |
| | | | 5 | 21 | 23 | 23 | 23 | 24 | 24 | 24 | 24 |
| | | | 6 | 21 | 22 | 23 | 22 | 22 | 20 | 19 | 21 |
| | | | Mean | 20.2 | 21.2 | 22.2 | 22.8 | 23.2 | 22.8 | 23.2 | 23.0 |
| | | | SEM | 0.4 | 0.7 | 0.4 | 0.5 | 0.5 | 0.7 | 0.9 | 0.5 |
| | | | $p < 0.05$ | | | | | | | | |
| 9 | OBI-888 | 1 mg/ kg × 6 IV | 1 | 20 | 21 | 23 | 24 | 25 | 25 | 25 | 25 |
| | | | 2 | 20 | 20 | 21 | 22 | 23 | 22 | 23 | 23 |
| | | | 3 | 18 | 19 | 20 | 21 | 21 | 21 | 22 | 21 |

TABLE 5-1-continued

Body weight, Xenograft, Breast, MCF-7 in Nude Mice (Day 1-Day 26)

| Gr. | Treatment | Dose (mg/kg) (Route) | No. | Day1 | Day5 | Day8 | Day12 | Day15 | Day19 | Day22 | Day26 |
|---|---|---|---|---|---|---|---|---|---|---|---|
| | | (Once weekly) | 4 | 21 | 23 | 25 | 25 | 26 | 26 | 26 | 26 |
| | | | 5 | 22 | 22 | 23 | 24 | 25 | 25 | 25 | 25 |
| | | | 6 | 21 | 23 | 25 | 26 | 26 | 26 | 26 | 26 |
| | | | Mean | 20.3 | 21.3 | 22.8 | 23.7 | 24.3 | 24.2 | 24.5 | 24.3 |
| | | | SEM | 0.6 | 0.7 | 0.8 | 0.8 | 0.8 | 0.9 | 0.7 | 0.8 |
| 10 | OBI-888 | 3 mg/kg × 6 IV (Once weekly) | 1 | 20 | 20 | 22 | 22 | 23 | 23 | 24 | 24 |
| | | | 2 | 22 | 23 | 23 | 24 | 25 | 24 | 25 | 25 |
| | | | 3 | 22 | 23 | 24 | 25 | 25 | 25 | 26 | 26 |
| | | | 4 | 22 | 23 | 24 | 26 | 26 | 26 | 26 | 26 |
| | | | 5 | 21 | 22 | 23 | 24 | 25 | 24 | 25 | 24 |
| | | | 6 | 22 | 23 | 25 | 27 | 27 | 27 | 27 | 27 |
| | | | Mean | 21.5 | 22.3 | 23.5 | 24.7 | 25.2 | 24.8 | 25.5 | 25.3 |
| | | | SEM | 0.3 | 0.5 | 0.4 | 0.7 | 0.5 | 0.6 | 0.4 | 0.5 |
| | | | $p < 0.05$ | | | | | | | | |
| 11 | MMAE | 0.057 mg/kg × 6 IV (Once weekly) | 1 | 23 | 24 | 26 | 26 | 27 | 26 | 27 | 27 |
| | | | 2 | 22 | 22 | 23 | 24 | 25 | 24 | 25 | 25 |
| | | | 3 | 22 | 22 | 24 | 25 | 25 | 25 | 24 | 24 |
| | | | 4 | 24 | 24 | 25 | 25 | 26 | 25 | 26 | 26 |
| | | | 5 | 21 | 22 | 23 | 24 | 25 | 25 | 25 | 24 |
| | | | 6 | 23 | 24 | 24 | 25 | 25 | 25 | 26 | 25 |
| | | | Mean | 22.5 | 23.0 | 24.2 | 24.8 | 25.5 | 25.0 | 25.5 | 25.2 |
| | | | SEM | 0.4 | 0.4 | 0.5 | 0.3 | 0.3 | 0.3 | 0.4 | 0.5 |
| | | | $p < 0.05$ | | | | | | | | |

TABLE 5-2

Body weight, Xenograft, Breast, MCF-7 in Nude Mice (Day 29-Day 49)

| Gr. | Treatment | Dose (mg/kg) (Route) | No. | Day29 | Day33 | Day36 | Day40 | Day43 | Day46 | Day49 |
|---|---|---|---|---|---|---|---|---|---|---|
| 1 | Vehicle (25 mM Sodium Citrate, pH 6.5 + 100 mM NaCl) | 10 mL/kg × 6 IV (Once weekly) | 1 | 26 | 26 | 26 | 26 | 26 | 26 | 26 |
| | | | 2 | 28 | 28 | 28 | 28 | 28 | 28 | 29 |
| | | | 3 | 27 | 28 | 28 | 28 | 27 | 27 | 27 |
| | | | 4 | 26 | 26 | 27 | 26 | 26 | 27 | 27 |
| | | | 5 | 28 | 28 | 28 | 29 | 28 | 28 | 28 |
| | | | 6 | 24 | 23 | 23 | 23 | 22 | 23 | 24 |
| | | | Mean | 26.5 | 26.5 | 26.7 | 26.7 | 26 | 26.5 | 26.8 |
| | | | SEM | 0.6 | 0.8 | 0.8 | 0.9 | 1 | 0.8 | 0.7 |
| 2 | Vehicle (25 mM Sodium Citrate, pH 6.5 + 100 mM NaCl) | 10 mL/kg × 2 IV (Once weekly) | 1 | 25 | 25 | 25 | 25 | 26 | 26 | 26 |
| | | | 2 | 25 | 23 | 23 | 24 | 24 | 23 | 23 |
| | | | 3 | 23 | 22 | 24 | 23 | 23 | 24 | 23 |
| | | | 4 | 28 | 28 | 28 | 28 | 27 | 27 | 28 |
| | | | 5 | 28 | 29 | 29 | 29 | 29 | 28 | 29 |
| | | | 6 | 27 | 27 | 28 | 28 | 27 | 28 | 29 |
| | | | Mean | 26.0 | 25.7 | 26.2 | 26.2 | 26 | 26.0 | 26.3 |
| | | | SEM | 0.8 | 1.1 | 1.0 | 1.0 | 1 | 0.9 | 1.1 |
| | | | $p < 0.05$ | | | | | | | |
| 3 | ADC (OBI-999) | 10 mg/kg × 2 IV (Once weekly) | 1 | 26 | 26 | 27 | 27 | 27 | 26 | 28 |
| | | | 2 | 24 | 24 | 24 | 25 | 24 | 24 | 24 |
| | | | 3 | 27 | 28 | 28 | 27 | 28 | 27 | 28 |
| | | | 4 | 22 | 22 | 23 | 23 | 23 | 23 | 23 |
| | | | 5 | 24 | 24 | 24 | 24 | 25 | 25 | 25 |
| | | | 6 | 25 | 25 | 25 | 25 | 25 | 25 | 25 |
| | | | Mean | 24.7 | 24.8 | 25.2 | 25.2 | 25 | 25.0 | 25.5 |
| | | | SEM | 0.7 | 0.8 | 0.8 | 0.7 | 1 | 0.6 | 0.8 |
| | | | $p < 0.05$ | | | | | | | |
| 4 | ADC (OBI-999) | 0.3 mg/kg × 6 IV (Once weekly) | 1 | 24 | 24 | 25 | 25 | 25 | 25 | 25 |
| | | | 2 | 26 | 27 | 28 | 27 | 27 | 27 | 28 |
| | | | 3 | 25 | 25 | 25 | 25 | 25 | 25 | 25 |
| | | | 4 | 25 | 25 | 26 | 26 | 26 | 26 | 27 |
| | | | 5 | 25 | 24 | 25 | 25 | 25 | 25 | 25 |
| | | | 6 | 26 | 26 | 27 | 26 | 26 | 26 | 27 |
| | | | Mean | 25.2 | 25.2 | 26.0 | 25.7 | 26 | 25.7 | 26.2 |
| | | | SEM | 0.3 | 0.5 | 0.5 | 0.3 | 0 | 0.3 | 0.5 |
| | | | $p < 0.05$ | | | | | | | |

TABLE 5-2-continued

Body weight, Xenograft, Breast, MCF-7 in Nude Mice (Day 29-Day 49)

| Gr. | Treatment | Dose (mg/kg) (Route) | No. | Day29 | Day33 | Day36 | Day40 | Day43 | Day46 | Day49 |
|---|---|---|---|---|---|---|---|---|---|---|
| 5 | ADC (OBI-999) | 1 mg/ kg × 6 IV (Once weekly) | 1 | 24 | 24 | 24 | 24 | 24 | 24 | 24 |
| | | | 2 | 26 | 26 | 26 | 26 | 26 | 26 | 27 |
| | | | 3 | 24 | 25 | 25 | 25 | 25 | 25 | 25 |
| | | | 4 | 27 | 27 | 27 | 27 | 27 | 28 | 28 |
| | | | 5 | 26 | 25 | 26 | 26 | 25 | 25 | 26 |
| | | | 6 | 26 | 26 | 27 | 26 | 25 | 26 | 26 |
| | | | Mean | 25.5 | 25.5 | 25.8 | 25.7 | 25.3 | 25.7 | 26.0 |
| | | | SEM | 0.5 | 0.4 | 0.5 | 0.4 | 0.4 | 0.6 | 0.6 |
| 6 | ADC (OBI-999) | 3 mg/ kg × 6 IV (Once weekly) | 1 | 27 | 26 | 27 | 26 | 27 | 27 | 28 |
| | | | 2 | 24 | 24 | 25 | 24 | 24 | 24 | 24 |
| | | | 3 | 24 | 24 | 25 | 24 | 24 | 24 | 25 |
| | | | 4 | 26 | 24 | 24 | 25 | 24 | 25 | 27 |
| | | | 5 | 23 | 23 | 24 | 24 | 24 | 24 | 24 |
| | | | 6 | 24 | 24 | 25 | 25 | 25 | 24 | 24 |
| | | | Mean | 24.7 | 24.2 | 25.0 | 24.7 | 24.7 | 24.7 | 25.3 |
| | | | SEM | 0.6 | 0.4 | 0.4 | 0.3 | 0.5 | 0.5 | 0.7 |
| | | | $P < 0.05$ | | | | | | | |
| 7 | OBI-888 | 10 mg/ kg × 2 IV (Once weekly) | 1 | 24 | 25 | 25 | 24 | 24 | 24 | 25 |
| | | | 2 | 28 | 28 | 28 | 27 | 28 | 28 | 28 |
| | | | 3 | 24 | 24 | 24 | 24 | 25 | 24 | 25 |
| | | | 4 | 26 | 26 | 26 | 22 | 21 | 22 | 24 |
| | | | 5 | 25 | 25 | 26 | 26 | 26 | 26 | 28 |
| | | | 6 | 25 | 25 | 25 | 25 | 23 | 25 | 24 |
| | | | Mean | 25.3 | 25.5 | 25.7 | 24.7 | 24.5 | 24.8 | 25.7 |
| | | | SEM | 0.6 | 0.6 | 0.6 | 0.7 | 1.0 | 0.8 | 0.8 |
| | | | $P < 0.05$ | | | | | | | |
| 8 | OBI-888 | 0.3 mg/ kg × 6 IV (Once weekly) | 1 | 25 | 25 | 25 | 25 | 25 | 25 | 26 |
| | | | 2 | 23 | 22 | 23 | 22 | 23 | 23 | 24 |
| | | | 3 | 24 | 25 | 24 | 25 | 24 | 24 | 26 |
| | | | 4 | 24 | 23 | 24 | 24 | 24 | 24 | 24 |
| | | | 5 | 24 | 24 | 24 | 24 | 24 | 24 | 24 |
| | | | 6 | 24 | 24 | 25 | 24 | 25 | 24 | 25 |
| | | | Mean | 24.0 | 23.8 | 24.2 | 24.0 | 24.2 | 24.0 | 24.8 |
| | | | SEM | 0.3 | 0.5 | 0.3 | 0.4 | 0.3 | 0.3 | 0.4 |
| | | | $P < 0.05$ | | | | | | | |
| 9 | OBI-888 | 1 mg/ kg × 6 IV (Once weekly) | 1 | 25 | 25 | 23 | 20 | 24 | 25 | 26 |
| | | | 2 | 24 | 23 | 24 | 23 | 23 | 23 | 25 |
| | | | 3 | 22 | 22 | 22 | 23 | 23 | 22 | 22 |
| | | | 4 | 26 | 25 | 26 | 26 | 26 | 26 | 27 |
| | | | 5 | 25 | 24 | 25 | 25 | 25 | 25 | 26 |
| | | | 6 | 27 | 26 | 27 | 27 | 27 | 28 | 27 |
| | | | Mean | 24.8 | 24.2 | 24.5 | 24.0 | 24.7 | 24.8 | 25.5 |
| | | | SEM | 0.7 | 0.6 | 0.8 | 1.0 | 0.7 | 0.9 | 0.8 |
| 10 | OBI-888 | 3 mg/ kg × 6 IV (Once weekly) | 1 | 25 | 24 | 25 | 25 | 25 | 24 | 26 |
| | | | 2 | 26 | 26 | 27 | 26 | 26 | 27 | 28 |
| | | | 3 | 25 | 25 | 26 | 26 | 26 | 26 | 27 |
| | | | 4 | 27 | 26 | 27 | 26 | 24 | 24 | 24 |
| | | | 5 | 25 | 26 | 26 | 26 | 26 | 26 | 27 |
| | | | 6 | 27 | 26 | 26 | 25 | 25 | 25 | 27 |
| | | | Mean | 25.8 | 25.5 | 26.2 | 25.7 | 25.3 | 25.3 | 26.5 |
| | | | SEM | 0.4 | 0.3 | 0.3 | 0.2 | 0.3 | 0.5 | 0.6 |
| | | | $P < 0.05$ | | | | | | | |
| 11 | MMAE | 0.057 mg/ kg × 6 IV (Once weekly) | 1 | 27 | 27 | 27 | 26 | 26 | 26 | 28 |
| | | | 2 | 25 | 24 | 25 | 25 | 25 | 25 | 26 |
| | | | 3 | 25 | 24 | 24 | 24 | 22 | 21 | 21 |
| | | | 4 | 26 | 26 | 27 | 28 | 27 | 27 | 25 |
| | | | 5 | 24 | 25 | 25 | 26 | 25 | 26 | 26 |
| | | | 6 | 25 | 26 | 26 | 26 | 26 | 26 | 27 |
| | | | Mean | 25.3 | 25.3 | 25.7 | 25.8 | 25.2 | 25.2 | 25.5 |
| | | | SEM | 0.4 | 0.5 | 0.5 | 0.5 | 0.7 | 0.9 | 1.0 |
| | | | $P < 0.05$ | | | | | | | |

TABLE 5-3

Body weight, Xenograft, Breast, MCF-7 in Nude Mice (Day 53-Day 77)

| Gr. | Treatment | Dose (mg/kg) (Route) | No. | Day53 | Day56 | Day60 | Day63 | Day67 | Day70 | Day74 | Day77 |
|---|---|---|---|---|---|---|---|---|---|---|---|
| 1 | Vehicle (25 mM Sodium Citrate, pH 6.5 + 100 mM NaCl) | 10 mL/ kg × 6 IV (Once weekly) | 1 | 27 | 26 | 27 | 27 | 27 | 27 | 27 | 27 |
| | | | 2 | 29 | 28 | 28 | 27 | 28 | 28 | 27 | 28 |
| | | | 3 | 28 | 27 | 28 | 28 | 27 | 26 | 26 | 26 |
| | | | 4 | 27 | 27 | 27 | 27 | 28 | 28 | 28 | 28 |
| | | | 5 | 27 | 28 | 29 | 29 | 28 | 28 | 28 | 27 |
| | | | 6 | 25 | 26 | 27 | 26 | 26 | 26 | 26 | 25 |
| | | | Mean | 27.2 | 27.0 | 27.7 | 27.3 | 27.3 | 27.2 | 27.0 | 26.8 |
| | | | SEM | 0.5 | 0.4 | 0.3 | 0.4 | 0.3 | 0.4 | 0.4 | 0.5 |
| 2 | Vehicle (25 mM Sodium Citrate, pH 6.5 + 100 mM NaCl) | 10 mL/ kg × 2 IV (Once weekly) | 1 | 26 | 26 | 27 | 26 | 27 | 27 | 27 | 27 |
| | | | 2 | 23 | 21 | 21 | 21 | 21 | 21 | 22 | 22 |
| | | | 3 | 24 | 24 | 25 | 25 | 25 | 25 | 25 | 25 |
| | | | 4 | 28 | 28 | 29 | 28 | 28 | 29 | 29 | 29 |
| | | | 5 | 28 | 28 | 28 | 28 | 29 | 29 | 29 | 29 |
| | | | 6 | 28 | 27 | 26 | 26 | 26 | 26 | 27 | 27 |
| | | | Mean | 26.2 | 25.7 | 26.0 | 25.7 | 26.0 | 26.2 | 26.5 | 26.5 |
| | | | SEM | 0.9 | 1.1 | 1.2 | 1.1 | 1.2 | 1.2 | 1.1 | 1.1 |
| | | | P < 0.05 | | | | | | | | |
| 3 | ADC (OBI-999) | 10 mg/ kg × 2 IV (Once weekly) | 1 | 28 | 27 | 28 | 27 | 28 | 28 | 27 | 28 |
| | | | 2 | 24 | 24 | 24 | 24 | 25 | 24 | 24 | 24 |
| | | | 3 | 28 | 28 | 29 | 28 | 30 | 30 | 29 | 29 |
| | | | 4 | 24 | 23 | 24 | 21 | 23 | 24 | 24 | 25 |
| | | | 5 | 25 | 25 | 26 | 24 | 24 | 25 | 26 | 26 |
| | | | 6 | 25 | 24 | 25 | 26 | 25 | 26 | 23 | 22 |
| | | | Mean | 25.7 | 25.2 | 26.0 | 25.0 | 25.8 | 26.2 | 25.5 | 25.7 |
| | | | SEM | 0.8 | 0.8 | 0.9 | 1.0 | 1.1 | 1.0 | 0.9 | 1.1 |
| | | | P < 0.05 | | | | | | | | |
| 4 | ADC (OBI-999) | 0.3 mg/ kg × 6 IV (Once weekly) | 1 | 25 | 25 | 26 | 26 | 26 | 26 | 26 | 26 |
| | | | 2 | 28 | 28 | 28 | 28 | 28 | 28 | 28 | 28 |
| | | | 3 | 26 | 26 | 26 | 25 | 23 | 24 | 21 | 22 |
| | | | 4 | 28 | 28 | 28 | 27 | 28 | 28 | 28 | 28 |
| | | | 5 | 23 | 24 | 26 | 25 | 26 | 27 | 28 | 27 |
| | | | 6 | 27 | 27 | 29 | 28 | 29 | 27 | 27 | 28 |
| | | | Mean | 26.2 | 26.3 | 27.2 | 26.5 | 26.7 | 26.7 | 26.3 | 26.5 |
| | | | SEM | 0.8 | 0.7 | 0.5 | 0.6 | 0.9 | 0.6 | 1.1 | 1.0 |
| | | | P < 0.05 | | | | | | | | |
| 5 | ADC (OBI-999) | 1 mg/ kg × 6 IV (Once weekly) | 1 | 24 | 24 | 24 | 22 | 23 | 23 | 23 | 23 |
| | | | 2 | 28 | 27 | 29 | 27 | 29 | 29 | 25 | 25 |
| | | | 3 | 25 | 24 | 25 | 25 | 27 | 26 | 25 | 25 |
| | | | 4 | 28 | 27 | 28 | 28 | 28 | 28 | 29 | 28 |
| | | | 5 | 26 | 26 | 27 | 26 | 26 | 27 | 27 | 26 |
| | | | 6 | 26 | 26 | 27 | 27 | 27 | 27 | 29 | 28 |
| | | | Mean | 26.2 | 25.7 | 26.7 | 25.8 | 26.7 | 26.7 | 26.3 | 25.8 |
| | | | SEM | 0.7 | 0.6 | 0.8 | 0.9 | 0.8 | 0.8 | 1.0 | 0.8 |
| | | | P < 0.05 | | | | | | | | |
| 6 | ADC (OBI-999) | 3 mg/ kg × 6 IV (Once weekly) | 1 | 28 | 27 | 28 | 28 | 29 | 29 | 30 | 29 |
| | | | 2 | 24 | 22 | 22 | 21 | 22 | 21 | 22 | 22 |
| | | | 3 | 25 | 25 | 26 | 26 | 26 | 26 | 26 | 26 |
| | | | 4 | 26 | 27 | 28 | 28 | 28 | 28 | 28 | 27 |
| | | | 5 | 24 | 24 | 25 | 24 | 24 | 25 | 24 | 24 |
| | | | 6 | 24 | 23 | 24 | 23 | 23 | 23 | 23 | 23 |
| | | | Mean | 25.2 | 24.7 | 25.5 | 25.0 | 25.3 | 25.3 | 25.5 | 25.2 |
| | | | SEM | 0.7 | 0.8 | 1.0 | 1.2 | 1.1 | 1.2 | 1.3 | 1.1 |
| | | | P < 0.05 | | | | | | | | |
| 7 | OBI-888 | 10 mg/ kg × 2 IV (Once weekly) | 1 | 25 | 25 | 27 | 26 | 26 | 26 | died | died |
| | | | 2 | 28 | 28 | 29 | 29 | 28 | died | died | died |
| | | | 3 | 24 | 24 | 26 | 21 | 23 | 24 | 24 | 24 |
| | | | 4 | 25 | 27 | 28 | 27 | 27 | 27 | 26 | 25 |
| | | | 5 | 27 | 22 | 23 | 27 | 28 | 31 | 35 | 26 |
| | | | 6 | 23 | 22 | 21 | 24 | 24 | 24 | 22 | 20 |
| | | | Mean | 25.3 | 24.7 | 25.7 | 25.7 | 26.0 | 26.4 | 26.6 | 24.2 |
| | | | SEM | 0.8 | 1.0 | 1.3 | 1.1 | 0.9 | 1.3 | 2.2 | 1.1 |
| | | | P < 0.05 | | | | | | | | |
| 8 | OBI-888 | 0.3 mg/ kg × 6 IV (Once weekly) | 1 | 26 | 26 | 26 | 26 | 27 | 27 | 28 | 27 |
| | | | 2 | 24 | 23 | 24 | 25 | 26 | 26 | 27 | 26 |
| | | | 3 | 26 | 24 | 25 | 25 | 25 | 25 | 26 | 26 |
| | | | 4 | 24 | 24 | 25 | 25 | 25 | 26 | 26 | 25 |
| | | | 5 | 24 | 25 | 27 | 25 | 24 | 25 | 25 | 25 |
| | | | 6 | 26 | 25 | 26 | 26 | 26 | 26 | 26 | 26 |
| | | | Mean | 25.0 | 24.5 | 25.5 | 25.3 | 25.5 | 25.8 | 26.3 | 25.8 |
| | | | SEM | 0.4 | 0.4 | 0.4 | 0.2 | 0.4 | 0.3 | 0.4 | 0.3 |
| | | | P < 0.05 | | | | | | | | |

TABLE 5-3-continued

Body weight, Xenograft, Breast, MCF-7 in Nude Mice (Day 53-Day 77)

| Gr. | Treatment | Dose (mg/kg) (Route) | No. | Day53 | Day56 | Day60 | Day63 | Day67 | Day70 | Day74 | Day77 |
|---|---|---|---|---|---|---|---|---|---|---|---|
| 9 | OBI-888 | 1 mg/kg × 6 IV (Once weekly) | 1 | 26 | 26 | 26 | 26 | 25 | 26 | 26 | 24 |
|   |   |   | 2 | 24 | 25 | 25 | 24 | 26 | 26 | 24 | 25 |
|   |   |   | 3 | 22 | 27 | 28 | 20 | 21 | 21 | 22 | 21 |
|   |   |   | 4 | 27 | 25 | 26 | 26 | 27 | 27 | 24 | 24 |
|   |   |   | 5 | 25 | 26 | 26 | 26 | 26 | 26 | 26 | 26 |
|   |   |   | 6 | 26 | 19 | 19 | 26 | 26 | 27 | 27 | 27 |
|   |   |   | Mean | 25.0 | 24.7 | 25.0 | 24.7 | 25.2 | 25.5 | 24.8 | 24.5 |
|   |   |   | SEM | 0.7 | 1.2 | 1.3 | 1.0 | 0.9 | 0.9 | 0.7 | 0.8 |
|   |   |   | $P < 0.05$ | | | | | | | | |
| 10 | OBI-888 | 3 mg/kg × 6 IV (Once weekly) | 1 | 26 | 24 | 26 | 26 | 27 | 27 | 26 | 27 |
|   |   |   | 2 | 26 | 27 | 27 | 24 | 23 | 21 | 23 | 24 |
|   |   |   | 3 | 26 | 23 | 23 | 25 | 22 | 25 | 25 | 25 |
|   |   |   | 4 | 24 | 26 | 28 | 23 | 24 | 22 | 23 | 25 |
|   |   |   | 5 | 27 | 26 | 27 | 27 | 27 | 27 | 27 | 28 |
|   |   |   | 6 | 26 | 25 | 27 | 26 | 26 | 27 | 27 | 28 |
|   |   |   | Mean | 25.8 | 25.2 | 26.3 | 25.2 | 24.8 | 24.8 | 25.2 | 26.2 |
|   |   |   | SEM | 0.4 | 0.6 | 0.7 | 0.6 | 0.9 | 1.1 | 0.7 | 0.7 |
|   |   |   | $P < 0.05$ | | | | | | | | |
| 11 | MMAE | 0.057 mg/kg × 6 IV (Once weekly) | 1 | 28 | 26 | 28 | 29 | 27 | 25 | 24 | 23 |
|   |   |   | 2 | 26 | 26 | 27 | 26 | 26 | 26 | 27 | 27 |
|   |   |   | 3 | 22 | 23 | 24 | 24 | 25 | 25 | 25 | 24 |
|   |   |   | 4 | 24 | 25 | 26 | 27 | 28 | 28 | 28 | 27 |
|   |   |   | 5 | 26 | 24 | 27 | 27 | 27 | 27 | 27 | 28 |
|   |   |   | 6 | 26 | 27 | 27 | 26 | 28 | 28 | 29 | 29 |
|   |   |   | Mean | 25.3 | 25.2 | 26.5 | 26.5 | 26.8 | 26.5 | 26.7 | 26.3 |
|   |   |   | SEM | 0.8 | 0.6 | 0.6 | 0.7 | 0.5 | 0.6 | 0.8 | 1.0 |
|   |   |   | $P < 0.05$ | | | | | | | | |

Figure 4A:
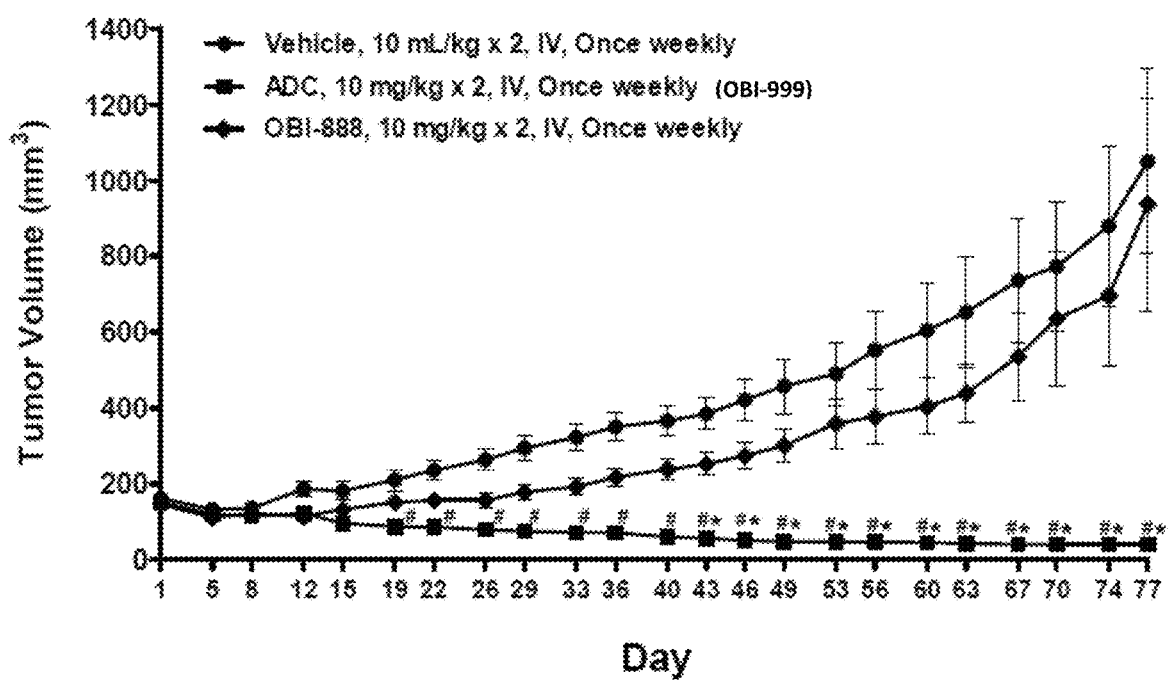
FIGS. 4A and 4B show tumor growth curves in MCF-7 implanted female nude (nu/nu) mice. Test substances were administered as 10 mg/kg once weekly×2 weeks (FIG. 4A) and lower doses at 3, 1, and 0.3 mg/kg once weekly×6 weeks (FIG. 4B). T/C value≤42% was considered significant antitumor activity (#) compared to the vehicle group. Two-way ANOVA followed by Bonferroni post-tests were applied for comparison between the vehicle and test substance-treated groups. Differences are considered significant at $*p<0.05$.
Figure 4B:
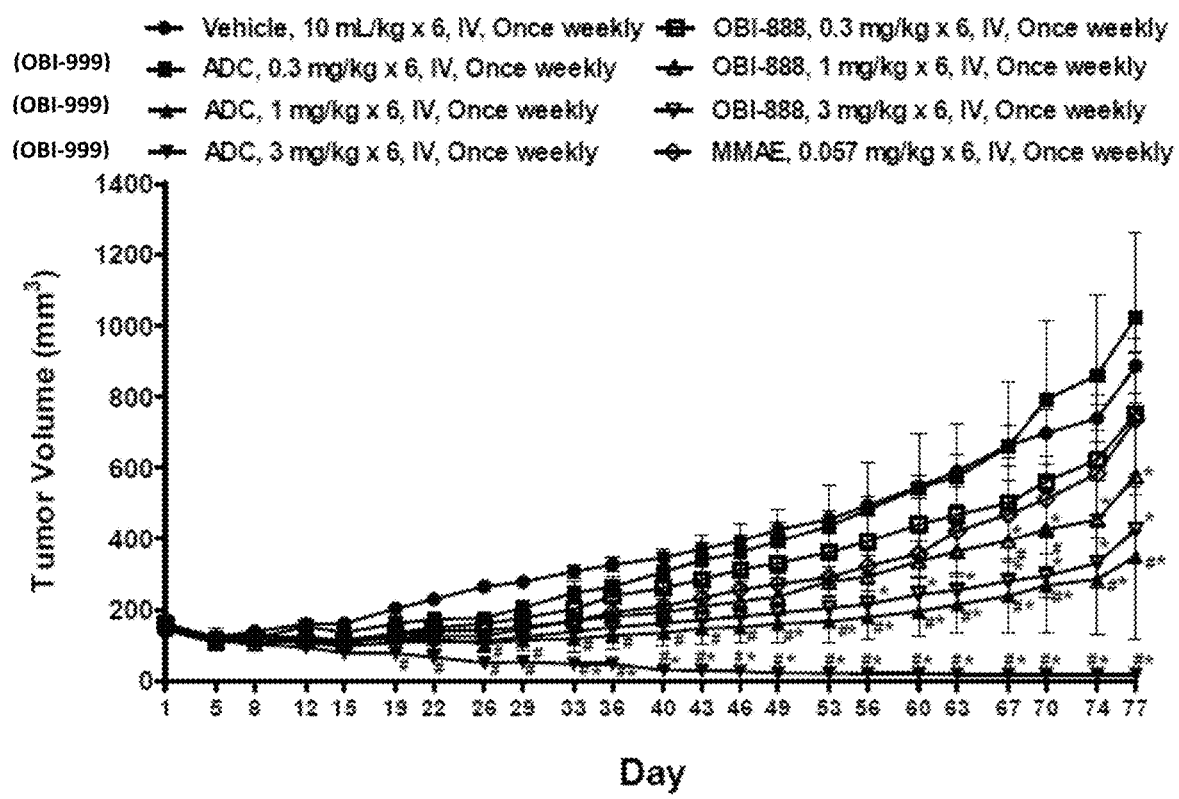

FIGS. 4A and 4B show the tumor growth curves in MCF-7 implanted female nude (nu/nu) mice. Intravenous administration of ADC (OBI-999) at 10 mg/kg once weekly for two weeks was associated with significant (T/C value ≤42%) anti-tumor activity from Day 19 to Day 77 compared to the corresponding vehicle control group (FIG. 4A). Furthermore, evidence of a dose-dependent effect was observed in the ADC (OBI-999) treated groups which received once weekly administrations for six weeks. Intravenous administration of ADC (OBI-999) at 0.3 mg/kg once weekly for six weeks was not associated with anti-tumor activity over the course of the study. However, intravenous administration of ADC (OBI-999) at 1 mg/kg and 3 mg/kg once weekly for six weeks was associated with significant (T/C value ≤42%) anti-tumor activity from Day 26 to Day 77 and Day 19 to Day 77, respectively, compared to the corresponding vehicle control group (FIG. 4B).

Intravenous administration of OBI-888 at 10 mg/kg once weekly for two weeks was associated with modest-to-moderate anti-tumor activity both during and for a short time after the dosing phase of the study compared to the corresponding vehicle control group (FIG. 4A). Furthermore, evidence of a dose-dependent effect was observed in the OBI-888 treated groups which received once weekly administrations for six weeks. Intravenous administration of OBI-888 at 0.3 mg/kg once weekly for six weeks was associated with modest anti-tumor activity over the course of the study. Intravenous administration of OBI-888 at 1 mg/kg once weekly for six weeks was associated with moderate anti-tumor activity over the course of the study. Intravenous administration of OBI-888 at 3 mg/kg once weekly for six weeks reached significant (T/C value ≤42%) anti-tumor activity on Day 67 and Day 70, although anti-tumor activity remained close to significant (T/C value ≤42%) as early as Day 26 compared to the corresponding vehicle control group (FIG. 4B).

Intravenous administration of MMAE at 0.057 mg/kg once weekly for six weeks was associated with modest-to-moderate anti-tumor activity both during and for a short time after the dosing phase of the study compared to the corresponding vehicle control group (FIG. 4B).

Figure 5A:
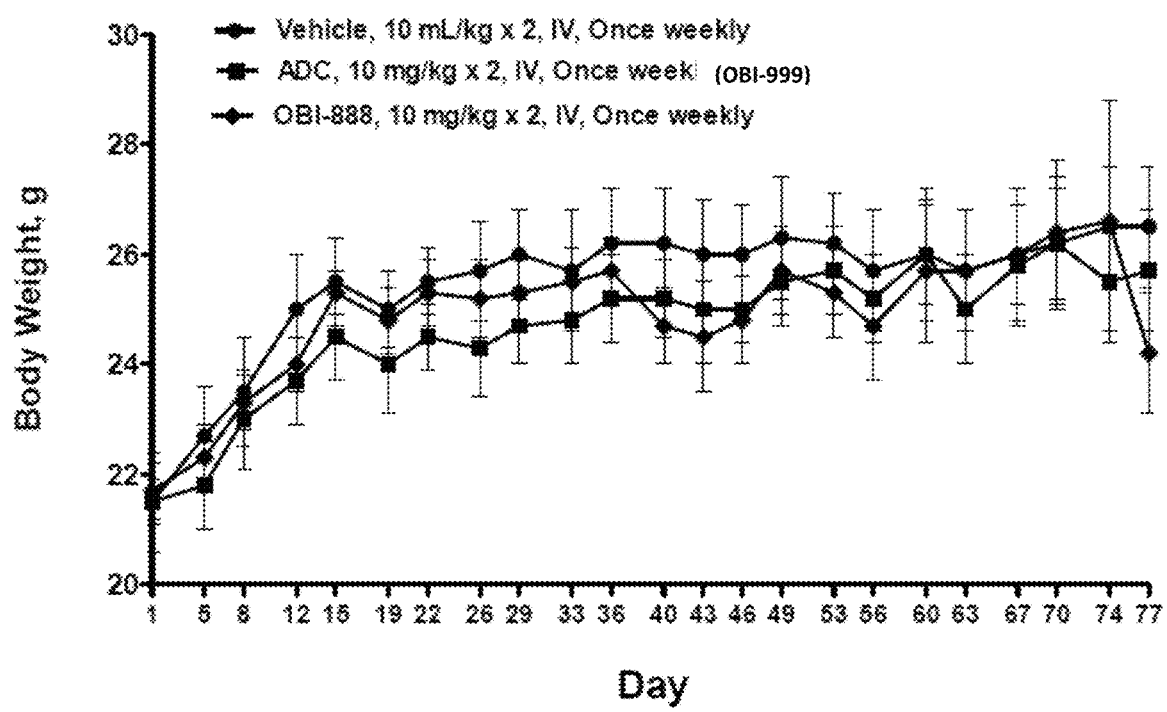
FIGS. 5A and 5B show body weight changes in MCF-7 implanted female nude (nu/nu) mice. Test substances were administered as 10 mg/kg once weekly×2 weeks (FIG. 5A) and lower doses at 3, 1, and 0.3 mg/kg once weekly×6 weeks (FIG. 5B). T/C value 42% was considered significant antitumor activity (#) compared to the vehicle group. Two-way≤ANOVA followed by Bonferroni post-tests were applied for comparison between the vehicle and test substance-treated groups. Differences are considered significant at $*p<0.05$.
Figure 5B:
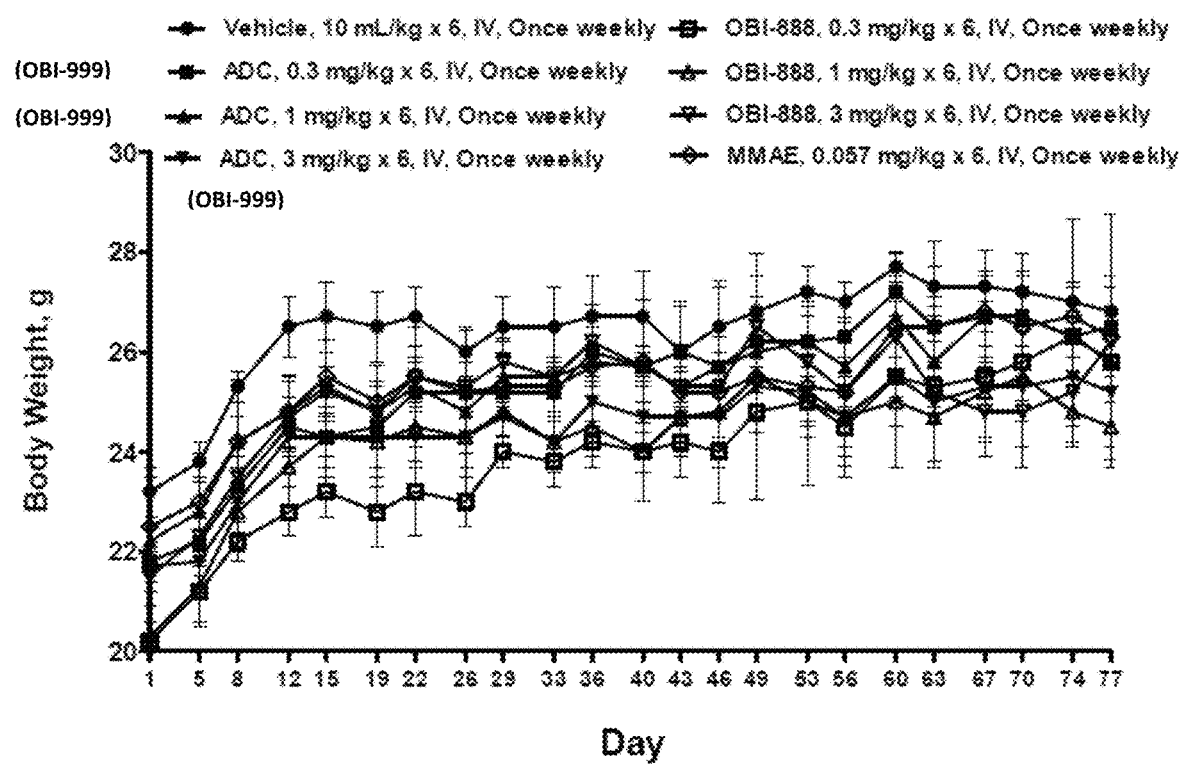
Figure 6:
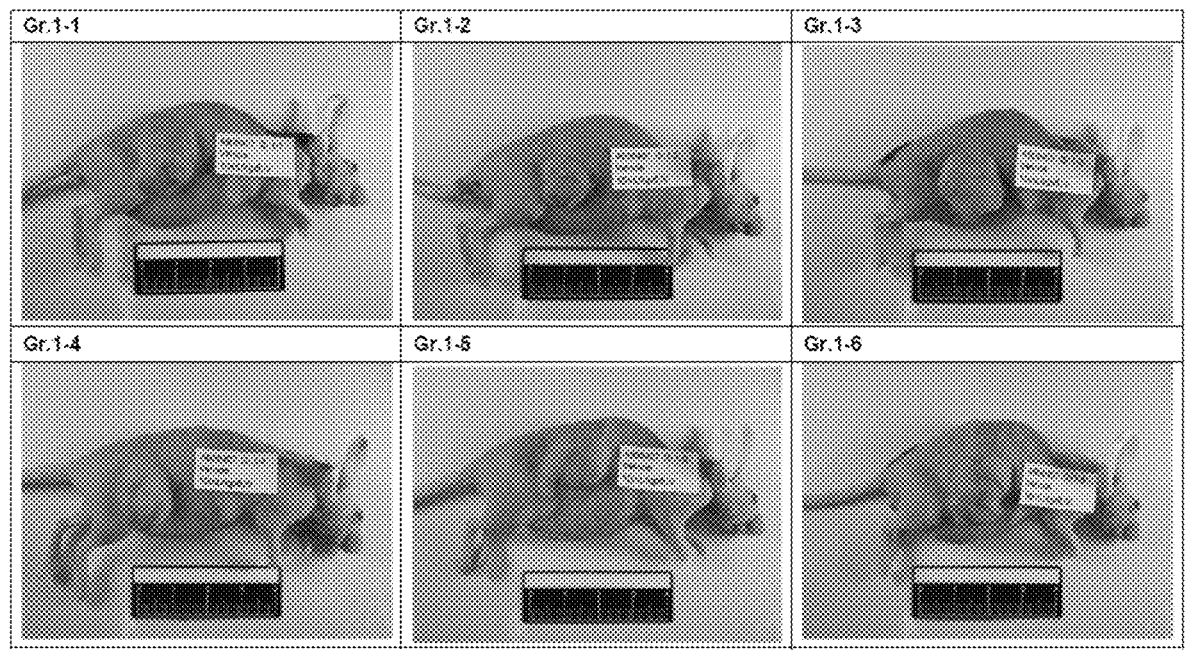
FIG. 6 showed pictures of female (nu/nu) nude mice with MCF-7 implanted tumors after treatment with Vehicle (25 mM Sodium Citrate, pH 6.5+100 mM NaCl) 10 mL/kg, IV, once weekly×6 weeks.
Figure 7:
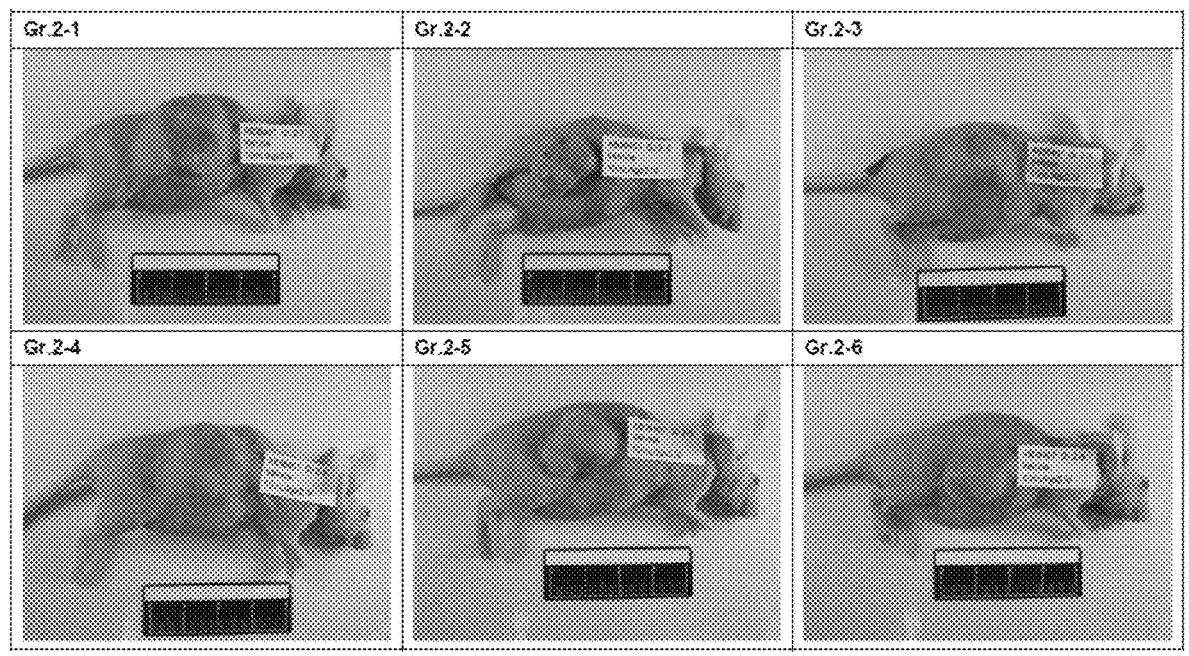
FIG. 7 showed pictures of female (nu/nu) nude mice with MCF-7 implanted tumors after treatment with Vehicle (25 mM Sodium Citrate, pH 6.5+100 mM NaCl) 10 mL/kg, IV, once weekly×2 weeks.
Figure 8:
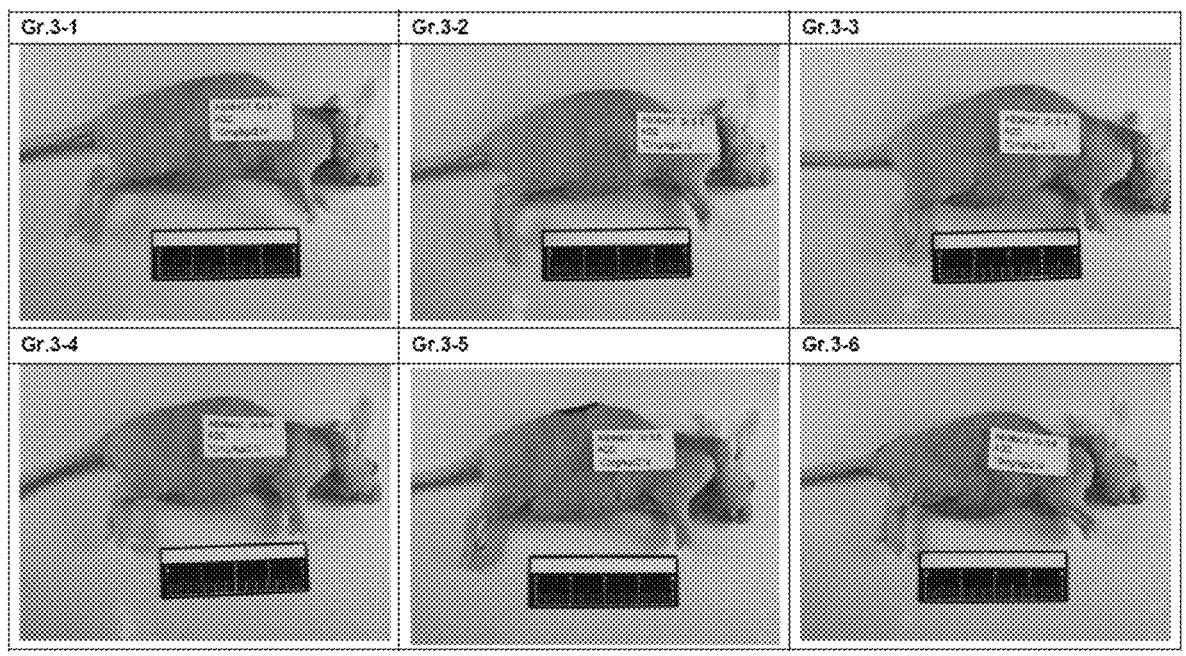
FIG. 8 showed pictures of female (nu/nu) nude mice with MCF-7 implanted tumors after treatment with ADC (OBI-999) 10 mg/kg, IV, once weekly×2 weeks.
Figure 9:
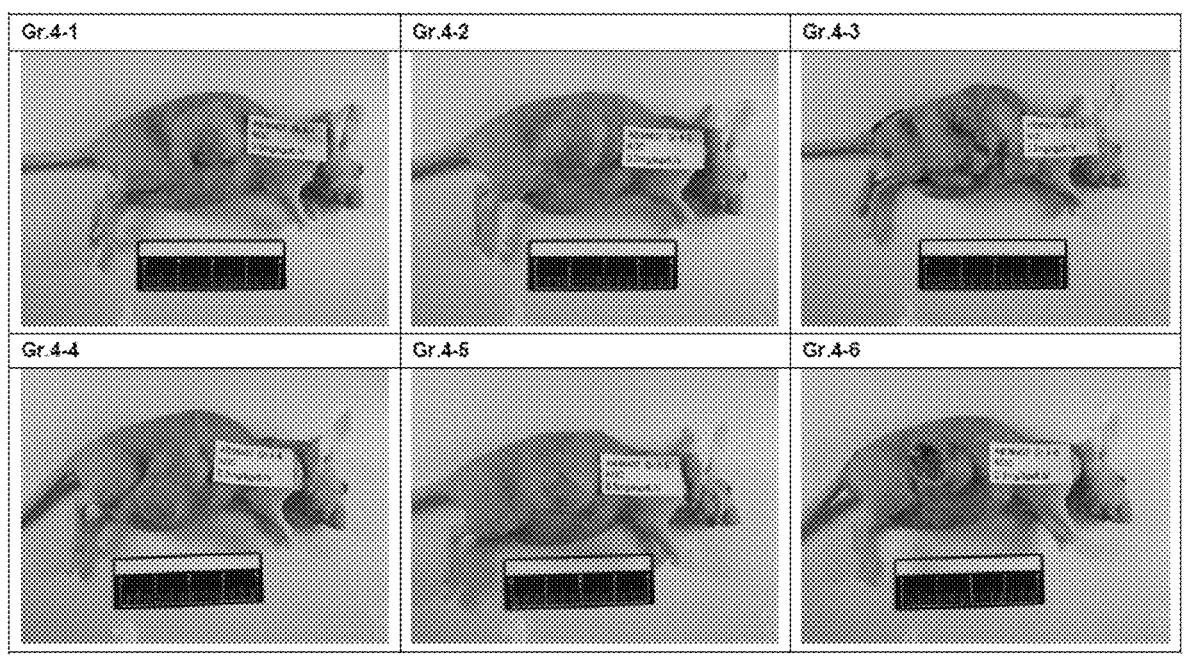
FIG. 9 showed pictures of female (nu/nu) nude mice with MCF-7 implanted tumors after treatment with ADC (OBI-999) 0.3 mg/kg, IV, once weekly×6 weeks.
Figure 10:
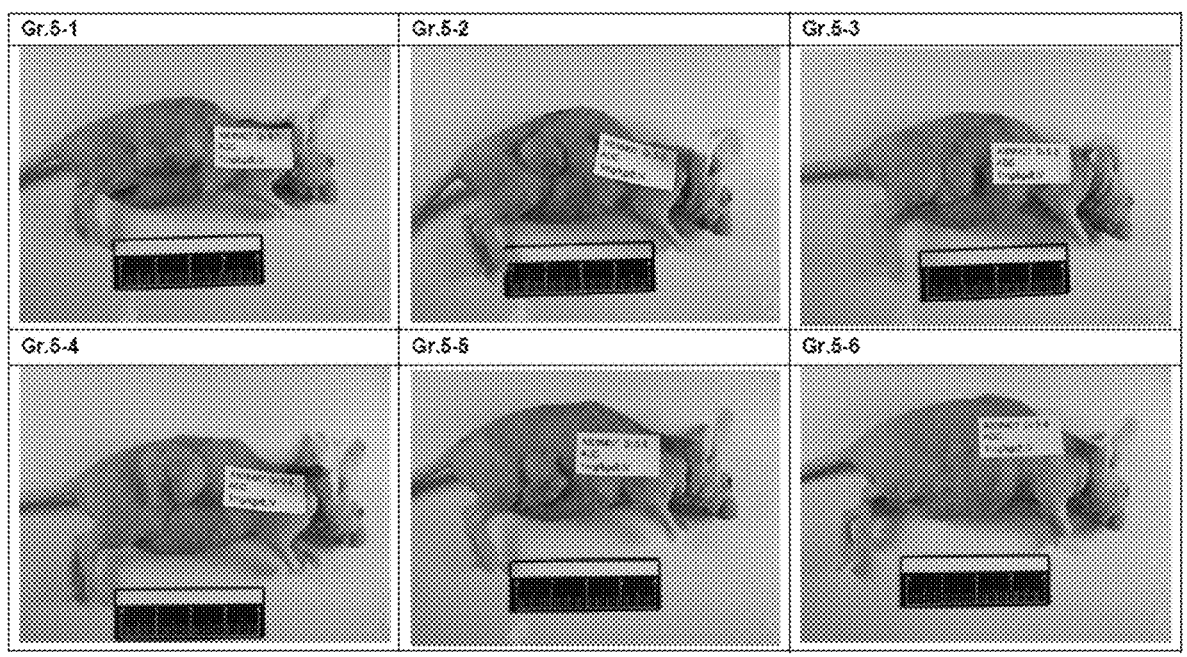
FIG. 10 showed pictures of female (nu/nu) nude mice with MCF-7 implanted tumors after treatment with ADC (OBI-999) 1 mg/kg, IV, once weekly×6 weeks.
Figure 11:
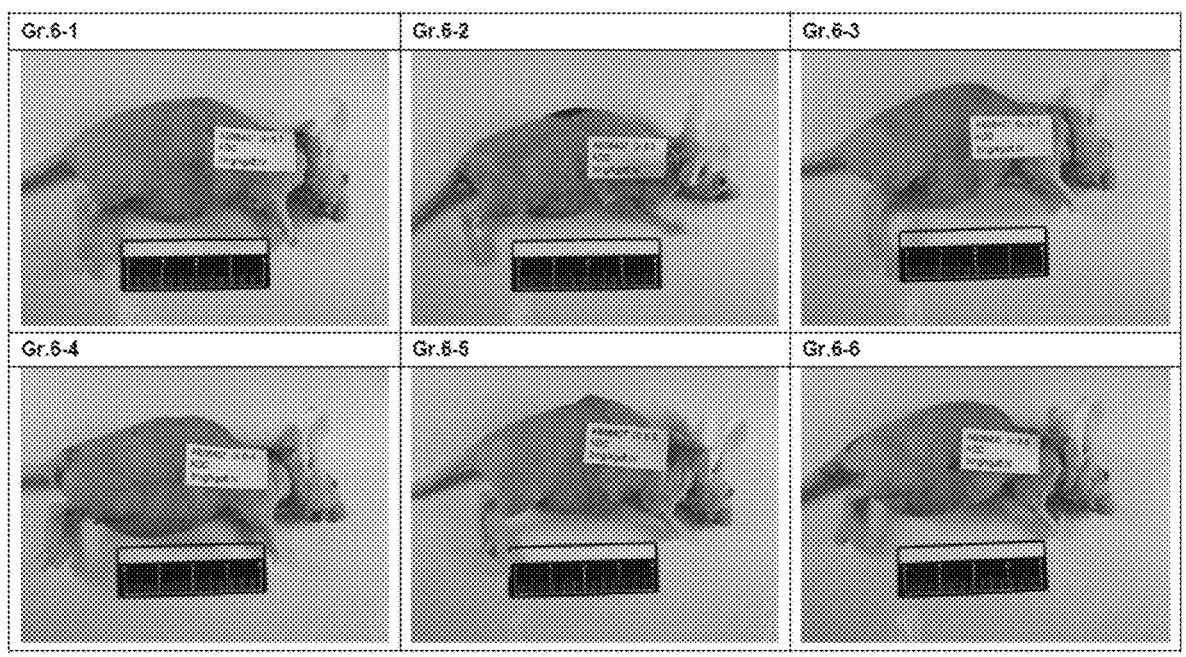
FIG. 11 showed pictures of female (nu/nu) nude mice with MCF-7 implanted tumors after treatment with ADC (OBI-999) 3 mg/kg, IV, once weekly×6 weeks.
Figure 12:
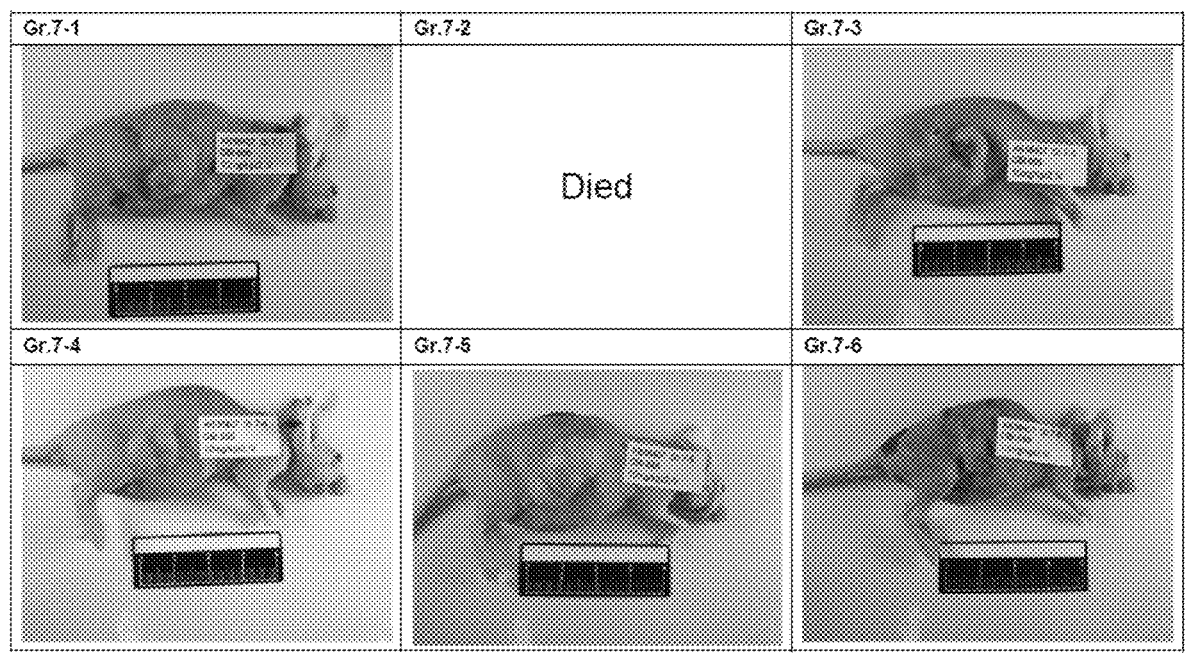
FIG. 12 showed pictures of female (nu/nu) nude mice with MCF-7 implanted tumors after treatment with OBI-888 10 mg/kg, IV, once weekly×2 weeks.
Figure 13:
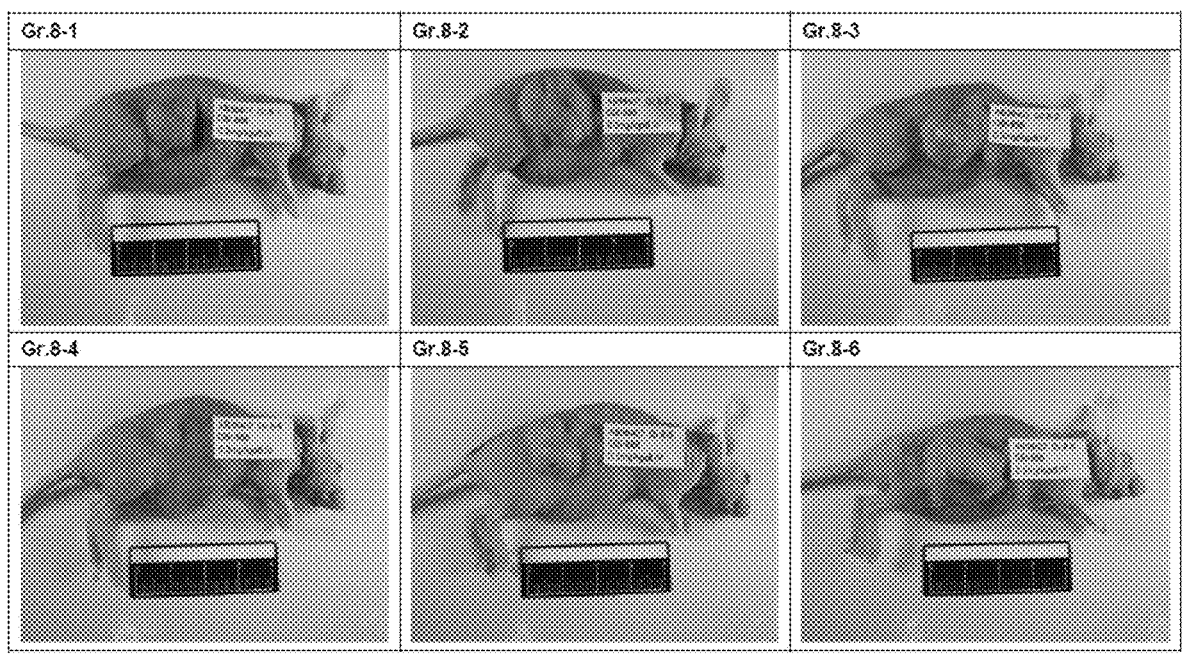
FIG. 13 showed pictures of female (nu/nu) nude mice with MCF-7 implanted tumors after treatment with OBI-888 0.3 mg/kg, IV, once weekly×6 weeks.
Figure 14:
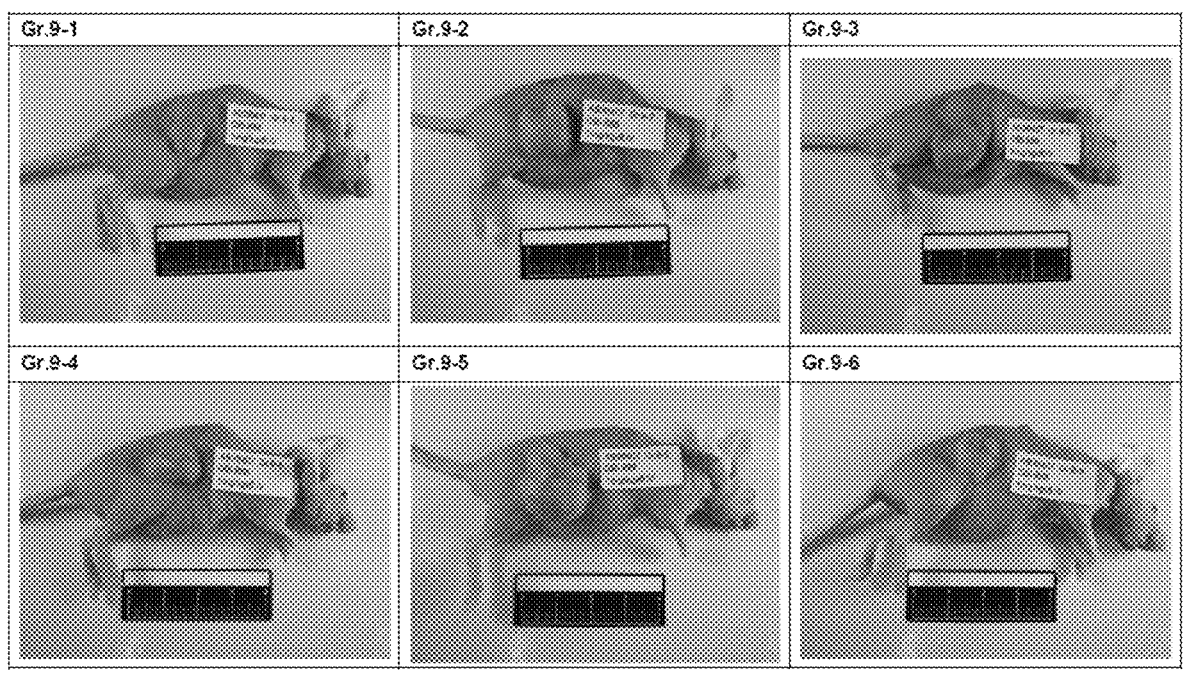
FIG. 14 showed pictures of female (nu/nu) nude mice with MCF-7 implanted tumors after treatment with OBI-888 1 mg/kg, IV, once weekly×6 weeks.
Figure 15:
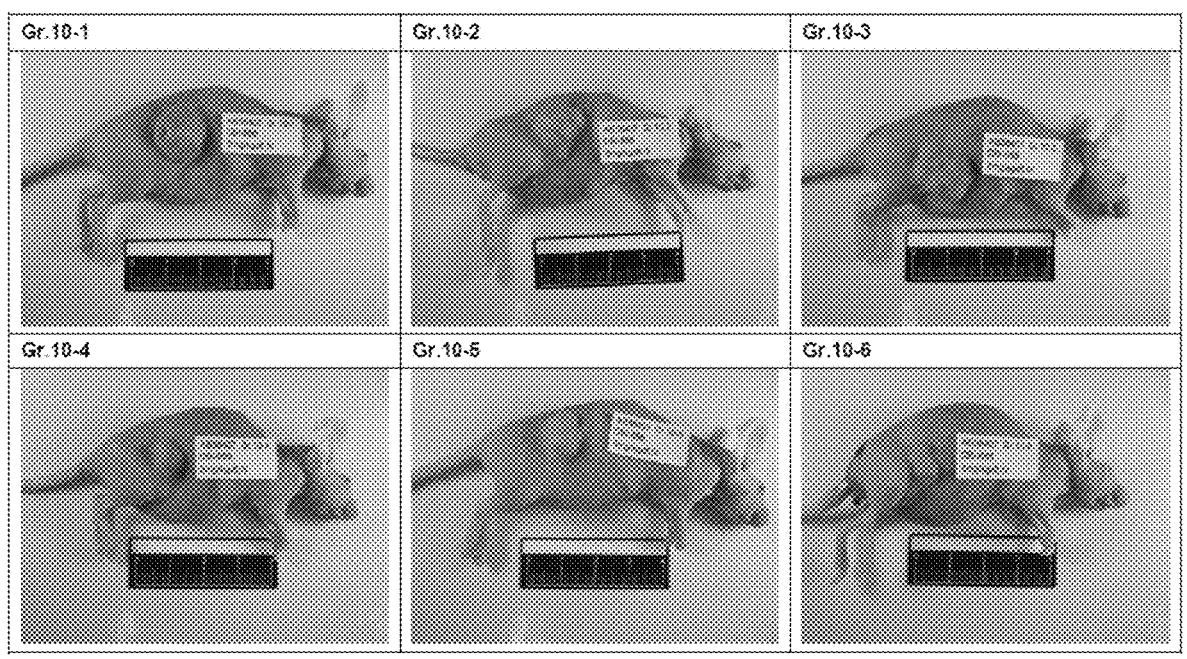
FIG. 15 showed pictures of female (nu/nu) nude mice with MCF-7 implanted tumors after treatment with OBI-888 3 mg/kg, IV, once weekly×6 weeks.
Figure 16:
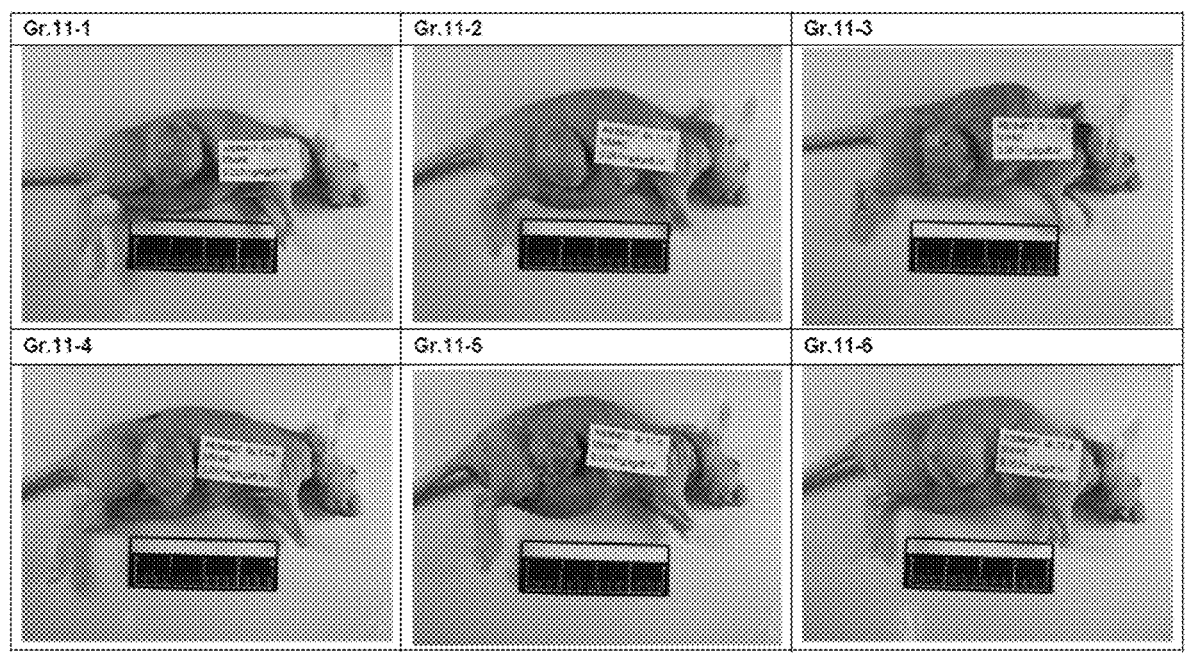
FIG. 16 showed pictures of female (nu/nu) nude mice with MCF-7 implanted tumors after treatment with MMAE 0.057 mg/kg, IV, once weekly×2 weeks.

FIGS. 5A and 5B show the body weight changes in MCF-7 implanted female nude (nu/nu) mice. All test substances at all dose levels were well-tolerated in animals, and were not associated with significant loss in body weight over the course of the study. No overt toxicities were observed during the study period. It also proved the safety of ADC (OBI-999), OBI-888 and MMAE compared to the corresponding vehicle control group.

Example 4: Measurement of the Anti-Tumor Activity of the Exemplary Antibody in Nude Mice (Gastric Cancer)

In a xenograft tumor model of human gastric carcinoma, viable NCI-N87 (ATCC CRL-5822) cells were subcutaneously (SC) implanted (2.5×10$^6$ cells/mL with matrigel (1:1) at 0.2 mL/mouse) into the right flank of female nu/nu mice. Tumor implanted mice were divided into seven treatment groups, each group containing eight animals, and one group containing five animals, and dose administrations were initiated one day after cell implantation (denoted as Day 1).

4.1 Test Substances and Dosing Pattern

Test substances ADC (OBI-999), OBI-888, and corresponding vehicle were formulated by diluting stock with a 25 mM sodium citrate, 100 mM NaCl buffer (pH 6.5) and administered intravenously (IV) once weekly for four weeks. Standard agent, MMAE antibody at 0.191 mg/kg, and corresponding vehicle (PBS pH 7.4) were administered intraperitoneally (IP) once weekly for four weeks. One treatment group received combination therapy of test substance, OBI-888 at 10 mg/kg, with MMAE at 0.191 mg/kg.

TABLE 6

Study Design for Anti-Tumor Activity of the exemplary antibody in Nude Mice (Gastric cancer)

| Group | Test Compound | Route | Dosage mL/kg | Dosage mg/kg | Mice[c,d] (nu/nu) (female) |
|---|---|---|---|---|---|
| 1 | Vehicle[a] + Vehicle[b] | IP + IV | 10 | N/A | 8 |
| 2 | ADC (OBI-999)[b] | IV | 10 | 1 | 8 |
| 3 | ADC (OBI-999)[b] | IV | 10 | 3 | 8 |
| 4 | ADC (OBI-999)[b] | IV | 10 | 10 | 8 |
| 5 | OBI-888[b] | IV | 10 | 10 | 8 |
| 6 | Anti-CD30 ADC[b] (OBI-910) | IV | 10 | 3 | 5 |
| 7 | MMAE[a] + OBI-888[b] | IP + IV | 10 | 0.191 + 10 | 8 |
| 8 | MMAE[a] | IP | 10 | 0.191 | 8 |

[a] PBS, pH 7.4 (high concentration of MMAE will be stored in 100% DMSO and then is diluted with PBS, pH 7.4)
[b] 25 mM Sodium Citrate + 100 mM NaCl, pH 6.5
[c] Vehicle and test substances are administered once weekly for four weeks starting one day after tumor cell implantation (denoted as Day 1).
[d] NCI-N87 at 2.5 × 10^6 cells/mouse with matrigel (1:1) in 200 uL are injected subcutaneously into right flank of female nu/nu mice.
Tumor size/body weight monitoring: twice weekly till Day 70 or the study is terminated when mean tumor volume in the vehicle control group reaches 2000 mm$^3$. Pictures are required to be taken at sacrifice.

4.2 Cell Line

Viable human gastric carcinoma NCI-N87 (ATCC CRL-5822) cell line was purchased and cultured in Eurofins Panlabs Taiwan, Ltd. The cells were cultured in RPMI-1640 medium containing 10% fetal bovine serum (FBS) at 37° C. in 5% $CO_2$ incubator and implanted subcutaneously in the right flank of each mouse.

4.3 Animals

Female nude (nu/nu) mice aged 5-6 weeks obtained from BioLasco Taiwan (under Charles River Laboratories Licensee) were used. The animals were housed in individually ventilated cages (IVC, 36 Mini Isolator system). The allocation for 3 animals was 27×20×14 in cm. All animals were maintained in a hygienic environment under controlled temperature (20-24° C.) and humidity (30%-70%) with 12-hour light/dark cycle. Free access to standard lab diet [MFG (Oriental Yeast Co., Ltd., Japan)] and autoclaved tap water in bottles were granted. All aspects of this work including housing, experimentation, and animal disposal were performed in general accordance with the "Guide for the Care and Use of Laboratory Animals: Eighth Edition" (National Academies Press, Washington, D.C., 2011) in our AAALAC-accredited laboratory animal facility. In addition, the animal care and use protocol was reviewed and approved by the IACUC at Eurofins Panlabs Taiwan, Ltd.

4.4 Chemicals 0.9% NaCl (Sin-Tong, Taiwan), Fetal bovine serum (HyClone, USA), Matrigel (BD, USA) and RPMI-1640 (HyClone, USA).

4.5 Equipment

Animal cage (Tecniplast, Italy), Beaker 1000 mL (Kimax, USA), Calipers (Mitutoyo, Japan), Class II biological safety cabinet (NuAire, USA), Individually ventilated cages (IVC, 36 Mini Isolator system) (Tecniplast, Italy), Mouse scale #Z-40 (Taconic, USA), Stainless forceps (Klappenecker, Germany) and Vertical laminar flow (Tsao-Hsin, Taiwan).

4.6 Methods

The tumor volumes, body weights, mortality, and signs of overt toxicity were monitored and recorded twice weekly for 100 days. Tumor growth inhibition was calculated as T/C (treatment/control)×100%. A T/C value ≤42% compared to that of the vehicle control group was considered significant anti-tumor activity. Two-way ANOVA followed by Bonferroni test was used to ascertain the statistically significant significance of groups compared to respective vehicle control (*p<0.05).

4.7 Results

TABLE 7-1

Tumor volume, Xenograft, Gastric, NCI-N87 in Female nu/nu Mice (Day 1-Day 25)

| Gr. | Treatment | Dose (mg/kg) (Route) | No. | Day1 | Day4 | Day8 | Day11 | Day15 | Day18 | Day22 | Day25 |
|---|---|---|---|---|---|---|---|---|---|---|---|
| 1 | Vehicle (PBS, pH 7.4) + Vehicle (25 mM Sodium Citrate, + 100 mM NaCl, pH 6.5) | 10 mL/ kg × 4 (Once weekly) IP + IV | 1 | 93 | 100 | 137 | 258 | 372 | 453 | 635 | 613 |
| | | | 2 | 118 | 117 | 131 | 166 | 175 | 216 | 219 | 225 |
| | | | 3 | 108 | 141 | 177 | 333 | 392 | 432 | 600 | 704 |
| | | | 4 | 99 | 123 | 146 | 332 | 332 | 375 | 442 | 498 |
| | | | 5 | 103 | 157 | 162 | 289 | 292 | 335 | 455 | 493 |
| | | | 6 | 96 | 124 | 146 | 303 | 325 | 514 | 560 | 664 |
| | | | 7 | 86 | 106 | 144 | 268 | 271 | 321 | 329 | 489 |
| | | | 8 | 98 | 123 | 133 | 296 | 344 | 406 | 510 | 510 |
| | | | Mean | 100 | 124 | 147 | 281 | 313 | 382 | 469 | 525 |
| | | | SEM | 3 | 6 | 5 | 19 | 24 | 32 | 50 | 52 |
| 2 | ADC (OBI-999) | 1 mg/ kg × 4 IV (Once weekly) | 1 | 85 | 98 | 110 | 152 | 92 | 104 | 108 | 115 |
| | | | 2 | 88 | 112 | 99 | 131 | 117 | 141 | 139 | 159 |
| | | | 3 | 93 | 113 | 97 | 144 | 129 | 143 | 169 | 208 |
| | | | 4 | 94 | 119 | 88 | 176 | 119 | 103 | 77 | 121 |
| | | | 5 | 103 | 117 | 103 | 104 | 113 | 113 | 85 | 80 |
| | | | 6 | 88 | 97 | 83 | 144 | 131 | 131 | 139 | 145 |
| | | | 7 | 103 | 104 | 96 | 135 | 121 | 131 | 143 | 150 |
| | | | 8 | 101 | 123 | 94 | 97 | 88 | 78 | 91 | 133 |
| | | | Mean | 94 | 110 | 96 | 135 | 114 | 118* | 119* | 139* |
| | | | SEM | 3 | 3 | 3 | 9 | 6 | 8 | 12 | 13 |
| | | | % T/C | — | 89 | 65 | 48 | 36# | 31# | 25# | 26# |
| | | | % TGI | — | 11 | 35 | 52 | 64 | 69 | 75 | 74 |
| 3 | ADC (OBI-999) | 3 mg/ kg × 4 IV (Once weekly) | 1 | 80 | 102 | 121 | 91 | 60 | 60 | 68 | 73 |
| | | | 2 | 96 | 131 | 89 | 91 | 79 | 79 | 79 | 65 |
| | | | 3 | 97 | 125 | 89 | 96 | 99 | 79 | 69 | 66 |
| | | | 4 | 97 | 93 | 71 | 93 | 94 | 86 | 77 | 76 |
| | | | 5 | 90 | 131 | 80 | 89 | 84 | 77 | 53 | 57 |

TABLE 7-1-continued

Tumor volume, Xenograft, Gastric, NCI-N87 in Female nu/nu Mice (Day 1-Day 25)

| Gr. | Treatment | Dose (mg/kg) (Route) | No. | Day1 | Day4 | Day8 | Day11 | Day15 | Day18 | Day22 | Day25 |
|---|---|---|---|---|---|---|---|---|---|---|---|
| | | | 6 | 127 | 160 | 77 | 81 | 91 | 70 | 43 | 68 |
| | | | 7 | 94 | 127 | 101 | 87 | 108 | 85 | 79 | 77 |
| | | | 8 | 77 | 88 | 60 | 72 | 93 | 99 | 69 | 70 |
| | | | Mean | 95 | 120 | 86 | 88 | 89 | 79* | 67* | 69* |
| | | | SEM | 5 | 8 | 7 | 3 | 5 | 4 | 5 | 2 |
| | | | % T/C | — | 97 | 59 | 31# | 28# | 21# | 14# | 13# |
| | | | % TGI | — | 3 | 41 | 69 | 72 | 79 | 86 | 87 |
| 4 | ADC (OBI-999) | 10 mg/ kg × 4 IV (Once weekly) | 1 | 93 | 89 | 82 | 66 | 61 | 86 | 54 | 68 |
| | | | 2 | 110 | 115 | 97 | 85 | 72 | 71 | 51 | 73 |
| | | | 3 | 88 | 125 | 85 | 86 | 93 | 51 | 41 | 58 |
| | | | 4 | 94 | 104 | 101 | 86 | 93 | 89 | 73 | 85 |
| | | | 5 | 96 | 86 | 73 | 81 | 74 | 40 | 41 | 69 |
| | | | 6 | 87 | 127 | 96 | 104 | 101 | 86 | 53 | 57 |
| | | | 7 | 82 | 108 | 110 | 82 | 86 | 73 | 70 | 70 |
| | | | 8 | 96 | 115 | 88 | 85 | 77 | 68 | 66 | 62 |
| | | | Mean | 93 | 109 | 92 | 84 | 82 | 71* | 56* | 68* |
| | | | SEM | 3 | 5 | 4 | 4 | 5 | 6 | 4 | 3 |
| | | | % T/C | — | 88 | 63 | 30# | 26# | 19# | 12# | 13# |
| | | | % TGI | — | 12 | 37 | 70 | 74 | 81 | 88 | 87 |
| 5 | OBI-888 | 10 mg/ kg × 4 IV (Once weekly) | 1 | 94 | 106 | 117 | 179 | 214 | 248 | 356 | 358 |
| | | | 2 | 101 | 133 | 157 | 272 | 318 | 321 | 409 | 394 |
| | | | 3 | 94 | 104 | 114 | 199 | 238 | 295 | 307 | 396 |
| | | | 4 | 78 | 135 | 125 | 150 | 281 | 426 | 455 | 460 |
| | | | 5 | 123 | 150 | 144 | 236 | 252 | 458 | 522 | 551 |
| | | | 6 | 91 | 111 | 115 | 195 | 256 | 279 | 401 | 401 |
| | | | 7 | 94 | 111 | 106 | 211 | 233 | 348 | 359 | 432 |
| | | | 8 | 86 | 113 | 89 | 144 | 216 | 288 | 385 | 467 |
| | | | Mean | 95 | 120 | 121 | 198 | 251 | 333 | 399 | 432 |
| | | | SEM | 5 | 6 | 8 | 15 | 12 | 26 | 23 | 21 |
| | | | % T/C | — | 97 | 82 | 70 | 80 | 87 | 85 | 82 |
| | | | % TGI | — | 3 | 18 | 30 | 20 | 13 | 15 | 18 |
| 6 | Anti-CD30 ADC (OBI-910) | 3 mg/ kg × 4 IV (Once weekly) | 1 | 108 | 110 | 112 | 101 | 91 | 91 | 97 | 104 |
| | | | 2 | 97 | 81 | 94 | 121 | 117 | 121 | 129 | 130 |
| | | | 3 | 78 | 94 | 111 | 125 | 106 | 110 | 129 | 166 |
| | | | 4 | 117 | 89 | 94 | 108 | 127 | 128 | 155 | 133 |
| | | | 5 | 111 | 121 | 111 | 127 | 129 | 146 | 172 | 174 |
| | | | SEM | 102 | 99 | 104 | 116 | 114 | 119* | 136* | 141* |
| | | | Mean | 7 | 7 | 4 | 5 | 7 | 9 | 13 | 13 |
| | | | % T/C | — | 80 | 71 | 41# | 36# | 31# | 29# | 27# |
| | | | % TGI | — | 20 | 29 | 59 | 67 | 69 | 71 | 73 |
| 7 | MMAE + OBI-888 | 0.191 mg/ kg × 4 IP (Once weekly) + 10 mg/ kg × 4 IV (Once weekly) | 1 | 99 | 104 | 146 | 164 | 214 | 214 | 222 | 243 |
| | | | 2 | 111 | 121 | 112 | 146 | 161 | 211 | 243 | 269 |
| | | | 3 | 121 | 88 | 103 | 103 | 159 | 145 | 119 | 130 |
| | | | 4 | 112 | 99 | 119 | 119 | 163 | 233 | 320 | 415 |
| | | | 5 | 83 | 125 | 112 | 146 | 164 | 186 | 237 | 236 |
| | | | 6 | 87 | 74 | died | died | died | died | died | died |
| | | | 7 | 81 | 99 | 111 | 132 | 181 | 214 | 239 | 269 |
| | | | 8 | 78 | 104 | 108 | 113 | 192 | 179 | 181 | 217 |
| | | | Mean | 97 | 102 | 116 | 132 | 176 | 197 | 223 | 254* |
| | | | SEM | 6 | 6 | 5 | 8 | 8 | 11 | 23 | 32 |
| | | | % T/C | — | 82 | 79 | 47 | 56 | 52 | 48 | 48 |
| | | | % TGI | — | 18 | 21 | 53 | 44 | 48 | 52 | 52 |
| 8 | MMAE | 0.191 mg/ kg × 4 IP (Once weekly) | 1 | 61 | 106 | 117 | 162 | 153 | 152 | 144 | 146 |
| | | | 2 | 89 | 102 | 142 | 158 | 189 | 213 | 201 | 216 |
| | | | 3 | 83 | 115 | 127 | 137 | 178 | 234 | 246 | 259 |
| | | | 4 | 88 | 115 | 115 | 169 | 231 | 255 | 303 | 356 |
| | | | 5 | 125 | 115 | 110 | 174 | 175 | 231 | 252 | 315 |
| | | | 6 | 88 | died | died | died | died | died | died | died |
| | | | 7 | 110 | 104 | 125 | 187 | 208 | 228 | 322 | 353 |
| | | | 8 | 121 | 109 | 119 | 166 | 189 | 211 | 296 | 296 |
| | | | Mean | 96 | 109 | 122 | 165 | 189 | 218 | 252 | 277 |
| | | | SEM | 8 | 2 | 4 | 6 | 9 | 12 | 24 | 29 |
| | | | % T/C | — | 88 | 83 | 59 | 60 | 57 | 54 | 53 |
| | | | % TGI | — | 12 | 17 | 41 | 40 | 43 | 46 | 47 |

TABLE 7-2

Tumor volume, Xenograft, Gastric, NCI-N87 in Female nu/nu Mice (Day 29-Day 53)

| Gr. | Treatment | Dose (mg/kg) (Route) | No. | Tumor Volume (mm$^3$) | | | | | | | |
|---|---|---|---|---|---|---|---|---|---|---|---|
| | | | | Day29 | Day32 | Day36 | Day39 | Day43 | Day46 | Day50 | Day53 |
| 1 | Vehicle (PBS, pH 7.4) + Vehicle (25 mM Sodium Citrate, + 100 mM NaCl, pH 6.5) | 10 mL/kg × 4 (Once weekly) IP + IV | 1 | 645 | 706 | 853 | 926 | 1062 | 1069 | 1116 | 1127 |
| | | | 2 | 299 | 299 | 416 | 432 | 451 | 455 | 484 | 513 |
| | | | 3 | 779 | 1079 | 1355 | 1479 | 1592 | 1862 | 2039 | 2546 |
| | | | 4 | 623 | 628 | 719 | 756 | 792 | 792 | 798 | 811 |
| | | | 5 | 702 | 864 | 895 | 1201 | 1309 | 1553 | 1800 | 2004 |
| | | | 6 | 862 | 956 | 1034 | 1135 | 1236 | 1420 | 1849 | 2009 |
| | | | 7 | 489 | 489 | 503 | 508 | 564 | 630 | 653 | 719 |
| | | | 8 | 665 | 707 | 746 | 828 | 863 | 900 | 968 | 1036 |
| | | | Mean | 633 | 716 | 815 | 908 | 984 | 1085 | 1213 | 1346 |
| | | | SEM | 62 | 89 | 105 | 125 | 137 | 172 | 212 | 262 |
| 2 | ADC (OBI-999) | 1 mg/ kg × 4 IV (Once weekly) | 1 | 113 | 73 | 72 | 72 | 64 | 58 | 53 | 51 |
| | | | 2 | 164 | 192 | 228 | 234 | 258 | 299 | 324 | 346 |
| | | | 3 | 222 | 240 | 243 | 252 | 275 | 310 | 345 | 345 |
| | | | 4 | 121 | 121 | 121 | 125 | 125 | 113 | died | died |
| | | | 5 | 94 | 110 | 112 | 97 | 96 | 96 | 104 | 108 |
| | | | 6 | 145 | 148 | 152 | 168 | 183 | 202 | 208 | 225 |
| | | | 7 | 152 | 176 | 184 | 199 | 216 | 218 | 248 | 271 |
| | | | 8 | 133 | 133 | 137 | 148 | 152 | 187 | 208 | 231 |
| | | | Mean | 143* | 149* | 156* | 162* | 171* | 185* | 213* | 225* |
| | | | SEM | 14 | 19 | 21 | 23 | 27 | 33 | 40 | 42 |
| | | | % T/C | 23# | 21# | 19# | 18# | 17# | 17# | 18# | 17# |
| | | | % TGI | 77 | 79 | 81 | 82 | 83 | 83 | 82 | 83 |
| 3 | ADC (OBI-999) | 3 mg/ kg × 4 IV (Once weekly) | 1 | 56 | 72 | 72 | 66 | 64 | 63 | 60 | 58 |
| | | | 2 | 68 | 68 | 73 | 76 | 72 | 64 | 61 | 59 |
| | | | 3 | 59 | 40 | 41 | 43 | 38 | 34 | 33 | 32 |
| | | | 4 | 54 | 48 | 44 | 36 | 38 | 38 | 38 | 38 |
| | | | 5 | 88 | 32 | 0 | 0 | 0 | 0 | 0 | 0 |
| | | | 6 | 64 | 64 | 62 | 56 | 55 | 54 | 52 | 50 |
| | | | 7 | 104 | 89 | 85 | 82 | 76 | 72 | 69 | 36 |
| | | | 8 | 70 | 69 | 66 | 65 | 62 | 60 | 60 | 57 |
| | | | Mean | 70* | 60* | 55* | 53* | 51* | 48* | 47* | 42* |
| | | | SEM | 6 | 7 | 9 | 9 | 9 | 8 | 8 | 8 |
| | | | % T/C | 11# | 8# | 7# | 6# | 5# | 4# | 4# | 3# |
| | | | % TGI | 89 | 92 | 93 | 94 | 95 | 96 | 96 | 97 |
| 4 | ADC (OBI-999) | 10 mg/ kg × 4 IV (Once weekly) | 1 | 66 | 61 | 51 | 51 | 50 | 49 | 48 | 47 |
| | | | 2 | 56 | 57 | 64 | 61 | 59 | 59 | 58 | 58 |
| | | | 3 | 44 | 47 | 46 | 40 | 38 | 0 | 0 | 0 |
| | | | 4 | 77 | 69 | 65 | 65 | 64 | 64 | 61 | 61 |
| | | | 5 | 52 | 59 | 56 | 54 | 52 | 51 | 49 | 46 |
| | | | 6 | 70 | 59 | 53 | 53 | 53 | 52 | 50 | 49 |
| | | | 7 | 67 | 68 | 68 | 62 | 60 | 60 | 60 | 57 |
| | | | 8 | 66 | 77 | 66 | 61 | 60 | 57 | 55 | 54 |
| | | | Mean | 62* | 62* | 59* | 56* | 55* | 49* | 48* | 47* |
| | | | SEM | 4 | 3 | 3 | 3 | 3 | 7 | 7 | 7 |
| | | | % T/C | 10# | 9# | 7# | 6# | 6# | 5# | 4# | 3# |
| | | | % TGI | 90 | 91 | 93 | 94 | 94 | 95 | 96 | 97 |
| 5 | OBI-888 | 10 mg/ kg × 4 IV (Once weekly) | 1 | 418 | 583 | 605 | 612 | 698 | 801 | 819 | 926 |
| | | | 2 | 590 | 689 | 694 | 694 | 773 | 845 | 1016 | 1074 |
| | | | 3 | 460 | 466 | 508 | 588 | 668 | 770 | 828 | 1030 |
| | | | 4 | 714 | 830 | 859 | 1040 | 1103 | 1359 | 1614 | 1885 |
| | | | 5 | 739 | 744 | 835 | 886 | 968 | 1230 | 1238 | 1342 |
| | | | 6 | 565 | 565 | 652 | 723 | 840 | 979 | 1012 | 1074 |
| | | | 7 | 530 | 728 | 780 | 780 | 900 | 1057 | 1072 | 1258 |
| | | | 8 | 533 | 652 | 719 | 722 | 869 | 958 | 1065 | 1065 |
| | | | Mean | 569 | 657 | 707 | 756 | 852 | 1000 | 1083 | 1207 |
| | | | SEM | 40 | 41 | 42 | 52 | 51 | 74 | 90 | 107 |
| | | | % T/C | 90 | 92 | 87 | 83 | 87 | 92 | 89 | 90 |
| | | | % TGI | 10 | 8 | 13 | 17 | 13 | 8 | 11 | 10 |
| 6 | Anti-CD30 ADC (OBI-910) | 3 mg/ kg × 4 IV (Once weekly) | 1 | 181 | 187 | 192 | 179 | 171 | 164 | 148 | 141 |
| | | | 2 | 208 | 231 | 189 | 191 | 210 | 256 | 292 | 320 |
| | | | 3 | 225 | 243 | 243 | 246 | 252 | 296 | 327 | 355 |
| | | | 4 | 197 | 207 | 217 | 217 | 217 | 259 | 262 | 262 |
| | | | 5 | 282 | 272 | 377 | 381 | 411 | 546 | 546 | 579 |
| | | | Mean | 219* | 228* | 244* | 243* | 252* | 304* | 315* | 331* |
| | | | SEM | 17 | 15 | 35 | 36 | 42 | 64 | 65 | 72 |
| | | | % T/C | 35# | 32# | 30# | 27# | 26# | 28# | 26# | 25# |
| | | | % TGI | 65 | 68 | 70 | 73 | 74 | 72 | 74 | 75 |
| 7 | MMAE + OBI-888 | 0.191 mg/ kg × 4 IP (Once weekly) + | 1 | 293 | 292 | 356 | 394 | 407 | 509 | 562 | 578 |
| | | | 2 | 286 | 272 | 279 | 293 | 352 | 356 | 385 | 407 |
| | | | 3 | 143 | 189 | 199 | 159 | 156 | 164 | 166 | 192 |
| | | | 4 | 465 | 465 | 469 | 484 | 484 | 515 | 538 | 614 |
| | | | 5 | 283 | 325 | 387 | 405 | 417 | 458 | 476 | 521 |
| | | | 6 | died | died | died | died | died | died | died | died |

TABLE 7-2-continued

Tumor volume, Xenograft, Gastric, NCI-N87 in Female nu/nu Mice (Day 29-Day 53)

| Gr. | Treatment | Dose (mg/kg) (Route) | No. | Day29 | Day32 | Day36 | Day39 | Day43 | Day46 | Day50 | Day53 |
|---|---|---|---|---|---|---|---|---|---|---|---|
| | | 10 mg/ | 7 | 325 | 405 | 515 | 514 | 540 | 617 | 688 | 819 |
| | | kg × 4 | 8 | 314 | 293 | 289 | 292 | 295 | 360 | 372 | 432 |
| | | IV | Mean | 301* | 320* | 356* | 363* | 379* | 426* | 455* | 509* |
| | | (Once | SEM | 36 | 34 | 42 | 47 | 48 | 56 | 63 | 74 |
| | | weekly) | % T/C | 48 | 45 | 44 | 40# | 39# | 39# | 38# | 38# |
| | | | % TGI | 52 | 55 | 56 | 60 | 61 | 61 | 62 | 62 |
| 8 | MMAE | 0.191 mg/ | 1 | 162 | 160 | 94 | 94 | 97 | 91 | 89 | 88 |
| | | kg × 4 | 2 | 277 | 318 | 345 | 385 | 414 | 606 | 623 | 682 |
| | | IP | 3 | 399 | 397 | 390 | 407 | 429 | 535 | 569 | 590 |
| | | (Once | 4 | 406 | 385 | 389 | 442 | 489 | 495 | 550 | 581 |
| | | weekly) | 5 | 439 | 446 | 506 | 530 | 581 | 719 | 766 | 816 |
| | | | 6 | died | died | died | died | died | died | died | died |
| | | | 7 | 525 | 584 | 658 | 671 | 780 | 878 | 936 | 1094 |
| | | | 8 | 387 | 432 | 459 | 487 | 549 | 561 | 590 | 620 |
| | | | Mean | 371* | 389* | 406* | 431* | 477* | 555* | 589* | 639* |
| | | | SEM | 44 | 49 | 65 | 67 | 78 | 92 | 98 | 114 |
| | | | % T/C | 59 | 54 | 50 | 47 | 48 | 51 | 49 | 47 |
| | | | % TGI | 41 | 46 | 50 | 53 | 52 | 49 | 51 | 53 |

TABLE 7-3

Tumor volume, Xenograft, Gastric, NCI-N87 in Female nu/nu Mice (Day 57-Day 85)

| Gr. | Treatment | Dose/Route (mg/kg) | No. | Day57 | Day60 | Day 64 | Day67 | Day70 | Day74 | Day78 | Day81 | Day85 |
|---|---|---|---|---|---|---|---|---|---|---|---|---|
| 1 | Vehicle | 10 mL/ | 1 | NA | NA | NA | NA | NA | NA | NA | NA | NA |
| | (PBS, pH 7.4) | kg × 4 | 2 | NA | NA | NA | NA | NA | NA | NA | NA | NA |
| | + | (Once | 3 | NA | NA | NA | NA | NA | NA | NA | NA | NA |
| | Vehicle | weekly) | 4 | NA | NA | NA | NA | NA | NA | NA | NA | NA |
| | (25 mM Sodium Citrate, | IP + IV | 5 | NA | NA | NA | NA | NA | NA | NA | NA | NA |
| | + | | 6 | NA | NA | NA | NA | NA | NA | NA | NA | NA |
| | 100 mM | | 7 | NA | NA | NA | NA | NA | NA | NA | NA | NA |
| | NaCl, pH 6.5) | | 8 | NA | NA | NA | NA | NA | NA | NA | NA | NA |
| | | | Mean | — | — | — | — | — | — | — | — | — |
| | | | SEM | — | — | — | — | — | — | — | — | — |
| 2 | ADC (OBI-999) | 1 mg/ | 1 | 48 | 48 | 47 | 44 | 36 | 35 | 35 | 37 | 37 |
| | | kg × 4 | 2 | 386 | 417 | 426 | 471 | 496 | 519 | 528 | 553 | 567 |
| | | IV | 3 | 373 | 424 | 456 | 536 | 556 | 578 | 630 | 690 | 760 |
| | | (Once | 4 | died | died | died | died | died | died | died | died | died |
| | | weekly) | 5 | 104 | 104 | 101 | 101 | 94 | 91 | 97 | 97 | 94 |
| | | | 6 | 231 | 206 | 223 | 229 | 254 | 277 | 292 | 298 | 306 |
| | | | 7 | 328 | 396 | 455 | 521 | 544 | 593 | 658 | 684 | 778 |
| | | | 8 | 251 | 309 | 347 | 489 | 529 | 570 | 680 | 717 | 833 |
| | | | Mean | 246 | 272 | 294 | 342 | 358 | 380 | 417 | 439 | 482 |
| | | | SEM | 49 | 58 | 65 | 80 | 85 | 92 | 103 | 110 | 127 |
| | | | % T/C | — | — | — | — | — | — | — | — | — |
| 3 | ADC (OBI-999) | 3 mg/ | 1 | 55 | 55 | 53 | 53 | 54 | 55 | 57 | 60 | 62 |
| | | kg × 4 | 2 | 56 | 56 | 56 | 59 | 61 | 64 | 65 | 68 | 70 |
| | | IV | 3 | 30 | 29 | 29 | 27 | 27 | 26 | 25 | 25 | 24 |
| | | (Once | 4 | 39 | 40 | 41 | 41 | 45 | 51 | 54 | 59 | 64 |
| | | weekly) | 5 | 0 | 0 | 0 | 0 | 0 | 0 | 0 | 0 | 0 |
| | | | 6 | 50 | 51 | 53 | 55 | 58 | 60 | 63 | 63 | 64 |
| | | | 7 | died | died | died | died | died | died | died | died | died |
| | | | 8 | 55 | 55 | 57 | 60 | 60 | 57 | 55 | 53 | 52 |
| | | | Mean | 41 | 41 | 41 | 42 | 44 | 45 | 46 | 47 | 48 |
| | | | SEM | 8 | 8 | 8 | 8 | 9 | 9 | 9 | 9 | 10 |
| | | | % T/C | — | — | — | — | — | — | — | — | — |
| 4 | ADC (OBI-999) | 10 mg/ | 1 | 46 | 46 | 49 | 51 | 54 | 54 | 52 | 52 | 52 |
| | | kg × 4 | 2 | 55 | 58 | 55 | 55 | 53 | 51 | 48 | 48 | 51 |
| | | IV | 3 | 0 | 0 | 0 | 0 | 0 | 0 | 0 | 0 | 0 |
| | | (Once | 4 | 61 | 61 | 64 | 65 | 65 | 65 | 62 | 60 | 57 |
| | | weekly) | 5 | 45 | 45 | 45 | 44 | 42 | 40 | 38 | 38 | 36 |
| | | | 6 | 46 | 45 | 45 | 45 | 44 | 44 | 42 | 40 | 40 |
| | | | 7 | 57 | 57 | 60 | 62 | 62 | 57 | 55 | 53 | 40 |
| | | | 8 | 54 | 53 | 51 | 51 | 48 | 46 | 45 | 45 | 45 |
| | | | Mean | 46 | 46 | 46 | 47 | 46 | 45 | 43 | 42 | 40 |
| | | | SEM | 7 | 7 | 7 | 7 | 7 | 7 | 7 | 7 | 6 |
| | | | % T/C | — | — | — | — | — | — | — | — | — |

TABLE 7-3-continued

Tumor volume, Xenograft, Gastric, NCI-N87 in Female nu/nu Mice (Day 57-Day 85)

| Gr. | Treatment | Dose/Route (mg/kg) | No. | Day57 | Day60 | Day 64 | Day67 | Day70 | Day74 | Day78 | Day81 | Day85 |
|---|---|---|---|---|---|---|---|---|---|---|---|---|
| 5 | OBI-888 | 10 mg/ kg × 4 IV (Once weekly) | 1 | 1005 | 1145 | 1152 | 1220 | 1281 | NA | NA | NA | NA |
|   |   |   | 2 | 1135 | 1369 | 1406 | 1458 | 1458 | NA | NA | NA | NA |
|   |   |   | 3 | 1048 | 1090 | 1146 | 1331 | 1371 | NA | NA | NA | NA |
|   |   |   | 4 | 2137 | 2313 | 2334 | 2669 | 2692 | NA | NA | NA | NA |
|   |   |   | 5 | 1429 | 1475 | 1483 | 1491 | 1491 | NA | NA | NA | NA |
|   |   |   | 6 | 1324 | 1371 | 1433 | 1571 | 1694 | NA | NA | NA | NA |
|   |   |   | 7 | 1302 | 1378 | 1468 | 1617 | 1628 | NA | NA | NA | NA |
|   |   |   | 8 | 1310 | 1371 | 1415 | 1553 | 1580 | NA | NA | NA | NA |
|   |   |   | Mean | 1336 | 1439 | 1480 | 1614 | 1649 | — | — | — | — |
|   |   |   | SEM | 126 | 133 | 131 | 158 | 156 | — | — | — | — |
|   |   |   | % T/C | — | — | — | — | — | — | — | — | — |
| 6 | Anti-CD30 ADC (OBI-910) | 3 mg/ kg × 4 IV (Once weekly) | 1 | 135 | 133 | 127 | 123 | 119 | 117 | 115 | 113 | 113 |
|   |   |   | 2 | 360 | 437 | 467 | 610 | 631 | 733 | 862 | 905 | 999 |
|   |   |   | 3 | 427 | 453 | 503 | 634 | 634 | 706 | 854 | 928 | 1006 |
|   |   |   | 4 | 269 | 352 | 368 | 415 | 411 | 485 | 515 | 539 | 559 |
|   |   |   | 5 | 584 | 605 | 611 | 633 | 645 | 689 | 689 | 729 | 749 |
|   |   |   | Mean | 355 | 396 | 415 | 483 | 488 | 546 | 607 | 643 | 685 |
|   |   |   | SEM | 75 | 77 | 82 | 99 | 102 | 116 | 138 | 150 | 166 |
|   |   |   | % T/C | — | — | — | — | — | — | — | — | — |
| 7 | MMAE + OBI-888 | 0.191 mg/ kg × 4 IP (Once weekly) + 10 mg/ kg × 4 IV (Once weekly) | 1 | 640 | 701 | 721 | 814 | 841 | 930 | 969 | 1065 | 1175 |
|   |   |   | 2 | 461 | 490 | 510 | 540 | 551 | 584 | 623 | 623 | 623 |
|   |   |   | 3 | 199 | 206 | 200 | 228 | 234 | 240 | 248 | 255 | 276 |
|   |   |   | 4 | 663 | 663 | 677 | 723 | 728 | 743 | 757 | 767 | 772 |
|   |   |   | 5 | 567 | 681 | 708 | 796 | 808 | 951 | 958 | 965 | 1064 |
|   |   |   | 6 | died | died | died | died | died | died | died | died | died |
|   |   |   | 7 | 845 | 897 | 897 | 965 | 1044 | 1051 | 1111 | 1171 | 1171 |
|   |   |   | 8 | 436 | 409 | 409 | 404 | 420 | 467 | 477 | 477 | 482 |
|   |   |   | Mean | 544 | 578 | 589 | 639 | 661 | 709 | 735 | 760 | 795 |
|   |   |   | SEM | 77 | 86 | 88 | 98 | 104 | 111 | 116 | 125 | 134 |
|   |   |   | % T/C | — | — | — | — | — | — | — | — | — |
| 8 | MMAE | 0.191 mg/ kg × 4 IP (Once weekly) | 1 | 85 | 83 | 82 | 79 | 76 | 74 | 74 | 77 | 77 |
|   |   |   | 2 | 694 | 745 | 765 | 883 | 943 | 1012 | 1042 | 1064 | 1097 |
|   |   |   | 3 | 663 | 783 | 788 | 827 | 870 | 909 | 955 | 961 | 1033 |
|   |   |   | 4 | 627 | 664 | 702 | 726 | 726 | 856 | 890 | 903 | 933 |
|   |   |   | 5 | 870 | 854 | 920 | 1070 | 1090 | 1117 | 1197 | 1197 | 1331 |
|   |   |   | 6 | died | died | died | died | died | died | died | died | died |
|   |   |   | 7 | 1141 | 1234 | 1272 | 1300 | 1358 | 1422 | 1431 | 1517 | 1558 |
|   |   |   | 8 | 650 | 676 | 703 | 840 | 859 | 916 | 928 | 935 | 988 |
|   |   |   | Mean | 676 | 720 | 747 | 818 | 846 | 901 | 931 | 951 | 1002 |
|   |   |   | SEM | 120 | 129 | 134 | 143 | 150 | 156 | 160 | 166 | 175 |
|   |   |   | % T/C | — | — | — | — | — | — | — | — | — |

TABLE 7-4

Tumor volume, Xenograft, Gastric, NCI-N87 in Female nu/nu Mice (Day 88-Day 100)

| Gr. | Treatment | Dose (mg/kg) (Route) | No. | Day88 | Day91 | Day95 | Day98 | Day100 |
|---|---|---|---|---|---|---|---|---|
| 1 | Vehicle (PBS, pH 7.4) + Vehicle (25 mM Sodium Citrate, + 100 mM NaCl, pH 6.5) | 10 mL/kg × 4 (Once weekly) IP + IV | 1 | NA | NA | NA | NA | NA |
|   |   |   | 2 | NA | NA | NA | NA | NA |
|   |   |   | 3 | NA | NA | NA | NA | NA |
|   |   |   | 4 | NA | NA | NA | NA | NA |
|   |   |   | 5 | NA | NA | NA | NA | NA |
|   |   |   | 6 | NA | NA | NA | NA | NA |
|   |   |   | 7 | NA | NA | NA | NA | NA |
|   |   |   | 8 | NA | NA | NA | NA | NA |
|   |   |   | Mean | — | — | — | — | — |
|   |   |   | SEM | — | — | — | — | — |
| 2 | ADC (OBI-999) | 1 mg/kg × 4 IV (Once weekly) | 1 | 36 | 36 | 34 | 34 | 34 |
|   |   |   | 2 | 588 | 719 | 817 | 832 | 881 |
|   |   |   | 3 | 814 | 841 | 868 | 898 | 959 |
|   |   |   | 4 | died | died | died | died | died |
|   |   |   | 5 | 91 | 91 | 94 | 94 | 96 |
|   |   |   | 6 | 306 | 298 | 295 | 292 | 289 |
|   |   |   | 7 | 802 | 817 | 866 | 942 | 996 |
|   |   |   | 8 | 834 | 924 | 1163 | 1284 | 1338 |
|   |   |   | Mean | 496 | 532 | 591 | 625 | 656 |

TABLE 7-4-continued

Tumor volume, Xenograft, Gastric, NCI-N87 in Female nu/nu Mice (Day 88-Day 100)

| Gr. | Treatment | Dose (mg/kg) (Route) | No. | Day88 | Day91 | Day95 | Day98 | Day100 |
|---|---|---|---|---|---|---|---|---|
| | | | SEM | 132 | 143 | 167 | 182 | 193 |
| | | | % T/C | — | — | — | — | — |
| 3 | ADC (OBI-999) | 3 mg/kg × 4 | 1 | 65 | 65 | 68 | 70 | 73 |
| | | IV | 2 | 70 | 70 | 68 | 65 | 62 |
| | | (Once weekly) | 3 | 23 | 22 | 21 | 21 | 0 |
| | | | 4 | 66 | 72 | 76 | 85 | 117 |
| | | | 5 | 0 | 0 | 0 | 0 | 0 |
| | | | 6 | 65 | 65 | 65 | 57 | 55 |
| | | | 7 | died | died | died | died | died |
| | | | 8 | 52 | 52 | 51 | 50 | 49 |
| | | | Mean | 49 | 49 | 50 | 50 | 51 |
| | | | SEM | 10 | 10 | 11 | 11 | 16 |
| | | | % T/C | — | — | — | — | — |
| 4 | ADC (OBI-999) | 10 mg/kg × 4 | 1 | 52 | 50 | 49 | 48 | 47 |
| | | IV | 2 | 53 | 55 | 55 | 53 | 51 |
| | | (Once weekly) | 3 | 0 | 0 | 0 | 0 | 0 |
| | | | 4 | 55 | 55 | 55 | 54 | 53 |
| | | | 5 | 36 | 36 | 36 | 35 | 28 |
| | | | 6 | 40 | 40 | 37 | 34 | 0 |
| | | | 7 | NA | NA | NA | NA | NA |
| | | | 8 | 43 | 42 | 40 | 37 | 24 |
| | | | Mean | 40 | 40 | 39 | 37 | 29 |
| | | | SEM | 7 | 7 | 7 | 7 | 9 |
| | | | % T/C | — | — | — | — | — |
| 5 | OBI-888 | 10 mg/kg × 4 | 1 | NA | NA | NA | NA | NA |
| | | IV | 2 | NA | NA | NA | NA | NA |
| | | (Once weekly) | 3 | NA | NA | NA | NA | NA |
| | | | 4 | NA | NA | NA | NA | NA |
| | | | 5 | NA | NA | NA | NA | NA |
| | | | 6 | NA | NA | NA | NA | NA |
| | | | 7 | NA | NA | NA | NA | NA |
| | | | 8 | NA | NA | NA | NA | NA |
| | | | Mean | — | — | — | — | — |
| | | | SEM | — | — | — | — | — |
| | | | % T/C | — | — | — | — | — |
| 6 | Anti-CD30 ADC (OBI-910) | 3 mg/kg × 4 | 1 | 112 | 110 | 106 | 103 | 99 |
| | | IV | 2 | 1038 | 1183 | 1347 | 1408 | 1455 |
| | | (Once weekly) | 3 | 1014 | 1081 | 1176 | 1236 | 1311 |
| | | | 4 | 573 | 597 | 657 | 693 | 719 |
| | | | 5 | 804 | 888 | 895 | 856 | 942 |
| | | | Mean | 708 | 772 | 836 | 859 | 905 |
| | | | SEM | 171 | 193 | 217 | 228 | 240 |
| | | | % T/C | — | — | — | — | — |
| 7 | MMAE + OBI-888 | 0.191 mg/kg × 4 IP (Once weekly) + 10 mg/kg × 4 IV (Once weekly) | 1 | 1253 | 1329 | 1466 | 1595 | 1732 |
| | | | 2 | 628 | 628 | 640 | 646 | 628 |
| | | | 3 | 290 | 293 | 296 | 296 | 296 |
| | | | 4 | 788 | 820 | 815 | 810 | 753 |
| | | | 5 | 1087 | 1122 | 1226 | 1284 | 1301 |
| | | | 6 | died | died | died | died | died |
| | | | 7 | 1171 | 1208 | 1217 | 1225 | 1242 |
| | | | 8 | 468 | 454 | 436 | 408 | 386 |
| | | | Mean | 812 | 836 | 871 | 895 | 905 |
| | | | SEM | 140 | 150 | 167 | 184 | 201 |
| | | | % T/C | — | — | — | — | — |
| 8 | MMAE | 0.191 mg/kg × 4 | 1 | 74 | 72 | 68 | 68 | 62 |
| | | IP | 2 | 1104 | 1122 | 1192 | 1215 | 1254 |
| | | (Once weekly) | 3 | 1117 | 1130 | 1184 | 1265 | 1273 |
| | | | 4 | 933 | 933 | 947 | 1061 | 1076 |
| | | | 5 | 1346 | 1346 | 1354 | 1398 | 1444 |
| | | | 6 | died | died | died | died | died |
| | | | 7 | 1626 | 1636 | 1646 | 1656 | 1590 |
| | | | 8 | 1023 | 1023 | 1029 | 1043 | 1043 |
| | | | Mean | 1032 | 1037 | 1060 | 1101 | 1106 |
| | | | SEM | 182 | 183 | 186 | 189 | 189 |
| | | | % T/C | — | — | — | — | — |

TABLE 8-1

Body Weight, Xenograft, Gastric, NCI-N87 in Female nu/nu Mice (Day 1-Day 25)

| Gr. | Treatment | Dose (mg/kg) (Route) | No. | Day1 | Day4 | Day8 | Day11 | Day15 | Day18 | Day22 | Day25 |
|---|---|---|---|---|---|---|---|---|---|---|---|
| 1 | Vehicle (PBS, pH 7.4) + Vehicle (25 mM Sodium Citrate, + 100 mM NaCl, pH 6.5) | 10 mL/kg × 4 (Once weekly) IP + IV | 1 | 22 | 24 | 24 | 25 | 24 | 24 | 25 | 25 |
| | | | 2 | 23 | 24 | 25 | 25 | 24 | 24 | 24 | 25 |
| | | | 3 | 21 | 22 | 23 | 24 | 24 | 24 | 24 | 25 |
| | | | 4 | 22 | 24 | 22 | 22 | 23 | 24 | 24 | 24 |
| | | | 5 | 22 | 23 | 24 | 25 | 26 | 26 | 26 | 25 |
| | | | 6 | 23 | 24 | 25 | 26 | 25 | 26 | 25 | 25 |
| | | | 7 | 23 | 23 | 24 | 25 | 24 | 25 | 25 | 24 |
| | | | 8 | 24 | 24 | 25 | 26 | 25 | 25 | 25 | 26 |
| | | | Mean | 22.5 | 23.5 | 24.0 | 24.8 | 24.4 | 24.8 | 24.8 | 24.9 |
| | | | SEM | 0.3 | 0.3 | 0.4 | 0.5 | 0.3 | 0.3 | 0.3 | 0.2 |
| 2 | ADC (OBI-999) | 1 mg/kg × 4 IV (Once weekly) | 1 | 22 | 23 | 23 | 24 | 24 | 24 | 24 | 24 |
| | | | 2 | 22 | 24 | 25 | 25 | 24 | 24 | 24 | 24 |
| | | | 3 | 21 | 22 | 23 | 24 | 23 | 23 | 23 | 23 |
| | | | 4 | 22 | 23 | 24 | 24 | 23 | 23 | 22 | 24 |
| | | | 5 | 23 | 23 | 26 | 26 | 27 | 27 | 27 | 27 |
| | | | 6 | 20 | 22 | 23 | 23 | 24 | 24 | 24 | 24 |
| | | | 7 | 22 | 22 | 24 | 25 | 24 | 23 | 24 | 24 |
| | | | 8 | 23 | 23 | 24 | 24 | 24 | 24 | 24 | 24 |
| | | | Mean | 21.9 | 22.8 | 24.0 | 24.4 | 24.1 | 24.0 | 24.0 | 24.3 |
| | | | SEM | 0.4 | 0.3 | 0.4 | 0.3 | 0.4 | 0.5 | 0.5 | 0.4 |
| 3 | ADC (OBI-999) | 3 mg/kg × 4 IV (Once weekly) | 1 | 22 | 23 | 23 | 24 | 23 | 24 | 24 | 24 |
| | | | 2 | 21 | 22 | 23 | 24 | 25 | 25 | 25 | 26 |
| | | | 3 | 23 | 22 | 22 | 23 | 22 | 23 | 24 | 24 |
| | | | 4 | 23 | 23 | 23 | 22 | 22 | 23 | 24 | 23 |
| | | | 5 | 23 | 24 | 25 | 24 | 24 | 24 | 24 | 24 |
| | | | 6 | 22 | 22 | 23 | 24 | 24 | 24 | 24 | 24 |
| | | | 7 | 21 | 22 | 23 | 24 | 25 | 25 | 25 | 25 |
| | | | 8 | 22 | 22 | 21 | 21 | 22 | 22 | 23 | 22 |
| | | | Mean | 22.1 | 22.5 | 22.9 | 23.3 | 23.4 | 23.8 | 24.1 | 24.0 |
| | | | SEM | 0.3 | 0.3 | 0.4 | 0.4 | 0.5 | 0.4 | 0.2 | 0.4 |
| 4 | ADC (OBI-999) | 10 mg/kg × 4 IV (Once weekly) | 1 | 22 | 22 | 22 | 22 | 23 | 24 | 23 | 24 |
| | | | 2 | 21 | 21 | 23 | 23 | 24 | 23 | 24 | 24 |
| | | | 3 | 22 | 23 | 23 | 22 | 22 | 23 | 23 | 24 |
| | | | 4 | 21 | 21 | 22 | 22 | 23 | 23 | 23 | 23 |
| | | | 5 | 23 | 23 | 24 | 24 | 23 | 23 | 24 | 24 |
| | | | 6 | 22 | 23 | 24 | 24 | 24 | 24 | 24 | 24 |
| | | | 7 | 21 | 22 | 22 | 23 | 22 | 23 | 23 | 22 |
| | | | 8 | 23 | 23 | 25 | 26 | 26 | 25 | 26 | 26 |
| | | | Mean | 21.9 | 22.4 | 23.1 | 23.3 | 23.4 | 23.5 | 23.8 | 23.9 |
| | | | SEM | 0.3 | 0.4 | 0.4 | 0.5 | 0.5 | 0.3 | 0.4 | 0.4 |
| 5 | OBI-888 | 10 mg/kg × 4 IV (Once weekly) | 1 | 21 | 21 | 22 | 23 | 24 | 24 | 23 | 24 |
| | | | 2 | 22 | 23 | 24 | 24 | 25 | 25 | 25 | 26 |
| | | | 3 | 19 | 19 | 19 | 20 | 21 | 22 | 22 | 23 |
| | | | 4 | 22 | 22 | 22 | 23 | 23 | 23 | 23 | 24 |
| | | | 5 | 21 | 22 | 23 | 23 | 22 | 22 | 23 | 23 |
| | | | 6 | 21 | 21 | 22 | 23 | 23 | 23 | 24 | 24 |
| | | | 7 | 20 | 22 | 22 | 22 | 21 | 21 | 22 | 22 |
| | | | 8 | 21 | 21 | 22 | 22 | 21 | 21 | 22 | 22 |
| | | | Mean | 20.9 | 21.4 | 22.0 | 22.5 | 22.5 | 22.6 | 23.0 | 23.5 |
| | | | SEM | 0.4 | 0.4 | 0.5 | 0.4 | 0.5 | 0.5 | 0.4 | 0.5 |
| 6 | Anti-CD30 ADC (OBI-910) | 3 mg/kg × 4 IV (Once weekly) | 1 | 21 | 22 | 23 | 23 | 23 | 24 | 24 | 22 |
| | | | 2 | 20 | 21 | 22 | 22 | 22 | 23 | 23 | 22 |
| | | | 3 | 21 | 22 | 22 | 23 | 22 | 23 | 24 | 24 |
| | | | 4 | 22 | 22 | 22 | 23 | 24 | 24 | 25 | 25 |
| | | | 5 | 22 | 23 | 23 | 23 | 24 | 25 | 25 | 26 |
| | | | Mean | 21.2 | 22.0 | 22.4 | 22.8 | 23.0 | 23.8 | 24.2 | 23.8 |
| | | | SEM | 0.4 | 0.3 | 0.2 | 0.2 | 0.4 | 0.4 | 0.4 | 0.8 |
| 7 | MMAE + OBI-888 | 0.191 mg/kg × 4 IP (Once weekly) + 10 mg/kg × 4 IV (Once weekly) | 1 | 20 | 18 | 22 | 21 | 23 | 24 | 24 | 23 |
| | | | 2 | 21 | 20 | 22 | 22 | 21 | 22 | 23 | 23 |
| | | | 3 | 21 | 20 | 22 | 22 | 22 | 22 | 22 | 22 |
| | | | 4 | 21 | 20 | 22 | 23 | 23 | 22 | 23 | 22 |
| | | | 5 | 23 | 21 | 24 | 24 | 25 | 24 | 25 | 26 |
| | | | 6 | 23 | 21 | died | died | died | died | died | died |
| | | | 7 | 22 | 22 | 24 | 23 | 24 | 23 | 24 | 24 |
| | | | 8 | 22 | 21 | 23 | 23 | 23 | 24 | 24 | 25 |
| | | | Mean | 21.6 | 20.4 | 22.7 | 22.6 | 23.0 | 23.0 | 23.6 | 23.6 |
| | | | SEM | 0.4 | 0.4 | 0.4 | 0.4 | 0.5 | 0.4 | 0.4 | 0.6 |
| 8 | MMAE | 0.191 mg/kg × 4 IP (Once weekly) | 1 | 20 | 18 | 22 | 22 | 24 | 22 | 24 | 24 |
| | | | 2 | 20 | 19 | 22 | 22 | 23 | 22 | 22 | 22 |
| | | | 3 | 22 | 22 | 22 | 23 | 23 | 23 | 24 | 24 |
| | | | 4 | 24 | 21 | 23 | 25 | 25 | 26 | 25 | 25 |
| | | | 5 | 22 | 20 | 23 | 24 | 24 | 24 | 25 | 24 |
| | | | 6 | 21 | died | died | died | died | died | died | died |

TABLE 8-1-continued

Body Weight, Xenograft, Gastric, NCI-N87 in Female nu/nu Mice (Day 1-Day 25)

| Gr. | Treatment | Dose (mg/kg) (Route) | No. | Day1 | Day4 | Day8 | Day11 | Day15 | Day18 | Day22 | Day25 |
|---|---|---|---|---|---|---|---|---|---|---|---|
| | | | 7 | 24 | 24 | 24 | 23 | 23 | 24 | 25 | 25 |
| | | | 8 | 22 | 19 | 19 | 19 | 22 | 22 | 24 | 24 |
| | | | Mean | 21.9 | 20.4 | 22.1 | 22.6 | 23.4 | 23.6 | 24.1 | 24.0 |
| | | | SEM | 0.5 | 0.8 | 0.6 | 0.7 | 0.4 | 0.5 | 0.4 | 0.4 |

TABLE 8-2

Body Weight, Xenograft, Gastric, NCI-N87 in Female nu/nu Mice (Day 29-Day 53)

| Gr. | Treatment | Dose (mg/kg) (Route) | No. | Day29 | Day32 | Day36 | Day39 | Day43 | Day46 | Day50 | Day 53 |
|---|---|---|---|---|---|---|---|---|---|---|---|
| 1 | Vehicle (PBS, pH 7.4) + Vehicle (25 mM Sodium Citrate, + 100 mM NaCl, pH 6.5) | 10 mL/kg × 4 (Once weekly) IP + IV | 1 | 27 | 26 | 26 | 27 | 26 | 27 | 27 | 29 |
| | | | 2 | 26 | 26 | 26 | 27 | 26 | 27 | 28 | 29 |
| | | | 3 | 26 | 27 | 27 | 27 | 27 | 27 | 28 | 28 |
| | | | 4 | 25 | 25 | 26 | 26 | 26 | 26 | 27 | 28 |
| | | | 5 | 27 | 27 | 28 | 28 | 28 | 29 | 29 | 29 |
| | | | 6 | 25 | 25 | 26 | 26 | 26 | 27 | 25 | 27 |
| | | | 7 | 25 | 26 | 26 | 27 | 26 | 26 | 26 | 27 |
| | | | 8 | 27 | 27 | 27 | 27 | 27 | 27 | 27 | 28 |
| | | | Mean | 26.0 | 26.1 | 26.5 | 26.9 | 26.5 | 27.0 | 27.1 | 28.1 |
| | | | SEM | 0.3 | 0.3 | 0.3 | 0.2 | 0.3 | 0.3 | 0.4 | 0.3 |
| 2 | ADC (OBI-999) | 1 mg/kg × 4 IV (Once weekly) | 1 | 24 | 24 | 26 | 25 | 25 | 25 | 25 | 25 |
| | | | 2 | 26 | 26 | 26 | 27 | 26 | 27 | 26 | 27 |
| | | | 3 | 24 | 24 | 25 | 26 | 26 | 26 | 26 | 26 |
| | | | 4 | 23 | 24 | 24 | 23 | 20 | 19 | died | died |
| | | | 5 | 28 | 28 | 28 | 29 | 29 | 30 | 29 | 29 |
| | | | 6 | 25 | 25 | 26 | 27 | 27 | 28 | 27 | 28 |
| | | | 7 | 25 | 25 | 26 | 26 | 25 | 26 | 26 | 28 |
| | | | 8 | 26 | 25 | 26 | 27 | 26 | 27 | 27 | 28 |
| | | | Mean | 25.1 | 25.1 | 25.9 | 26.3 | 25.5 | 26.0 | 26.6 | 27.3 |
| | | | SEM | 0.5 | 0.5 | 0.4 | 0.6 | 0.9 | 1.1 | 0.5 | 0.5 |
| 3 | ADC (OBI-999) | 3 mg/kg × 4 IV (Once weekly) | 1 | 25 | 25 | 26 | 26 | 26 | 27 | 27 | 28 |
| | | | 2 | 27 | 27 | 29 | 29 | 25 | 24 | 26 | 27 |
| | | | 3 | 24 | 24 | 25 | 26 | 26 | 27 | 26 | 27 |
| | | | 4 | 24 | 24 | 24 | 25 | 25 | 25 | 25 | 26 |
| | | | 5 | 26 | 25 | 26 | 27 | 27 | 27 | 27 | 27 |
| | | | 6 | 25 | 25 | 26 | 26 | 26 | 26 | 26 | 27 |
| | | | 7 | 26 | 26 | 25 | 24 | 23 | 21 | 18 | 17 |
| | | | 8 | 23 | 23 | 24 | 25 | 23 | 24 | 24 | 25 |
| | | | Mean | 25.0 | 24.9 | 25.6 | 26.0 | 25.1 | 25.1 | 24.9 | 25.5 |
| | | | SEM | 0.5 | 0.4 | 0.6 | 0.5 | 0.5 | 0.7 | 1.0 | 1.3 |
| 4 | ADC (OBI-999) | 10 mg/kg × 4 IV (Once weekly) | 1 | 24 | 25 | 26 | 26 | 26 | 26 | 27 | 28 |
| | | | 2 | 25 | 25 | 25 | 25 | 26 | 25 | 26 | 26 |
| | | | 3 | 24 | 25 | 25 | 26 | 26 | 26 | 26 | 26 |
| | | | 4 | 24 | 25 | 25 | 26 | 25 | 26 | 26 | 26 |
| | | | 5 | 25 | 24 | 25 | 26 | 26 | 26 | 26 | 26 |
| | | | 6 | 26 | 26 | 27 | 28 | 27 | 27 | 27 | 27 |
| | | | 7 | 23 | 24 | 25 | 25 | 24 | 26 | 25 | 25 |
| | | | 8 | 28 | 28 | 27 | 28 | 27 | 28 | 28 | 29 |
| | | | Mean | 24.9 | 25.3 | 25.6 | 26.3 | 25.9 | 26.3 | 26.4 | 26.6 |
| | | | SEM | 0.5 | 0.5 | 0.3 | 0.4 | 0.4 | 0.3 | 0.3 | 0.5 |
| 5 | OBI-888 | 10 mg/kg × 4 IV (Once weekly) | 1 | 24 | 25 | 25 | 26 | 26 | 27 | 26 | 27 |
| | | | 2 | 27 | 25 | 27 | 28 | 28 | 29 | 29 | 30 |
| | | | 3 | 23 | 23 | 24 | 26 | 25 | 26 | 25 | 27 |
| | | | 4 | 25 | 25 | 26 | 27 | 27 | 27 | 27 | 28 |
| | | | 5 | 24 | 24 | 24 | 24 | 24 | 25 | 25 | 26 |
| | | | 6 | 25 | 25 | 26 | 26 | 27 | 26 | 26 | 27 |
| | | | 7 | 23 | 23 | 23 | 24 | 24 | 25 | 25 | 26 |
| | | | 8 | 22 | 23 | 24 | 24 | 25 | 25 | 25 | 26 |
| | | | Mean | 24.1 | 24.1 | 24.9 | 25.6 | 25.8 | 26.3 | 26.0 | 27.1 |
| | | | SEM | 0.5 | 0.4 | 0.5 | 0.5 | 0.5 | 0.5 | 0.5 | 0.5 |
| 6 | Anti-CD30 ADC (OBI-910) | 3 mg/kg × 4 IV (Once weekly) | 1 | 23 | 24 | 25 | 27 | 26 | 26 | 25 | 26 |
| | | | 2 | 22 | 23 | 24 | 25 | 25 | 26 | 26 | 27 |
| | | | 3 | 25 | 25 | 25 | 26 | 26 | 27 | 27 | 28 |
| | | | 4 | 26 | 26 | 26 | 26 | 26 | 27 | 27 | 28 |
| | | | 5 | 26 | 26 | 27 | 28 | 27 | 27 | 26 | 25 |

TABLE 8-2-continued

Body Weight, Xenograft, Gastric, NCI-N87 in Female nu/nu Mice (Day 29-Day 53)

| Gr. | Treatment | Dose (mg/kg) (Route) | No. | Day29 | Day32 | Day36 | Day39 | Day43 | Day46 | Day50 | Day53 |
|---|---|---|---|---|---|---|---|---|---|---|---|
| | | | Mean | 24.4 | 24.8 | 25.4 | 26.4 | 26.0 | 26.6 | 26.2 | 26.8 |
| | | | SEM | 0.8 | 0.6 | 0.5 | 0.5 | 0.3 | 0.2 | 0.4 | 0.6 |
| 7 | MMAE + OBI-888 | 0.191 mg/kg × 4 IP (Once weekly) + 10 mg/kg × 4 IV (Once weekly) | 1 | 24 | 24 | 24 | 26 | 26 | 26 | 26 | 27 |
| | | | 2 | 23 | 23 | 24 | 24 | 24 | 24 | 24 | 25 |
| | | | 3 | 23 | 23 | 23 | 24 | 22 | 23 | 23 | 25 |
| | | | 4 | 24 | 24 | 25 | 25 | 24 | 25 | 24 | 25 |
| | | | 5 | 28 | 27 | 27 | 29 | 28 | 29 | 29 | 30 |
| | | | 6 | died | died | died | died | died | died | died | died |
| | | | 7 | 25 | 25 | 26 | 26 | 25 | 26 | 25 | 26 |
| | | | 8 | 25 | 24 | 25 | 26 | 25 | 26 | 26 | 27 |
| | | | Mean | 24.6 | 24.3 | 24.9 | 25.7 | 24.9 | 25.6 | 25.3 | 26.4 |
| | | | SEM | 0.6 | 0.5 | 0.5 | 0.6 | 0.7 | 0.7 | 0.7 | 0.7 |
| 8 | MMAE | 0.191 mg/kg × 4 IP (Once weekly) | 1 | 25 | 25 | 26 | 26 | 26 | 26 | 26 | 27 |
| | | | 2 | 24 | 23 | 24 | 24 | 24 | 25 | 24 | 24 |
| | | | 3 | 25 | 24 | 25 | 26 | 26 | 27 | 26 | 27 |
| | | | 4 | 26 | 27 | 25 | 26 | 26 | 27 | 26 | 27 |
| | | | 5 | 26 | 26 | 26 | 26 | 26 | 27 | 27 | 27 |
| | | | 6 | died | died | died | died | died | died | died | died |
| | | | 7 | 25 | 26 | 25 | 26 | 26 | 26 | 26 | 26 |
| | | | 8 | 26 | 25 | 25 | 26 | 26 | 26 | 27 | 28 |
| | | | Mean | 25.3 | 25.1 | 25.1 | 25.7 | 25.7 | 26.3 | 26.0 | 26.6 |
| | | | SEM | 0.3 | 0.5 | 0.3 | 0.3 | 0.3 | 0.3 | 0.4 | 0.5 |

TABLE 8-3

Body Weight, Xenograft, Gastric, NCI-N87 in Female nu/nu Mice (Day 57-Day 85)

| Gr. | Treatment | Dose (mg/kg) (Route) | No. | Day57 | Day60 | Day64 | Day67 | Day70 | Day74 | Day78 | Day81 | Day85 |
|---|---|---|---|---|---|---|---|---|---|---|---|---|
| 1 | Vehicle (PBS, pH 7.4) + Vehicle (25 mM Sodium Citrate, + 100 mM NaCl, pH 6.5) | 10 mL/kg 4 (Once weekly) IP + IV | 1 | NA | NA | NA | NA | NA | NA | NA | NA | NA |
| | | | 2 | NA | NA | NA | NA | NA | NA | NA | NA | NA |
| | | | 3 | NA | NA | NA | NA | NA | NA | NA | NA | NA |
| | | | 4 | NA | NA | NA | NA | NA | NA | NA | NA | NA |
| | | | 5 | NA | NA | NA | NA | NA | NA | NA | NA | NA |
| | | | 6 | NA | NA | NA | NA | NA | NA | NA | NA | NA |
| | | | 7 | NA | NA | NA | NA | NA | NA | NA | NA | NA |
| | | | 8 | NA | NA | NA | NA | NA | NA | NA | NA | NA |
| | | | Mean | — | — | — | — | — | — | — | — | — |
| | | | SEM | — | — | — | — | — | — | — | — | — |
| 2 | ADC (OBI-999) | 1 mg/kg × 4 IV (Once weekly) | 1 | 25 | 25 | 26 | 26 | 26 | 26 | 26 | 26 | 27 |
| | | | 2 | 27 | 28 | 28 | 28 | 28 | 28 | 28 | 28 | 29 |
| | | | 3 | 27 | 27 | 27 | 27 | 28 | 28 | 28 | 29 | 30 |
| | | | 4 | died | died | died | died | died | died | died | died | died |
| | | | 5 | 29 | 28 | 28 | 30 | 28 | 29 | 28 | 28 | 29 |
| | | | 6 | 28 | 28 | 28 | 28 | 28 | 30 | 29 | 29 | 30 |
| | | | 7 | 27 | 26 | 25 | 26 | 25 | 27 | 29 | 28 | 27 |
| | | | 8 | 28 | 28 | 28 | 29 | 28 | 28 | 29 | 29 | 30 |
| | | | Mean | 27.3 | 27.1 | 27.1 | 27.7 | 27.1 | 28.0 | 28.1 | 28.1 | 28.9 |
| | | | SEM | 0.5 | 0.5 | 0.5 | 0.6 | 0.5 | 0.5 | 0.4 | 0.4 | 0.5 |
| 3 | ADC (OBI-999) | 3 mg/kg × 4 IV (Once weekly) | 1 | 27 | 28 | 27 | 27 | 28 | 28 | 28 | 28 | 28 |
| | | | 2 | 27 | 28 | 29 | 29 | 29 | 29 | 30 | 31 | 31 |
| | | | 3 | 26 | 27 | 27 | 27 | 27 | 28 | 27 | 27 | 27 |
| | | | 4 | 26 | 26 | 26 | 26 | 26 | 26 | 27 | 26 | 27 |
| | | | 5 | 27 | 27 | 27 | 27 | 27 | 27 | 27 | 27 | 28 |
| | | | 6 | 26 | 27 | 26 | 26 | 26 | 27 | 27 | 27 | 28 |
| | | | 7 | died | died | died | died | died | died | died | died | died |
| | | | 8 | 25 | 26 | 25 | 26 | 25 | 26 | 26 | 26 | 26 |
| | | | Mean | 26.3 | 27.0 | 26.7 | 26.9 | 26.9 | 27.3 | 27.4 | 27.4 | 27.9 |
| | | | SEM | 0.3 | 0.3 | 0.5 | 0.4 | 0.5 | 0.4 | 0.5 | 0.6 | 0.6 |
| 4 | ADC (OBI-999) | 10 mg/kg × 4 IV (Once weekly) | 1 | 27 | 28 | 28 | 29 | 28 | 29 | 29 | 28 | 29 |
| | | | 2 | 27 | 27 | 28 | 28 | 28 | 28 | 27 | 28 | 26 |
| | | | 3 | 26 | 28 | 27 | 27 | 28 | 26 | 26 | 25 | 26 |
| | | | 4 | 27 | 25 | 26 | 28 | 27 | 27 | 28 | 27 | 28 |
| | | | 5 | 27 | 27 | 26 | 27 | 27 | 27 | 26 | 27 | 27 |
| | | | 6 | 28 | 28 | 28 | 28 | 27 | 27 | 26 | 25 | 26 |
| | | | 7 | 24 | 24 | 22 | 22 | 21 | 19 | 19 | 19 | 15 |
| | | | 8 | 28 | 29 | 28 | 28 | 28 | 29 | 28 | 27 | 28 |

TABLE 8-3-continued

Body Weight, Xenograft, Gastric, NCI-N87 in Female nu/nu Mice (Day 57-Day 85)

| Gr. | Treatment | Dose (mg/kg) (Route) | No. | Day57 | Day60 | Day64 | Day67 | Day70 | Day74 | Day78 | Day81 | Day85 |
|---|---|---|---|---|---|---|---|---|---|---|---|---|
| | | | Mean | 26.8 | 27.0 | 26.6 | 27.1 | 26.8 | 26.5 | 26.1 | 25.6 | 25.6 |
| | | | SEM | 0.5 | 0.6 | 0.7 | 0.8 | 0.8 | 1.1 | 1.1 | 1.0 | 1.6 |
| 5 | OBI-888 | 10 mg/kg × 4 IV (Once weekly) | 1 | 27 | 28 | 27 | 28 | 27 | NA | NA | NA | NA |
| | | | 2 | 29 | 30 | 30 | 30 | 30 | NA | NA | NA | NA |
| | | | 3 | 26 | 26 | 26 | 27 | 28 | NA | NA | NA | NA |
| | | | 4 | 27 | 28 | 27 | 28 | 28 | NA | NA | NA | NA |
| | | | 5 | 25 | 26 | 26 | 26 | 26 | NA | NA | NA | NA |
| | | | 6 | 26 | 26 | 27 | 27 | 27 | NA | NA | NA | NA |
| | | | 7 | 26 | 26 | 26 | 27 | 26 | NA | NA | NA | NA |
| | | | 8 | 26 | 26 | 26 | 26 | 26 | NA | NA | NA | NA |
| | | | Mean | 26.5 | 27.0 | 26.9 | 27.4 | 27.3 | — | — | — | — |
| | | | SEM | 0.4 | 0.5 | 0.5 | 0.5 | 0.5 | — | — | — | — |
| 6 | Anti-CD30 ADC (OBI-910) | 3 mg/kg × 4 IV (Once weekly) | 1 | 25 | 27 | 27 | 27 | 27 | 27 | 27 | 27 | 27 |
| | | | 2 | 26 | 28 | 27 | 28 | 28 | 28 | 29 | 29 | 29 |
| | | | 3 | 26 | 27 | 27 | 28 | 27 | 27 | 27 | 27 | 27 |
| | | | 4 | 27 | 28 | 29 | 29 | 30 | 29 | 30 | 29 | 31 |
| | | | 5 | 24 | 25 | 25 | 25 | 25 | 24 | 26 | 26 | 26 |
| | | | Mean | 25.6 | 27.0 | 27.0 | 27.4 | 27.4 | 27.0 | 27.8 | 27.6 | 28.0 |
| | | | SEM | 0.5 | 0.5 | 0.6 | 0.7 | 0.8 | 0.8 | 0.7 | 0.6 | 0.9 |
| 7 | MMAE + OBI-888 | 0.191 mg/kg × 4 IP (Once weekly) + 10 mg/kg × 4 IV (Once weekly) | 1 | 27 | 27 | 27 | 28 | 28 | 28 | 28 | 28 | 29 |
| | | | 2 | 25 | 25 | 25 | 26 | 25 | 24 | 24 | 24 | 25 |
| | | | 3 | 24 | 25 | 26 | 26 | 25 | 25 | 25 | 24 | 24 |
| | | | 4 | 24 | 25 | 24 | 25 | 23 | 24 | 24 | 24 | 25 |
| | | | 5 | 30 | 30 | 30 | 31 | 30 | 31 | 32 | 31 | 32 |
| | | | 6 | died | died | died | died | died | died | died | died | died |
| | | | 7 | 26 | 26 | 26 | 26 | 26 | 26 | 26 | 26 | 26 |
| | | | 8 | 26 | 27 | 27 | 27 | 26 | 27 | 27 | 27 | 26 |
| | | | Mean | 26.0 | 26.4 | 26.4 | 27.0 | 26.1 | 26.4 | 26.6 | 26.3 | 26.7 |
| | | | SEM | 0.8 | 0.7 | 0.7 | 0.8 | 0.9 | 0.9 | 1.1 | 1.0 | 1.1 |
| 8 | MMAE | 0.191 mg/kg × 4 IP (Once weekly) | 1 | 27 | 27 | 27 | 27 | 26 | 27 | 28 | 28 | 27 |
| | | | 2 | 24 | 25 | 24 | 25 | 25 | 24 | 25 | 25 | 25 |
| | | | 3 | 27 | 28 | 28 | 28 | 27 | 28 | 28 | 28 | 28 |
| | | | 4 | 27 | 26 | 27 | 28 | 27 | 28 | 28 | 28 | 29 |
| | | | 5 | 27 | 28 | 27 | 28 | 27 | 28 | 28 | 27 | 28 |
| | | | 6 | died | died | died | died | died | died | died | died | died |
| | | | 7 | 26 | 27 | 27 | 27 | 26 | 24 | 25 | 24 | 23 |
| | | | 8 | 27 | 27 | 27 | 28 | 27 | 27 | 29 | 28 | 28 |
| | | | Mean | 26.4 | 26.9 | 26.7 | 27.3 | 26.4 | 26.6 | 27.3 | 26.9 | 26.9 |
| | | | SEM | 0.4 | 0.4 | 0.5 | 0.4 | 0.3 | 0.7 | 0.6 | 0.6 | 0.8 |

TABLE 8-4

Body Weight, Xenograft, Gastric, NCI-N87 in Female nu/nu Mice (Day 88-Day 100)

| Gr. | Treatment | Dose (mg/kg) (Route) | No. | Day88 | Day91 | Day95 | Day98 | Day100 |
|---|---|---|---|---|---|---|---|---|
| 1 | Vehicle (PBS, pH 7.4) + Vehicle (25 mM Sodium Citrate, + 100 mM NaCl, pH 6.5) | 10 mL/kg × 4 (Once weekly) IP + IV (Once weekly) | 1 | NA | NA | NA | NA | NA |
| | | | 2 | NA | NA | NA | NA | NA |
| | | | 3 | NA | NA | NA | NA | NA |
| | | | 4 | NA | NA | NA | NA | NA |
| | | | 5 | NA | NA | NA | NA | NA |
| | | | 6 | NA | NA | NA | NA | NA |
| | | | 7 | NA | NA | NA | NA | NA |
| | | | 8 | NA | NA | NA | NA | NA |
| | | | Mean | — | — | — | — | — |
| | | | SEM | — | — | — | — | — |
| 2 | ADC (OBI-999) | 1 mg/kg × 4 IV (Once weekly) | 1 | 27 | 26 | 27 | 27 | 28 |
| | | | 2 | 29 | 28 | 28 | 29 | 29 |
| | | | 3 | 29 | 29 | 29 | 29 | 30 |
| | | | 4 | died | died | died | died | died |
| | | | 5 | 29 | 29 | 30 | 29 | 29 |
| | | | 6 | 30 | 29 | 30 | 29 | 30 |
| | | | 7 | 26 | 26 | 26 | 26 | 27 |
| | | | 8 | 30 | 29 | 30 | 30 | 31 |
| | | | Mean | 28.6 | 28.0 | 28.6 | 28.4 | 29.1 |
| | | | SEM | 0.6 | 0.5 | 0.6 | 0.5 | 0.5 |

TABLE 8-4-continued

Body Weight, Xenograft, Gastric, NCI-N87 in Female nu/nu Mice (Day 88-Day 100)

| Gr. | Treatment | Dose (mg/kg) (Route) | No. | Day88 | Day91 | Day95 | Day98 | Day100 |
|---|---|---|---|---|---|---|---|---|
| 3 | ADC (OBI-999) | 3 mg/kg × 4 IV (Once weekly) | 1 | 29 | 29 | 28 | 29 | 29 |
| | | | 2 | 31 | 31 | 31 | 31 | 31 |
| | | | 3 | 28 | 28 | 28 | 28 | 28 |
| | | | 4 | 27 | 27 | 27 | 27 | 28 |
| | | | 5 | 27 | 28 | 28 | 27 | 29 |
| | | | 6 | 27 | 27 | 28 | 27 | 28 |
| | | | 7 | died | died | died | died | died |
| | | | 8 | 26 | 26 | 27 | 26 | 26 |
| | | | Mean | 27.9 | 28.0 | 28.1 | 27.9 | 28.4 |
| | | | SEM | 0.6 | 0.6 | 0.5 | 0.6 | 0.6 |
| 4 | ADC (OBI-999) | 10 mg/kg × 4 IV (Once weekly) | 1 | 28 | 28 | 28 | 29 | 29 |
| | | | 2 | 27 | 28 | 28 | 28 | 29 |
| | | | 3 | 26 | 25 | 26 | 25 | 25 |
| | | | 4 | 28 | 27 | 27 | 27 | 28 |
| | | | 5 | 26 | 25 | 25 | 23 | 23 |
| | | | 6 | 26 | 26 | 28 | 29 | 30 |
| | | | 7 | NA | NA | NA | NA | NA |
| | | | 8 | 27 | 27 | 27 | 26 | 26 |
| | | | Mean | 26.9 | 26.6 | 27.0 | 26.7 | 27.1 |
| | | | SEM | 0.3 | 0.5 | 0.4 | 0.8 | 1.0 |
| 5 | OBI-888 | 10 mg/kg × 4 IV (Once weekly) | 1 | NA | NA | NA | NA | NA |
| | | | 2 | NA | NA | NA | NA | NA |
| | | | 3 | NA | NA | NA | NA | NA |
| | | | 4 | NA | NA | NA | NA | NA |
| | | | 5 | NA | NA | NA | NA | NA |
| | | | 6 | NA | NA | NA | NA | NA |
| | | | 7 | NA | NA | NA | NA | NA |
| | | | 8 | NA | NA | NA | NA | NA |
| | | | Mean | — | — | — | — | — |
| | | | SEM | — | — | — | — | — |
| 6 | Anti-CD30 ADC (OBI-910) | 3 mg/kg × 4 IV (Once weekly) | 1 | 27 | 27 | 27 | 27 | 28 |
| | | | 2 | 29 | 29 | 30 | 30 | 30 |
| | | | 3 | 26 | 25 | 25 | 25 | 25 |
| | | | 4 | 31 | 31 | 31 | 30 | 32 |
| | | | 5 | 26 | 25 | 25 | 25 | 25 |
| | | | Mean | 27.8 | 27.4 | 27.6 | 27.4 | 28.0 |
| | | | SEM | 1.0 | 1.2 | 1.2 | 1.1 | 1.4 |
| 7 | MMAE + OBI-888 | 0.191 mg/kg × 4 IP (Once weekly) + 10 mg/kg × 4 IV (Once weekly) | 1 | 29 | 28 | 29 | 29 | 30 |
| | | | 2 | 26 | 26 | 26 | 25 | 25 |
| | | | 3 | 24 | 23 | 22 | 21 | 21 |
| | | | 4 | 26 | 25 | 25 | 26 | 25 |
| | | | 5 | 32 | 32 | 33 | 32 | 33 |
| | | | 6 | died | died | died | died | died |
| | | | 7 | 25 | 25 | 25 | 24 | 24 |
| | | | 8 | 27 | 25 | 26 | 25 | 25 |
| | | | Mean | 27.0 | 26.3 | 26.6 | 26.0 | 26.1 |
| | | | SEM | 1.0 | 1.1 | 1.3 | 1.3 | 1.5 |
| 8 | MMAE | 0.191 mg/kg × 4 IP (Once weekly) | 1 | 28 | 28 | 28 | 29 | 28 |
| | | | 2 | 25 | 26 | 26 | 27 | 27 |
| | | | 3 | 29 | 29 | 29 | 29 | 30 |
| | | | 4 | 29 | 29 | 29 | 29 | 29 |
| | | | 5 | 28 | 28 | 29 | 29 | 30 |
| | | | 6 | died | died | died | died | died |
| | | | 7 | 23 | 23 | 22 | 22 | 22 |
| | | | 8 | 28 | 28 | 29 | 28 | 29 |
| | | | Mean | 27.1 | 27.3 | 27.4 | 27.6 | 27.9 |
| | | | SEM | 0.9 | 0.8 | 1.0 | 1.0 | 1.1 |

Figure 17:
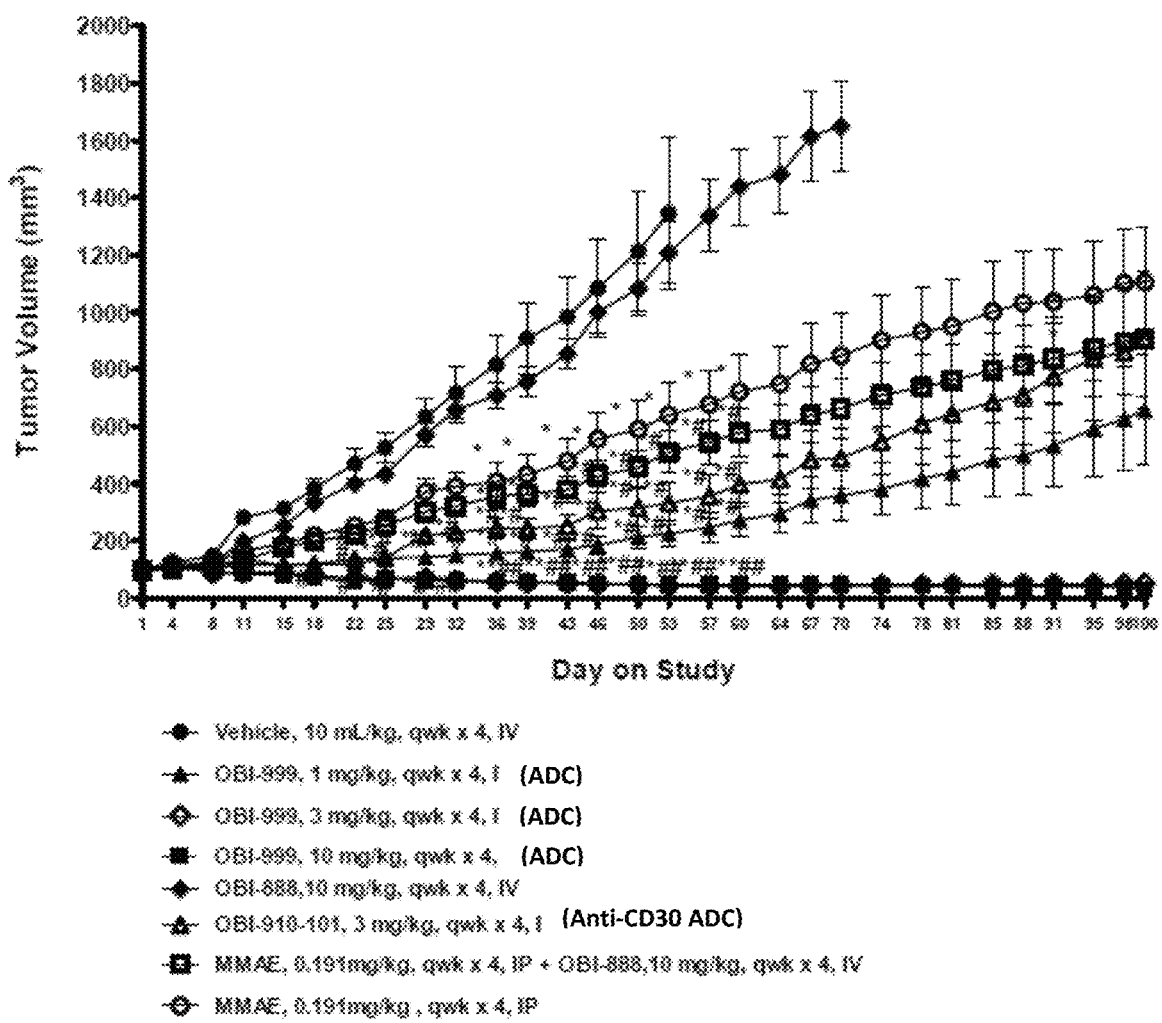
FIG. 17 showed tumor growth curves in NCI-N87 implanted female nude (nu/nu) mice. Vehicle and test substances were administered as detailed in the study design. T/C value ≤42% was considered significant anti-tumor activity (#) compared to the vehicle group. Two-way ANOVA followed by Bonferroni post-tests were applied for comparison between the vehicle and test substance-treated groups. Differences are considered significant at *p<0.05.

FIG. 17 showed the tumor growth curves in NCI-H526 implanted female nude (nu/nu) mice. Intravenous administration of ADC (OBI-999) at 1 mg/kg, exhibited robust anti-tumor activity over the course of the study compared to the vehicle control group. Significant anti-tumor activity (T/C value ≤42%) was achieved starting on Day 15 and continuing through to Day 53 with a maximum percent TGI of 83% on Day 53. Intravenous administration of ADC (OBI-999) at 3 mg/kg, exhibited robust anti-tumor activity over the course of the study compared to the vehicle control group. Significant anti-tumor activity (T/C value ≤42%) was achieved starting on Day 11 and continuing through to Day 53 with a maximum percent TGI of 97% on Day 53. Intravenous administration of ADC (OBI-999) at 10 mg/kg, exhibited robust anti-tumor activity over the course of the study compared to the vehicle control group. Significant anti-tumor activity (T/C value ≤42%) was achieved starting on Day 11 and continuing through to Day 53 with a maximum percent TGI of 97% on Day 53.

Weekly intravenous (IV) administration of OBI-888 at 10 mg/kg, exhibited modest anti-tumor activity over the course of the study compared to the vehicle control group (FIG. 17).

Weekly intravenous (IV) administration of test substance, Anti-CD30 ADC (OBI-910) at 10 mg/kg, exhibited robust anti-tumor activity over the course of the study compared to the vehicle control group. Significant anti-tumor activity (T/C value ≤42%) was achieved starting on Day 11 and continuing through to Day 53 with a maximum percent TGI of 75% on Day 53 (FIG. 17).

Weekly intraperitoneal (IP) administration of standard agent, MMAE at 0.191 mg/kg, exhibited moderate anti-tumor activity over the course of the study compared to the vehicle control group with a maximum percent TGI of 53% on Day 53 (FIG. 17).

Combination therapy of test substance OBI-888 at 10 mg/kg with standard agent MMAE at 0.191 mg/kg was associated with significant inhibition of tumor growth over the course of the study compared to the vehicle control group. Significant anti-tumor activity (T/C value ≤42%) was achieved starting on Day 11 and continuing through to Day 53 with a maximum percent TGI of 62% on Day 53 (FIG. 17).

Figure 18:
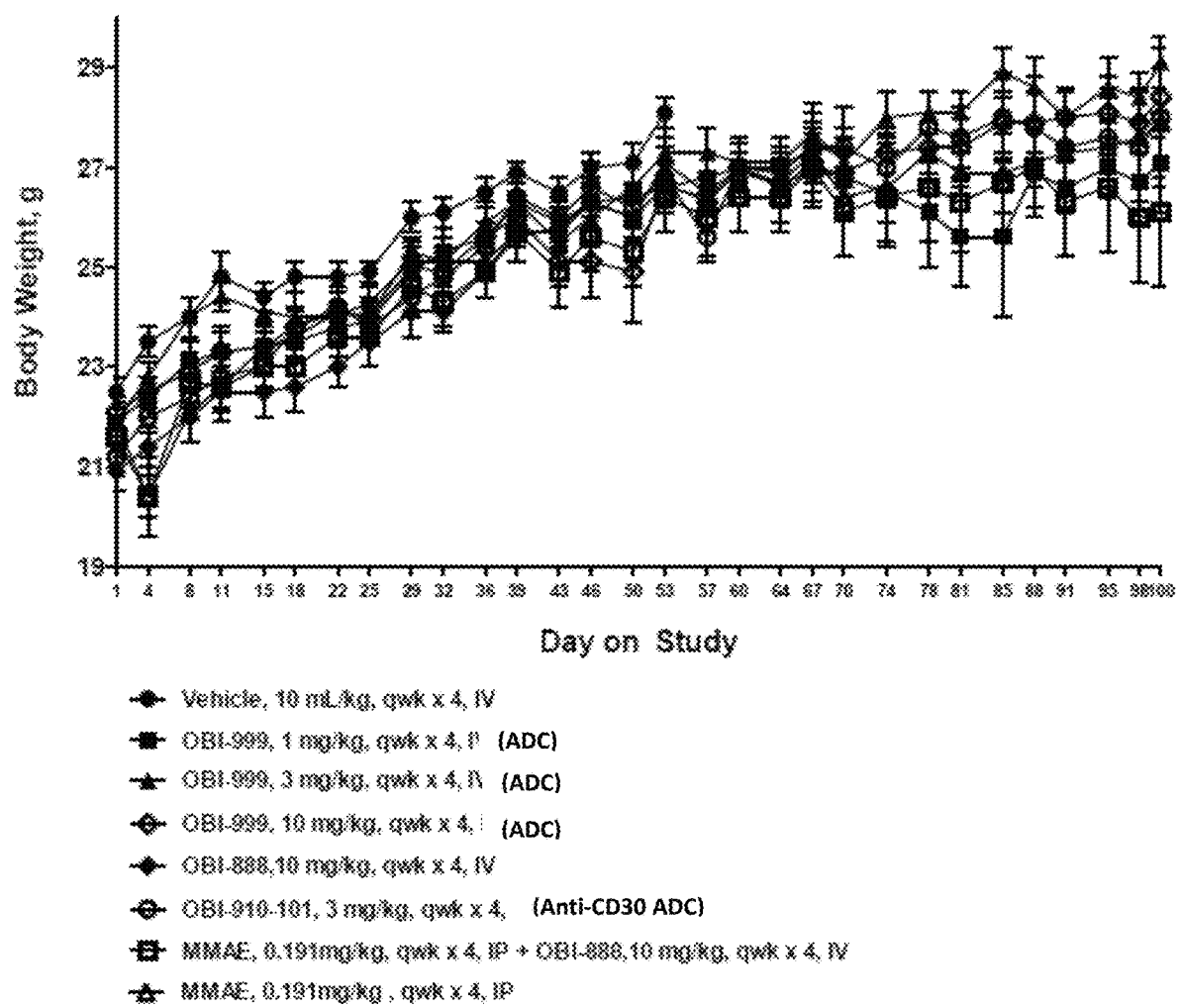
FIG. 18 showed body weight changes in NCI-N87 implanted female nude (nu/nu) mice. Vehicle and test substances were administered as detailed in the study design. The body weights were measured and recorded twice weekly until Day 100.
Figure 19:
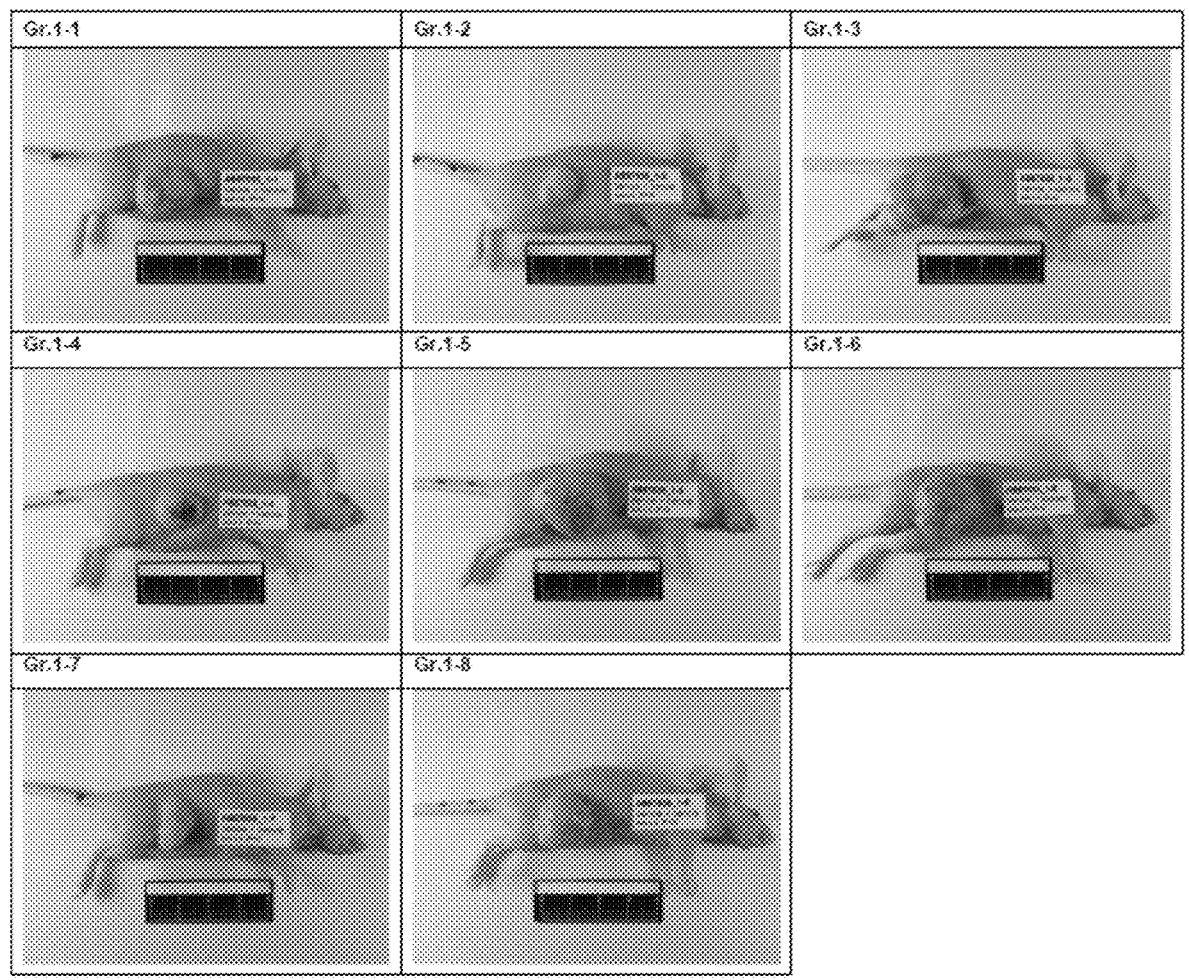
FIG. 19 showed pictures of female (nu/nu) nude mice with NCI-N87 implanted tumors after treatment with Vehicle (25 mM Sodium Citrate, pH 6.5+100 mM NaCl) 10 mL/kg, IV, once weekly×4 weeks+Vehicle (PBS, pH 7.4) 10 mL/kg, IP, once weekly×4 weeks.
Figure 20:
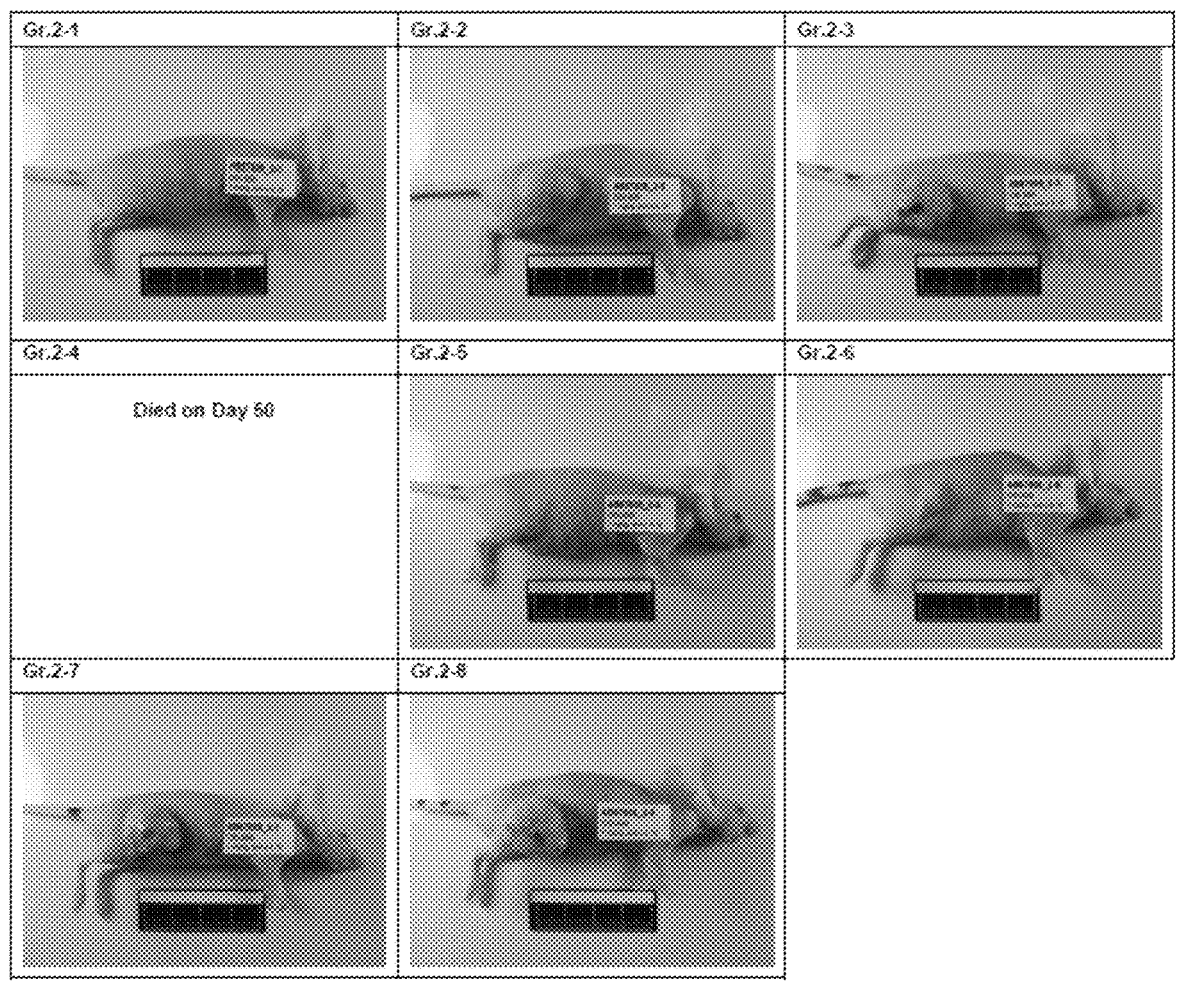
FIG. 20 showed pictures of female (nu/nu) nude mice with NCI-N87 implanted tumors after treatment with ADC (OBI-999) 1 mg/kg, IV, once weekly×4 weeks.
Figure 21:
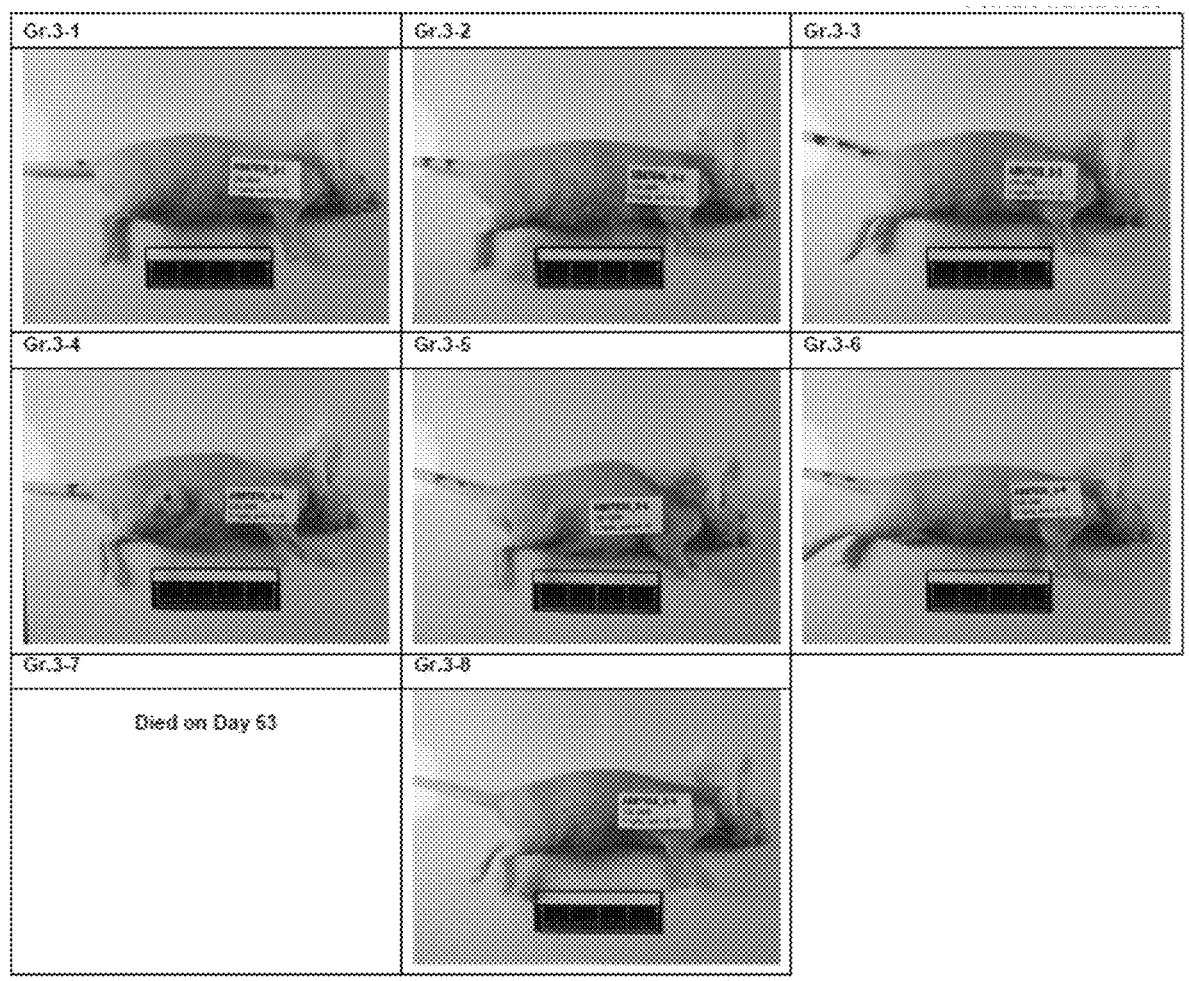
FIG. 21 showed pictures of female (nu/nu) nude mice with NCI-N87 implanted tumors after treatment with ADC (OBI-999) 3 mg/kg, IV, once weekly×4 weeks.
Figure 22:
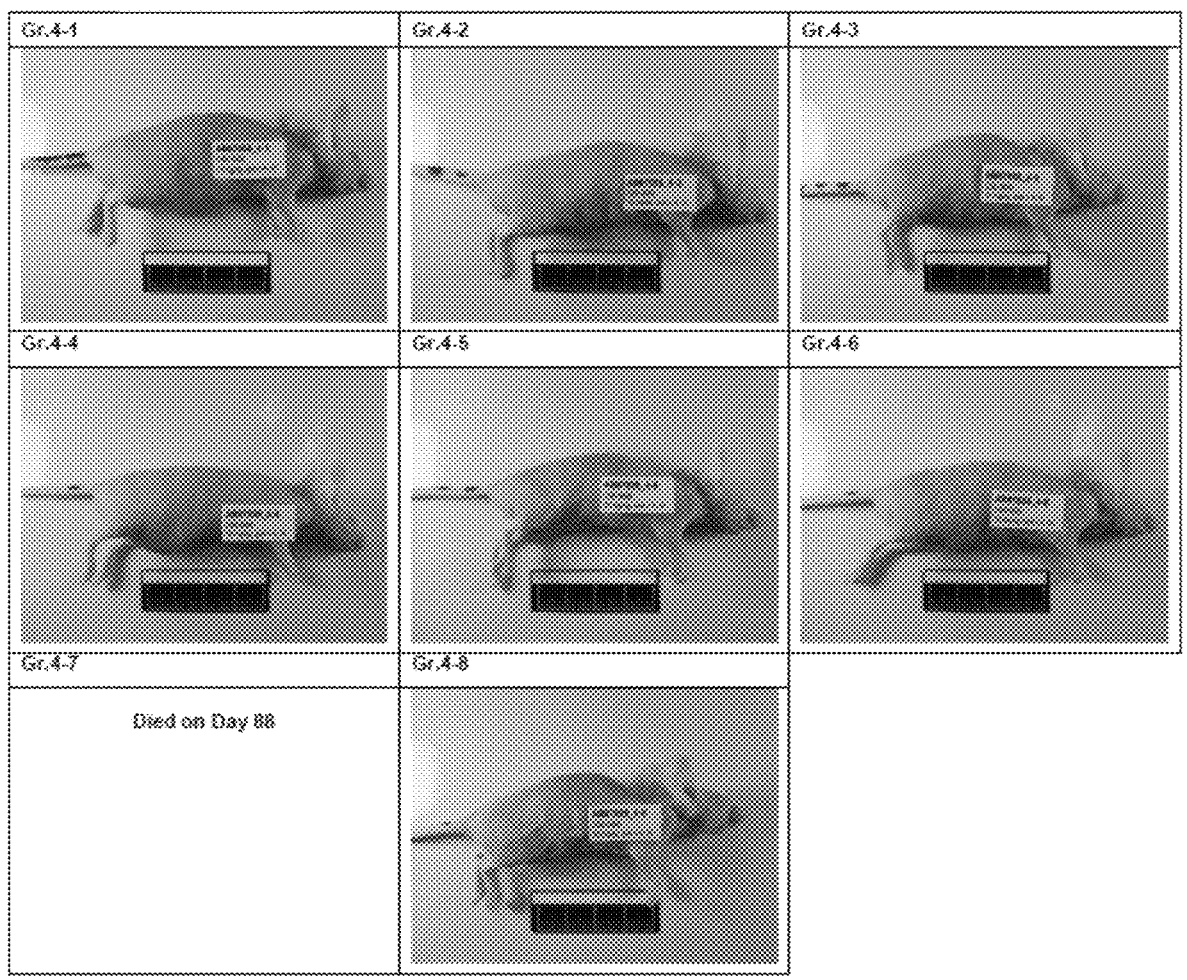
FIG. 22 showed pictures of female (nu/nu) nude mice with NCI-N87 implanted tumors after treatment with ADC (OBI-999) 10 mg/kg, IV, once weekly×4 weeks.
Figure 23:
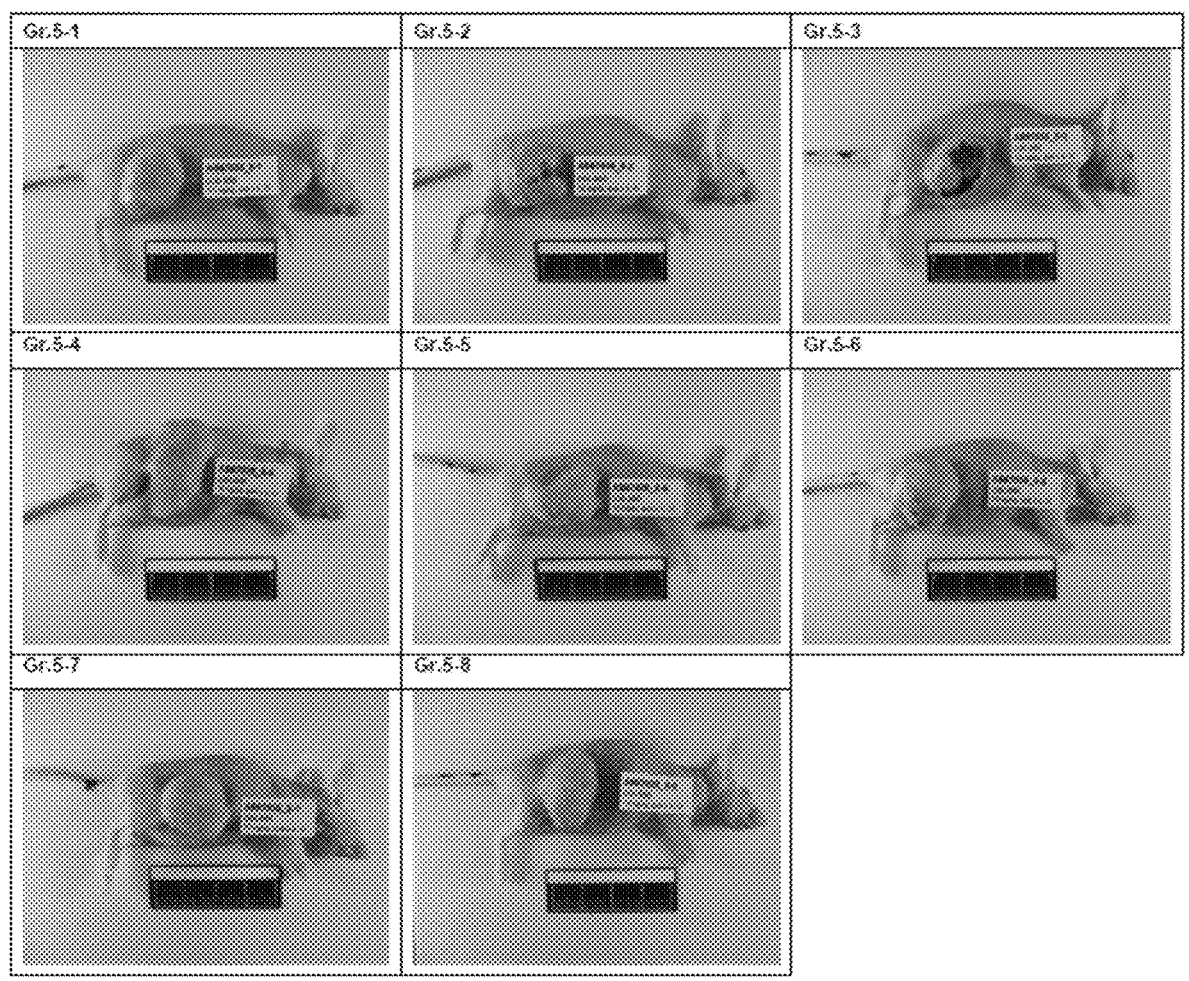
FIG. 23 showed pictures of female (nu/nu) nude mice with NCI-N87 implanted tumors after treatment with OBI-888 10 mg/kg, IV, once weekly×4 weeks.
Figure 24:
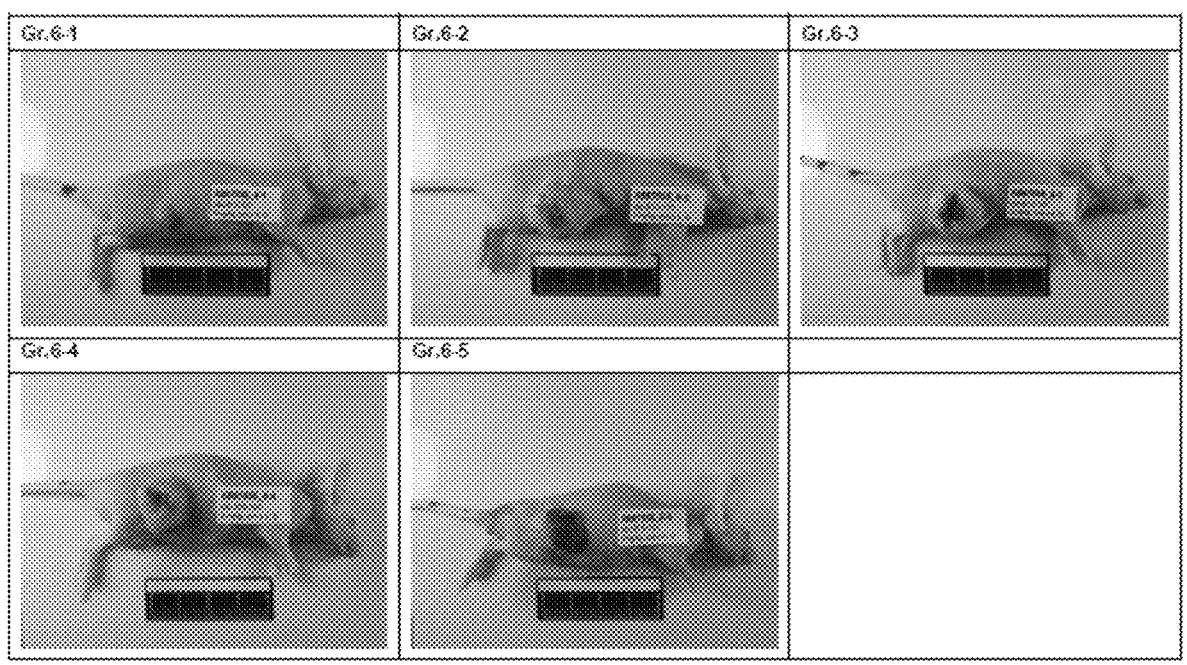
FIG. 24 showed pictures of female (nu/nu) nude mice with NCI-N87 implanted tumors after treatment with OBI-910 (Anti-CD30 ADC) 3 mg/kg, IV, once weekly×4 weeks.
Figure 25:
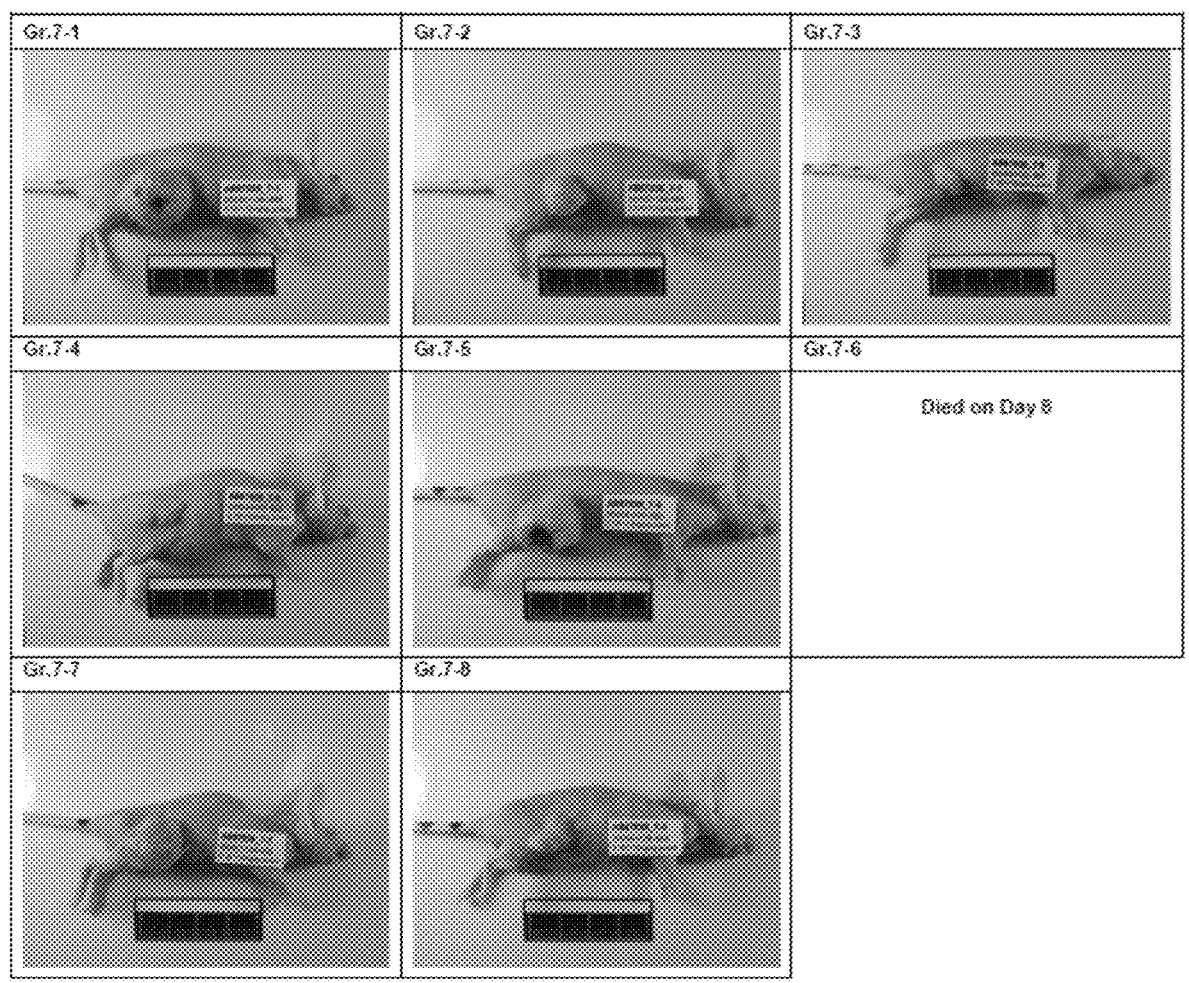
FIG. 25 showed pictures of female (nu/nu) nude mice with NCI-N87 implanted tumors after treatment with MMAE 0.191 mg/kg, IP, once weekly×4 weeks+OBI-888 10 mg/kg, IV, once weekly×4 weeks.
Figure 26:
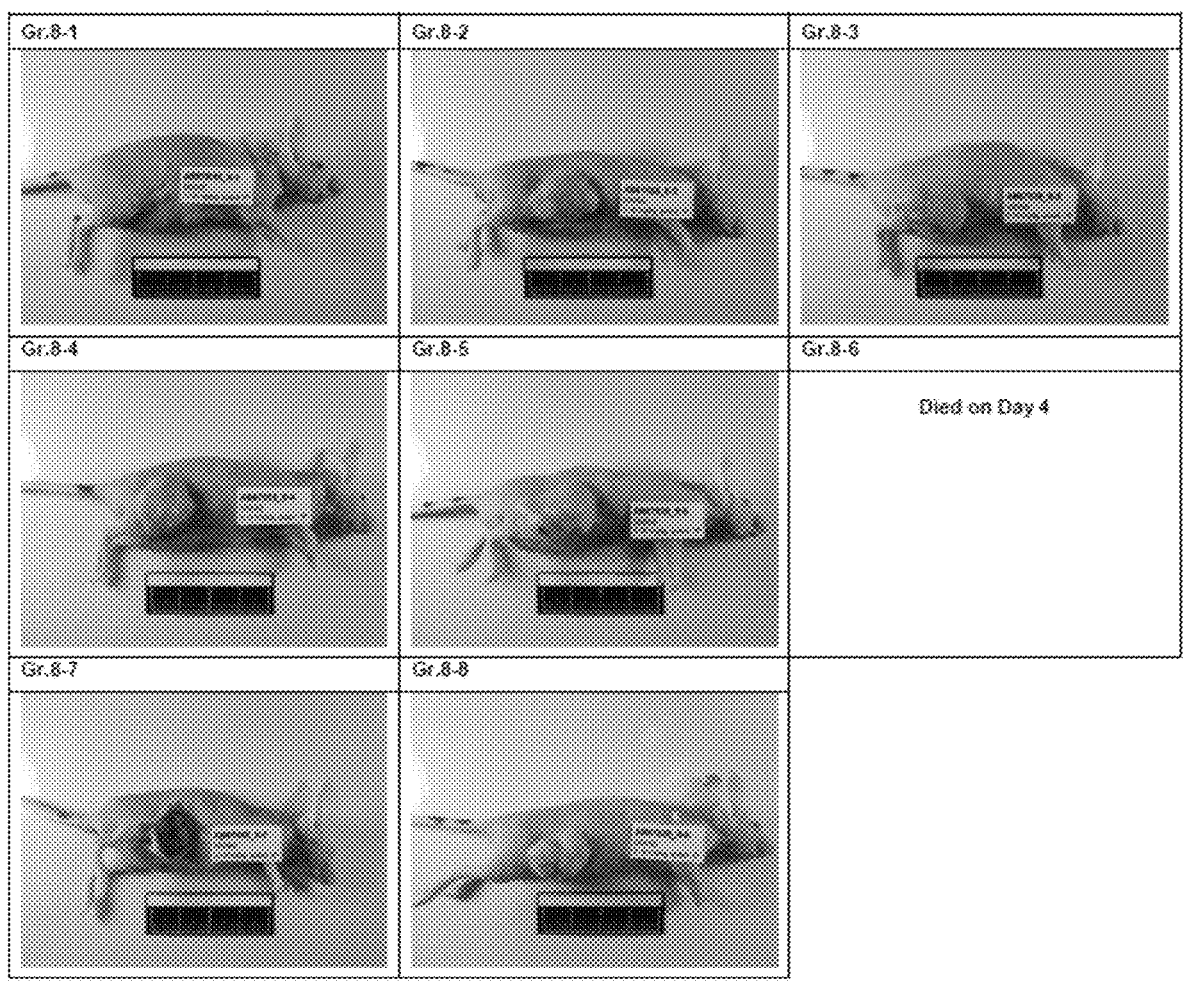
FIG. 26 showed pictures of female (nu/nu) nude mice with NCI-N87 implanted tumors after treatment with MMAE 0.191 mg/kg, IP, once weekly×4 weeks.

FIG. 18 showed the body weight changes in NCI-H526 implanted female nude (nu/nu) mice. All test substances were well-tolerated and not associated with any significant body weight loss over the course of the study.

Example 5: Measurement of the Anti-Tumor Activity of the Exemplary Antibody in Nude Mice (Lung Cancer)

In a xenograft tumor model of human small cell lung cancer, viable NCI-H526 stage E carcinoma; variant small cell lung cancer cells (ATCC CRL-5811), were subcutaneously (SC) implanted ($1\times10^6$ cells with matrigel (1:0.8) in 0.2 mL/mouse) into the right flank of female nu/nu mice. Tumor implanted mice were divided into five treatment groups, each group containing eight animals, and test agent administrations were initiated one day after cell implantation (denoted as Day 1).

5.1 Test Substances and Dosing Pattern

Test substances ADC (OBI-999), OBI-888, and corresponding vehicle were formulated by diluting stock with a 25 mM sodium citrate, 100 mM NaCl buffer (pH 6.5) and administered intravenously (IV) once weekly for four weeks. Standard agent, MMAE antibody at 0.191 mg/kg, and corresponding vehicle (PBS pH 7.4) were administered intraperitoneally (IP) once weekly for four weeks. One treatment group received combination therapy of test substance, OBI-888 at 10 mg/kg, with MMAE at 0.191 mg/kg.

TABLE 9

Study Design for Anti-Tumor Activity of the exemplary antibody in Nude Mice (Lung cancer)

| Group | Test Compound | Route | Dosage mL/kg | Dosage mg/kg | Mice[c,d] (nu/nu) (female) |
|---|---|---|---|---|---|
| 1 | Vehicle[a] + Vehicle[b] | IP + IV | 10 | N/A | 8 |
| 2 | ADC (OBI-999)[b] | IV | 10 | 10 | 8 |
| 3 | OBI-888[b] | IV | 10 | 10 | 8 |
| 4 | MMAE[a] + OBI-888[b] | IP + IV | 10 | 0.191 + 10 | 8 |
| 5 | MMAE[a] | IP | 10 | 0.191 | 8 |

[a]PBS, pH 7.4 (high concentration of MMAE will be stored in 100% DMSO and then is diluted with PBS, pH 7.4)
[b]25 mM Sodium Citrate + 100 mM NaCl, pH 6.5
[c]Vehicle and test substances are administered once weekly for four weeks starting one day after tumor cell implantation (denoted as Day 1).
[d]NCI-H526 at $1 \times 10^6$ cells/mouse with matrigel (1:0.8) in 200 μL are injected subcutaneously into right flank of female nu/nu mice.
Tumor size/body weight monitoring: twice weekly till Day 70 or the study is terminated when mean tumor volume in the vehicle control group reaches 2000 mm³. Pictures are required to be taken at sacrifice.

5.2 Cell Line

The NCI-H526 tumor cell line was purchased from American Type Culture Collection (ATCC CRL-5811, variant small cell lung carcinoma) and cultured in Eurofins Panlabs Taiwan, Ltd. The cells were cultured in RPMI-1640 medium containing 10% fetal bovine serum (FBS) at 37° C. in 5% $CO_2$ incubator and implanted subcutaneously in the right flank of each mouse.

5.3 Animals

Female nu/nu nude, aged 6-7 weeks, were obtained from BioLasco Taiwan (under Charles River Laboratories Licensee) and used. The animals were housed in individually ventilated cages (IVC, 36 Mini Isolator system). The allocation for 5 animals was 27×20×14 in cm. All animals were maintained in a hygienic environment under controlled temperature (20-24° C.) and humidity (30-70%) with 12-hour light/dark cycle. Free access to standard lab diet [MFG (Oriental Yeast Co., Ltd., Japan)] and autoclaved tap water were granted. All aspects of this work including housing, experimentation, and animal disposal were performed in general accordance with the "Guide for the Care and Use of Laboratory Animals: Eighth Edition" (National Academies Press, Washington, D.C., 2011) in our AAALAC-accredited laboratory animal facility. In addition, the animal care and use protocol was reviewed and approved by the IACUC at Eurofins Panlabs Taiwan, Ltd.

5.4 Chemicals

Fetal bovine serum (Hyclone, USA), RPMI-1640 medium (ThermoFisher, USA) and Matrigel (Corning, USA) were used in this experiment.

5.5 Equipment

Calipers (Mitutoyo, Japan), Centrifuge 5810R (Eppendorf, Germany), $CO_2$ Incubator (Forma Scientific Inc., USA), Hematocytometer (Hausser Scientific Horsham, USA), Individually ventilated cages racks (36 Mini Isolator system, Tecniplast, Italy), Inverted microscope CK-40 (Olympus, Japan), System microscope E-400 (Nikon, Japan) and Vertical laminar flow (Tsao-Hsin, Taiwan).

5.6 Methods

The tumor volumes, body weights, mortality, and signs of overt toxicity were monitored and recorded twice weekly for 45 days. Tumor growth inhibition was calculated as T/C (treatment/control)×100%. A T/C value ≤42% compared to that of the vehicle control group was considered significant anti-tumor activity. Two-way ANOVA followed by Bonferroni test was used to ascertain the statistically significant significance of groups compared to respective vehicle control (*$p<0.05$).

5.7 Results

TABLE 10-1

Tumor volume, Xenograft, Lung, NCI-H526 in Female nu/nu Mice (Day 1-Day 25)

| Gr. | Treatment | Dose (mg/kg) (Route) | No. | Tumor Volume (mm$^3$) | | | | | | | |
|---|---|---|---|---|---|---|---|---|---|---|---|
| | | | | Day1 | Day4 | Day8 | Day11 | Day15 | Day18 | Day22 | Day25 |
| 1 | Vehicle (PBS, pH 7.4) + Vehicle (25 mM Sodium Citrate, + 100 mM NaCl, pH 6.5) | 10 mL/kg × 4 (Once weekly) IP + IV | 1 | 66 | 61 | 92 | 104 | 159 | 536 | 942 | 1548 |
| | | | 2 | 86 | 91 | 86 | 111 | 101 | 157 | 190 | 428 |
| | | | 3 | 71 | 76 | 85 | 99 | 157 | 368 | 949 | 1578 |
| | | | 4 | 89 | 103 | 137 | 164 | 180 | 401 | 965 | 1383 |
| | | | 5 | 80 | 80 | 80 | 172 | 221 | 474 | 757 | 1303 |
| | | | 6 | 70 | 73 | 69 | 123 | 189 | 356 | 615 | 920 |
| | | | 7 | 90 | 89 | 99 | 121 | 203 | 490 | 647 | 787 |
| | | | 8 | 65 | 82 | 72 | 133 | 183 | 449 | 760 | 1004 |
| | | | Mean | 77 | 82 | 90 | 128 | 174 | 404 | 728 | 1119 |
| | | | SEM | 4 | 4 | 8 | 9 | 13 | 41 | 91 | 143 |
| 2 | ADC (OBI-999) | 10 mg/kg × 4 IV (Once weekly) | 1 | 66 | 31 | 92 | 104 | 159 | 536 | 942 | 1548 |
| | | | 2 | 86 | 91 | 86 | 111 | 101 | 157 | 190 | 428 |
| | | | 3 | 71 | 76 | 85 | 99 | 157 | 368 | 949 | 1578 |
| | | | 4 | 89 | 103 | 137 | 164 | 180 | 401 | 965 | 1383 |
| | | | 5 | 80 | 80 | 80 | 172 | 221 | 474 | 757 | 1303 |
| | | | 6 | 70 | 73 | 69 | 123 | 189 | 356 | 615 | 920 |
| | | | 7 | 90 | 89 | 99 | 121 | 203 | 490 | 647 | 787 |
| | | | 8 | 65 | 82 | 72 | 133 | 183 | 449 | 760 | 1004 |
| | | | Mean | 77 | 82 | 90 | 128 | 174 | 404 | 728 | 1119 |
| | | | SEM | 5 | 9 | 4 | 4 | 5 | 11 | 33 | 46 |
| | | | % TGI | N/A | −24 | −8 | 34 | 49 | 76 | 83 | 85 |
| | | | % T/C | 99 | 124 | 108 | 66 | 51 | 24[#] | 17[#] | 15[#] |
| 3 | OBI-888 | 10 mg/kg × 4 IV (Once weekly) | 1 | 66 | 101 | 94 | 108 | 171 | 216 | 551 | 981 |
| | | | 2 | 86 | 87 | 81 | 99 | 113 | 183 | 504 | 725 |
| | | | 3 | 80 | 121 | 81 | 91 | 136 | 201 | 415 | 681 |
| | | | 4 | 66 | 97 | 104 | 127 | 135 | 222 | 511 | 913 |
| | | | 5 | 86 | 93 | 98 | 96 | 166 | 170 | 483 | 756 |
| | | | 6 | 86 | 86 | 81 | 93 | 62 | 76 | 113 | 289 |
| | | | 7 | 94 | 94 | 79 | 79 | 89 | 77 | 87 | 99 |
| | | | 8 | 71 | 99 | 69 | 89 | 82 | 99 | 93 | 83 |
| | | | Mean | 79 | 97 | 86 | 98 | 119 | 156 | 345 | 566* |
| | | | SEM | 4 | 4 | 4 | 5 | 14 | 22 | 74 | 126 |
| | | | % TGI | NA | −18 | 4 | 23 | 32 | 61 | 53 | 49 |
| | | | % T/C | 103 | 118 | 96 | 77 | 68 | 39[#] | 47 | 51 |
| 4 | MMAE + OBI-888 | 0.191 mg/kg × 4 IP (Once weekly) + 10 mg/kg × 4 IV (Once weekly) | 1 | 82 | 86 | 93 | 119 | 112 | 179 | 323 | 511 |
| | | | 2 | 63 | 82 | 83 | 69 | 69 | 66 | 68 | 118 |
| | | | 3 | 68 | 108 | 94 | 83 | 61 | 95 | 148 | 346 |
| | | | 4 | 87 | 80 | 79 | 148 | 142 | 181 | 525 | 938 |
| | | | 5 | 97 | 81 | 93 | 96 | 121 | 141 | 402 | 590 |
| | | | 6 | 101 | 111 | 88 | 93 | 98 | 98 | 119 | 171 |
| | | | 7 | 93 | 99 | 89 | 99 | 115 | 137 | 388 | 540 |
| | | | 8 | 87 | 94 | 94 | 88 | 115 | 122 | 333 | 507 |
| | | | Mean | 85 | 93 | 89 | 99 | 104 | 127 | 288* | 465* |
| | | | SEM | 5 | 4 | 2 | 9 | 10 | 14 | 57 | 92 |
| | | | % TGI | NA | −13 | 1 | 23 | 40 | 69 | 60 | 58 |
| | | | % T/C | 110 | 113 | 99 | 77 | 60 | 31[#] | 40[#] | 42[#] |
| 5 | MMAE | 0.191 mg/kg × 4 IP (Once weekly) | 1 | 75 | 80 | 94 | 74 | 82 | 80 | 74 | 70 |
| | | | 2 | 108 | 127 | 74 | 86 | 133 | 199 | 618 | 1163 |
| | | | 3 | 81 | 101 | 94 | 89 | 137 | 246 | 530 | 1095 |
| | | | 4 | 83 | 88 | 83 | 104 | 101 | 169 | 337 | 483 |
| | | | 5 | 99 | 115 | 70 | 121 | 144 | 187 | 317 | 525 |
| | | | 6 | 60 | 85 | 82 | 67 | 89 | 101 | 152 | 249 |
| | | | 7 | 68 | 80 | 121 | 77 | 172 | 281 | 621 | 1078 |
| | | | 8 | 91 | 108 | 74 | 79 | 123 | 202 | 401 | 535 |
| | | | Mean | 83 | 98 | 87 | 87 | 123 | 183 | 381 | 650* |
| | | | SEM | 6 | 6 | 6 | 6 | 11 | 24 | 72 | 146 |
| | | | % TGI | NA | −20 | 3 | 32 | 29 | 55 | 48 | 42 |
| | | | % T/C | 108 | 120 | 97 | 68 | 71 | 45 | 52 | 58 |

TABLE 10-2

Tumor volume, Xenograft, Lung, NCI-H526 in Female nu/nu Mice (Day 29-Day 45)

| Gr. | Treatment | Dose (mg/kg) (Route) | No. | Day29 | Day31 | Day36 | Day39 | Day43 | Day45 |
|---|---|---|---|---|---|---|---|---|---|
| 1 | Vehicle (PBS, pH 7.4) + Vehicle (25 mM Sodium Citrate, + 100 mM NaCl, pH 6.5) | 10 mL/kg × 4 (Once weekly) IP + IV | 1 | 1968 | 2452 | NA | NA | NA | NA |
|  |  |  | 2 | 968 | 1251 | NA | NA | NA | NA |
|  |  |  | 3 | 2579 | 3369 | NA | NA | NA | NA |
|  |  |  | 4 | 2218 | 2803 | NA | NA | NA | NA |
|  |  |  | 5 | 2342 | 2329 | NA | NA | NA | NA |
|  |  |  | 6 | 1594 | 1794 | NA | NA | NA | NA |
|  |  |  | 7 | 1561 | 2022 | NA | NA | NA | NA |
|  |  |  | 8 | 1942 | 2363 | NA | NA | NA | NA |
|  |  |  | Mean | 1897 | 2298 | — | — | — | — |
|  |  |  | SEM | 181 | 226 | — | — | — | — |
| 2 | ADC (OBI-999) | 10 mg/kg × 4 IV (Once weekly) | 1 | 517 | 717 | 922 | died | died | died |
|  |  |  | 2 | 207 | 289 | 612 | 615 | 953 | 1095 |
|  |  |  | 3 | 811 | 983 | 1886 | 2403 | 3693 | 4092 |
|  |  |  | 4 | 99 | 79 | 0 | 0 | 0 | 0 |
|  |  |  | 5 | 507 | 644 | 1349 | 1798 | 2982 | 3948 |
|  |  |  | 6 | 231 | 333 | 789 | 1094 | 1727 | 2190 |
|  |  |  | 7 | 150 | 265 | 461 | 702 | 1109 | 1369 |
|  |  |  | 8 | 80 | 111 | 144 | 218 | 318 | 395 |
|  |  |  | Mean | 325* | 428* | 770 | 976 | 1540 | 1870 |
|  |  |  | SEM | 92 | 113 | 220 | 305 | 482 | 575 |
|  |  |  | % TGI | 83 | 81 | — | — | — | — |
|  |  |  | % T/C | 17[#] | 19[#] | — | — | — | — |
| 3 | OBI-888 | 10 mg/kg × 4 IV (Once weekly) | 1 | 1640 | 1837 | 3370 | 3941 | NA | NA |
|  |  |  | 2 | 1227 | 1519 | 2820 | 3803 | NA | NA |
|  |  |  | 3 | 931 | 1246 | 2045 | 2174 | NA | NA |
|  |  |  | 4 | 1318 | 1714 | 2856 | 3617 | NA | NA |
|  |  |  | 5 | 1176 | 1539 | 1998 | 2177 | NA | NA |
|  |  |  | 6 | 500 | 550 | 1159 | 1802 | NA | NA |
|  |  |  | 7 | 120 | 214 | 322 | 410 | NA | NA |
|  |  |  | 8 | 77 | 101 | 70 | 63 | NA | NA |
|  |  |  | Mean | 874* | 1090* | 1830 | 2248 | — | — |
|  |  |  | SEM | 205 | 246 | 429 | 526 | — | — |
|  |  |  | % TGI | 54 | 53 | — | — | — | — |
|  |  |  | % T/C | 46 | 47 | — | — | — | — |
| 4 | MMAE + OBI-888 | 0.191 mg/kg × 4 IP (Once weekly) + 10 mg/kg × 4 IV (Once weekly) | 1 | 747 | 866 | 1514 | 2347 | NA | NA |
|  |  |  | 2 | 184 | 321 | 877 | 1485 | NA | NA |
|  |  |  | 3 | 632 | 887 | 1897 | 2822 | NA | NA |
|  |  |  | 4 | 1654 | 2176 | 3764 | 5272 | NA | NA |
|  |  |  | 5 | 1150 | 1437 | 2654 | 3181 | NA | NA |
|  |  |  | 6 | 389 | 636 | 982 | 1333 | NA | NA |
|  |  |  | 7 | 1046 | 1204 | 2056 | 3536 | NA | NA |
|  |  |  | 8 | 1034 | 1367 | 2251 | 3438 | NA | NA |
|  |  |  | Mean | 855* | 1112* | 1999 | 2927 | — | — |
|  |  |  | SEM | 165 | 202 | 331 | 446 | — | — |
|  |  |  | % TGI | 55 | 52 | — | — | — | — |
|  |  |  | % T/C | 45 | 48 | — | — | — | — |
| 5 | MMAE | 0.191 mg/kg × 4 IP (Once weekly) | 1 | 90 | 173 | 126 | 56 | NA | NA |
|  |  |  | 2 | 1756 | 1901 | 3047 | 4380 | NA | NA |
|  |  |  | 3 | 1410 | 1682 | 2480 | 2713 | NA | NA |
|  |  |  | 4 | 853 | 1172 | 2090 | 2836 | NA | NA |
|  |  |  | 5 | 522 | 657 | 759 | 841 | NA | NA |
|  |  |  | 6 | 431 | 550 | 1032 | 1304 | NA | NA |
|  |  |  | 7 | 1313 | 1595 | 2538 | 3040 | NA | NA |
|  |  |  | 8 | 845 | 1044 | 1318 | 1339 | NA | NA |
|  |  |  | Mean | 903* | 1097* | 1674 | 2064 | — | — |
|  |  |  | SEM | 198 | 215 | 359 | 499 | — | — |
|  |  |  | % TGI | 52 | 52 | — | — | — | — |
|  |  |  | % T/C | 48 | 48 | — | — | — | — |

TABLE 11-1

Body weight, Xenograft, Lung, NCI-H526 in Female nu/nu Mice (Day 1-Day 25)

| Gr. | Treatment | Dose (mg/kg) (Route) | No. | Day1 | Day4 | Day8 | Day11 | Day15 | Day18 | Day22 | Day25 |
|---|---|---|---|---|---|---|---|---|---|---|---|
| 1 | Vehicle (PBS, pH 7.4) + Vehicle (25 mM Sodium Citrate, + 100 mM NaCl, pH 6.5) | 10 mL/kg × 4 (Once weekly) IP + IV | 1 | 23 | 24 | 24 | 23 | 24 | 25 | 26 | 27 |
|   |   |   | 2 | 23 | 25 | 26 | 25 | 26 | 25 | 25 | 26 |
|   |   |   | 3 | 23 | 24 | 24 | 25 | 25 | 26 | 25 | 26 |
|   |   |   | 4 | 25 | 25 | 25 | 24 | 24 | 25 | 26 | 27 |
|   |   |   | 5 | 24 | 24 | 24 | 24 | 24 | 26 | 26 | 27 |
|   |   |   | 6 | 25 | 26 | 26 | 25 | 26 | 26 | 27 | 27 |
|   |   |   | 7 | 24 | 25 | 26 | 25 | 24 | 26 | 26 | 26 |
|   |   |   | 8 | 22 | 23 | 22 | 22 | 23 | 24 | 24 | 25 |
|   |   |   | Mean | 23.6 | 24.5 | 24.6 | 24.1 | 24.5 | 25.4 | 25.6 | 26.4 |
|   |   |   | SEM | 0.4 | 0.3 | 0.5 | 0.4 | 0.4 | 0.3 | 0.3 | 0.3 |
| 2 | ADC (OBI-999) | 10 mg/kg × 4 IV (Once weekly) | 1 | 24 | 25 | 25 | 25 | 25 | 26 | 26 | 26 |
|   |   |   | 2 | 24 | 24 | 25 | 25 | 25 | 25 | 25 | 25 |
|   |   |   | 3 | 26 | 26 | 28 | 28 | 27 | 28 | 28 | 28 |
|   |   |   | 4 | 24 | 25 | 24 | 24 | 25 | 27 | 27 | 27 |
|   |   |   | 5 | 25 | 26 | 28 | 28 | 28 | 28 | 28 | 29 |
|   |   |   | 6 | 24 | 25 | 26 | 26 | 25 | 26 | 25 | 26 |
|   |   |   | 7 | 23 | 24 | 25 | 24 | 24 | 24 | 24 | 24 |
|   |   |   | 8 | 24 | 24 | 25 | 25 | 25 | 25 | 25 | 26 |
|   |   |   | Mean | 24.3 | 24.9 | 25.8 | 25.6 | 25.5 | 26.1 | 26.0 | 26.4 |
|   |   |   | SEM | 0.3 | 0.3 | 0.5 | 0.6 | 0.5 | 0.5 | 0.5 | 0.6 |
| 3 | OBI-888 | 10 mg/kg × 4 IV (Once weekly) | 1 | 25 | 25 | 27 | 27 | 27 | 28 | 28 | 29 |
|   |   |   | 2 | 24 | 24 | 25 | 25 | 25 | 25 | 26 | 27 |
|   |   |   | 3 | 24 | 23 | 24 | 23 | 24 | 25 | 24 | 25 |
|   |   |   | 4 | 25 | 25 | 27 | 28 | 28 | 29 | 29 | 30 |
|   |   |   | 5 | 24 | 24 | 24 | 25 | 25 | 26 | 26 | 27 |
|   |   |   | 6 | 26 | 27 | 28 | 28 | 28 | 29 | 29 | 30 |
|   |   |   | 7 | 25 | 26 | 26 | 26 | 27 | 27 | 27 | 27 |
|   |   |   | 8 | 24 | 24 | 25 | 25 | 26 | 25 | 26 | 26 |
|   |   |   | Mean | 24.6 | 24.8 | 25.8 | 25.9 | 26.3 | 26.8 | 26.9 | 27.6 |
|   |   |   | SEM | 0.3 | 0.5 | 0.5 | 0.6 | 0.5 | 0.6 | 0.6 | 0.7 |
| 4 | MMAE + OBI-888 | 0.191 mg/kg × 4 IP (Once weekly) + 10 mg/kg × 4 IV (Once weekly) | 1 | 25 | 25 | 26 | 25 | 26 | 26 | 27 | 27 |
|   |   |   | 2 | 24 | 24 | 27 | 27 | 28 | 29 | 29 | 28 |
|   |   |   | 3 | 24 | 24 | 26 | 25 | 26 | 27 | 26 | 26 |
|   |   |   | 4 | 25 | 22 | 24 | 25 | 26 | 26 | 26 | 27 |
|   |   |   | 5 | 24 | 24 | 26 | 27 | 28 | 28 | 28 | 28 |
|   |   |   | 6 | 25 | 26 | 27 | 27 | 28 | 28 | 28 | 29 |
|   |   |   | 7 | 25 | 26 | 27 | 27 | 28 | 27 | 28 | 29 |
|   |   |   | 8 | 21 | 21 | 23 | 24 | 25 | 25 | 25 | 25 |
|   |   |   | Mean | 24.1 | 24.0 | 25.8 | 25.9 | 26.9 | 27.0 | 27.1 | 27.4 |
|   |   |   | SEM | 0.5 | 0.6 | 0.5 | 0.4 | 0.4 | 0.5 | 0.5 | 0.5 |
| 5 | MMAE | 0.191 mg/kg × 4 IP (Once weekly) | 1 | 24 | 22 | 24 | 24 | 25 | 25 | 24 | 26 |
|   |   |   | 2 | 25 | 25 | 26 | 28 | 28 | 28 | 28 | 30 |
|   |   |   | 3 | 26 | 27 | 28 | 28 | 28 | 28 | 28 | 29 |
|   |   |   | 4 | 24 | 21 | 21 | 23 | 24 | 24 | 25 | 26 |
|   |   |   | 5 | 24 | 23 | 25 | 24 | 25 | 25 | 25 | 25 |
|   |   |   | 6 | 23 | 23 | 23 | 23 | 23 | 24 | 24 | 25 |
|   |   |   | 7 | 23 | 24 | 24 | 24 | 24 | 24 | 25 | 25 |
|   |   |   | 8 | 22 | 24 | 25 | 25 | 26 | 25 | 25 | 26 |
|   |   |   | Mean | 23.9 | 23.6 | 24.5 | 24.9 | 25.4 | 25.4 | 25.5 | 26.5 |
|   |   |   | SEM | 0.4 | 0.7 | 0.7 | 0.7 | 0.7 | 0.6 | 0.6 | 0.7 |

TABLE 11-2

Body weight, Xenograft, Lung, NCI-H526 in Female nu/nu Mice (Day 29-Day 45)

| Gr. | Treatment | Dose (mg/kg) (Route) | No. | Day29 | Day31 | Day36 | Day39 | Day43 | Day45 |
|---|---|---|---|---|---|---|---|---|---|
| 1 | Vehicle (PBS, pH 7.4) + Vehicle (25 mM Sodium Citrate, + 100 mM NaCl, pH 6.5) | 10 mL/kg × 4 (Once weekly) IP + IV | 1 | 28 | 29 | NA | NA | NA | NA |
|   |   |   | 2 | 27 | 28 | NA | NA | NA | NA |
|   |   |   | 3 | 28 | 30 | NA | NA | NA | NA |
|   |   |   | 4 | 30 | 30 | NA | NA | NA | NA |
|   |   |   | 5 | 29 | 30 | NA | NA | NA | NA |
|   |   |   | 6 | 29 | 30 | NA | NA | NA | NA |
|   |   |   | 7 | 28 | 29 | NA | NA | NA | NA |
|   |   |   | 8 | 26 | 28 | NA | NA | NA | NA |
|   |   |   | Mean | 28.1 | 29.3 | — | — | — | — |
|   |   |   | SEM | 0.4 | 0.3 | — | — | — | — |

TABLE 11-2-continued

Body weight, Xenograft, Lung, NCI-H526 in Female nu/nu Mice (Day 29-Day 45)

| Gr. | Treatment | Dose (mg/kg) (Route) | No. | Day29 | Day31 | Day36 | Day39 | Day43 | Day45 |
|---|---|---|---|---|---|---|---|---|---|
| 2 | ADC (OBI-999) | 10 mg/kg × 4 | 1 | 27 | 25 | 24 | died | died | died |
|   |   | IV | 2 | 26 | 26 | 27 | 27 | 27 | 28 |
|   |   | (Once weekly) | 3 | 29 | 29 | 31 | 32 | 34 | 36 |
|   |   |   | 4 | 28 | 27 | 28 | 29 | 28 | 29 |
|   |   |   | 5 | 32 | 31 | 32 | 34 | 33 | 35 |
|   |   |   | 6 | 27 | 27 | 28 | 29 | 30 | 31 |
|   |   |   | 7 | 25 | 25 | 26 | 27 | 26 | 28 |
|   |   |   | 8 | 26 | 26 | 27 | 28 | 27 | 28 |
|   |   |   | Mean | 27.5 | 27.0 | 27.9 | 29.4 | 29.3 | 30.7 |
|   |   |   | SEM | 0.8 | 0.7 | 0.9 | 0.9 | 1.1 | 1.2 |
| 3 | OBI-888 | 10 mg/kg × 4 | 1 | 32 | 31 | 35 | 36 | NA | NA |
|   |   | IV | 2 | 28 | 28 | 30 | 30 | NA | NA |
|   |   | (Once weekly) | 3 | 26 | 25 | 27 | 28 | NA | NA |
|   |   |   | 4 | 32 | 31 | 33 | 36 | NA | NA |
|   |   |   | 5 | 28 | 27 | 27 | 28 | NA | NA |
|   |   |   | 6 | 31 | 31 | 32 | 34 | NA | NA |
|   |   |   | 7 | 27 | 27 | 29 | 29 | NA | NA |
|   |   |   | 8 | 27 | 27 | 27 | 27 | NA | NA |
|   |   |   | Mean | 28.9 | 28.4 | 30.0 | 31.0 | — | — |
|   |   |   | SEM | 0.9 | 0.8 | 1.1 | 1.3 | — | — |
| 4 | MMAE + OBI-888 | 0.191 mg/kg × 4 IP (Once weekly) + 10 mg/kg × 4 IV (Once weekly) | 1 | 29 | 29 | 31 | 33 | NA | NA |
|   |   |   | 2 | 30 | 30 | 31 | 32 | NA | NA |
|   |   |   | 3 | 28 | 28 | 31 | 32 | NA | NA |
|   |   |   | 4 | 30 | 30 | 33 | 35 | NA | NA |
|   |   |   | 5 | 30 | 30 | 32 | 34 | NA | NA |
|   |   |   | 6 | 30 | 30 | 30 | 34 | NA | NA |
|   |   |   | 7 | 32 | 32 | 33 | 35 | NA | NA |
|   |   |   | 8 | 27 | 27 | 29 | 33 | NA | NA |
|   |   |   | Mean | 29.5 | 29.5 | 31.3 | 33.5 | — | — |
|   |   |   | SEM | 0.5 | 0.5 | 0.5 | 0.4 | — | — |
| 5 | MMAE | 0.191 mg/kg × 4 | 1 | 25 | 25 | 26 | 27 | NA | NA |
|   |   | IP | 2 | 32 | 32 | 33 | 38 | NA | NA |
|   |   | (Once weekly) | 3 | 31 | 32 | 33 | 34 | NA | NA |
|   |   |   | 4 | 26 | 26 | 28 | 30 | NA | NA |
|   |   |   | 5 | 27 | 27 | 27 | 27 | NA | NA |
|   |   |   | 6 | 26 | 26 | 26 | 27 | NA | NA |
|   |   |   | 7 | 27 | 27 | 29 | 30 | NA | NA |
|   |   |   | 8 | 27 | 27 | 29 | 29 | NA | NA |
|   |   |   | Mean | 27.6 | 27.8 | 28.9 | 30.3 | — | — |
|   |   |   | SEM | 0.9 | 1.0 | 1.0 | 1.4 | — | — |

Figure 27:
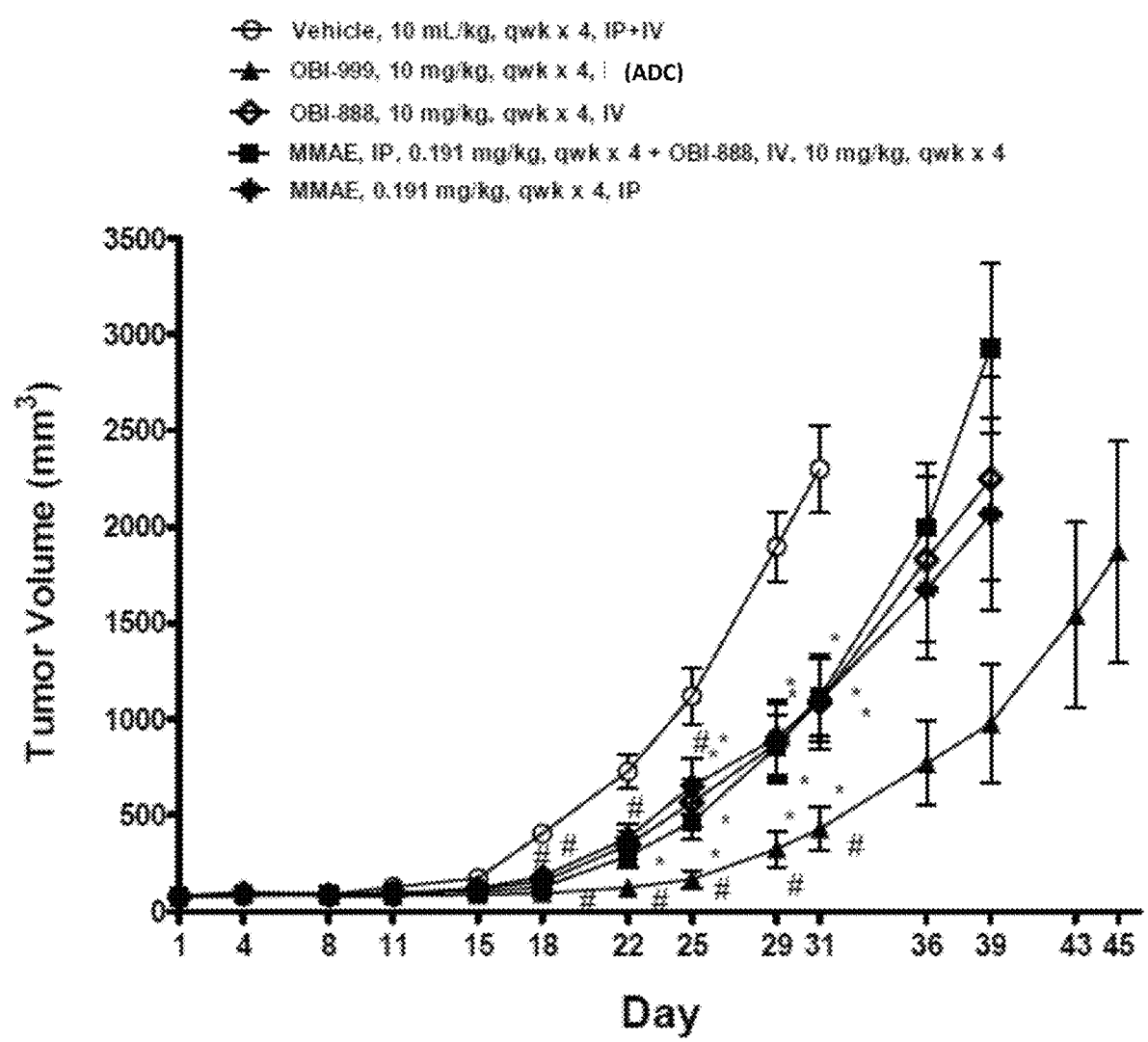
FIG. 27 showed tumor growth curves in NCI-H526 implanted female nude (nu/nu) mice. Vehicle and test substances were administered as detailed in the study design. T/C value ≤42% was considered significant anti-tumor activity (#) compared to the vehicle group. Two-way ANOVA followed by Bonferroni post-tests were applied for comparison between the vehicle and test substance-treated groups. Differences are considered significant at *p<0.05.

FIG. 27 showed the tumor growth curves in NCI-H526 implanted female nude (nu/nu) mice. Intravenous administration of ADC (OBI-999) at 10 mg/kg once weekly for four weeks was associated with significant anti-tumor activity (T/C value ≤42%) starting on Day 15 and continued through to Day 31 with a maximum percent TGI of 85% on Day 25.

Weekly intravenous (IV) administration of test substance, OBI-888 at 10 mg/kg, exhibited moderate anti-tumor activity over the course of the study compared to the vehicle control group; however, significant anti-tumor activity (T/C value ≤42%) was achieved on Day 18 of the study with a maximum percent TGI of 61% on Day 18.

Weekly intraperitoneal (IP) administration of standard agent, MMAE at 0.191 mg/kg, exhibited moderate anti-tumor activity over the course of the study compared to the vehicle control group with a maximum percent TGI of 55% on Day 18.

Combination therapy of test substance OBI-888 at 10 mg/kg with standard agent MMAE at 0.191 mg/kg was associated with moderate inhibition of tumor growth over the course of the study compared to the vehicle control group; however, significant anti-tumor activity (T/C value ≤42%) was achieved on Day 18, Day 22, and Day 25 with a maximum percent TGI of 69% on Day 18.

Figure 28:
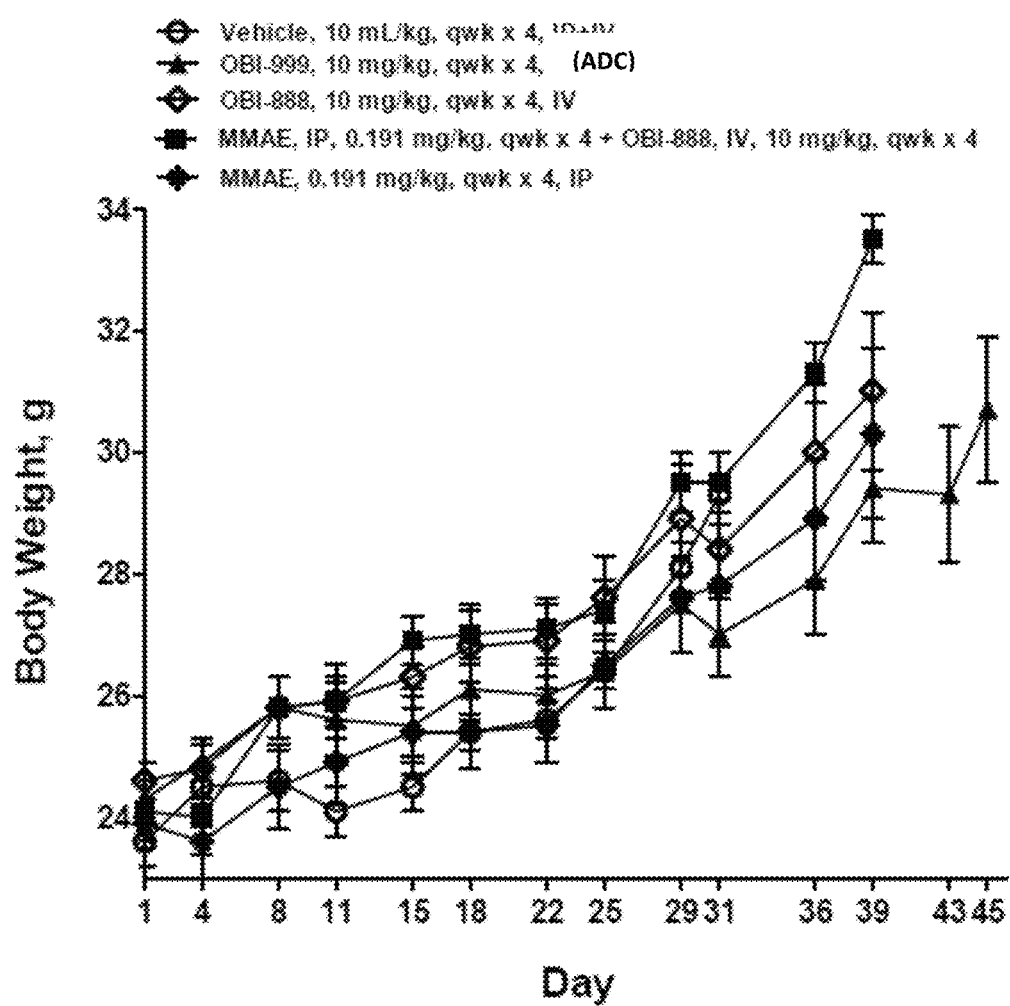
FIG. 28 showed body weight changes in NCI-H526 implanted female nude (nu/nu) mice. Vehicle and test substances were administered as detailed in the study design. The body weights were measured and recorded twice weekly until Day 45.
Figure 29:
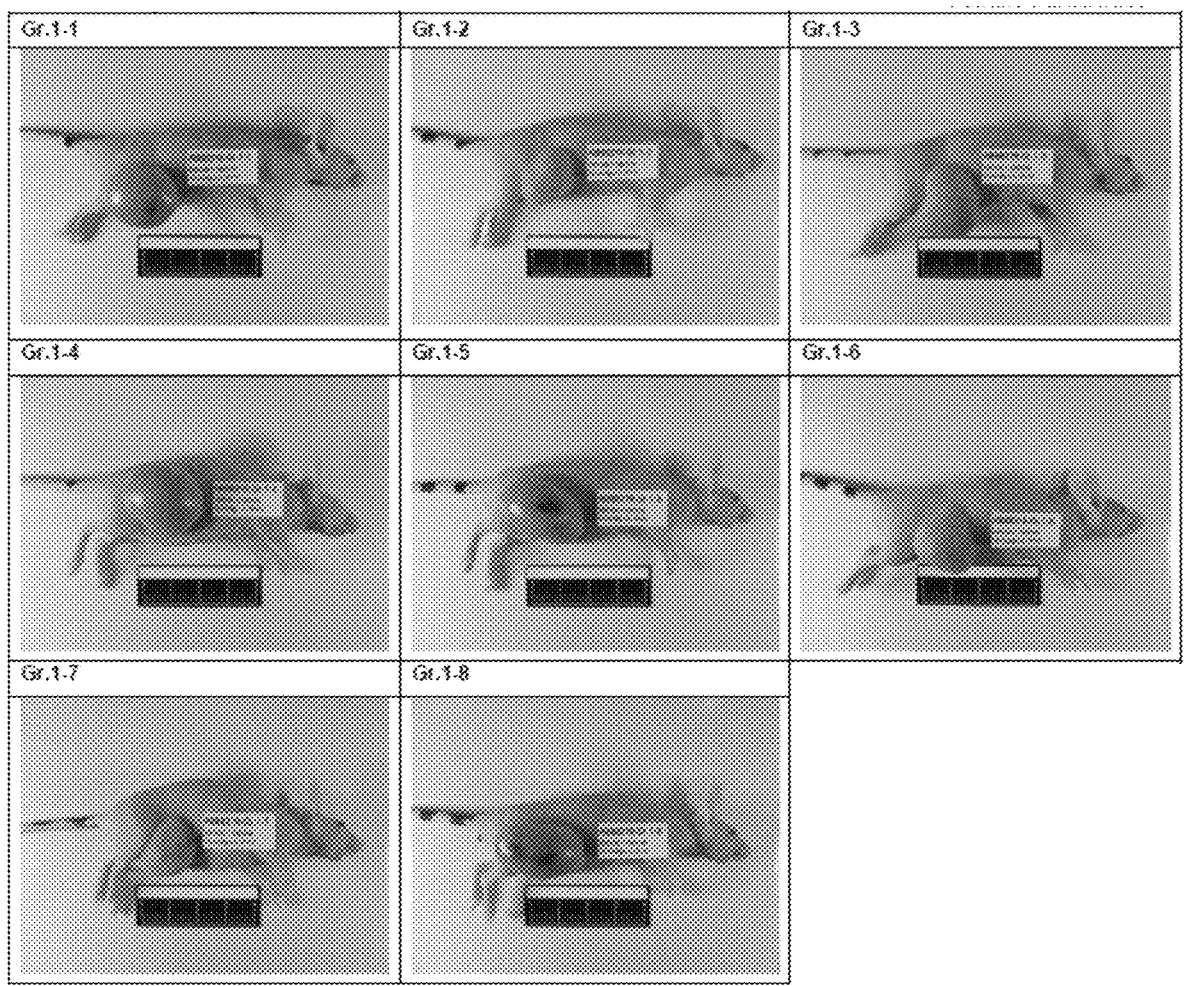
FIG. 29 showed pictures of female (nu/nu) nude mice with NCI-H526 implanted tumors after treatment with Vehicle (25 mM Sodium Citrate, pH 6.5+100 mM NaCl) 10 mL/kg, IV, once weekly×4 weeks+Vehicle (PBS, pH 7.4) 10 mL/kg, IP, once weekly×4 weeks.
Figure 30:
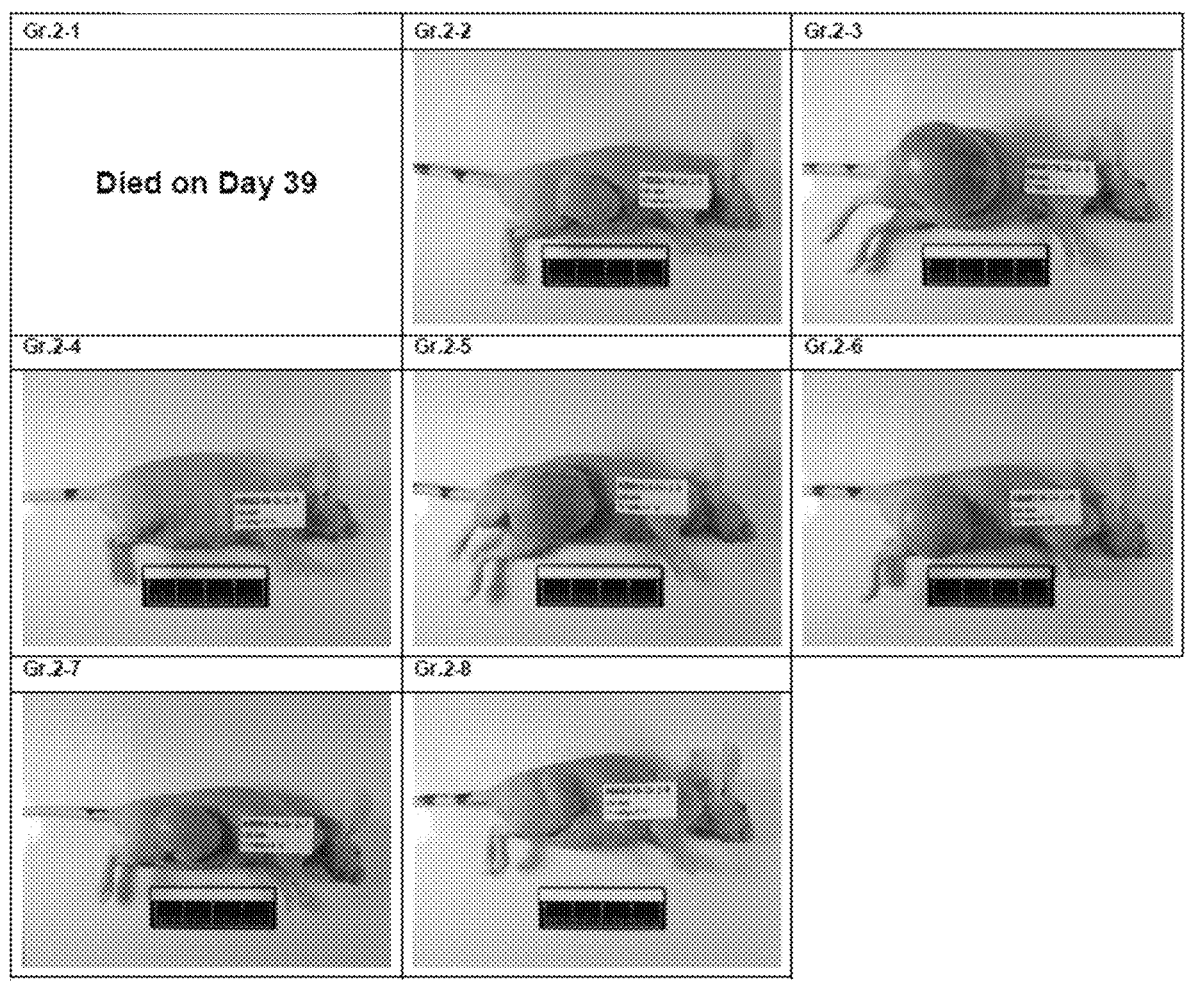
FIG. 30 showed pictures of female (nu/nu) nude mice with NCI-H526 implanted tumors after treatment with ADC (OBI-999) 10 mg/kg, IV, once weekly×4 weeks.
Figure 31:
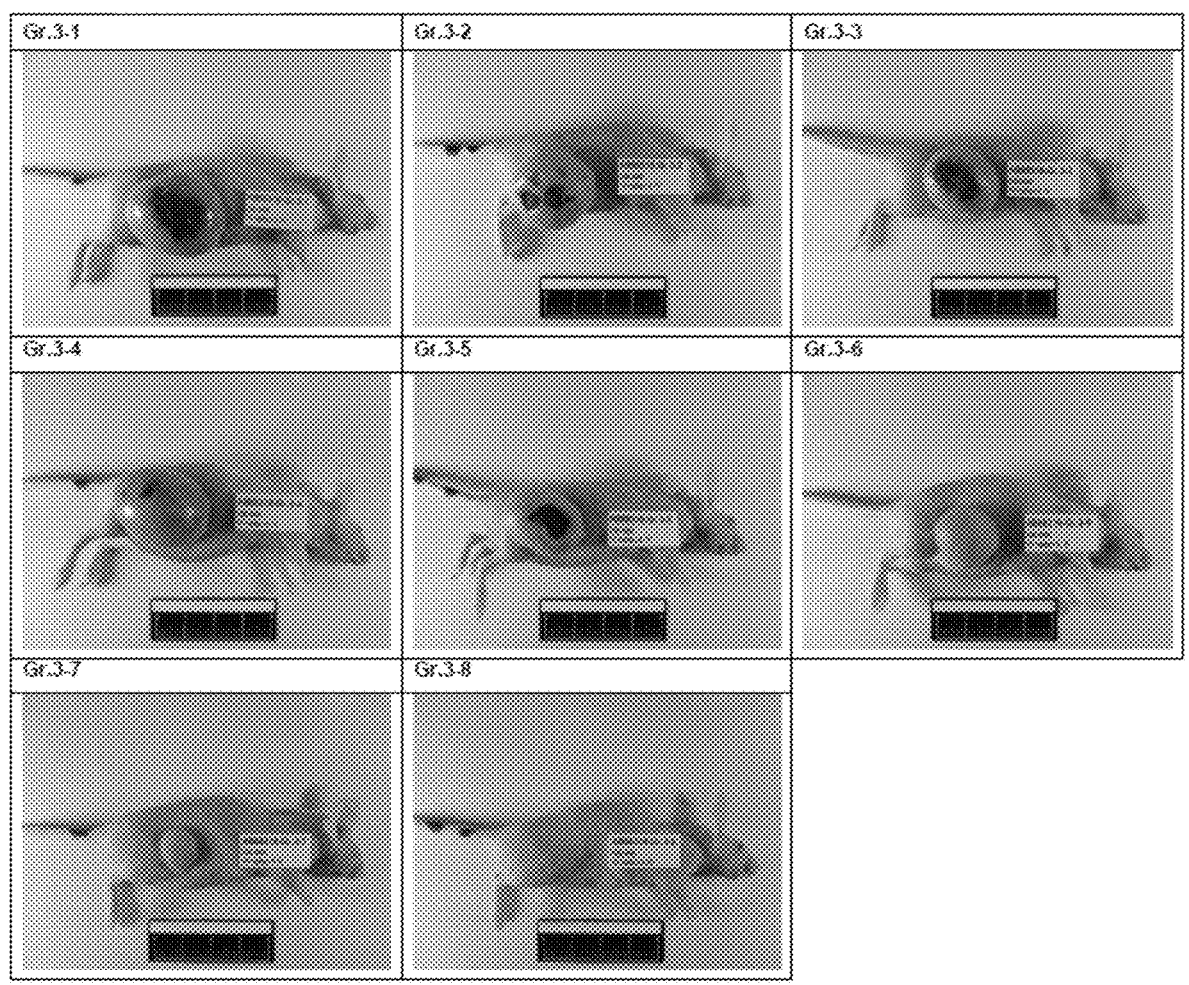
FIG. 31 showed pictures of female (nu/nu) nude mice with NCI-H526 implanted tumors after treatment with OBI-888 10 mg/kg, IV, once weekly×4 weeks.
Figure 32:
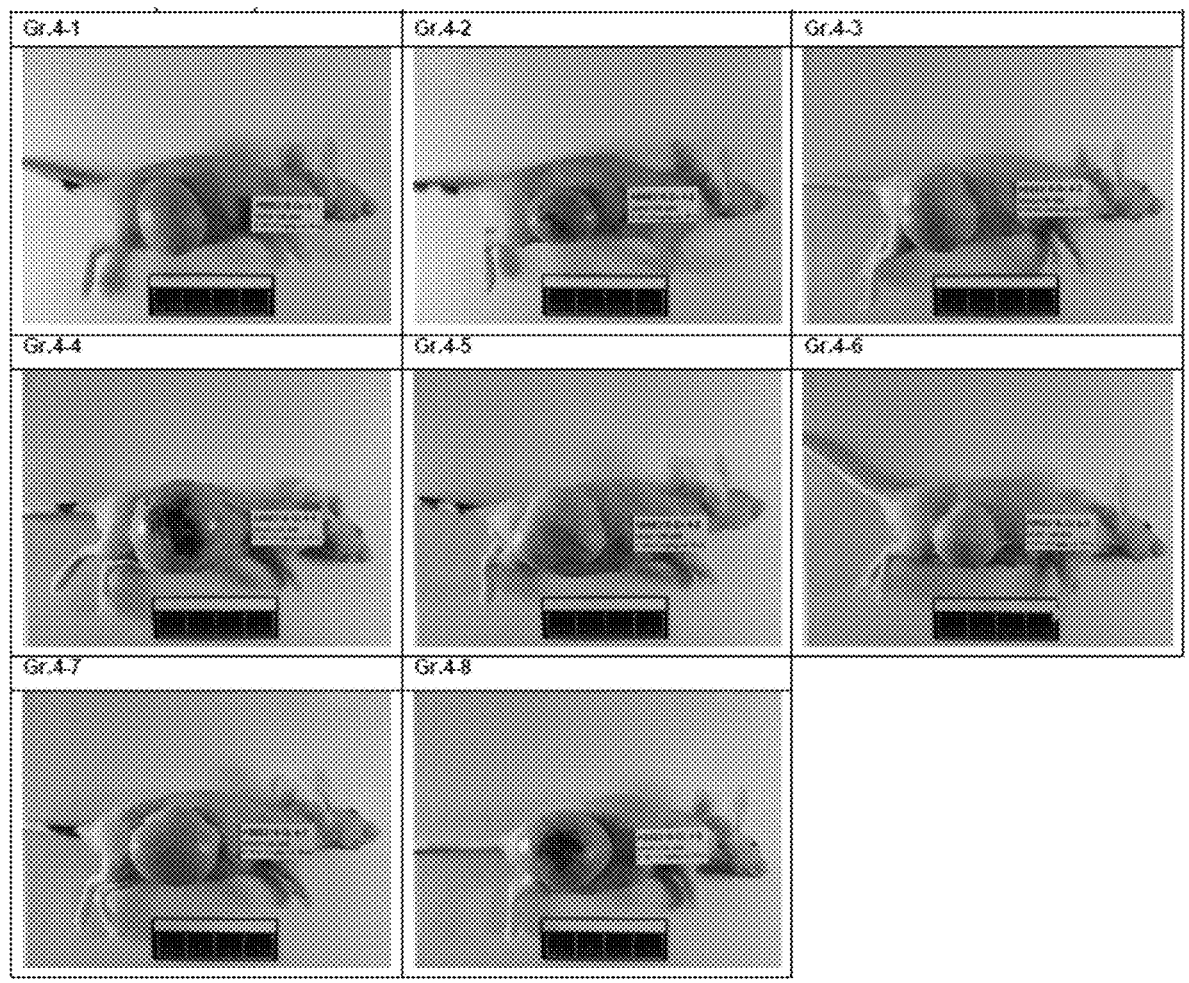
FIG. 32 showed pictures of female (nu/nu) nude mice with NCI-H526 implanted tumors after treatment with MMAE 0.191 mg/kg, IP, once weekly×4 weeks+OBI-888 10 mg/kg, IV, once weekly×4 weeks.
Figure 33:
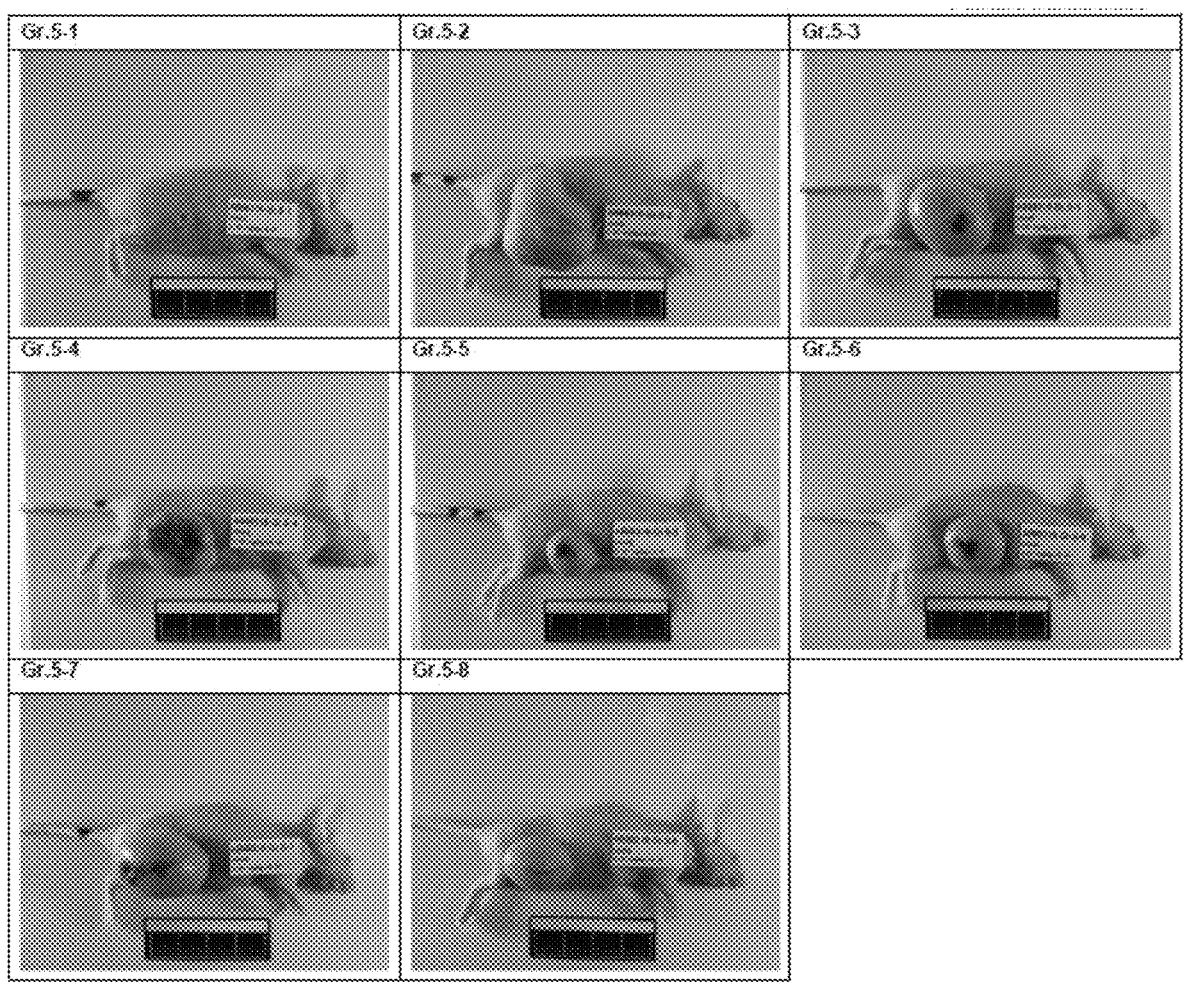
FIG. 33 showed pictures of female (nu/nu) nude mice with NCI-H526 implanted tumors after treatment with MMAE 0.191 mg/kg, IP, once weekly×4 weeks.

FIG. 28 showed the body weight changes in NCI-H526 implanted female nude (nu/nu) mice. All test substances were well-tolerated and not associated with any significant body weight loss over the course of the study.

Example 6: Measurement of the Anti-Tumor Activity of the Exemplary Antibody in Nude Mice (Pancreatic Cancer)

The objective of this study was to evaluate the in vivo anti-tumor efficacy of OBI-888, ADC (OBI-999), MMAE and OBI-888 combined with MMAE in HPAC human pancreatic cancer xenograft model in male BALB/c nude mice.

6.1 Test Substances and Dosing Pattern

Test substances ADC (OBI-999), OBI-888, and corresponding vehicle were formulated by diluting stock with a 25 mM sodium citrate, 100 mM NaCl buffer (pH 6.5) and administered intravenously (IV) once weekly for four weeks. Standard agent, MMAE antibody at 0.191 mg/kg, and corresponding vehicle (PBS pH 7.4) were administered intraperitoneally (IP) once weekly for four weeks. One treatment group received combination therapy of test substance, OBI-888 at 10 mg/kg, with MMAE at 0.191 mg/kg.

TABLE 12

Study Design for Anti-Tumor Activity of the exemplary antibody in Nude Mice (Pancreatic cancer)

| Group | Test Compound | Route | Dosage mL/kg | Dosage mg/kg | Mice[c,d] (nu/nu) (male) |
|---|---|---|---|---|---|
| 1 | Vehicle[a] + Vehicle[b] | IP + IV | 10 | N/A | 8 |
| 2 | ADC (OBI-999)[b] | IV | 10 | 10 | 8 |
| 3 | OBI-888[b] | IV | 10 | 10 | 8 |
| 4 | MMAE[a] + OBI-888[b] | IP + IV | 10 | 0.191[a] + 10[b] | 8 |
| 5 | MMAE[a] | IP | 10 | 0.191 | 8 |

[a]PBS, pH 7.4 (high concentration of MMAE will be stored in 100% DMSO and then is diluted with PBS, pH 7.4)
[b]25 mM Sodium Citrate + 100 mM NaCl, , pH 6.5
[c]Vehicle and test substances are administered once weekly for four weeks starting one day after tumor cell implantation (denoted as Day 1).
[d]Each mouse was inoculated subcutaneously with HPAC tumor cells (3 × 10^6) in 0.2 mL of PBS for tumor development. Treatments were started on day 6 after tumor inoculation when the average tumor size reached 85 mm³.

6.2 Cell Line

The HPAC tumor cells (ATCC CRL-2119) were maintained in vitro as a monolayer culture in 1:1 mixture of Dulbecco's modified Eagle's medium and Ham's F12 medium containing 1.2 g/L sodium bicarbonate, 2.5 mM L-glutamine, 15 mM HEPES and 0.5 mM sodium pyruvate supplemented with 0.002 mg/mL insulin, 0.005 mg/mL transferrin, 40 ng/mL hydrocortisone, 10 ng/mL epidermal growth factor and 5% fetal bovine serum, 100 U/mL penicillin and 100 µg/mL streptomycin at 37° C. in an atmosphere of 5% $CO_2$ in air. The tumor cells were routinely subcultured twice weekly by trypsin-EDTA treatment. The cells growing in an exponential growth phase were harvested and counted for tumor inoculation.

6.3 Animals

Male nu/nu nude, aged 6-8 weeks, were obtained from Shanghai Lingchang and used. The mice were kept in individual ventilation cages at constant temperature and humidity with four animals in each cage (temperature: 20-26° C. and humidity: 40-70%). The cages were made of polycarbonate and the size was 300 mm×200 mm×180 mm. The bedding material was corn cob, which was changed twice per week. Animals had free access to irradiation sterilized dry granule food and drinking water during the entire study period. The identification labels for each cage contained the following information: number of animals, sex, strain, date received, treatment, study number, group number and the starting date of the treatment.

6.4 Methods

The endpoint was to determine the anti-tumor effects of testing compounds. Tumor size was measured twice weekly in two dimensions using a caliper, and the volume was expressed in mm³ using the formula: $V=0.5\ a \times b^2$ where a and b are the long and short diameters of the tumor, respectively. The tumor size was then used for calculation of T/C values. The T/C value (in percent) is an indication of antitumor effectiveness; T and C are the mean volumes of the treated and control groups, respectively, on a given day. TGI was calculated for each group using the formula: TGI (%)=[1−(Ti−T0)/(Vi−V0)]×100; Ti is the average tumor volume of a treatment group on a given day, T0 is the average tumor volume of the treatment group on day 0, Vi is the average tumor volume of the vehicle control group on the same day with Ti, and V0 is the average tumor volume of the vehicle group on day 0.

Summary statistics, including mean and the standard error of the mean (SEM), are provided for the tumor volume of each group at each time point. Statistical analysis of difference in the tumor volume among the groups were conducted on the data obtained at the best therapeutic time point after the final dose (the 37th day after grouping). A one-way ANOVA was performed to compare the tumor volume among groups, and when a significant F-statistics (a ratio of treatment variance to the error variance) was obtained, comparisons between groups were carried out with Games-Howell test, otherwise they were carried out with Dunnett (2 sided) test. The potential synergistic effect between OBI-888 and MMAE was analyzed by two-way ANOVA. All data were analyzed using SPSS 17.0. $p<0.05$ was considered to be statistically significant.

6.5 Results

TABLE 13

Tumor volume, pancreas, HPAC in nu/nu Mice

| Treatment | No. | Tumor Volume (mm³) 0[a] | 3 | 7 | 10 | 14 | 17 | 21 | 24 | 28 | 31 | 35 | 37 |
|---|---|---|---|---|---|---|---|---|---|---|---|---|---|
| Group-1 | 1 | 87 | 432 | 503 | 628 | 1060 | 1179 | 1259 | 1508 | 2143 | 2950 | 4426 | 4239 |
| Vehicle A + B | 2 | 93 | 104 | 203 | 251 | 468 | 654 | 929 | 1287 | 1471 | 1589 | 1560 | 1792 |
| IP + IV | 3 | 134 | 176 | 208 | 284 | 485 | 636 | 842 | 939 | 1263 | 1431 | 1465 | 1881 |
| 10 µL/g + | 4 | 80 | 124 | 161 | 252 | 341 | 735 | 979 | 1024 | 1729 | 1627 | 1692 | 1866 |
| 10 µL/g | 5 | 61 | 204 | 253 | 378 | 492 | 595 | 896 | 876 | 1079 | 1292 | 1289 | 1953 |
| QW × 4 | 6 | 111 | 161 | 203 | 343 | 501 | 637 | 670 | 725 | 1078 | 1549 | 1629 | 2178 |
|  | 7 | 54 | 77 | 141 | 188 | 334 | 388 | 513 | 567 | 818 | 1033 | 1161 | 1450 |
|  | 8 | 59 | 71 | 135 | 186 | 320 | 428 | 653 | 762 | 994 | 1227 | 1359 | 1998 |
|  | Mean | 85 | 169 | 226 | 314 | 500 | 656 | 843 | 961 | 1322 | 1587 | 1823 | 2170 |
|  | SEM | 10 | 41 | 42 | 51 | 85 | 85 | 82 | 109 | 155 | 207 | 377 | 305 |
| Group-2 | 1 | 59 | 75 | 104 | 135 | 53 | 26 | 4 | 1 | 0 | 0 | 0 | 0 |
| ADC (OBI-999) | 2 | 80 | 115 | 124 | 116 | 43 | 4 | 1 | 0 | 0 | 0 | 0 | 0 |
| IV | 3 | 100 | 74 | 75 | 61 | 0 | 0 | 0 | 0 | 0 | 0 | 0 | 0 |
| 10 mg/kg | 4 | 56 | 94 | 115 | 91 | 0 | 0 | 0 | 0 | 0 | 0 | 0 | 0 |
| QW × 4 | 5 | 101 | 148 | 196 | 178 | 102 | 76 | 15 | 14 | 12 | 4 | 1 | 0 |
|  | 6 | 122 | 149 | 264 | 180 | 134 | 65 | 52 | 22 | 18 | 20 | 4 | 12 |
|  | 7 | 72 | 76 | 101 | 87 | 42 | 16 | 4 | 1 | 1 | 0 | 0 | 0 |
|  | 8 | 89 | 154 | 175 | 79 | 0 | 0 | 0 | 0 | 0 | 0 | 0 | 0 |
|  | Mean | 85 | 111 | 144 | 116 | 47 | 23 | 9 | 5 | 4 | 3 | 1 | 1 |
|  | SEM | 8 | 13 | 22 | 16 | 18 | 11 | 6 | 3 | 2 | 2 | 0 | 1 |

TABLE 13-continued

Tumor volume, pancreas, HPAC in nu/nu Mice

| Treatment | No. | Tumor Volume (mm³) | | | | | | | | | | |
|---|---|---|---|---|---|---|---|---|---|---|---|---|
| | | 0[a] | 3 | 7 | 10 | 14 | 17 | 21 | 24 | 28 | 31 | 35 | 37 |
| Group-3 | 1 | 140 | 155 | 170 | 251 | 384 | 404 | 781 | 874 | 1471 | 1952 | 2063 | 2073 |
| OBI-888 | 2 | 52 | 61 | 154 | 209 | 412 | 523 | 695 | 952 | 999 | 1489 | 1535 | 1839 |
| IV | 3 | 84 | 128 | 169 | 331 | 481 | 571 | 772 | 908 | 1480 | 1722 | 2696 | 2620 |
| 10 mg/kg | 4 | 90 | 100 | 140 | 296 | 323 | 442 | 671 | 992 | 1590 | 1915 | 2275 | 2269 |
| QW × x 4 | 5 | 109 | 98 | 129 | 252 | 458 | 615 | 727 | 870 | 1200 | 1627 | 1836 | 1838 |
| | 6 | 58 | 71 | 116 | 214 | 255 | 303 | 645 | 635 | 1134 | 1175 | 1485 | 1791 |
| | 7 | 75 | 98 | 219 | 367 | 529 | 641 | 724 | 857 | 1150 | 1422 | 1584 | 1852 |
| | 8 | 69 | 151 | 164 | 288 | 610 | 706 | 930 | 1132 | 1663 | 1876 | 2046 | 2074 |
| | Mean | 85 | 108 | 158 | 276 | 432 | 526 | 743 | 902 | 1336 | 1647 | 1940 | 2044 |
| | SEM | 10 | 12 | 11 | 20 | 40 | 48 | 31 | 50 | 86 | 96 | 148 | 101 |
| Group-4 | 1 | 128 | 166 | 189 | 302 | 520 | 578 | 656 | 844 | 971 | 1370 | 1440 | 1640 |
| MMAE + | 2 | 118 | 100 | 108 | 154 | 286 | 366 | 453 | 717 | 863 | 904 | 1332 | 1577 |
| OBI-888 | 3 | 45 | 79 | | | | Died | | | | | | |
| IP + IV | 4 | 88 | 93 | 143 | 243 | 371 | 824 | 898 | 1134 | 1606 | 1632 | 1830 | 2226 |
| 0.191 mg/kg + | 5 | 71 | 75 | 161 | 200 | 279 | 451 | 486 | 693 | 840 | 1186 | 1218 | 1227 |
| 10 mg/kg | 6 | 79 | 112 | 121 | 220 | 288 | 414 | 483 | 577 | 985 | 1063 | 1192 | 1638 |
| QW × 4 | 7 | 91 | 111 | 244 | 274 | 561 | 653 | 735 | 1292 | 1507 | 2073 | 2400 | 2523 |
| | 8 | 57 | 53 | 73 | 89 | 110 | 189 | 293 | 359 | 554 | 844 | 940 | 931 |
| | Mean | 85 | 99 | 148 | 212 | 345 | 496 | 572 | 802 | 1047 | 1296 | 1479 | 1680 |
| | SEM | 10 | 12 | 21 | 27 | 59 | 79 | 77 | 121 | 143 | 165 | 185 | 206 |
| Group-5 | 1 | 58 | 128 | | | | Died | | | | | | |
| MMAE | 2 | 53 | 76 | 104 | | | | Euthanized | | | | | |
| IP | 3 | 132 | 148 | | | | Died | | | | | | |
| 0.191 mg/kg | 4 | 72 | 82 | 114 | 444 | 429 | 590 | 649 | 748 | 1080 | 1174 | 1650 | 1652 |
| QW × 4 | 5 | 86 | 158 | 177 | 196 | 418 | 452 | 692 | 705 | 888 | 1340 | 1656 | 1963 |
| | 6 | 116 | 128 | 144 | 219 | 418 | 510 | 581 | 822 | 913 | 1439 | 1496 | 1828 |
| | 7 | 71 | 57 | 97 | 160 | 268 | 321 | 383 | 511 | 623 | 1030 | 1236 | 1196 |
| | 8 | 91 | 137 | 167 | 207 | 390 | 448 | 451 | 571 | 785 | 989 | 1208 | 1580 |
| | Mean | 85 | 114 | 134 | 245 | 385 | 464 | 551 | 672 | 858 | 1194 | 1449 | 1644 |
| | SEM | 10 | 13 | 14 | 51 | 30 | 44 | 59 | 57 | 75 | 87 | 97 | 130 |

TABLE 14

Body weight, pancreas, HPAC in nu/nu Mice

| Treatment | No. | Body weight (g) | | | | | | | | | | | | |
|---|---|---|---|---|---|---|---|---|---|---|---|---|---|---|
| | | 0[a] | 3 | 4 | 7 | 9 | 10 | 14 | 17 | 21 | 24 | 28 | 31 | 35 | 37 |
| Group-1 | 1 | 24.8 | 24.7 | 24.4 | 25.3 | 25.5 | 25.6 | 26.6 | 26.8 | 27.2 | 27.2 | 27.4 | 26.9 | 27.9 | 28.5 |
| Vehicle | 2 | 21.9 | 22.0 | 22.2 | 22.7 | 23.0 | 22.9 | 23.5 | 23.6 | 23.8 | 23.9 | 24.5 | 23.7 | 24.4 | 24.8 |
| A + B | 3 | 24.7 | 24.3 | 24.5 | 25.3 | 25.5 | 25.5 | 26.6 | 26.5 | 26.6 | 26.8 | 27.1 | 26.4 | 28.2 | 28.3 |
| IP + IV | 4 | 21.0 | 21.4 | 21.8 | 22.5 | 22.5 | 22.7 | 23.2 | 23.3 | 24.2 | 24.3 | 25.1 | 24.7 | 25.2 | 26.2 |
| 10 μL/g+ | 5 | 23.3 | 24.1 | 24.6 | 25.4 | 25.0 | 25.0 | 25.5 | 25.4 | 25.6 | 26.0 | 27.0 | 26.2 | 27.0 | 27.2 |
| 10 μL/g | 6 | 21.4 | 22.3 | 22.4 | 23.0 | 23.0 | 23.4 | 23.5 | 23.2 | 23.2 | 23.6 | 23.5 | 23.9 | 23.5 | 24.3 |
| QW × 4 | 7 | 22.8 | 23.0 | 23.5 | 24.2 | 24.2 | 24.1 | 24.4 | 24.2 | 24.9 | 25.0 | 25.4 | 25.6 | 26.8 | 27.2 |
| | 8 | 24.4 | 24.8 | 25.0 | 25.7 | 26.9 | 25.7 | 26.3 | 22.2 | 26.6 | 27.0 | 27.4 | 27.5 | 28.3 | 28.5 |
| | Mean | 23.0 | 23.3 | 23.5 | 24.2 | 24.4 | 24.4 | 25.0 | 24.3 | 25.3 | 25.5 | 25.9 | 25.6 | 26.4 | 26.9 |
| | SEM | 0.5 | 0.5 | 0.4 | 0.5 | 0.6 | 0.4 | 0.5 | 0.6 | 0.5 | 0.5 | 0.5 | 0.5 | 0.6 | 0.6 |
| Group-2 | 1 | 24.4 | 24.9 | 24.8 | 25.5 | 25.7 | 25.9 | 26.6 | 26.4 | 26.2 | 26.3 | 26.3 | 26.6 | 26.8 | 27.0 |
| ADC | 2 | 24.1 | 24.9 | 25.5 | 25.6 | 25.8 | 25.7 | 26.9 | 26.7 | 27.3 | 27.4 | 27.1 | 27.7 | 27.9 | 28.1 |
| (OBI-999) | 3 | 23.8 | 23.9 | 23.9 | 24.6 | 24.8 | 24.6 | 25.6 | 25.6 | 25.9 | 26.1 | 26.0 | 26.2 | 26.4 | 27.8 |
| IV | 4 | 23.2 | 24.6 | 24.4 | 24.9 | 25.3 | 25.1 | 25.1 | 24.6 | 25.1 | 25.3 | 25.3 | 25.3 | 24.3 | 24.9 |
| 10 mg/kg | 5 | 24.5 | 25.1 | 25.3 | 25.9 | 25.8 | 25.8 | 26.8 | 26.5 | 27.4 | 27.4 | 27.4 | 27.5 | 27.6 | 28.9 |
| QW × 4 | 6 | 24.8 | 24.4 | 25.1 | 25.8 | 26.2 | 26.3 | 27.4 | 26.7 | 26.3 | 26.3 | 26.9 | 26.9 | 27.3 | 27.9 |
| | 7 | 22.8 | 23.0 | 23.1 | 24.0 | 23.8 | 23.8 | 24.3 | 24.0 | 24.5 | 24.6 | 24.7 | 24.3 | 24.5 | 25.6 |
| | 8 | 24.6 | 24.3 | 24.4 | 25.4 | 25.4 | 25.3 | 26.1 | 26.3 | 26.4 | 26.1 | 26.4 | 26.4 | 27.1 | 27.6 |
| | Mean | 24.0 | 24.4 | 24.6 | 25.2 | 25.3 | 25.3 | 26.1 | 25.9 | 26.1 | 26.2 | 26.3 | 26.4 | 26.6 | 27.2 |
| | SEM | 0.3 | 0.2 | 0.3 | 0.2 | 0.3 | 0.3 | 0.4 | 0.4 | 0.3 | 0.3 | 0.3 | 0.4 | 0.5 | 0.5 |
| Group-3 | 1 | 25.1 | 24.3 | 24.5 | 25.5 | 25.4 | 25.8 | 26.5 | 26.9 | 26.4 | 27.3 | 26.9 | 26.8 | 28.8 | 28.4 |
| OBI-888 | 2 | 25.5 | 25.5 | 25.9 | 26.6 | 27.3 | 27.4 | 27.0 | 27.3 | 27.8 | 29.4 | 28.8 | 28.4 | 28.9 | 29.0 |
| IV | 3 | 24.9 | 24.4 | 24.9 | 25.5 | 26.2 | 26.5 | 27.0 | 27.6 | 27.7 | 27.9 | 28.5 | 27.8 | 29.1 | 29.1 |
| 10 mg/kg | 4 | 25.0 | 25.5 | 26.1 | 27.1 | 27.0 | 27.1 | 24.5 | 27.6 | 27.3 | 26.8 | 27.9 | 27.5 | 28.5 | 27.9 |
| QW × 4 | 5 | 24.3 | 23.7 | 24.0 | 24.1 | 24.8 | 25.0 | 26.0 | 26.5 | 25.0 | 26.2 | 26.1 | 27.1 | 27.1 | 27.1 |
| | 6 | 23.9 | 24.5 | 24.7 | 25.2 | 25.3 | 25.1 | 25.6 | 25.7 | 26.7 | 26.9 | 26.8 | 26.5 | 26.8 | 26.9 |
| | 7 | 24.4 | 24.6 | 24.7 | 25.0 | 25.4 | 25.5 | 25.9 | 26.2 | 26.4 | 26.5 | 27.2 | 26.8 | 27.5 | 27.7 |
| | 8 | 23.0 | 23.5 | 23.7 | 23.9 | 24.5 | 24.9 | 25.1 | 24.9 | 24.6 | 24.7 | 25.3 | 25.4 | 25.9 | 25.3 |
| | Mean | 24.5 | 24.5 | 24.8 | 25.4 | 25.7 | 25.9 | 25.9 | 26.6 | 26.5 | 26.8 | 27.2 | 26.9 | 27.8 | 27.7 |
| | SEM | 0.3 | 0.3 | 0.3 | 0.4 | 0.4 | 0.3 | 0.3 | 0.3 | 0.4 | 0.5 | 0.4 | 0.3 | 0.4 | 0.4 |

TABLE 14-continued

Body weight, pancreas, HPAC in nu/nu Mice

| Treatment | No. | 0[a] | 3 | 4 | 7 | 9 | 10 | 14 | 17 | 21 | 24 | 28 | 31 | 35 | 37 |
|---|---|---|---|---|---|---|---|---|---|---|---|---|---|---|---|
| Group-4 | 1 | 27.2 | 23.6 | 23.9 | 26.9 | 27.1 | 27.5 | 28.3 | 28.0 | 28.2 | 27.8 | 28.3 | 29.7 | 30.4 | 29.9 |
| MMAE + | 2 | 25.1 | 23.7 | 24.0 | 26.3 | 25.9 | 26.2 | 26.7 | 26.6 | 26.9 | 27.0 | 26.9 | 27.4 | 28.2 | 28.0 |
| OBI-888 | 3 | 23.6 | 21.6 | 20.7 | | | | | | Died | | | | | |
| IP + IV | 4 | 24.1 | 21.7 | 22.6 | 25.6 | 25.4 | 25.3 | 25.8 | 25.4 | 26.2 | 25.2 | 25.4 | 24.9 | 25.5 | 25.6 |
| 0.191 mg/kg + | 5 | 23.9 | 22.6 | 23.6 | 24.3 | 24.0 | 24.3 | 25.1 | 24.6 | 24.5 | 24.7 | 24.3 | 23.8 | 25.0 | 25.1 |
| 10 mg/kg | 6 | 25.2 | 23.7 | 25.0 | 27.5 | 27.7 | 27.9 | 28.8 | 26.9 | 28.3 | 28.4 | 28.3 | 28.4 | 29.7 | 30.0 |
| QW × 4 | 7 | 24.3 | 22.3 | 21.2 | 23.7 | 23.9 | 24.2 | 25.4 | 26.0 | 26.1 | 26.7 | 26.3 | 26.8 | 28.1 | 28.3 |
| | 8 | 23.3 | 23.7 | 24.1 | 24.6 | 25.2 | 25.6 | 25.2 | 26.0 | 26.1 | 26.7 | 26.3 | 26.8 | 27.5 | 27.6 |
| | Mean | 24.6 | 22.8 | 23.1 | 25.5 | 25.6 | 25.8 | 26.5 | 26.2 | 26.6 | 26.6 | 26.5 | 26.8 | 27.8 | 27.8 |
| | SEM | 0.4 | 0.3 | 0.5 | 0.5 | 0.5 | 0.5 | 0.6 | 0.4 | 0.5 | 0.5 | 0.6 | 0.7 | 0.8 | 0.7 |
| Group-5 | 1 | 25.4 | 21.8 | 21.0 | | | | | | Died | | | | | |
| MMAE | 2 | 24.3 | 22.4 | 21.3 | 18.8 | | | | | Euthanized | | | | | |
| IP | 3 | 24.8 | 21.5 | 20.5 | | | | | | Died | | | | | |
| 0.191 mg/kg | 4 | 24.2 | 21.6 | 22.0 | 25.1 | 24.9 | 25.9 | 25.7 | 23.9 | 25.6 | 24.8 | 26.2 | 25.0 | 26.9 | 26.7 |
| QW × 4 | 5 | 24.5 | 24.0 | 24.9 | 27.0 | 25.9 | 26.0 | 26.2 | 26.0 | 26.2 | 25.7 | 25.3 | 25.2 | 25.6 | 25.3 |
| | 6 | 23.3 | 20.7 | 19.6 | 21.7 | 22.2 | 26.3 | 24.4 | 24.5 | 24.7 | 24.9 | 24.9 | 25.4 | 25.6 | 25.5 |
| | 7 | 24.0 | 23.1 | 23.7 | 25.2 | 24.9 | 25.3 | 26.0 | 25.3 | 25.7 | 25.6 | 26.3 | 26.4 | 27.2 | 27.1 |
| | 8 | 22.7 | 21.6 | 22.1 | 23.8 | 23.5 | 24.1 | 24.5 | 23.6 | 23.8 | 23.7 | 24.1 | 24.1 | 24.5 | 24.0 |
| | Mean | 24.2 | 22.1 | 21.9 | 23.6 | 24.3 | 25.5 | 25.3 | 24.6 | 25.2 | 24.9 | 25.4 | 25.2 | 26.0 | 25.7 |
| | SEM | 0.3 | 0.4 | 0.6 | 1.2 | 0.7 | 0.4 | 0.4 | 0.4 | 0.4 | 0.4 | 0.4 | 0.4 | 0.5 | 0.5 |

Figure 34:
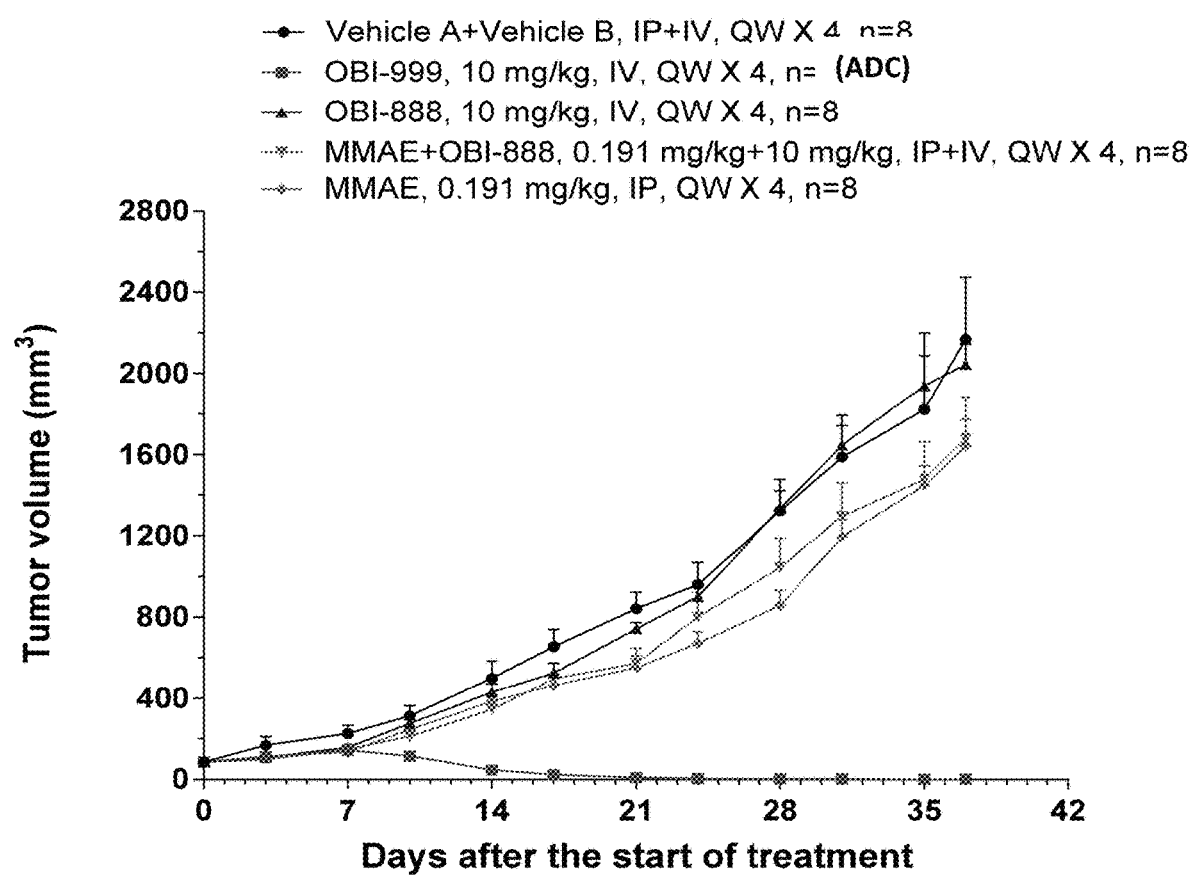
FIG. 34 showed tumor growth curves in different treatment groups of male BALB/c nude mice bearing HPAC established tumors. Vehicle and test substances were administered as detailed in the study design. Data points represent group mean, error bars represent standard error of the mean (SEM).

FIG. 34 showed the tumor growth curves in HPAC implanted nude (nu/nu) mice. Treatment with the test article ADC (OBI-999) at 10 mg/kg produced a significant antitumor activity starting on Day 14 and continued through to Day 37. Its mean tumor size was 1 mm$^3$ (T/C=0.1%, TGI=104.0%, p<0.001). OBI-888 at 10 mg/kg as a single agent didn't produce significant antitumor activity. Its mean tumor size was 2,044 mm$^3$ (T/C=94.2%, TGI=6.0%, p=0.967). MMAE at 0.191 mg/kg as a single agent or combined with OBI-888 at 10 mg/kg produced a minor antitumor activity with a mean tumor size of 1,644 mm$^3$ (T/C=75.8%, TGI=25.2%, p=0.231) and 1,680 mm$^3$ (T/C=77.4%, TGI=23.5%, p=0.213), respectively.

Figure 35:
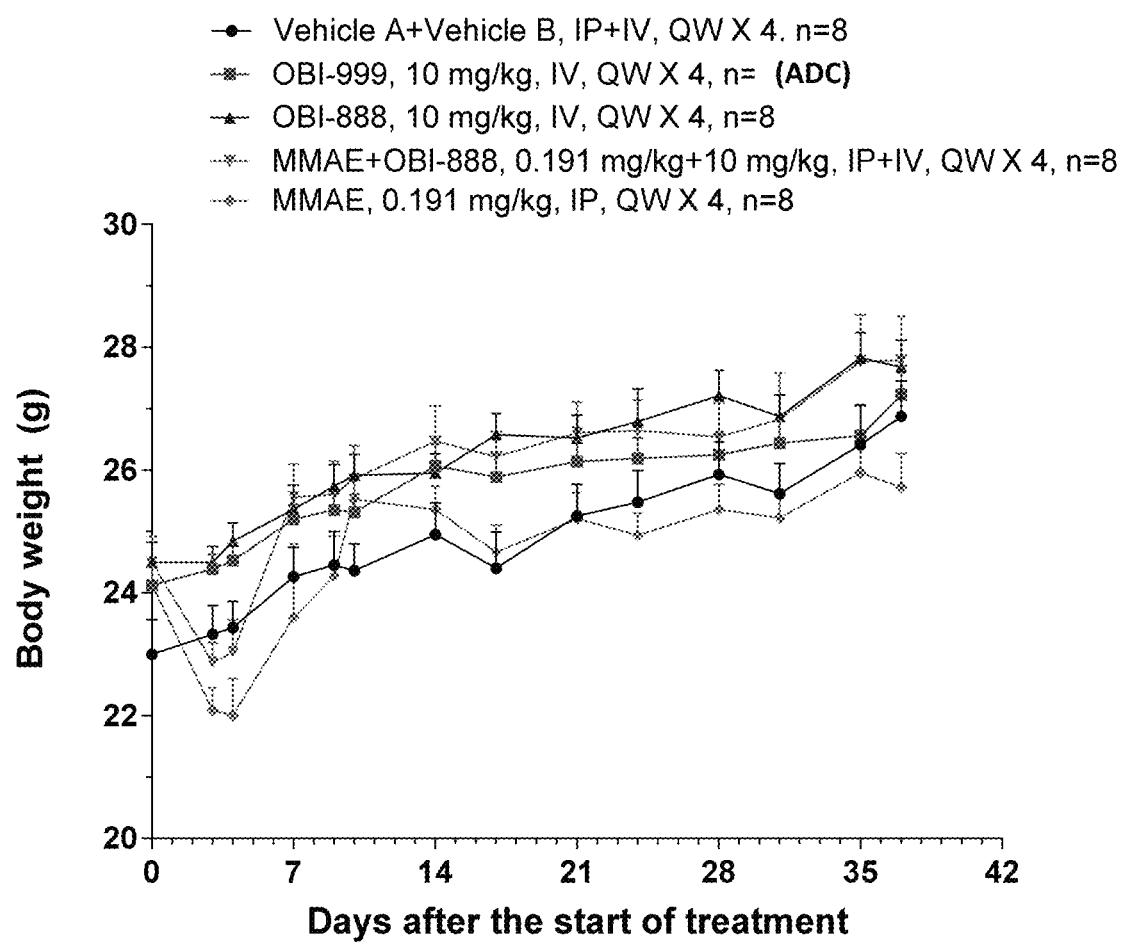
FIG. 35 showed the body weight changes of different treatment groups in male BALB/c nude mice bearing HPAC established tumors. Vehicle and test substances were administered as detailed in the study design. Data points represent group mean body weight. Error bars represent standard error of the mean (SEM).
Figure 36:
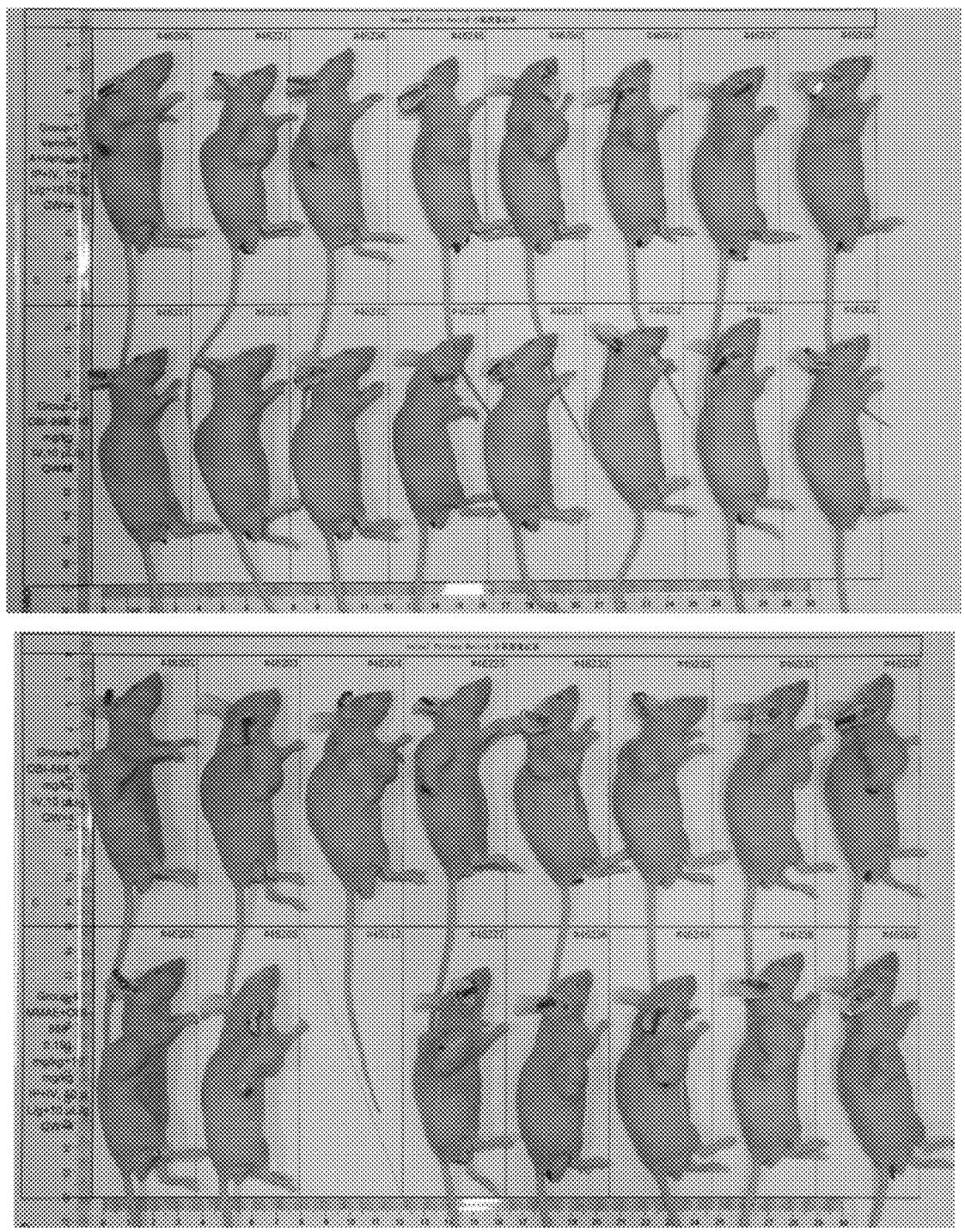
FIG. 36 showed pictures of different treatment groups in male BALB/c nude mice bearing HPAC established tumors.
Figure 36:
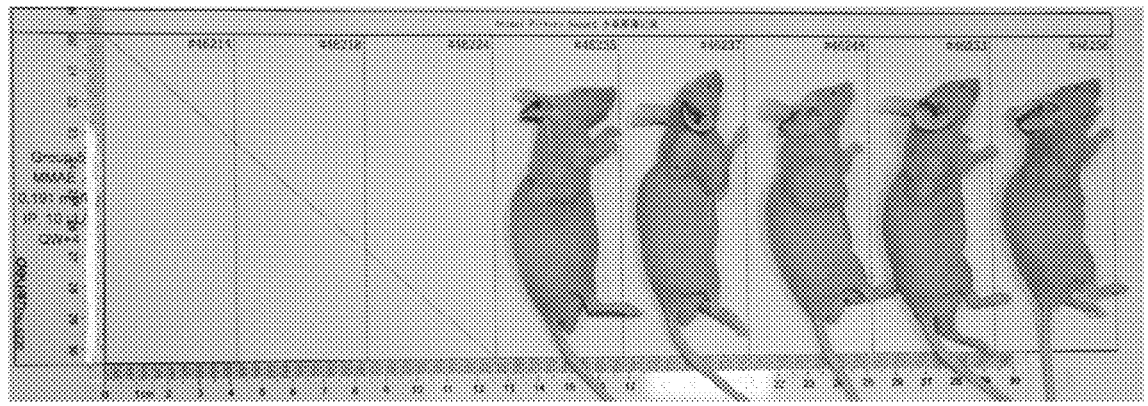

FIG. 35 showed the body weight changes in HPAC implanted nude (nu/nu) mice. All test substances were well-tolerated and not associated with any significant body weight loss over the course of the study.

Unless defined otherwise, all technical and scientific terms and any acronyms used herein have the same meanings as commonly understood by one of ordinary skill in the art in the field of this invention. Although any compositions, methods, kits, and means for communicating information similar or equivalent to those described herein can be used to practice this invention, the preferred compositions, methods, kits, and means for communicating information are described herein.

All references cited herein are incorporated herein by reference to the full extent allowed by law. The discussion of those references is intended merely to summarize the assertions made by their authors. No admission is made that any reference (or a portion of any reference) is relevant prior art. Applicants reserve the right to challenge the accuracy and pertinence of any cited reference.

What is claimed is:

1. A method of treating cancer in a subject, the method comprising administering to the subject in need thereof an effective amount of an antibody-drug conjugate (ADC);
   wherein the ADC comprising a therapeutic agent and an antibody or an antigen-binding fragment that binds Globo H (Fucα1→2 Galβ1→3 GalNAcβ1→3 Galα1→4 Galβ1→4 Glc);
   wherein the therapeutic agent is covalently conjugated to the antibody or the antigen-binding fragment by a linker;
   wherein the anti-Globo H antibody is OBI-888; and
   wherein the therapeutic agent is monomethyl auristatin E (MMAE).

2. The method of claim 1, wherein the cancer is Globo H expressing cancer.

3. The method of claim 2, wherein the Globo H expressing cancer is selected from the group consisting of sarcoma, skin cancer, leukemia, lymphoma, brain cancer, glioblastoma, lung cancer, breast cancer, oral cancer, head-and-neck cancer, nasopharyngeal cancer, esophagus cancer, stomach cancer, liver cancer, bile duct cancer, gallbladder cancer, bladder cancer, pancreatic cancer, intestinal cancer, colorectal cancer, kidney cancer, cervix cancer, endometrial cancer, ovarian cancer, testical cancer, buccal cancer, oropharyngeal cancer, laryngeal cancer, prostate cancer and gastric cancer.

4. The method of claim 3, wherein the Globo H expressing cancer is selected from the group consisting of breast cancer, pancreatic cancer, gastric cancer and lung cancer.

5. The method of claim 1, wherein the subject is human.

6. The method of claim 1, wherein the effective amount of the ADC is administered intravenously.

7. The method of claim 1, wherein the ADC is administered in combination with an effective amount of an additional agent selected from the group consisting of an anti-cancer agent, an immunosuppressant agent, and an anti-infectious agent, for the treatment of muscular disorders, ubiquitin-pathway-related genetic disorders, immune/inflammatory disorders, and neurological disorders.

8. The method of claim 7, wherein the combination is administered via combined administration or separate administration.

* * * * *

SEQUENCE LISTING

```
<160> NUMBER OF SEQ ID NOS: 54

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Phe Ser Leu Tyr Thr Phe Asp Met Gly Val Gly
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2
```

```
His Ile Trp Trp Asp Asp Asp Lys Tyr Tyr Asn Pro Ala Leu Lys Ser
1               5                   10                  15

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Arg Gly Leu His Asp Tyr Tyr Tyr Trp Phe Ala Tyr
1               5                   10

<210> SEQ ID NO 4
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Ile Thr Leu Lys Glu Ser Gly Pro Thr Leu Val Lys Pro Thr Gln
1               5                   10                  15

Thr Leu Thr Leu Thr Cys Thr Phe Ser
            20                  25

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Ile Arg Gln Pro Pro Gly Lys Gly Leu Glu Trp Leu Ala
1               5                   10

<210> SEQ ID NO 6
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ala Ser Ser Ser Val Ser Tyr Met His
1               5                   10
```

```
<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Thr Ser Asn Leu Ala Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Gln Trp Ser Arg Asn Pro Phe Thr
1               5

<210> SEQ ID NO 10
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Trp Tyr Gln Gln Lys Pro Gly Lys Ser Pro Lys Pro Trp Ile Tyr
1               5                   10                  15

<210> SEQ ID NO 12
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 13
```

-continued

<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Tyr Thr Phe
            20                  25                  30

Asp Met Gly Val Gly Trp Ile Arg Gln Pro Pro Gly Lys Gly Leu Glu
        35                  40                  45

Trp Leu Ala His Ile Trp Trp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Val Arg Gly Leu His Asp Tyr Tyr Tyr Trp Phe Ala Tyr
            100                 105                 110

<210> SEQ ID NO 14
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
            20                  25                  30

His Trp Tyr Gln Gln Lys Pro Gly Lys Ser Pro Lys Pro Trp Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Arg Asn Pro Phe Thr
                85                  90                  95

<210> SEQ ID NO 15
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Tyr Thr Phe
            20                  25                  30

Asp Met Gly Val Gly Trp Ile Arg Gln Pro Ser Gly Lys Gly Leu Glu
        35                  40                  45

```
Trp Leu Ala His Ile Trp Trp Asp Asp Asp Lys Tyr Tyr Asn Pro Ala
 50                  55                  60

Leu Lys Ser Arg Leu Thr Val Ser Lys Asp Thr Ser Lys Asn Gln Val
 65                  70                  75                  80

Phe Leu Lys Ile Pro Asn Val Asp Thr Ala Asp Ser Ala Thr Tyr Tyr
                 85                  90                  95

Cys Ala Arg Val Arg Gly Leu His Asp Tyr Tyr Tyr Trp Phe Ala Tyr
            100                 105                 110

<210> SEQ ID NO 16
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Ile Val Leu Ser Gln Ser Pro Thr Ile Leu Ser Ala Ser Pro Gly
 1               5                  10                  15

Glu Lys Val Thr Met Thr Cys Arg Ala Ser Ser Ser Val Ser Tyr Met
             20                  25                  30

His Trp Tyr Gln Gln Lys Pro Gly Ser Ser Pro Lys Pro Trp Ile Tyr
         35                  40                  45

Ala Thr Ser Asn Leu Ala Ser Gly Val Pro Ala Arg Phe Ser Gly Ser
 50                  55                  60

Gly Ser Gly Thr Ser Tyr Ser Leu Thr Ile Ser Arg Val Glu Ala Glu
 65                  70                  75                  80

Asp Ala Ala Thr Tyr Phe Cys Gln Gln Trp Ser Arg Asn Pro Phe Thr
                 85                  90                  95

<210> SEQ ID NO 17
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Ile Thr Leu Lys Glu Ser Gly Pro Thr Leu Val Lys Pro Thr Gln
 1               5                  10                  15

Thr Leu Thr Leu Thr Cys Thr Phe Ser Gly Phe Ser Leu Tyr Thr Phe
             20                  25                  30

Asp Met Gly Val Gly Trp Ile Arg Gln Pro Pro Gly Lys Gly Leu Glu
         35                  40                  45

Trp Leu Ala His Ile Trp Trp Asp Gly Asp Lys Tyr Tyr Asn Pro Ala
 50                  55                  60

Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Val Arg Gly Leu His Arg Tyr Tyr Tyr Trp Phe Ala Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140
```

```
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
    195                 200                 205

Asn His Lys Pro Ser Asn Thr Lys Val Asp Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 18
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
            20                  25                  30

His Trp Tyr Gln Gln Lys Pro Gly Lys Ser Pro Lys Pro Trp Ile Tyr
        35                  40                  45
```

Ala Thr Ser Asn Lys Ala Ser Gly Val Pro Ser Arg Phe Ser Gly Ser
            50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Arg Arg Pro Phe Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 19
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ile Ser Tyr
            20                  25                  30

Gly Val Asp Trp Val Arg Gln Pro Pro Gly Lys Gly Leu Glu Trp Leu
        35                  40                  45

Gly Val Ile Trp Gly Gly Gly Asn Thr Asn Tyr Asn Ser Ser Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Lys Thr Gly Thr Gly Tyr Ala Leu Glu Tyr Trp Gly Gln Gly Thr Ser
            100                 105                 110

Val Thr Val Ser Ser
        115

<210> SEQ ID NO 20
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Glu Asn Val Leu Thr Gln Ser Pro Ala Ile Met Ser Ala Ser Pro Gly
1               5                   10                  15

Glu Lys Val Thr Met Thr Cys Ser Ala Arg Ser Ser Val Ser Tyr Met
                20                  25                  30

His Trp Tyr Gln Gln Lys Ser Thr Ala Ser Pro Lys Leu Trp Ile Tyr
            35                  40                  45

Asp Thr Ser Lys Leu Ala Ser Gly Val Pro Gly Arg Phe Ser Gly Ser
        50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Ala Ser Gly Tyr Pro Leu Thr
                85                  90                  95

Phe Gly Ala Gly Thr Lys Leu Glu Leu Lys Arg
            100                 105
```

<210> SEQ ID NO 21
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

```
Glu Asn Val Leu Thr Gln Ser Pro Ala Ile Met Ser Ala Ser Pro Gly
1               5                   10                  15

Glu Lys Val Thr Met Thr Cys
                20
```

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

```
Ser Ala Arg Ser Ser Val Ser Tyr Met His
1               5                   10
```

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

```
Trp Tyr Gln Gln Lys Ser Thr Ala Ser Pro Lys Leu Trp Ile Tyr
1               5                   10                  15
```

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Thr Ser Lys Leu Ala Ser

```
<210> SEQ ID NO 25
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gly Val Pro Gly Arg Phe Ser Gly Ser Gly Asn Ser Tyr Ser
1               5                   10                  15

Leu Thr Ile Ser Ser Met Glu Ala Glu Asp Val Ala Thr Tyr Tyr Cys
            20                  25                  30

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Phe Gln Ala Ser Gly Tyr Pro Leu Thr
1               5

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Phe Gly Ala Gly Thr Lys Leu Glu Leu Lys Arg
1               5                   10

<210> SEQ ID NO 28
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Val Gln Leu Lys Glu Ser Gly Pro Gly Leu Val Ala Pro Ser Gln
1               5                   10                  15

Ser Leu Ser Ile Thr Cys Thr Val Ser
            20                  25

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Phe Ser Leu Ile Ser Tyr Gly Val Asp
1               5                   10
```

```
<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Trp Val Arg Gln Pro Pro Gly Lys Gly Leu Glu Trp Leu Gly
1               5                   10

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Val Ile Trp Gly Gly Gly Asn Thr Asn Tyr Asn Ser Ser Leu Met Ser
1               5                   10                  15

<210> SEQ ID NO 32
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Arg Leu Ser Ile Ser Lys Asp Asn Ser Lys Ser Gln Val Phe Leu Lys
1               5                   10                  15

Met Asn Ser Leu Gln Thr Asp Asp Thr Ala Met Tyr Tyr Cys Ala Lys
                20                  25                  30

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Thr Gly Thr Gly Tyr Ala Leu Glu Tyr
1               5

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Trp Gly Gln Gly Thr Ser Val Thr Val Ser Ser
1               5                   10

<210> SEQ ID NO 35
<211> LENGTH: 117
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 35

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Ser Ser Tyr
            20                  25                  30

Gly Val Asp Trp Val Arg Gln Pro Pro Gly Lys Gly Leu Glu Trp Val
        35                  40                  45

Gly Val Ile Trp Gly Gly Gly Asn Thr Asn Tyr Asn Ser Ser Leu Met
    50                  55                  60

Ser Arg Phe Thr Ile Ser Arg Asp Asn Ser Lys Asn Thr Leu Tyr Leu
65                  70                  75                  80

Gln Met Asn Ser Leu Lys Thr Glu Asp Thr Ala Val Tyr Tyr Cys Ala
                85                  90                  95

Lys Thr Gly Thr Gly Tyr Ala Leu Glu Tyr Trp Gly Gln Gly Thr Thr
            100                 105                 110

Val Thr Val Ser Ser
        115

<210> SEQ ID NO 36
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Lys Leu Lys Glu Ser Gly Pro Gly Leu Val Lys Pro Thr Gln
1               5                   10                  15

Thr Leu Thr Leu Thr Cys Thr Val Ser Gly Phe Ser Leu Ser Ser Tyr
            20                  25                  30

Gly Val Asp Trp Val Arg Gln Pro Pro Gly Lys Gly Leu Glu Trp Val
        35                  40                  45

Gly Val Ile Trp Gly Gly Gly Asn Thr Asn Tyr Asn Ser Ser Leu Met
    50                  55                  60

Ser Arg Phe Thr Ile Ser Arg Asp Asn Ser Lys Asn Thr Leu Tyr Leu
65                  70                  75                  80

Gln Met Asn Ser Leu Lys Thr Glu Asp Thr Ala Val Tyr Tyr Cys Ala
                85                  90                  95

Lys Thr Gly Thr Gly Tyr Ala Leu Glu Tyr Trp Gly Gln Gly Thr Thr
            100                 105                 110

Val Thr Val Ser Ser
        115

<210> SEQ ID NO 37
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Lys Leu Lys Glu Ser Gly Pro Gly Leu Val Lys Pro Thr Gln
1               5                   10                  15

Thr Leu Thr Leu Thr Cys Thr Val Ser Gly Phe Ser Leu Ser Ser Tyr
            20                  25                  30

```
Gly Val Asp Trp Val Arg Gln Pro Pro Gly Lys Gly Leu Glu Trp Val
            35                  40                  45

Gly Val Ile Trp Gly Gly Ser Thr Asn Tyr Asn Ser Ser Leu Met
        50                  55                  60

Ser Arg Phe Thr Ile Ser Arg Asp Asn Ser Lys Asn Thr Leu Tyr Leu
65                  70                  75                  80

Gln Met Asn Ser Leu Lys Thr Glu Asp Thr Ala Val Tyr Tyr Cys Ala
                85                  90                  95

Lys Thr Gly Thr Gly Tyr Ala Leu Glu Tyr Trp Gly Gln Gly Thr Thr
            100                 105                 110

Val Thr Val Ser Ser
        115

<210> SEQ ID NO 38
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Val Lys Leu Lys Glu Ser Gly Pro Gly Leu Val Lys Pro Thr Gln
1               5                   10                  15

Thr Leu Thr Leu Thr Cys Thr Val Ser Gly Phe Ser Leu Ser Ser Tyr
            20                  25                  30

Gly Val Asp Trp Val Arg Gln Pro Pro Gly Lys Gly Leu Glu Trp Val
            35                  40                  45

Gly Val Ile Trp Gly Gly Gln Thr Asn Tyr Asn Ser Ser Leu Met
        50                  55                  60

Ser Arg Phe Thr Ile Ser Arg Asp Asn Ser Lys Asn Thr Leu Tyr Leu
65                  70                  75                  80

Gln Met Asn Ser Leu Lys Thr Glu Asp Thr Ala Val Tyr Tyr Cys Ala
                85                  90                  95

Lys Thr Gly Thr Gly Tyr Ala Leu Glu Tyr Trp Gly Gln Gly Thr Thr
            100                 105                 110

Val Thr Val Ser Ser
        115

<210> SEQ ID NO 39
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Lys Leu Lys Glu Ser Gly Pro Gly Leu Val Lys Pro Thr Gln
1               5                   10                  15

Thr Leu Thr Leu Thr Cys Thr Val Ser Gly Phe Ser Leu Ser Ser Tyr
            20                  25                  30

Gly Val Asp Trp Val Arg Gln Pro Pro Gly Lys Gly Leu Glu Trp Val
            35                  40                  45

Gly Val Ile Trp Gly Gly Gly Asn Thr Tyr Tyr Asn Ser Ser Leu Met
        50                  55                  60

Ser Arg Phe Thr Ile Ser Arg Asp Asn Ser Lys Asn Thr Leu Tyr Leu
65                  70                  75                  80
```

Gln Met Asn Ser Leu Lys Thr Glu Asp Thr Ala Val Tyr Tyr Cys Ala
                85                  90                  95

Lys Thr Gly Thr Gly Tyr Ala Leu Glu Tyr Trp Gly Gln Gly Thr Thr
            100                 105                 110

Val Thr Val Ser Ser
        115

<210> SEQ ID NO 40
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Val Thr Leu Lys Glu Ser Gly Pro Gly Leu Val Lys Pro Thr Gln
1               5                   10                  15

Thr Leu Thr Leu Thr Cys Thr Val Ser Gly Phe Ser Leu Ser Ser Tyr
            20                  25                  30

Gly Val Asp Trp Val Arg Gln Pro Pro Gly Lys Gly Leu Glu Trp Val
        35                  40                  45

Gly Val Ile Trp Gly Gly Gly Ser Thr Asn Tyr Asn Ser Ser Leu Met
    50                  55                  60

Ser Arg Phe Thr Ile Ser Arg Asp Asn Ser Lys Asn Thr Leu Tyr Leu
65                  70                  75                  80

Gln Met Asn Ser Leu Lys Thr Glu Asp Thr Ala Val Tyr Tyr Cys Ala
                85                  90                  95

Lys Thr Gly Thr Gly Tyr Ala Leu Glu Tyr Trp Gly Gln Gly Thr Thr
            100                 105                 110

Val Thr Val Ser Ser
        115

<210> SEQ ID NO 41
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Thr Leu Lys Glu Ser Gly Pro Gly Leu Val Lys Pro Thr Gln
1               5                   10                  15

Thr Leu Thr Leu Thr Cys Thr Val Ser Gly Phe Ser Leu Ser Ser Tyr
            20                  25                  30

Gly Val Asp Trp Val Arg Gln Pro Pro Gly Lys Gly Leu Glu Trp Val
        35                  40                  45

Gly Val Ile Trp Gly Gly Gly Gln Thr Asn Tyr Asn Ser Ser Leu Met
    50                  55                  60

Ser Arg Phe Thr Ile Ser Arg Asp Asn Ser Lys Asn Thr Leu Tyr Leu
65                  70                  75                  80

Gln Met Asn Ser Leu Lys Thr Glu Asp Thr Ala Val Tyr Tyr Cys Ala
                85                  90                  95

Lys Thr Gly Thr Gly Tyr Ala Leu Glu Tyr Trp Gly Gln Gly Thr Thr
            100                 105                 110

Val Thr Val Ser Ser
        115

```
<210> SEQ ID NO 42
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Val Thr Leu Lys Glu Ser Gly Pro Gly Leu Val Lys Pro Thr Gln
1               5                   10                  15

Thr Leu Thr Leu Thr Cys Thr Val Ser Gly Phe Ser Leu Ser Ser Tyr
            20                  25                  30

Gly Val Asp Trp Val Arg Gln Pro Pro Gly Lys Gly Leu Glu Trp Val
        35                  40                  45

Gly Val Ile Trp Gly Gly Gly Asn Thr Tyr Tyr Asn Ser Ser Leu Met
    50                  55                  60

Ser Arg Phe Thr Ile Ser Arg Asp Asn Ser Lys Asn Thr Leu Tyr Leu
65                  70                  75                  80

Gln Met Asn Ser Leu Lys Thr Glu Asp Thr Ala Val Tyr Tyr Cys Ala
                85                  90                  95

Lys Thr Gly Thr Gly Tyr Ala Leu Glu Tyr Trp Gly Gln Gly Thr Thr
            100                 105                 110

Val Thr Val Ser Ser
        115

<210> SEQ ID NO 43
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Thr Leu Lys Glu Ser Gly Pro Ala Leu Val Lys Pro Thr Gln
1               5                   10                  15

Thr Leu Thr Leu Thr Cys Thr Val Ser Gly Phe Ser Leu Ser Ser Tyr
            20                  25                  30

Gly Val Asp Trp Val Arg Gln Pro Pro Gly Lys Gly Leu Glu Trp Val
        35                  40                  45

Gly Val Ile Trp Gly Gly Gly Asn Thr Asn Tyr Asn Ser Ser Leu Met
    50                  55                  60

Ser Arg Phe Thr Ile Ser Arg Asp Asn Ser Lys Asn Thr Leu Tyr Leu
65                  70                  75                  80

Gln Met Asn Ser Leu Lys Thr Glu Asp Thr Ala Val Tyr Tyr Cys Ala
                85                  90                  95

Lys Thr Gly Thr Gly Tyr Ala Leu Glu Tyr Trp Gly Gln Gly Thr Thr
            100                 105                 110

Val Thr Val Ser Ser
        115

<210> SEQ ID NO 44
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 44

Gln Val Lys Leu Lys Glu Ser Gly Pro Ala Leu Val Lys Pro Ser Gln
1               5                   10                  15

Thr Leu Thr Leu Thr Cys Thr Val Ser Gly Phe Ser Leu Ser Ser Tyr
            20                  25                  30

Gly Val Asp Trp Val Arg Gln Pro Pro Gly Lys Gly Leu Glu Trp Val
        35                  40                  45

Gly Val Ile Trp Gly Gly Asn Thr Asn Tyr Asn Ser Ser Leu Met
    50                  55                  60

Ser Arg Phe Thr Ile Ser Arg Asp Asn Ser Lys Asn Thr Leu Tyr Leu
65                  70                  75                  80

Gln Met Asn Ser Leu Lys Thr Glu Asp Thr Ala Val Tyr Tyr Cys Ala
                85                  90                  95

Lys Thr Gly Thr Gly Tyr Ala Leu Glu Tyr Trp Gly Gln Gly Thr Thr
            100                 105                 110

Val Thr Val Ser Ser
        115

<210> SEQ ID NO 45
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Lys Leu Lys Glu Ser Gly Pro Gly Leu Val Lys Pro Ser Gln
1               5                   10                  15

Thr Leu Thr Leu Thr Cys Thr Val Ser Gly Phe Ser Leu Ser Ser Tyr
            20                  25                  30

Gly Val Asp Trp Val Arg Gln Pro Pro Gly Lys Gly Leu Glu Trp Val
        35                  40                  45

Gly Val Ile Trp Gly Gly Asn Thr Asn Tyr Asn Ser Ser Leu Met
    50                  55                  60

Ser Arg Phe Thr Ile Ser Arg Asp Asn Ser Lys Asn Thr Leu Tyr Leu
65                  70                  75                  80

Gln Met Asn Ser Leu Lys Thr Glu Asp Thr Ala Val Tyr Tyr Cys Ala
                85                  90                  95

Lys Thr Gly Thr Gly Tyr Ala Leu Glu Tyr Trp Gly Gln Gly Thr Thr
            100                 105                 110

Val Thr Val Ser Ser
        115

<210> SEQ ID NO 46
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Val Lys Leu Gln Glu Ser Gly Pro Ala Leu Val Lys Pro Ser Gln
1               5                   10                  15

Thr Leu Thr Leu Thr Cys Thr Val Ser Gly Phe Ser Leu Ser Ser Tyr
            20                  25                  30

```
Gly Val Asp Trp Val Arg Gln Pro Pro Gly Lys Gly Leu Glu Trp Val
            35                  40                  45
Gly Val Ile Trp Gly Gly Gly Asn Thr Asn Tyr Asn Ser Ser Leu Met
        50                  55                  60
Ser Arg Phe Thr Ile Ser Arg Asp Asn Ser Lys Asn Thr Leu Tyr Leu
65                  70                  75                  80
Gln Met Asn Ser Leu Lys Thr Glu Asp Thr Ala Val Tyr Tyr Cys Ala
                85                  90                  95
Lys Thr Gly Thr Gly Tyr Ala Leu Glu Tyr Trp Gly Gln Gly Thr Thr
            100                 105                 110
Val Thr Val Ser Ser
        115

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Phe Ser Leu Ser Ser Tyr Gly Val Asp Trp
1               5                   10

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Val Ile Trp Gly Gly Gly Asn Thr Asn Tyr Asn Ser Ser Leu Met Ser
1               5                   10                  15
Arg

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Thr Gly Thr Gly Tyr Ala Leu Glu
1               5

<210> SEQ ID NO 50
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Gln Met Thr Gln Ser Pro Ser Ser Leu Ser Ala Ser Val Gly
1               5                   10                  15
Asp Arg Val Thr Ile Thr Cys Ser Ala Arg Ser Ser Val Ser Tyr Met
            20                  25                  30
```

His Trp Tyr Gln Gln Lys Pro Gly Lys Val Pro Lys Leu Leu Ile Tyr
            35                  40                  45

Asp Thr Ser Lys Leu Ala Ser Gly Val Pro Ser Arg Phe Ser Gly Ser
 50                  55                  60

Gly Ser Gly Thr Asp Phe Thr Leu Thr Ile Ser Ser Leu Gln Pro Glu
 65                  70                  75                  80

Asp Val Ala Thr Tyr Tyr Cys Phe Gln Ala Ser Gly Tyr Pro Leu Thr
                 85                  90                  95

Phe Gly Gly Gly Thr Lys Val Glu Ile Lys Arg
            100                 105

<210> SEQ ID NO 51
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Ile Val Leu Thr Gln Ser Pro Ala Thr Leu Ser Leu Ser Pro Gly
 1               5                   10                  15

Glu Arg Ala Thr Leu Ser Cys Ser Ala Arg Ser Ser Val Ser Tyr Met
            20                  25                  30

His Trp Tyr Gln Gln Lys Pro Gly Gln Ala Pro Arg Leu Leu Ile Tyr
            35                  40                  45

Asp Thr Ser Lys Leu Ala Ser Gly Ile Pro Ala Arg Phe Ser Gly Ser
 50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Phe Gln Ala Ser Gly Tyr Pro Leu Thr
                 85                  90                  95

Phe Gly Gly Gly Thr Lys Val Glu Ile Lys Arg
            100                 105

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ser Ala Arg Ser Ser Val Ser Tyr Met His
 1               5                   10

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asp Thr Ser Lys Leu Ala Ser
 1               5

<210> SEQ ID NO 54
<211> LENGTH: 9
<212> TYPE: PRT

-continued

```
<213> ORGANISM: Artificial Sequence
<220> FEATURE:
<223> OTHER INFORMATION: Description of Artificial Sequence: Synthetic
      peptide

<400> SEQUENCE: 54

Phe Gln Ala Ser Gly Tyr Pro Leu Thr
1               5
```